(12) United States Patent
Verdine et al.

(10) Patent No.: US 10,280,192 B2
(45) Date of Patent: May 7, 2019

(54) METHODS FOR THE SYNTHESIS OF FUNCTIONALIZED NUCLEIC ACIDS

(71) Applicant: WAVE LIFE SCIENCES LTD., Singapore (SG)

(72) Inventors: Gregory L. Verdine, Boston, MA (US); Meena, Belmont, MA (US); Naoki Iwamoto, Brighton, MA (US); David Charles Donnell Butler, Medford, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 0 days.

(21) Appl. No.: 15/941,494

(22) Filed: Mar. 30, 2018

(65) Prior Publication Data
US 2018/0222936 A1   Aug. 9, 2018

Related U.S. Application Data

(63) Continuation of application No. 15/222,910, filed on Jul. 28, 2016, which is a continuation of application No. 14/233,579, filed as application No. PCT/US2012/046805 on Jul. 13, 2012, now Pat. No. 9,605,019.

(60) Provisional application No. 61/509,526, filed on Jul. 19, 2011.

(51) Int. Cl.
| | |
|---|---|
| *A61K 31/66* | (2006.01) |
| *A61K 31/70* | (2006.01) |
| *C07H 13/04* | (2006.01) |
| *C07H 21/04* | (2006.01) |
| *C07C 309/66* | (2006.01) |
| *C07D 295/108* | (2006.01) |

(52) U.S. Cl.
CPC ............. *C07H 21/04* (2013.01); *A61K 31/66* (2013.01); *A61K 31/70* (2013.01); *C07C 309/66* (2013.01); *C07D 295/108* (2013.01); *C07H 13/04* (2013.01)

(58) Field of Classification Search
CPC ........ A61K 31/66; A61K 31/70; C07H 21/04; C07H 13/04; C07D 295/108; C07C 309/66
See application file for complete search history.

(56) References Cited

U.S. PATENT DOCUMENTS

| | | | |
|---|---|---|---|
| 2,878,264 A | 3/1959 | Lunsford | |
| 3,135,766 A | 6/1964 | Gould | |
| 3,484,473 A | 12/1969 | Buckman et al. | |
| 3,687,808 A | 8/1972 | Merigan et al. | |
| 3,745,162 A | 7/1973 | Helsley | |
| 4,022,791 A | 5/1977 | Welch, Jr. | |
| 4,113,869 A | 9/1978 | Gardner | |
| 4,415,732 A | 11/1983 | Caruthers et al. | |
| 4,458,066 A | 7/1984 | Caruthers et al. | |
| 4,500,707 A | 2/1985 | Caruthers et al. | |
| 4,542,142 A | 9/1985 | Martel et al. | |
| 4,659,774 A | 4/1987 | Webb et al. | |
| 4,663,328 A | 5/1987 | Lafon | |
| 4,668,777 A | 5/1987 | Caruthers et al. | |
| 4,725,677 A | 2/1988 | Koster et al. | |
| 4,735,949 A | 4/1988 | Domagala et al. | |
| 4,840,956 A | 6/1989 | Domagala et al. | |
| 4,845,205 A | 7/1989 | Huynh Dinh et al. | |
| 4,923,901 A | 5/1990 | Koester et al. | |

(Continued)

FOREIGN PATENT DOCUMENTS

| CN | 102675386 A | 9/2012 |
|---|---|---|
| DE | 1144279 B | 2/1963 |

(Continued)

OTHER PUBLICATIONS

Aaronson, J.G. et al., Rapid HATU-Mediated Solution Phase siRNA Conjugation, Bioconjugate. Chem., 22: 1723-1728 (2011).

(Continued)

*Primary Examiner* — Lawrence E Crane

(74) *Attorney, Agent, or Firm* — Choate, Hall & Stewart LLP; Xiaodong Li; Surin Mong

(57) ABSTRACT

The present application, among other things, provides technologies, e.g., reagents, methods, etc. for preparing oligonucleotides comprising phosphorothiotriesters linkages. In some embodiments, provided methods comprise reacting an H-phosphonate of structure Ia or Ib with a silylating reagent to provide a silyloxyphosphonate, and reacting the silyloxyphosphonate with a thiosulfonate reagent of structure IIa or IIb to provide an oligonucleotide of structure IIIa or IIIb. In some embodiments, provided methods comprise reacting an H-phosphonate of structure Ic with a silylating reagent to provide a silyloxyphosphonate, reacting the silyloxyphosphonate with a bis(thiosulfonate) reagent of structure IVc to provide a phosphorothiotriester comprising a thiosulfonate group of structure Vc, and then reacting the phosphorothiotriester comprising a thiosulfonate group of structure Vc with a nucleophile of structure VIc to provide an oligonucleotide of structure IIIc. In some embodiments, the present application provides a thiosulfonate reagent of structure IIa:

Structure IIa

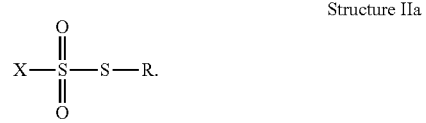

11 Claims, 6 Drawing Sheets

(56) References Cited

U.S. PATENT DOCUMENTS

| | | |
|---|---|---|
| 4,943,629 A | 7/1990 | DeVries et al. |
| 4,945,158 A | 7/1990 | DeVries et al. |
| 4,973,679 A | 11/1990 | Caruthers et al. |
| 4,981,957 A | 1/1991 | Lebleu et al. |
| 5,047,524 A | 9/1991 | Andrus et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,138,045 A | 8/1992 | Cook et al. |
| 5,141,813 A | 8/1992 | Nelson |
| 5,151,510 A | 9/1992 | Stec et al. |
| 5,175,273 A | 12/1992 | Bischofberger et al. |
| 5,200,553 A | 4/1993 | Nudelman et al. |
| 5,212,295 A | 5/1993 | Cook |
| 5,223,618 A | 6/1993 | Cook et al. |
| 5,262,530 A | 11/1993 | Andrus et al. |
| 5,292,875 A | 3/1994 | Stec et al. |
| 5,319,080 A | 6/1994 | Leumann |
| 5,359,044 A | 10/1994 | Cook et al. |
| 5,367,066 A | 11/1994 | Urdea et al. |
| 5,378,825 A | 1/1995 | Cook et al. |
| 5,386,023 A | 1/1995 | Sanghvi et al. |
| 5,432,272 A | 7/1995 | Benner |
| 5,457,187 A | 10/1995 | Gmeiner et al. |
| 5,457,191 A | 10/1995 | Cook et al. |
| 5,459,255 A | 10/1995 | Cook et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,506,212 A | 4/1996 | Hoke et al. |
| 5,512,668 A | 4/1996 | Stec et al. |
| 5,521,302 A | 5/1996 | Cook |
| 5,525,711 A | 6/1996 | Hawkins et al. |
| 5,541,307 A | 7/1996 | Cook et al. |
| 5,552,540 A | 9/1996 | Haralambidis |
| 5,565,488 A | 10/1996 | Braunlich et al. |
| 5,576,302 A | 11/1996 | Cook et al. |
| 5,587,361 A | 12/1996 | Cook et al. |
| 5,587,469 A | 12/1996 | Cook et al. |
| 5,594,121 A | 1/1997 | Froehler et al. |
| 5,596,091 A | 1/1997 | Switzer |
| 5,599,797 A | 2/1997 | Cook et al. |
| 5,602,240 A | 2/1997 | De Mesmaeker et al. |
| 5,607,923 A | 3/1997 | Cook et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,620,963 A | 4/1997 | Cook et al. |
| 5,622,989 A | 4/1997 | Br aunlich et al. |
| 5,623,070 A | 4/1997 | Cook et al. |
| 5,635,488 A | 6/1997 | Cook et al. |
| 5,643,889 A | 7/1997 | Suhadolnik et al. |
| 5,643,989 A | 7/1997 | Van De Grampel et al. |
| 5,646,267 A | 7/1997 | Stec et al. |
| 5,654,284 A | 8/1997 | Cook et al. |
| 5,661,134 A | 8/1997 | Cook et al. |
| 5,677,437 A | 10/1997 | Teng et al. |
| 5,681,940 A | 10/1997 | Wang et al. |
| 5,681,941 A | 10/1997 | Cook et al. |
| 5,688,941 A | 11/1997 | Cook et al. |
| 5,708,161 A | 1/1998 | Reese |
| 5,712,378 A | 1/1998 | Wang |
| 5,734,041 A | 3/1998 | Just et al. |
| 5,750,692 A | 5/1998 | Cook et al. |
| 5,777,092 A | 7/1998 | Cook et al. |
| 5,783,682 A | 7/1998 | Cook et al. |
| 5,792,844 A | 8/1998 | Sanghvi et al. |
| 5,795,765 A | 8/1998 | Izu et al. |
| 5,808,023 A | 9/1998 | Sanghvi et al. |
| 5,824,503 A | 10/1998 | Kurome et al. |
| 5,834,607 A | 11/1998 | Manoharan et al. |
| 5,846,466 A | 12/1998 | Abe et al. |
| 5,851,840 A | 12/1998 | Sluka et al. |
| 5,852,188 A | 12/1998 | Cook |
| 5,856,465 A | 1/1999 | Stec et al. |
| 5,883,237 A | 3/1999 | Stec et al. |
| 5,892,024 A | 4/1999 | Chaturvedula et al. |
| 5,898,031 A | 4/1999 | Crooke |
| 5,908,772 A | 6/1999 | Mitta et al. |
| 5,914,396 A | 6/1999 | Cook et al. |
| 5,932,450 A | 8/1999 | Dattagupta et al. |
| 5,936,080 A | 8/1999 | Stec et al. |
| 5,965,721 A | 10/1999 | Cook et al. |
| 5,969,118 A | 10/1999 | Sanghvi et al. |
| 5,976,855 A | 11/1999 | Svendsen et al. |
| 5,998,148 A | 12/1999 | Bennett et al. |
| 5,998,602 A | 12/1999 | Torrence et al. |
| 5,998,603 A | 12/1999 | Cook et al. |
| 6,004,813 A | 12/1999 | Serlupi-Crescenzi et al. |
| 6,005,107 A | 12/1999 | Nguyen-Ba et al. |
| 6,015,886 A | 1/2000 | Dale et al. |
| 6,015,887 A | 1/2000 | Teng |
| 6,017,700 A | 1/2000 | Horn et al. |
| 6,025,482 A | 2/2000 | Cook et al. |
| 6,031,092 A | 2/2000 | Just et al. |
| 6,056,973 A | 5/2000 | Allen et al. |
| 6,057,371 A | 5/2000 | Glennon |
| 6,066,500 A | 5/2000 | Bennett et al. |
| 6,080,543 A | 6/2000 | Engel et al. |
| 6,087,482 A | 7/2000 | Teng et al. |
| 6,107,094 A | 8/2000 | Crooke |
| 6,121,433 A | 9/2000 | Cook et al. |
| 6,124,445 A | 9/2000 | Imbach et al. |
| 6,127,540 A | 10/2000 | Nguyen-Ba et al. |
| 6,133,438 A | 10/2000 | Cook et al. |
| 6,140,096 A | 10/2000 | Kofod et al. |
| 6,146,829 A | 11/2000 | Cook et al. |
| 6,147,200 A | 11/2000 | Manoharan et al. |
| 6,159,728 A | 12/2000 | Stockley et al. |
| 6,160,109 A | 12/2000 | Just et al. |
| 6,166,197 A | 12/2000 | Cook et al. |
| 6,172,209 B1 | 1/2001 | Manoharan et al. |
| 6,191,266 B1 | 2/2001 | Wang |
| 6,194,576 B1 | 2/2001 | Nguyen-Ba et al. |
| 6,207,646 B1 | 3/2001 | Krieg et al. |
| 6,214,551 B1 | 4/2001 | Sanghvi et al. |
| 6,214,805 B1 | 4/2001 | Torrence et al. |
| 6,222,025 B1 | 4/2001 | Cook et al. |
| 6,232,463 B1 | 5/2001 | Cook et al. |
| 6,235,887 B1 | 5/2001 | Froehler et al. |
| 6,239,116 B1 | 5/2001 | Krieg et al. |
| 6,239,265 B1 | 5/2001 | Cook |
| 6,242,589 B1 | 6/2001 | Cook et al. |
| 6,248,519 B1 | 6/2001 | Engel et al. |
| 6,265,172 B1 | 7/2001 | St. Clair et al. |
| 6,270,968 B1 | 8/2001 | Dalb.o slashed.ge et al. |
| 6,271,004 B1 | 8/2001 | Warthoe |
| 6,271,357 B1 | 8/2001 | Cook et al. |
| 6,300,069 B1 | 10/2001 | Missel et al. |
| 6,306,627 B1 | 10/2001 | Decker |
| 6,316,024 B1 | 11/2001 | Allen et al. |
| 6,316,626 B1 | 11/2001 | Swayze et al. |
| 6,320,040 B1 | 11/2001 | Cook et al. |
| 6,322,985 B1 | 11/2001 | Kashi et al. |
| 6,326,199 B1 | 12/2001 | Cook et al. |
| 6,339,066 B1 | 1/2002 | Bennett et al. |
| 6,344,356 B1 | 2/2002 | Stemmer |
| 6,369,209 B1 | 4/2002 | Manoharan et al. |
| 6,369,237 B1 | 4/2002 | Verdine et al. |
| 6,372,492 B1 | 4/2002 | Bennett et al. |
| 6,380,368 B1 | 4/2002 | Froehler et al. |
| 6,383,808 B1 | 5/2002 | Monia et al. |
| 6,407,223 B1 | 6/2002 | Stec et al. |
| 6,440,739 B1 | 8/2002 | Bennett et al. |
| 6,440,943 B1 | 8/2002 | Cook et al. |
| 6,444,656 B1 | 9/2002 | Nguyen-Ba et al. |
| 6,451,524 B1 | 9/2002 | Ecker |
| 6,455,308 B1 | 9/2002 | Freier |
| 6,468,983 B2 | 10/2002 | Silverman et al. |
| 6,495,677 B1 | 12/2002 | Ramasamy et al. |
| 6,500,945 B2 | 12/2002 | Cook |
| 6,506,594 B1 | 1/2003 | Barany et al. |

(56) References Cited

U.S. PATENT DOCUMENTS

| | | |
|---|---|---|
| 6,506,894 B1 | 1/2003 | Reese et al. |
| 6,528,262 B1 | 3/2003 | Gilad et al. |
| 6,528,640 B1 | 3/2003 | Beigelman et al. |
| 6,538,126 B1 | 3/2003 | Cho et al. |
| 6,559,279 B1 | 5/2003 | Manoharan et al. |
| 6,562,960 B1 | 5/2003 | Baxter et al. |
| 6,582,936 B1 | 6/2003 | Serafini et al. |
| 6,608,186 B1 | 8/2003 | Miculka et al. |
| 6,610,837 B1 | 8/2003 | Guzaev et al. |
| 6,613,873 B1 | 9/2003 | Buchardt et al. |
| 6,617,438 B1 | 9/2003 | Beigelman et al. |
| 6,632,600 B1 | 10/2003 | Short |
| 6,639,022 B2 | 10/2003 | Michels et al. |
| 6,639,062 B2 | 10/2003 | Manoharan et al. |
| 6,649,750 B1 | 11/2003 | Capaldi et al. |
| 6,670,461 B1 | 12/2003 | Wengel et al. |
| 6,682,889 B1 | 1/2004 | Wang et al. |
| 6,699,979 B2 | 3/2004 | Cook |
| 6,737,520 B2 | 5/2004 | Manoharan et al. |
| 6,762,281 B2 | 7/2004 | Manoharan et al. |
| 6,767,739 B2 | 7/2004 | Crooke et al. |
| 6,809,195 B1 | 10/2004 | Sanghvi et al. |
| 6,811,975 B2 | 11/2004 | Cook et al. |
| 6,815,542 B2 | 11/2004 | Hong et al. |
| 6,861,518 B2 | 3/2005 | Just et al. |
| 6,867,294 B1 | 3/2005 | Sanghvi et al. |
| 6,900,301 B2 | 5/2005 | Cook et al. |
| 6,933,146 B2 | 8/2005 | Helliwell et al. |
| 6,933,288 B2 | 8/2005 | Migawa et al. |
| 6,936,432 B2 | 8/2005 | Gopalan et al. |
| 6,943,240 B2 | 9/2005 | Bauer et al. |
| 6,949,520 B1 | 9/2005 | Hartmann et al. |
| 6,977,245 B2 | 12/2005 | Klinman et al. |
| 6,995,259 B1 | 2/2006 | Vargeese et al. |
| 7,015,315 B1 | 3/2006 | Cook et al. |
| 7,018,793 B1 | 3/2006 | Short |
| 7,019,127 B2 | 3/2006 | Reese et al. |
| 7,022,833 B2 | 4/2006 | Reese |
| 7,030,230 B2 | 4/2006 | Ross et al. |
| 7,045,610 B2 | 5/2006 | Dempcy et al. |
| 7,049,122 B2 | 5/2006 | Chang et al. |
| 7,067,497 B2 | 6/2006 | Hanecak et al. |
| 7,101,993 B1 | 9/2006 | Cook et al. |
| 7,119,184 B2 | 10/2006 | Manoharan et al. |
| RE39,464 E | 1/2007 | Cook et al. |
| 7,160,920 B2 | 1/2007 | Garvey et al. |
| 7,205,399 B1 | 4/2007 | Vargeese et al. |
| 7,214,491 B2 | 5/2007 | Yadav et al. |
| 7,227,014 B2 | 6/2007 | Crooke et al. |
| 7,238,795 B2 | 7/2007 | Seela et al. |
| 7,247,621 B2 | 7/2007 | Hong et al. |
| 7,259,150 B2 | 8/2007 | Crooke et al. |
| 7,264,932 B2 | 9/2007 | Latham et al. |
| 7,268,119 B2 | 9/2007 | Cook et al. |
| 7,271,156 B2 | 9/2007 | Krieg et al. |
| 7,285,658 B2 | 10/2007 | Cook et al. |
| 7,288,376 B2 | 10/2007 | Sarma et al. |
| 7,303,895 B1 | 12/2007 | O'Regan et al. |
| 7,304,081 B2 | 12/2007 | Yao et al. |
| 7,354,909 B2 | 4/2008 | Klinman et al. |
| 7,381,527 B2 | 6/2008 | Sarma et al. |
| 7,399,845 B2 | 7/2008 | Seth et al. |
| 7,407,943 B2 | 8/2008 | Crooke et al. |
| 7,407,965 B2 | 8/2008 | Chen et al. |
| 7,410,975 B2 | 8/2008 | Lipford et al. |
| 7,414,116 B2 | 8/2008 | Milton et al. |
| 7,425,545 B2 | 9/2008 | Crooke et al. |
| 7,427,672 B2 | 9/2008 | Imanishi et al. |
| 7,429,565 B2 | 9/2008 | Boojamra et al. |
| 7,432,249 B2 | 10/2008 | Crooke |
| 7,432,250 B2 | 10/2008 | Crooke |
| 7,432,261 B2 | 10/2008 | Cannizzaro et al. |
| 7,452,901 B2 | 11/2008 | Boojamra et al. |
| 7,470,724 B2 | 12/2008 | Cannizzaro et al. |
| 7,495,088 B1 | 2/2009 | Brakel et al. |
| 7,501,091 B2 | 3/2009 | Munoz et al. |
| 7,507,808 B2 | 3/2009 | Dobie |
| 7,507,811 B2 | 3/2009 | Khvorova et al. |
| 7,511,131 B2 | 3/2009 | Crooke et al. |
| 7,517,520 B2 | 4/2009 | Manolova et al. |
| 7,534,879 B2 | 5/2009 | van Deutekom |
| 7,537,767 B2 | 5/2009 | Bachmann et al. |
| 7,547,684 B2 | 6/2009 | Seth et al. |
| 7,585,847 B2 | 9/2009 | Bratzler et al. |
| 7,598,031 B2 | 10/2009 | Liew |
| 7,598,227 B2 | 10/2009 | Crooke et al. |
| 7,598,230 B2 | 10/2009 | Cook et al. |
| 7,608,594 B2 | 10/2009 | Blagg et al. |
| 7,622,451 B2 | 11/2009 | Blagg et al. |
| 7,629,321 B2 | 12/2009 | Crooke |
| 7,645,747 B2 | 1/2010 | Boojamra et al. |
| 7,662,558 B2 | 2/2010 | Liew |
| 7,666,854 B2 | 2/2010 | Seth et al. |
| 7,666,888 B2 | 2/2010 | Bartberger et al. |
| 7,683,036 B2 | 3/2010 | Esau et al. |
| 7,695,902 B2 | 4/2010 | Crooke |
| 7,696,345 B2 | 4/2010 | Allerson et al. |
| 7,713,941 B2 | 5/2010 | Cook et al. |
| 7,718,623 B2 | 5/2010 | Kitagawa et al. |
| 7,723,508 B2 | 5/2010 | Crooke et al. |
| 7,732,590 B2 | 6/2010 | Bhanot et al. |
| 7,732,660 B2 | 6/2010 | Helliwell et al. |
| 7,741,305 B2 | 6/2010 | Crooke et al. |
| 7,741,457 B2 | 6/2010 | Seth et al. |
| 7,749,700 B2 | 7/2010 | Baird et al. |
| 7,750,131 B2 | 7/2010 | Seth et al. |
| 7,750,141 B2 | 7/2010 | Crooke et al. |
| 7,750,731 B2 | 7/2010 | Poulsen et al. |
| 7,759,318 B1 | 7/2010 | Perera et al. |
| 7,776,344 B2 | 8/2010 | Hartmann et al. |
| 7,776,874 B2 | 8/2010 | Yao et al. |
| 7,777,023 B2 | 8/2010 | Vargeese et al. |
| 7,803,930 B2 | 9/2010 | Crooke et al. |
| 7,807,653 B2 | 10/2010 | Cook et al. |
| 7,807,816 B2 | 10/2010 | Wilton et al. |
| 7,811,998 B2 | 10/2010 | Blagg et al. |
| 7,812,003 B2 | 10/2010 | Safe et al. |
| 7,838,287 B2 | 11/2010 | Goldsmith et al. |
| 7,863,252 B2 | 1/2011 | Crooke et al. |
| 7,884,086 B2 | 2/2011 | Bennett et al. |
| 7,884,117 B2 | 2/2011 | Zhang et al. |
| 7,888,324 B2 | 2/2011 | Crooke et al. |
| 7,893,039 B2 | 2/2011 | Swayze et al. |
| 7,919,472 B2 | 4/2011 | Monia et al. |
| 7,947,658 B2 | 5/2011 | Aronin et al. |
| 7,951,934 B2 | 5/2011 | Freier |
| 7,960,353 B2 | 6/2011 | Blagg |
| 7,960,541 B2 | 6/2011 | Wilton et al. |
| 7,973,015 B2 | 7/2011 | van Ommen et al. |
| 8,003,619 B2 | 8/2011 | Hartmann et al. |
| 8,008,011 B2 | 8/2011 | Schmutz et al. |
| 8,008,459 B2 | 8/2011 | Goldsmith et al. |
| 8,022,083 B2 | 9/2011 | Boojamra et al. |
| 8,039,235 B2 | 10/2011 | Lin et al. |
| 8,057,997 B2 | 11/2011 | Seela et al. |
| 8,058,288 B2 | 11/2011 | Yao et al. |
| 8,067,173 B2 | 11/2011 | Liew |
| 8,076,303 B2 | 12/2011 | Iyer et al. |
| 8,084,437 B2 | 12/2011 | Freier et al. |
| 8,084,600 B2 | 12/2011 | Natt et al. |
| 8,088,582 B2 | 1/2012 | Sampath et al. |
| 8,093,222 B2 | 1/2012 | Freier et al. |
| 8,093,225 B2 | 1/2012 | Mamet |
| 8,101,348 B2 | 1/2012 | Tuschl et al. |
| 8,101,358 B2 | 1/2012 | Liew |
| 8,101,585 B2 | 1/2012 | Yu et al. |
| 8,101,743 B2 | 1/2012 | Brown-Driver et al. |
| 8,106,025 B2 | 1/2012 | Bennett et al. |
| 8,110,358 B2 | 2/2012 | Liew |
| 8,110,558 B2 | 2/2012 | Bennett et al. |
| 8,114,597 B2 | 2/2012 | Liew |
| 8,124,745 B2 | 2/2012 | Allerson et al. |
| 8,133,674 B2 | 3/2012 | Liew |
| 8,133,675 B2 | 3/2012 | Liew |

(56) References Cited

U.S. PATENT DOCUMENTS

| | | |
|---|---|---|
| 8,133,876 B2 | 3/2012 | Bennett et al. |
| 8,138,328 B2 | 3/2012 | Crooke et al. |
| 8,143,230 B2 | 3/2012 | Bhanot et al. |
| 8,148,072 B2 | 4/2012 | Liew |
| 8,158,598 B2 | 4/2012 | Bhanot et al. |
| 8,163,707 B2 | 4/2012 | Qiu et al. |
| 8,178,506 B2 | 5/2012 | Lollo et al. |
| 8,188,059 B2 | 5/2012 | Bhanot et al. |
| 8,206,923 B2 | 6/2012 | Garza Gonzalez et al. |
| 8,207,263 B2 | 6/2012 | Popot et al. |
| 8,212,011 B2 | 7/2012 | Blagg |
| 8,212,012 B2 | 7/2012 | Blagg |
| 8,226,759 B2 | 7/2012 | Shin et al. |
| 8,232,384 B2 | 7/2012 | Wilton et al. |
| 8,257,922 B2 | 9/2012 | Liew |
| 8,258,289 B2 | 9/2012 | Bhanot et al. |
| 8,350,022 B2 | 1/2013 | Meier et al. |
| 8,361,977 B2 | 1/2013 | Baker et al. |
| 8,383,660 B2 | 2/2013 | Chang et al. |
| 8,410,070 B2 | 4/2013 | Miller et al. |
| 8,415,465 B2 | 4/2013 | Freier |
| 8,431,693 B2 | 4/2013 | Manoharan et al. |
| 8,450,474 B2 | 5/2013 | Wilton et al. |
| 8,455,634 B2 | 6/2013 | Wilton et al. |
| 8,455,635 B2 | 6/2013 | Wilton et al. |
| 8,455,636 B2 | 6/2013 | Wilton et al. |
| 8,470,987 B2 | 6/2013 | Wada et al. |
| 8,476,423 B2 | 7/2013 | Wilton et al. |
| 8,481,710 B2 | 7/2013 | Davidson et al. |
| 8,486,907 B2 | 7/2013 | Wilton et al. |
| 8,501,414 B2 | 8/2013 | Danzer et al. |
| 8,524,880 B2 | 9/2013 | Wilton et al. |
| 8,557,549 B2 | 10/2013 | Chang et al. |
| 8,557,844 B2 | 10/2013 | Platt et al. |
| 8,592,566 B2 | 11/2013 | Iwamura et al. |
| 8,632,963 B2 | 1/2014 | Shah et al. |
| 8,633,206 B2 | 1/2014 | Promo et al. |
| 8,647,742 B2 | 2/2014 | Dendukuri et al. |
| 8,648,186 B2 | 2/2014 | Monteleone |
| 8,653,254 B2 | 2/2014 | Umemoto et al. |
| 8,669,058 B2 | 3/2014 | Liew |
| 8,674,044 B2 | 3/2014 | Popot et al. |
| 8,679,750 B2 | 3/2014 | Hayden et al. |
| 8,680,063 B2 | 3/2014 | Aronin et al. |
| 8,729,036 B2 | 5/2014 | Zamore et al. |
| 8,735,417 B2 | 5/2014 | Altman et al. |
| 8,750,507 B2 | 6/2014 | Roosta et al. |
| 8,754,107 B2 | 6/2014 | George et al. |
| 8,759,507 B2 | 6/2014 | Van Deutekom |
| 8,802,659 B2 | 8/2014 | Thomas et al. |
| 8,809,516 B2 | 8/2014 | Manoharan et al. |
| 8,815,817 B2 | 8/2014 | Hessel et al. |
| 8,822,671 B2 | 9/2014 | Shimizu et al. |
| 8,859,755 B2 | 10/2014 | Wada et al. |
| 8,865,146 B2 | 10/2014 | Fukuhara et al. |
| 8,871,785 B2 | 10/2014 | Boojamra et al. |
| 8,877,435 B2 | 11/2014 | Helliwell et al. |
| 8,883,752 B2 | 11/2014 | Swayze et al. |
| 8,883,969 B2 | 11/2014 | Ide et al. |
| 8,927,513 B2 | 1/2015 | Manoharan et al. |
| 8,952,145 B2 | 2/2015 | Freier |
| 8,957,040 B2 | 2/2015 | Bennett et al. |
| 8,957,042 B2 | 2/2015 | Safe et al. |
| 8,975,389 B2 | 3/2015 | Manoharan et al. |
| 8,980,853 B2 | 3/2015 | Bennett et al. |
| 8,987,222 B2 | 3/2015 | Aronin et al. |
| 8,987,435 B2 | 3/2015 | Swayze et al. |
| 8,993,738 B2 | 3/2015 | Prakash et al. |
| 9,006,198 B2 | 4/2015 | Bennett et al. |
| 9,018,368 B2 | 4/2015 | Wilton et al. |
| 9,024,007 B2 | 5/2015 | Wilton et al. |
| 9,035,040 B2 | 5/2015 | Wilton et al. |
| 9,040,674 B2 | 5/2015 | Benson et al. |
| 9,057,066 B2 | 6/2015 | Hung et al. |
| 9,120,774 B2 | 9/2015 | Blagg et al. |
| 9,121,020 B2 | 9/2015 | Feinstein et al. |
| 9,126,927 B2 | 9/2015 | Yao et al. |
| 9,127,033 B2 | 9/2015 | Prakash et al. |
| 9,127,123 B2 | 9/2015 | Livingston et al. |
| 9,132,289 B2 | 9/2015 | Kawai |
| 9,139,604 B2 | 9/2015 | Boojamra et al. |
| 9,175,286 B2 | 11/2015 | Wilton et al. |
| 9,186,367 B2 | 11/2015 | Thomas et al. |
| 9,249,416 B2 | 2/2016 | Wilton et al. |
| 9,260,716 B2 | 2/2016 | Davidson et al. |
| 9,273,315 B2 | 3/2016 | Hung et al. |
| 9,284,344 B2 | 3/2016 | Kim et al. |
| 9,308,252 B2 | 4/2016 | Suckow et al. |
| 9,321,799 B2 | 4/2016 | Prakash et al. |
| 9,353,372 B2 | 5/2016 | Freier |
| 9,382,540 B2 | 7/2016 | Prakash et al. |
| 9,382,575 B2 | 7/2016 | Eom et al. |
| 9,394,333 B2 | 7/2016 | Wada et al. |
| 9,422,555 B2 | 8/2016 | Wilton et al. |
| 9,428,541 B2 | 8/2016 | Platt et al. |
| 9,441,229 B2 | 9/2016 | Wilton et al. |
| 9,447,415 B2 | 9/2016 | Wilton et al. |
| 9,453,228 B2 | 9/2016 | Kandimalla et al. |
| 9,476,044 B2 | 10/2016 | Tuschl et al. |
| 9,480,740 B2 | 11/2016 | Reed et al. |
| 9,481,704 B2 | 11/2016 | Clarke |
| 9,572,824 B2 | 2/2017 | Thomas et al. |
| 9,598,458 B2 | 3/2017 | Shimizu et al. |
| 9,605,019 B2 | 3/2017 | Verdine et al. |
| 9,605,262 B2 | 3/2017 | Wilton et al. |
| 9,605,263 B2 | 3/2017 | Rigo |
| 9,611,472 B2 | 4/2017 | Zamore et al. |
| 9,617,547 B2 | 4/2017 | Gemba |
| 9,695,211 B2 | 7/2017 | Wada et al. |
| 9,725,474 B2 | 8/2017 | Murata et al. |
| 9,738,895 B2 | 8/2017 | Swayze et al. |
| 9,744,183 B2 | 8/2017 | Verdine et al. |
| 9,809,616 B2 | 11/2017 | Amblard et al. |
| 9,827,258 B2 | 11/2017 | Thomas et al. |
| 9,885,082 B2 | 2/2018 | Hrdlicka |
| 9,896,688 B2 | 2/2018 | Chang et al. |
| 9,982,257 B2 * | 5/2018 | Butler .................. C12N 15/113 |
| 2001/0055761 A1 | 12/2001 | Kanemoto et al. |
| 2002/0013792 A1 | 1/2002 | Imielinski et al. |
| 2002/0082227 A1 | 6/2002 | Henry |
| 2002/0137921 A1 | 9/2002 | Cook |
| 2002/0183502 A1 | 12/2002 | Mesmaeker et al. |
| 2003/0045705 A1 | 3/2003 | Cook et al. |
| 2003/0049662 A1 | 3/2003 | Monia et al. |
| 2003/0050261 A1 | 3/2003 | Krieg et al. |
| 2003/0159938 A1 | 8/2003 | Hradil |
| 2003/0198982 A1 | 10/2003 | Seela et al. |
| 2003/0232978 A1 | 12/2003 | Seeberger et al. |
| 2003/0235845 A1 | 12/2003 | van Ommen et al. |
| 2004/0002596 A1 | 1/2004 | Hong et al. |
| 2004/0023901 A1 | 2/2004 | Cook et al. |
| 2004/0023921 A1 | 2/2004 | Hong et al. |
| 2004/0059104 A1 | 3/2004 | Cook et al. |
| 2004/0063647 A1 | 4/2004 | Johnson |
| 2004/0149587 A1 | 8/2004 | Hradil |
| 2004/0203145 A1 | 10/2004 | Zamore et al. |
| 2004/0213780 A1 | 10/2004 | Krainc |
| 2005/0042646 A1 | 2/2005 | Davidson et al. |
| 2005/0059619 A1 | 3/2005 | Krieg et al. |
| 2005/0096284 A1 | 5/2005 | McSwiggen |
| 2005/0159375 A1 | 7/2005 | Srivastava et al. |
| 2005/0169888 A1 | 8/2005 | Hartmann et al. |
| 2005/0176045 A1 | 8/2005 | Fedorov et al. |
| 2005/0203044 A1 | 9/2005 | Zinnen |
| 2005/0215513 A1 | 9/2005 | Boojamra et al. |
| 2005/0227947 A1 | 10/2005 | Chen et al. |
| 2005/0239102 A1 | 10/2005 | Verdine et al. |
| 2005/0261237 A1 | 11/2005 | Boojamra et al. |
| 2005/0277133 A1 | 12/2005 | McSwiggen |
| 2005/0277609 A1 | 12/2005 | Krieg et al. |
| 2006/0003962 A1 | 1/2006 | Ahluwalia et al. |
| 2006/0035858 A1 | 2/2006 | Geary et al. |
| 2006/0035866 A1 | 2/2006 | Cannizzaro et al. |
| 2006/0041115 A1 | 2/2006 | Ravikumar |

(56) References Cited

U.S. PATENT DOCUMENTS

| | | |
|---|---|---|
| 2006/0063730 A1 | 3/2006 | Monia et al. |
| 2006/0079478 A1 | 4/2006 | Boojamra et al. |
| 2006/0099616 A1 | 5/2006 | van Ommen et al. |
| 2006/0147952 A1 | 7/2006 | van Ommen et al. |
| 2006/0166910 A1 | 7/2006 | Tuschl et al. |
| 2006/0199776 A1 | 9/2006 | Blagg et al. |
| 2006/0199788 A1 | 9/2006 | Cannizzaro et al. |
| 2006/0211644 A1 | 9/2006 | Krieg et al. |
| 2006/0257912 A1 | 11/2006 | Kaemmerer et al. |
| 2006/0264404 A1 | 11/2006 | Boojamra et al. |
| 2007/0027116 A1 | 2/2007 | Cho et al. |
| 2007/0099851 A1 | 5/2007 | Linn |
| 2007/0099860 A1 | 5/2007 | Sah et al. |
| 2007/0123484 A1 | 5/2007 | Bhat et al. |
| 2007/0135363 A1 | 6/2007 | Cook et al. |
| 2007/0149462 A1 | 6/2007 | Iyer et al. |
| 2007/0161547 A1 | 7/2007 | Bhat et al. |
| 2007/0161590 A1 | 7/2007 | Van Bilsen et al. |
| 2007/0196852 A1 | 8/2007 | Heindl et al. |
| 2007/0249589 A1 | 10/2007 | Aebi et al. |
| 2007/0259832 A1 | 11/2007 | Cook et al. |
| 2007/0265224 A1 | 11/2007 | Cook et al. |
| 2007/0270452 A1 | 11/2007 | Blagg et al. |
| 2007/0282097 A1 | 12/2007 | Ohgi et al. |
| 2007/0287831 A1 | 12/2007 | Seth et al. |
| 2007/0299027 A1 | 12/2007 | Hung et al. |
| 2008/0015158 A1 | 1/2008 | Ichiro et al. |
| 2008/0015162 A1 | 1/2008 | Bhanot et al. |
| 2008/0039418 A1 | 2/2008 | Freier |
| 2008/0045473 A1 | 2/2008 | Uhlmann et al. |
| 2008/0064867 A1 | 3/2008 | Leuck et al. |
| 2008/0119426 A1 | 5/2008 | Dale |
| 2008/0200409 A1 | 8/2008 | Wilson et al. |
| 2008/0200423 A1 | 8/2008 | Cook et al. |
| 2008/0209581 A1 | 8/2008 | van Ommen et al. |
| 2008/0221055 A1 | 9/2008 | Sah et al. |
| 2008/0221303 A1 | 9/2008 | Katzhendler et al. |
| 2008/0249291 A1 | 10/2008 | Kwon et al. |
| 2008/0274989 A1 | 11/2008 | Davidson et al. |
| 2009/0012120 A1 | 1/2009 | Borhan et al. |
| 2009/0023675 A1 | 1/2009 | McSwiggen et al. |
| 2009/0053148 A1 | 2/2009 | Kandimalla et al. |
| 2009/0053205 A1 | 2/2009 | Kandimalla et al. |
| 2009/0060898 A1 | 3/2009 | Kandimalla et al. |
| 2009/0062224 A1 | 3/2009 | Kim et al. |
| 2009/0076246 A1 | 3/2009 | van Deutekom |
| 2009/0093425 A1 | 4/2009 | Dowdy et al. |
| 2009/0131372 A1 | 5/2009 | Chen et al. |
| 2009/0162316 A1 | 6/2009 | Verdine et al. |
| 2009/0163709 A1 | 6/2009 | Blagg |
| 2009/0186410 A1 | 7/2009 | Aronin et al. |
| 2009/0187014 A1 | 7/2009 | Blagg |
| 2009/0227543 A1 | 9/2009 | Cannizzaro et al. |
| 2009/0228998 A1 | 9/2009 | Van Ommen et al. |
| 2009/0247488 A1 | 10/2009 | Cannizzaro et al. |
| 2009/0263413 A1 | 10/2009 | Iwamura et al. |
| 2009/0275535 A1 | 11/2009 | Boojamra et al. |
| 2009/0306176 A1 | 12/2009 | Schlingensiepen et al. |
| 2010/0008937 A1 | 1/2010 | Peer et al. |
| 2010/0008981 A1 | 1/2010 | Kaemmerer et al. |
| 2010/0022467 A1 | 1/2010 | Boojamra et al. |
| 2010/0022620 A1 | 1/2010 | Crispin et al. |
| 2010/0038543 A1 | 2/2010 | Toda et al. |
| 2010/0048882 A1 | 2/2010 | Blagg et al. |
| 2010/0069472 A1 | 3/2010 | Hung et al. |
| 2010/0074889 A1 | 3/2010 | Qiu et al. |
| 2010/0105630 A1 | 4/2010 | Blagg |
| 2010/0120900 A1 | 5/2010 | van Bilsen et al. |
| 2010/0186626 A1 | 7/2010 | Shin et al. |
| 2010/0203002 A1 | 8/2010 | Fukuhara et al. |
| 2010/0204162 A1 | 8/2010 | Platt et al. |
| 2010/0215642 A1 | 8/2010 | Lan et al. |
| 2010/0273999 A1 | 10/2010 | Jung et al. |
| 2010/0299768 A1 | 11/2010 | Perrin et al. |
| 2010/0311684 A1 | 12/2010 | Cook et al. |
| 2010/0325746 A9 | 12/2010 | Kaemmerer et al. |
| 2011/0009477 A1 | 1/2011 | Yu et al. |
| 2011/0015253 A1 | 1/2011 | Wilton et al. |
| 2011/0015258 A1 | 1/2011 | Wilton et al. |
| 2011/0021365 A1 | 1/2011 | Seela et al. |
| 2011/0039334 A1 | 2/2011 | Bennett et al. |
| 2011/0046203 A1 | 2/2011 | Wilton et al. |
| 2011/0071101 A1 | 3/2011 | Boojamra et al. |
| 2011/0105587 A1 | 5/2011 | Fishcher et al. |
| 2011/0111491 A1 | 5/2011 | Davidson et al. |
| 2011/0136765 A1 | 6/2011 | Promo et al. |
| 2011/0178284 A1 | 7/2011 | Wada et al. |
| 2011/0201599 A1 | 8/2011 | Bahceci et al. |
| 2011/0212520 A1 | 9/2011 | Davidson et al. |
| 2011/0213010 A1 | 9/2011 | Hayden et al. |
| 2011/0257251 A1 | 10/2011 | Gude-Rodriguez et al. |
| 2011/0263686 A1 | 10/2011 | Wilton et al. |
| 2011/0269814 A1 | 11/2011 | Manoharan et al. |
| 2011/0269821 A1 | 11/2011 | Swayze et al. |
| 2011/0288053 A1 | 11/2011 | Boojamra et al. |
| 2011/0294124 A1 | 12/2011 | Wada et al. |
| 2011/0294869 A1 | 12/2011 | Petersen |
| 2011/0306652 A1 | 12/2011 | Freier |
| 2011/0312086 A1 | 12/2011 | Van Deutekom |
| 2012/0022144 A1 | 1/2012 | Wilton et al. |
| 2012/0022145 A1 | 1/2012 | Wilton et al. |
| 2012/0029057 A1 | 2/2012 | Wilton et al. |
| 2012/0029058 A1 | 2/2012 | Wilton et al. |
| 2012/0029059 A1 | 2/2012 | Wilton et al. |
| 2012/0029060 A1 | 2/2012 | Wilton et al. |
| 2012/0041050 A1 | 2/2012 | Wilton et al. |
| 2012/0059045 A1 | 3/2012 | Prakash et al. |
| 2012/0064137 A1 | 3/2012 | Kawai |
| 2012/0095076 A1 | 4/2012 | Sah et al. |
| 2012/0108800 A1 | 5/2012 | Murata et al. |
| 2012/0136039 A1 | 5/2012 | Aronin et al. |
| 2012/0156138 A1 | 6/2012 | Smith |
| 2012/0157511 A1 | 6/2012 | Manoharan et al. |
| 2012/0190649 A1 | 7/2012 | Thomas et al. |
| 2012/0208864 A1 | 8/2012 | Bhanot et al. |
| 2012/0214865 A1 | 8/2012 | Bennett et al. |
| 2012/0216823 A1 | 8/2012 | Fukuhara et al. |
| 2012/0246747 A1 | 9/2012 | Tuschl et al. |
| 2012/0252745 A1 | 10/2012 | Blagg et al. |
| 2012/0252879 A1 | 10/2012 | Hung et al. |
| 2012/0276037 A1 | 11/2012 | Suzuki et al. |
| 2012/0308609 A1 | 12/2012 | Gibbon et al. |
| 2012/0316224 A1 | 12/2012 | Verdine et al. |
| 2013/0005794 A1 | 1/2013 | Kaemmerer et al. |
| 2013/0046008 A1 | 2/2013 | Bennett et al. |
| 2013/0072671 A1 | 3/2013 | Van Deutekom |
| 2013/0084576 A1 | 4/2013 | Prakash et al. |
| 2013/0116310 A1 | 5/2013 | Wilton et al. |
| 2013/0116420 A1 | 5/2013 | Prakash et al. |
| 2013/0156845 A1 | 6/2013 | Manoharan et al. |
| 2013/0178612 A1 | 7/2013 | Wada et al. |
| 2013/0184450 A1 | 7/2013 | Wada et al. |
| 2013/0189782 A1 | 7/2013 | Hung et al. |
| 2013/0197061 A1 | 8/2013 | Hohjoh et al. |
| 2013/0217755 A1 | 8/2013 | Wilton et al. |
| 2013/0236536 A1 | 9/2013 | Phiasivongsa et al. |
| 2013/0243725 A1 | 9/2013 | Clarke |
| 2013/0253033 A1 | 9/2013 | Wilton et al. |
| 2013/0253178 A1 | 9/2013 | Shimizu et al. |
| 2013/0253180 A1 | 9/2013 | Wilton et al. |
| 2013/0274313 A1 | 10/2013 | Wilton et al. |
| 2013/0281684 A1 | 10/2013 | Freier |
| 2013/0302806 A1 | 11/2013 | Van Deutekom |
| 2013/0316969 A1 | 11/2013 | Boojamra et al. |
| 2013/0323836 A1 | 12/2013 | Manoharan et al. |
| 2013/0331438 A1 | 12/2013 | Wilton et al. |
| 2014/0080769 A1 | 3/2014 | Platt et al. |
| 2014/0080896 A1 | 3/2014 | Nelson et al. |
| 2014/0080898 A1 | 3/2014 | Wilton et al. |
| 2014/0107330 A1 | 4/2014 | Freier et al. |
| 2014/0120088 A1 | 5/2014 | Carpentier |
| 2014/0142160 A1 | 5/2014 | Lee et al. |
| 2014/0155587 A1 | 6/2014 | Wilton et al. |
| 2014/0163213 A1 | 6/2014 | Debelak et al. |

(56) References Cited

U.S. PATENT DOCUMENTS

| | | |
|---|---|---|
| 2014/0194610 A1 | 7/2014 | Verdine et al. |
| 2014/0213635 A1 | 7/2014 | Van Deutekom |
| 2014/0220573 A1 | 8/2014 | Hrdlicka |
| 2014/0221395 A1 | 8/2014 | Dhanoa |
| 2014/0235566 A1 | 8/2014 | Amblard et al. |
| 2014/0243515 A1 | 8/2014 | Wilton et al. |
| 2014/0243516 A1 | 8/2014 | Wilton et al. |
| 2014/0255936 A1 | 9/2014 | Rademakers et al. |
| 2014/0256578 A1 | 9/2014 | Hayden et al. |
| 2014/0275212 A1 | 9/2014 | van Deutekom |
| 2014/0303238 A1 | 10/2014 | Linsley et al. |
| 2014/0309190 A1 | 10/2014 | Thomas et al. |
| 2014/0309283 A1 | 10/2014 | Wilton et al. |
| 2014/0309284 A1 | 10/2014 | Wilton et al. |
| 2014/0309285 A1 | 10/2014 | Wilton et al. |
| 2014/0316121 A1 | 10/2014 | Prakash et al. |
| 2014/0323707 A1 | 10/2014 | Seth et al. |
| 2014/0350076 A1 | 11/2014 | van Deutekom |
| 2014/0357698 A1 | 12/2014 | Van Deutekom et al. |
| 2014/0357855 A1 | 12/2014 | Van Deutekom et al. |
| 2014/0373188 A1 | 12/2014 | Zamore et al. |
| 2014/0378527 A1 | 12/2014 | van Deutekom |
| 2015/0025039 A1 | 1/2015 | Boojamra et al. |
| 2015/0051389 A1 | 2/2015 | Seth et al. |
| 2015/0057330 A1 | 2/2015 | Wilton et al. |
| 2015/0080457 A1 | 3/2015 | Manoharan et al. |
| 2015/0080563 A2 | 3/2015 | van Deutekom |
| 2015/0096064 A1 | 4/2015 | Tuschl et al. |
| 2015/0126725 A1 | 5/2015 | Swayze et al. |
| 2015/0148404 A1 | 5/2015 | de Visser et al. |
| 2015/0159163 A1 | 6/2015 | Prakash et al. |
| 2015/0166999 A1 | 6/2015 | Gemba |
| 2015/0167006 A1 | 6/2015 | Swayze et al. |
| 2015/0197540 A1 | 7/2015 | Shimizu et al. |
| 2015/0211006 A1 | 7/2015 | Butler et al. |
| 2015/0218559 A1 | 8/2015 | Van Deutekom et al. |
| 2015/0259679 A1 | 9/2015 | Bennett et al. |
| 2015/0267197 A1 | 9/2015 | Bennett et al. |
| 2015/0275208 A1 | 10/2015 | Oestergaard et al. |
| 2015/0291636 A1 | 10/2015 | Atamanyuk et al. |
| 2015/0292015 A1 | 10/2015 | Bennett et al. |
| 2015/0307877 A1 | 10/2015 | Freier |
| 2015/0315594 A1 | 11/2015 | Prakash et al. |
| 2015/0322434 A1 | 11/2015 | van Deutekom |
| 2015/0329859 A1 | 11/2015 | Bennett et al. |
| 2015/0335708 A1 | 11/2015 | Froelich et al. |
| 2015/0353931 A1 | 12/2015 | Wilton et al. |
| 2015/0361424 A1 | 12/2015 | van Deutekom |
| 2015/0376615 A1 | 12/2015 | Wilton et al. |
| 2015/0376616 A1 | 12/2015 | Wilton et al. |
| 2015/0376624 A1 | 12/2015 | Gryaznov et al. |
| 2015/0376625 A1 | 12/2015 | Oestergaard et al. |
| 2016/0002281 A1 | 1/2016 | Mayes et al. |
| 2016/0002631 A1 | 1/2016 | Wilton et al. |
| 2016/0002632 A1 | 1/2016 | Wilton et al. |
| 2016/0002635 A1 | 1/2016 | Wilton et al. |
| 2016/0017327 A1 | 1/2016 | Rudnicki et al. |
| 2016/0024496 A1 | 1/2016 | Bennett et al. |
| 2016/0040161 A1 | 2/2016 | Packard et al. |
| 2016/0046939 A1 | 2/2016 | Prakash et al. |
| 2016/0050929 A1 | 2/2016 | Benfatti et al. |
| 2016/0050930 A1 | 2/2016 | Benfatti et al. |
| 2016/0053256 A1 | 2/2016 | Hung et al. |
| 2016/0068037 A1 | 3/2016 | Chang et al. |
| 2016/0076033 A1 | 3/2016 | Torii et al. |
| 2016/0108396 A1 | 4/2016 | Jensen et al. |
| 2016/0122761 A1 | 5/2016 | Prakash et al. |
| 2016/0128928 A1 | 5/2016 | Fukuhara et al. |
| 2016/0129023 A1 | 5/2016 | Thomas et al. |
| 2016/0138022 A1 | 5/2016 | Kandimalla et al. |
| 2016/0159846 A1 | 6/2016 | Prakash et al. |
| 2016/0168570 A1 | 6/2016 | Van Deutekom et al. |
| 2016/0186175 A1 | 6/2016 | Seth et al. |
| 2016/0186178 A1 | 6/2016 | Radovic-Moreno et al. |
| 2016/0186185 A1 | 6/2016 | Prakash et al. |
| 2016/0194349 A1 | 7/2016 | Prakash et al. |
| 2016/0194636 A1 | 7/2016 | Van Deutekom et al. |
| 2016/0214974 A1 | 7/2016 | Schaetzer et al. |
| 2016/0230172 A1 | 8/2016 | Rigo |
| 2016/0237108 A1 | 8/2016 | Fraley et al. |
| 2016/0237432 A1 | 8/2016 | Bennett et al. |
| 2016/0251653 A1 | 9/2016 | Davidson et al. |
| 2016/0251655 A1 | 9/2016 | Freier et al. |
| 2016/0251658 A1 | 9/2016 | Van Deutekom et al. |
| 2016/0264964 A1 | 9/2016 | Cancilla et al. |
| 2016/0312217 A1 | 10/2016 | Hung et al. |
| 2016/0331835 A1 | 11/2016 | Gemba et al. |
| 2016/0331836 A1 | 11/2016 | Gemba et al. |
| 2016/0333349 A1 | 11/2016 | Gemba et al. |
| 2016/0347780 A1 | 12/2016 | Wada et al. |
| 2016/0347784 A1 | 12/2016 | Verdine et al. |
| 2016/0355810 A1 | 12/2016 | Van Deutekom |
| 2016/0369273 A1 | 12/2016 | Freier |
| 2017/0009233 A1 | 1/2017 | Wilton et al. |
| 2017/0009234 A1 | 1/2017 | Wilton et al. |
| 2017/0029445 A1 | 2/2017 | Shimizu et al. |
| 2017/0029457 A1 | 2/2017 | Verdine et al. |
| 2017/0037399 A1 | 2/2017 | Meena et al. |
| 2017/0044526 A1 | 2/2017 | Wan et al. |
| 2017/0067050 A1 | 3/2017 | Tuschl et al. |
| 2017/0114086 A1 | 4/2017 | Clarke |
| 2017/0114340 A1 | 4/2017 | Mueller et al. |
| 2017/0130224 A1 | 5/2017 | Oestergaard et al. |
| 2017/0197903 A1 | 7/2017 | Hoashi |
| 2017/0239280 A1 | 8/2017 | Thomas et al. |
| 2017/0275621 A1 | 9/2017 | Butler et al. |
| 2017/0327824 A1 | 11/2017 | Oestergaard et al. |
| 2017/0349897 A1 | 12/2017 | Rigo |
| 2018/0111958 A1 | 4/2018 | Wada et al. |
| 2018/0216107 A1 | 8/2018 | Frank-Kamenetsky et al. |
| 2018/0216108 A1 | 8/2018 | Vargeese et al. |

FOREIGN PATENT DOCUMENTS

| | | |
|---|---|---|
| DE | 01934150 A1 | 1/1970 |
| EP | 0 002 322 A2 | 6/1979 |
| EP | 192521 A1 | 8/1986 |
| EP | 269258 A2 | 6/1988 |
| EP | 0506242 A1 | 9/1992 |
| EP | 0531447 A1 | 3/1993 |
| EP | 0604409 A1 | 7/1994 |
| EP | 0655088 A1 | 5/1995 |
| EP | 0779893 A2 | 6/1997 |
| EP | 0831854 A1 | 4/1998 |
| EP | 0973945 A1 | 1/2000 |
| EP | 1097162 A2 | 5/2001 |
| EP | 1100807 A1 | 5/2001 |
| EP | 1185305 | 3/2002 |
| EP | 1244682 A1 | 10/2002 |
| EP | 1311526 A1 | 5/2003 |
| EP | 1418179 A2 | 5/2004 |
| EP | 1499627 A2 | 1/2005 |
| EP | 1539188 A2 | 6/2005 |
| EP | 1556077 A2 | 7/2005 |
| EP | 1560840 A2 | 8/2005 |
| EP | 1562971 A2 | 8/2005 |
| EP | 1670810 A2 | 6/2006 |
| EP | 1670896 A2 | 6/2006 |
| EP | 1795536 A1 | 6/2007 |
| EP | 1957507 A2 | 8/2008 |
| EP | 1984381 A2 | 10/2008 |
| EP | 2021472 A2 | 2/2009 |
| EP | 2062980 A2 | 5/2009 |
| EP | 2066684 A2 | 6/2009 |
| EP | 2149571 A1 | 2/2010 |
| EP | 2161038 A1 | 3/2010 |
| EP | 2170917 A2 | 4/2010 |
| EP | 2173760 A2 | 4/2010 |
| EP | 2176280 A2 | 4/2010 |
| EP | 2282744 A1 | 2/2011 |
| EP | 2285819 A1 | 2/2011 |
| EP | 2316967 A1 | 5/2011 |
| EP | 2360166 A1 | 8/2011 |
| EP | 1 866 319 B1 | 11/2011 |

(56) References Cited

FOREIGN PATENT DOCUMENTS

| | | |
|---|---|---|
| EP | 2399588 A1 | 12/2011 |
| EP | 2422819 A2 | 2/2012 |
| EP | 2428227 A1 | 3/2012 |
| EP | 2458005 A1 | 5/2012 |
| EP | 2462153 A2 | 6/2012 |
| EP | 2479182 A1 | 7/2012 |
| EP | 1606407 B1 | 12/2013 |
| EP | 14193887.8 | 11/2014 |
| EP | 14198167.0 | 12/2014 |
| EP | 15182401.8 | 8/2015 |
| EP | 15191074.2 | 10/2015 |
| EP | 15191075.9 | 10/2015 |
| EP | 15191076.7 | 10/2015 |
| EP | 2982758 A1 | 2/2016 |
| EP | 2125852 B1 | 4/2016 |
| EP | 2370451 B1 | 11/2016 |
| EP | 2 534 262 B1 | 12/2016 |
| GB | 1448437 A | 9/1976 |
| GB | 2016273 A | 9/1979 |
| JP | H03-074398 A | 3/1991 |
| JP | 3072345 B1 | 7/2000 |
| JP | 2003/238586 A | 8/2003 |
| JP | 2009-190983 A | 8/2009 |
| JP | 4348044 B2 | 10/2009 |
| JP | 04348077 B2 | 10/2009 |
| JP | 2011/088935 A | 5/2011 |
| WO | WO-91/10671 A1 | 7/1991 |
| WO | WO-91/16331 A1 | 10/1991 |
| WO | WO-91/17755 A1 | 11/1991 |
| WO | WO-92/03452 A1 | 3/1992 |
| WO | WO-92/20822 A1 | 11/1992 |
| WO | WO-92/20823 A1 | 11/1992 |
| WO | WO-93/08296 A1 | 4/1993 |
| WO | WO-94/17093 A1 | 8/1994 |
| WO | WO-94/22886 A1 | 10/1994 |
| WO | WO-94/22888 A1 | 10/1994 |
| WO | WO-94/22890 A1 | 10/1994 |
| WO | WO-96/02555 A1 | 2/1996 |
| WO | WO-96/07392 A2 | 3/1996 |
| WO | WO-96/14329 A1 | 5/1996 |
| WO | WO-96/19572 A1 | 6/1996 |
| WO | WO-96/36627 A1 | 11/1996 |
| WO | WO-96/37504 A1 | 11/1996 |
| WO | WO-96/39413 A1 | 12/1996 |
| WO | WO-97/06183 A1 | 2/1997 |
| WO | WO-97/09443 A1 | 3/1997 |
| WO | WO-97/14710 A1 | 4/1997 |
| WO | WO-97/47637 A1 | 12/1997 |
| WO | WO-98/02582 A2 | 1/1998 |
| WO | WO-98/03542 A1 | 1/1998 |
| WO | WO-98/07734 A1 | 2/1998 |
| WO | WO-98/016535 A1 | 4/1998 |
| WO | WO-98/18810 A1 | 5/1998 |
| WO | WO-98/39334 A1 | 9/1998 |
| WO | WO-98/46794 A1 | 10/1998 |
| WO | WO-98/53801 A1 | 12/1998 |
| WO | WO-99/00377 A1 | 1/1999 |
| WO | WO-99/05160 A2 | 2/1999 |
| WO | WO-99/12034 A1 | 3/1999 |
| WO | WO-99/56755 A1 | 11/1999 |
| WO | WO-99/58118 A2 | 11/1999 |
| WO | WO-00/00499 A1 | 1/2000 |
| WO | WO-00/04034 A2 | 1/2000 |
| WO | WO-00/06588 A1 | 2/2000 |
| WO | WO-00/09159 A1 | 2/2000 |
| WO | WO-00/23444 A1 | 4/2000 |
| WO | WO-00/31110 A1 | 6/2000 |
| WO | WO-00/37658 A2 | 6/2000 |
| WO | WO-00/55179 A1 | 9/2000 |
| WO | WO-00/58329 A1 | 10/2000 |
| WO | WO-00/76554 A1 | 12/2000 |
| WO | WO-01/02415 A1 | 1/2001 |
| WO | WO-01/022990 A2 | 4/2001 |
| WO | WO-01/27126 A1 | 4/2001 |
| WO | WO-01/40515 A1 | 6/2001 |
| WO | WO-01/49701 A1 | 7/2001 |
| WO | WO-01/64702 A1 | 9/2001 |
| WO | WO-2001/068663 A1 | 9/2001 |
| WO | WO-01/81303 A1 | 11/2001 |
| WO | WO-01/85751 A1 | 11/2001 |
| WO | WO-01/88198 A1 | 11/2001 |
| WO | WO-02/12263 A1 | 2/2002 |
| WO | WO-02/14340 A1 | 2/2002 |
| WO | WO-02/15410 A2 | 2/2002 |
| WO | WO-02/20544 A1 | 3/2002 |
| WO | WO-02/22635 A1 | 3/2002 |
| WO | WO-02/24906 A1 | 3/2002 |
| WO | WO-02/32450 A2 | 4/2002 |
| WO | WO-02/57425 A2 | 7/2002 |
| WO | WO-2002/051716 A1 | 7/2002 |
| WO | WO-02/97134 A2 | 12/2002 |
| WO | WO-02/099317 A1 | 12/2002 |
| WO | WO-03/002065 A2 | 1/2003 |
| WO | WO-03/004602 A2 | 1/2003 |
| WO | WO-03/011887 A2 | 2/2003 |
| WO | WO-03/012057 A2 | 2/2003 |
| WO | WO-03/014306 A2 | 2/2003 |
| WO | WO-03/014307 A2 | 2/2003 |
| WO | WO-03/018600 A2 | 3/2003 |
| WO | WO-03/066633 A2 | 8/2003 |
| WO | WO-2003/071001 A1 | 8/2003 |
| WO | WO-2003/072757 A2 | 9/2003 |
| WO | WO-2003/073989 A2 | 9/2003 |
| WO | WO-03/097662 A1 | 11/2003 |
| WO | WO-03/099840 A1 | 12/2003 |
| WO | WO-03/100017 A2 | 12/2003 |
| WO | WO-03/106477 A1 | 12/2003 |
| WO | WO-2004/000351 A1 | 12/2003 |
| WO | WO-2004/003228 A1 | 1/2004 |
| WO | WO-2004/007718 A2 | 1/2004 |
| WO | WO-2004/014312 A2 | 2/2004 |
| WO | WO-2004/014933 A1 | 2/2004 |
| WO | WO-2004/016805 A2 | 2/2004 |
| WO | WO-2004010956 A2 | 2/2004 |
| WO | WO-2004/024919 A1 | 3/2004 |
| WO | WO-2004/039829 A2 | 5/2004 |
| WO | WO-2004041889 A2 | 5/2004 |
| WO | WO-2004044134 A2 | 5/2004 |
| WO | WO-2004044136 A2 | 5/2004 |
| WO | WO-2004044141 A2 | 5/2004 |
| WO | WO-2004044181 A2 | 5/2004 |
| WO | WO-2004/048522 A2 | 6/2004 |
| WO | WO-2004055162 A2 | 7/2004 |
| WO | WO-2004/080466 A1 | 9/2004 |
| WO | WO-2004/083432 A1 | 9/2004 |
| WO | WO-2004/083446 A2 | 9/2004 |
| WO | WO-2004/085454 A1 | 10/2004 |
| WO | WO-2004/096233 A2 | 11/2004 |
| WO | WO-2004/096235 A2 | 11/2004 |
| WO | WO-2004/096286 A2 | 11/2004 |
| WO | WO-2004093783 A2 | 11/2004 |
| WO | WO-2005/002626 A2 | 1/2005 |
| WO | WO-2005000201 A2 | 1/2005 |
| WO | WO-2005005599 A2 | 1/2005 |
| WO | WO-2005/014609 A2 | 2/2005 |
| WO | WO-2005013901 A2 | 2/2005 |
| WO | WO-2005/019236 A1 | 3/2005 |
| WO | WO-2005/019237 A1 | 3/2005 |
| WO | WO-2005/021568 A2 | 3/2005 |
| WO | WO-2005/023828 A1 | 3/2005 |
| WO | WO-2005/028494 A1 | 3/2005 |
| WO | WO-2005019418 A2 | 3/2005 |
| WO | WO-2005023825 A2 | 3/2005 |
| WO | WO-2005023995 A2 | 3/2005 |
| WO | WO-2005/039630 A2 | 5/2005 |
| WO | WO-2005/042018 A2 | 5/2005 |
| WO | WO-2005/042716 A2 | 5/2005 |
| WO | WO-2005040180 A2 | 5/2005 |
| WO | WO-2005063976 A2 | 7/2005 |
| WO | WO-2005/070859 A1 | 8/2005 |
| WO | WO-2005/085272 A1 | 9/2005 |
| WO | WO-2005/092909 A1 | 10/2005 |
| WO | WO-2006/000057 A1 | 1/2006 |
| WO | WO-2006020676 A2 | 2/2006 |

(56) References Cited

FOREIGN PATENT DOCUMENTS

| | | |
|---|---|---|
| WO | WO-2006/022323 A1 | 3/2006 |
| WO | WO-2006/029258 A2 | 3/2006 |
| WO | WO-2006/031267 A2 | 3/2006 |
| WO | WO-2006031461 A2 | 3/2006 |
| WO | WO-2006044531 A2 | 4/2006 |
| WO | WO-2006/049454 A1 | 5/2006 |
| WO | WO-2006/050501 A2 | 5/2006 |
| WO | WO-2006/053861 A2 | 5/2006 |
| WO | WO-2006/065751 A2 | 6/2006 |
| WO | WO-2006/066260 A2 | 6/2006 |
| WO | WO-2006/070284 A1 | 7/2006 |
| WO | WO-2006/080596 A1 | 8/2006 |
| WO | WO-2006/091915 A2 | 8/2006 |
| WO | WO-2006/117400 A2 | 11/2006 |
| WO | WO-2006/121960 A2 | 11/2006 |
| WO | WO-2007/002904 A2 | 1/2007 |
| WO | WO-2007/005941 A2 | 1/2007 |
| WO | WO-2007027775 A2 | 3/2007 |
| WO | WO-2007/041045 A2 | 4/2007 |
| WO | WO-2007/051045 A2 | 5/2007 |
| WO | WO-2007/059041 A2 | 5/2007 |
| WO | WO-2007/064291 A1 | 6/2007 |
| WO | WO-2007/070598 A2 | 6/2007 |
| WO | WO-2007064954 A2 | 6/2007 |
| WO | WO-2007/089584 A2 | 8/2007 |
| WO | WO-2007/089611 A2 | 8/2007 |
| WO | WO-2007/090071 A2 | 8/2007 |
| WO | WO-2007/095316 A2 | 8/2007 |
| WO | WO-2007131232 A2 | 11/2007 |
| WO | WO-2007131237 A2 | 11/2007 |
| WO | WO-2007131238 A2 | 11/2007 |
| WO | WO-2007134014 A2 | 11/2007 |
| WO | WO-2007136988 A2 | 11/2007 |
| WO | WO-2007/139190 A1 | 12/2007 |
| WO | WO-2007143315 A2 | 12/2007 |
| WO | WO-2007143316 A2 | 12/2007 |
| WO | WO-2007143317 A2 | 12/2007 |
| WO | WO-2007146511 A2 | 12/2007 |
| WO | WO-2008/005562 A2 | 1/2008 |
| WO | WO-2008/008476 A2 | 1/2008 |
| WO | WO-2008/021136 A2 | 2/2008 |
| WO | WO-2008017081 A1 | 2/2008 |
| WO | WO-2008/049085 A1 | 4/2008 |
| WO | WO-2008/051763 A1 | 5/2008 |
| WO | WO-2008/068638 A2 | 6/2008 |
| WO | WO-2008/073959 A2 | 6/2008 |
| WO | WO-2008066776 A2 | 6/2008 |
| WO | WO-2008/098104 A1 | 8/2008 |
| WO | WO-2008118883 A1 | 10/2008 |
| WO | WO-2008139262 A2 | 11/2008 |
| WO | WO-2008/148801 A2 | 12/2008 |
| WO | WO-2008/151833 A2 | 12/2008 |
| WO | WO-2009/001097 A2 | 12/2008 |
| WO | WO-2009/007855 A2 | 1/2009 |
| WO | WO-2009/014237 A2 | 1/2009 |
| WO | WO-2009046141 A2 | 4/2009 |
| WO | WO-2009/086264 A1 | 7/2009 |
| WO | WO-2009/089659 A1 | 7/2009 |
| WO | WO-2009/098197 A1 | 8/2009 |
| WO | WO-2009117589 A1 | 9/2009 |
| WO | WO-2009/124238 A1 | 10/2009 |
| WO | WO-2009/135322 A1 | 11/2009 |
| WO | WO-2009143387 A2 | 11/2009 |
| WO | WO-2009143390 A2 | 11/2009 |
| WO | WO-2009143391 A2 | 11/2009 |
| WO | WO-2009143463 A2 | 11/2009 |
| WO | WO-2009/146123 A2 | 12/2009 |
| WO | WO-2009148605 A2 | 12/2009 |
| WO | WO-2010/003133 A2 | 1/2010 |
| WO | WO-2010/030858 A1 | 3/2010 |
| WO | WO-2010/039543 A2 | 4/2010 |
| WO | WO-2010/042636 A2 | 4/2010 |
| WO | WO-2010/048549 A2 | 4/2010 |
| WO | WO-2010/048585 A2 | 4/2010 |
| WO | WO-2010036696 A1 | 4/2010 |
| WO | WO-2010036698 A1 | 4/2010 |
| WO | WO-2010048552 A2 | 4/2010 |
| WO | WO-2010/064146 A2 | 6/2010 |
| WO | WO-2010/072831 A1 | 7/2010 |
| WO | WO-2010080953 A1 | 7/2010 |
| WO | WO-2010/096650 A1 | 8/2010 |
| WO | WO-2010091301 A1 | 8/2010 |
| WO | WO-2010107838 A1 | 9/2010 |
| WO | WO-2010/113937 A1 | 10/2010 |
| WO | WO-2010/118263 A1 | 10/2010 |
| WO | WO-2010120262 A1 | 10/2010 |
| WO | WO-2010/129853 A2 | 11/2010 |
| WO | WO-2010/141471 A2 | 12/2010 |
| WO | WO-2010/146784 A1 | 12/2010 |
| WO | WO-2010/150789 A1 | 12/2010 |
| WO | WO-2011/005761 A1 | 1/2011 |
| WO | WO-2011/005764 A1 | 1/2011 |
| WO | WO-2011/005860 A2 | 1/2011 |
| WO | WO-2011/010706 A1 | 1/2011 |
| WO | WO-2011/015572 A1 | 2/2011 |
| WO | WO-2011/015573 A1 | 2/2011 |
| WO | WO-2011/017521 A2 | 2/2011 |
| WO | WO-2011/017561 A1 | 2/2011 |
| WO | WO-2011/034072 A1 | 3/2011 |
| WO | WO-2011038288 A1 | 3/2011 |
| WO | WO-2011/045702 A1 | 4/2011 |
| WO | WO-2011/062210 A1 | 5/2011 |
| WO | WO-2011/064974 A1 | 6/2011 |
| WO | WO-2011085271 A2 | 7/2011 |
| WO | WO-2011/097643 A1 | 8/2011 |
| WO | WO-2011/097644 A2 | 8/2011 |
| WO | WO-2011/108682 A1 | 9/2011 |
| WO | WO-2011/133871 A2 | 10/2011 |
| WO | WO-2011127175 A2 | 10/2011 |
| WO | WO-2011127307 A1 | 10/2011 |
| WO | WO-2011/139699 A2 | 11/2011 |
| WO | WO-2011/139911 A2 | 11/2011 |
| WO | WO-2011135396 A1 | 11/2011 |
| WO | WO-2012/030683 A2 | 3/2012 |
| WO | WO-2012/073857 A1 | 6/2012 |
| WO | WO-2012092367 A1 | 7/2012 |
| WO | WO-2012109395 A1 | 8/2012 |
| WO | WO-2012/151324 A1 | 11/2012 |
| WO | WO-2013/012758 A1 | 1/2013 |
| WO | WO-2013/013068 A2 | 1/2013 |
| WO | WO-2013/022984 A1 | 2/2013 |
| WO | WO-2013/022990 A1 | 2/2013 |
| WO | WO-2013022966 A1 | 2/2013 |
| WO | WO-2013022967 A1 | 2/2013 |
| WO | WO-2013/033223 A1 | 3/2013 |
| WO | WO-2013030588 A1 | 3/2013 |
| WO | WO-2013/089283 A1 | 6/2013 |
| WO | WO-2013/138236 A1 | 9/2013 |
| WO | WO-2014/010250 A1 | 1/2014 |
| WO | WO-2014/010718 A1 | 1/2014 |
| WO | WO-2014/012081 A2 | 1/2014 |
| WO | WO-2014/025805 A1 | 2/2014 |
| WO | WO-2014/028739 A1 | 2/2014 |
| WO | WO-2014/059356 A2 | 4/2014 |
| WO | WO-2014062686 A1 | 4/2014 |
| WO | WO-2014062691 A2 | 4/2014 |
| WO | WO-2014062736 A1 | 4/2014 |
| WO | WO-2014/067904 A1 | 5/2014 |
| WO | WO-2014/069520 A1 | 5/2014 |
| WO | WO-2014/076195 A1 | 5/2014 |
| WO | WO-2014/076196 A1 | 5/2014 |
| WO | WO-2014/080004 A1 | 5/2014 |
| WO | WO-2014070771 A1 | 5/2014 |
| WO | WO-2014/099941 A1 | 6/2014 |
| WO | WO-2014/118267 A1 | 8/2014 |
| WO | WO-2014/118272 A1 | 8/2014 |
| WO | WO-2014/130607 A1 | 8/2014 |
| WO | WO-2014/132671 A1 | 9/2014 |
| WO | WO-2014/154486 A1 | 10/2014 |
| WO | WO-2014/154488 A1 | 10/2014 |
| WO | WO-2014/179626 A2 | 11/2014 |
| WO | WO-2014/188001 A1 | 11/2014 |
| WO | WO-2014/192310 A1 | 12/2014 |
| WO | WO-2014/203518 A1 | 12/2014 |

(56) References Cited

FOREIGN PATENT DOCUMENTS

| | | |
|---|---|---|
| WO | WO-2014/205451 A2 | 12/2014 |
| WO | WO-2014/207232 A1 | 12/2014 |
| WO | WO-2015/010135 A2 | 1/2015 |
| WO | WO-2015/017675 A2 | 2/2015 |
| WO | WO-2015/032617 A1 | 3/2015 |
| WO | WO-2015/051169 A2 | 4/2015 |
| WO | WO-2015/051214 A1 | 4/2015 |
| WO | WO-2015/051366 A2 | 4/2015 |
| WO | WO-2015054676 A2 | 4/2015 |
| WO | WO-2015057727 A1 | 4/2015 |
| WO | WO-2015057738 A1 | 4/2015 |
| WO | WO-2015/070212 A1 | 5/2015 |
| WO | WO-2015/071388 A1 | 5/2015 |
| WO | WO-2015/089511 A2 | 6/2015 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2015143078 A1 | 9/2015 |
| WO | WO-2015/168172 A1 | 11/2015 |
| WO | WO-2015/168589 A2 | 11/2015 |
| WO | WO-2015/171932 A1 | 11/2015 |
| WO | WO-2015/179525 A1 | 11/2015 |
| WO | WO-2016/011226 A1 | 1/2016 |
| WO | WO-2016/020399 A1 | 2/2016 |
| WO | WO-2016/021683 A1 | 2/2016 |
| WO | WO-2016/027168 A2 | 2/2016 |
| WO | WO-2016/037191 A1 | 3/2016 |
| WO | WO-2016/079181 A1 | 5/2016 |
| WO | WO-2016/079183 A1 | 5/2016 |
| WO | WO-2016/081444 A1 | 5/2016 |
| WO | WO-2016/096938 A1 | 6/2016 |
| WO | WO-2016/102664 A1 | 6/2016 |
| WO | WO-2016112132 A1 | 7/2016 |
| WO | WO-2016/126995 A1 | 8/2016 |
| WO | WO-2016/127000 A1 | 8/2016 |
| WO | WO-2016/127002 A1 | 8/2016 |
| WO | WO-2016/130589 A2 | 8/2016 |
| WO | WO-2016/130806 A2 | 8/2016 |
| WO | WO-2016/138017 A1 | 9/2016 |
| WO | WO-2016/141236 A1 | 9/2016 |
| WO | WO-2016/145142 A1 | 9/2016 |
| WO | WO-2016/154096 A1 | 9/2016 |
| WO | WO-2016/161374 A1 | 10/2016 |
| WO | WO-2016/164896 A2 | 10/2016 |
| WO | WO-2016/167780 A1 | 10/2016 |
| WO | WO-2016168592 A2 | 10/2016 |
| WO | WO-2016/209862 A1 | 12/2016 |
| WO | WO-2017/004261 A1 | 1/2017 |
| WO | WO-2017/011276 A1 | 1/2017 |
| WO | WO-2017/011286 A1 | 1/2017 |
| WO | WO-2017/015109 A1 | 1/2017 |
| WO | WO-2017/015555 A1 | 1/2017 |
| WO | WO-2017/015575 A1 | 1/2017 |
| WO | WO-2017/019660 A1 | 2/2017 |
| WO | WO-2017/023660 A1 | 2/2017 |
| WO | WO-2017/032726 A1 | 3/2017 |
| WO | WO-2017/035340 A1 | 3/2017 |
| WO | WO-2017/040078 A1 | 3/2017 |
| WO | WO-2017-048620 A1 | 3/2017 |
| WO | WO-2017/055423 A1 | 4/2017 |
| WO | WO-2017/059411 A1 | 4/2017 |
| WO | WO-2017/059446 A1 | 4/2017 |
| WO | WO-2017/062862 A2 | 4/2017 |
| WO | WO-2017/067970 A1 | 4/2017 |
| WO | WO-2017/068087 A1 | 4/2017 |
| WO | WO-2017/079291 A1 | 5/2017 |
| WO | WO-2017/081223 A1 | 5/2017 |
| WO | WO-2017/157672 A1 | 9/2017 |
| WO | WO-2017/157899 A1 | 9/2017 |
| WO | WO-2017/160741 A1 | 9/2017 |
| WO | WO-2017/165489 A1 | 9/2017 |
| WO | WO-2017/178656 A1 | 10/2017 |
| WO | WO-2017180835 A1 | 10/2017 |
| WO | WO-2017/192664 A1 | 11/2017 |
| WO | WO-2017/192679 A1 | 11/2017 |
| WO | WO-2017/194498 A1 | 11/2017 |
| WO | WO-2017/194664 A1 | 11/2017 |
| WO | WO-2017/198775 A1 | 11/2017 |
| WO | WO-2017/210647 A1 | 12/2017 |
| WO | WO-2017/221883 A1 | 12/2017 |
| WO | WO-2018/022473 A1 | 2/2018 |
| WO | WO-2018/067973 A1 | 4/2018 |
| WO | WO-2018/098264 A1 | 5/2018 |

OTHER PUBLICATIONS

Aartsma-Rus, A. et al., Antisense-Induced Multiexon Skipping for Duchenne Muscular Dystrophy Makes More Sense, Am. J. Hum. Genet., 74:83-92 (2004).

Aartsma-Rus, A. et al., Targeted exon skipping as a potential gene correction therapy for Duchenne muscular dystrophy, Neuromuscular Disorders, 12: S71-S77 (2002).

Aartsma-Rus, A. et al., Therapeutic antisense-induced exon skipping in cultured muscle cells from six different DMD patients, Human Molecular Genetics, 12(8):907-914 (2003).

Adams, S.P. et al., Hindered dialkylamino nucleoside phosphite reagents in the synthesis of two DNA 51-mers, Journal of the American Chemical Society, 105(3): 661-663 (1983).

Adarsh, et al., Organelle Specific Targeted Drug Delivery—A Review, International Journal of Research in Pharmaceutical and Biomedical Sciences, 2(3): 895-912 (2011).

Ager, D.J. The Peterson olefination reaction, Organic Reactions, 38:1-223 (2004).

Agrawal, S. and Kandimalla, E.R., Antisense and/or Immunostimulatory Oligonucleotide THerapeutics, Current Cancer Drug Targets, Bentham Science, 1(3): 1 page. URL: <http:www.eurekaselect.com/65087/article> [Retrieved Apr. 3, 2016].

Agrawal, S. and Tang, J.Y., GEM 91—an antisense oligonucleotide phosphorothioate as a therapeutic agent for AIDS, Antisense Research and Development, 2(4):261-266 (1992).

Agrawal, S. et al., Mixed-backbone oligonucleotides as second generation antisense oligonucleotides: In vitro and in vivo studies, Proc. Natl. Acad. Sci. USA, 94: 2620-2625 (1997).

Aldaye, F.A. et al., Assembling materials with DNA as the guide, Science, 321(5897): 1795-1799 (2008).

Aldrich Chemical Co. Catalog, 2007-2008 Issue, only p. 1719 supplied: see first full entry at col. 1 (S-methyl methanethiosulfonate), Milwaukee, WI.

Almer et al., Synthesis of Stereochemically Homogeneous Oligoribonucleoside All-Rp-Phosphorothioates by Combining H-Phosphonate Chemistry and Enzymatic Digestion, J. Chem. Soc., Chem. Commun., 1459-1460 (1994).

Almer, et al. A New Approach to Stereospecific Synthesis of P-chiral Phosphorothioates. Preparation of Diastereomeric Dithymidyl-(3'-5') Phosphorothioates, Chem. Commun., (3): 290-1 (2004).

Almer, et al. Solid Support Synthesis of all-Rp-oligo(ribonucleoside phosphorothioate)s, Nucleic Acids Research 24(19): 3811-3820 (1996).

Almer, H. et al., Synthesis of Diribonucleoside Phosphorothioates via Sterospecific Sulfurization of H-Phosphonate Diesters, J. Org. Chem., 57(23): 6163-6169 (1992).

Altschul, S.F. et al., Basic local alignment search tool, Journal of Molecular Biology, 215(3):403-410 (1990).

Altschul, S.F. et al., Gapped BLAST and PSI-BLAST: a new generation of protein database search programs, Nucleic Acids Research, 25(17):3389-3402 (1997).

Alul, R.H. et al., Oxalyl-CPG: a labile support for synthesis of sensitive oligonucleotide, Nucleic Acids Research, 19(7):1527-1532 (1991).

Alvarez, K. et al., Photocleavable Protecting Groups as Nucleobase Protections Allowed the Solid-Phase Synthesis of Base-Sensitive SATE-Prooligonucleotides, Journal of Organic Chemistry, 64(17): 6319-6328(1999).

Amarzguioui et al., Tolerance for mutations and chemical modifications in a siRNA, Nucleic Acids Research 31(2): 589-595 (2003).

Anthony, K. et al., Exon Skipping Quantification by Quantitative Reverse-Transcription Polymerase Chain Reaction in Duchenne

(56) References Cited

OTHER PUBLICATIONS

Muscular Dystrophy Patients Treated with the Antisense Oligomer Eteplirsen, Human Gene Therapy Methods, 23: 336-345 (2012).
Arai, K. et al., Synthesis and properties of novel 2'-O-alkoxymethyl-modified nucleic acids, Bioorganic & Medicinal Chemistry Letters, 21(21): 6285-6287 (2011).
Aristarkhova, L.N. et al., Investigation in the field of thiosulfonic acids. 28. alkyl esters of cyclopentane- and cyclohexanethiosulfonic acids, Journal of Organic Chemistry of the USSR, 6: 2454-2458 (1970).
Athyros, V.G. et al., Antisense technology for the prevention or the treatment of cardiovascular disease: the next blockbuster?, Expert Opin. Investig. Drugs, 17(7): 969-72 (2008).
Ausin, C. et al., Assesment of heat-sensitive thiophosphate protecting groups in the development of thermolytic DNA oligonucleotide prodrugs, Tetrahedron, 66(1):68-79 (2010).
Bachelin et al., Structure of a Stereoregular Phosphorothioate DNA/RNA duplex, Nat. Struct. Biol., 5(4): 271-276 (1998).
Baek, M-S. et al., In Vitro Metabolic Stabilities and Metabolism of 2'-O-(Methoxyethyl) Partially Modified Phosphorothioate Antisense Oligonucleotides in Preincubated Rat or Human Whole Liver Homogenates, Oligonucleotides, 20(6): 309-316 (2010).
Ballas, Z.K. et al., Induction of NK Activity in Murine and Human Cells by CpG Motifs in Oligodeoxynucleotides and Bacterial DNA, J. Immunoll., 57: 1840-1845 (1996).
Barber, I. et al., the Prooligonucleotides Approach I: Esterase-Mediated Reversibility of Dithymidine S-Alkyl Phosphorothiolates to Dithymidine Phosphorothioates, Bioorganic and Medicinal Chemistry Letters, 5(6):563-568 (1995).
Barber, I. et al., the Prooligonucleotides Approach II: Synthesis and stability studies of chimeric oligonucleotide models, Bioorganic and Medicinal Chemistry Letters, 5(14):1441-1444 (1995).
Barnes, P.J. and Peterson, S. Efficacy and Safety of Inhaled Corticosteroids in Asthma, Am. Rev. Respir. Dis., 148: SI-S26 (1993).
Bartz, H. et al., Poly-guanosine strings improve cellular uptake and stimulatory activity of phosphodiester CpG oligonucleotides in human leukocytes, Vaccine, 23: 148-155 (2004).
Battistini et al., Stereoselective Synthesis of Cyclic Dinucloetide Phosphorothioates, Tetrahedron, 49(5): 1115-1132 (1993).
Bayever, E. et al., Systematic administration of a phosphorothioate oligonucleotide with a sequence complementary to p53 for acute myelogenous leukemia and myelodysplastic syndrome: intial results of a phase I trial, Antisense Research Development, 3(4):383-390 (1993).
Beal, P.A. et al., Second Structural Motif for Recognition of DNA by Oligonucleotide-Directed Triple-Helix Formation, Science, 251: 1360-1363 (1991).
Beaucage, S.L. and Iyer, R.P., Advances in the Synthesis of Oligonucleotides by the Phosphoramidite Approach, Tetrahedron, 48(12):2223-2311 (1992).
Benner, S.A. and Sismour, A.M., Synthetic biology, Nature Reviews Genetics, 6(7):533-543 (2005).
Berge, S.M. et al., Pharmaceutical salts, J. Pharm. Sci., 66(1):1-19 (1997).
Besch, R. et al, Specific Inhibition of ICAM-1 Expression Mediated by Gene Targeting with Triplex-forming Oligonucleotides, J. Biol. Chem., 277(26): 32473-32479 (2002).
Birts, C.N. et a., Transcription of Click-Linked DNA un Human Cells, Angew. Chem. Int. Ed., 53:2362-2365 (2014).
Bisbal, C. and Silverman, R.H., Diverse functions of RNase L and implication in pathology, Biochimie, 89(6-7):789-798 (2007).
Blade, H. et al., Modular Synthesis of Constrained Ethyl (cEt) Purine and Pyrimidine Nucleosides, J. Org. Chem., 80: 5337-5343 (2015).
Block, E. et al., Allium Chemistry: Synthesis and Sigmatropic Rearrangements of Alk(en)yl 1-Propenyl Disulfide S-Oxides from Cut Onion and Garlic, Journal of the Ameican Chemical Society, 118(12): 2799-2810 (1996).

Block, S.S. and Weidner, J.P, Vibrational Behavior and Structure of Disulfide Dioxides (Thiolsulfonates), Applied spectroscopy, 20(2): 73-79 (1966).
Bobkov, G.V. et al., Phosphoramidite building blocks for efficient incorporation of 2'-O-aminoethoxy(and propoxy)methyl nucleosides into oligonucleotides, Tetrahedron, 64: 6238-6251 (2008).
Bock, L.C. et al., Selections of single-stranded DNA molecules that bind and inhibit human thrombin, Nature, 355: 564-566 (1992).
Boczkowska, M. et al., Stereodefined Phosphorothioate Analogues of DNA: Relative Thermodynamic Stability of the Model PS-DNA/DNA and PS-DNA/RNA complexes, Biochemistry, 41: 12483-12487 (2002).
Bode, C. et al. CpG DNA as a vaccine adjuvant, Expert Rev. Vaccines, 10(4): 499-511 (2011).
Bodor, N. et al., A convenient synthesis of (acyloxy)alkyl .alpha.-ethers of phenols, The Journal of Organic Chemistry, 48(26):5280-5284 (1983).
Bohringer, M. et al., Why Pentose and not Hexose Nucleic Acids? Part II: Oligonucleotides of 2'3'-dideoxy-β-d-glucopyranosyl ('homo-DNA') production, Helvetica Chimica Acta, 75:1416-1477 (1992).
Bologna, J. et al., Uptake and Quantification of Intracellular Concentration of Lipophilic Pro-Oligonucleotides in HeLa Cells, Antisense and Nucleic Acid Drug Development, 12(1):33-41 (2002).
Bonora, G.M. et al., Large scale, liquid phase synthesis of oligonucleotides by the phosphoramidite approach, Nucleic Acids Research, 21(5): 1213-1217 (1993).
Boudreau, R.L. et al., Nonallele-specific silencing of mutant and wild-type huntingtin demonstrates therapeutic efficacy in Huntington's disease mice, 17(6): 1053-1063 (2009).
Braasch et al., RNA Interference in Mammalian Cells by Chemically-Modified RNA, Biochemistry 42(26): 7967-7975 (2003).
Brill, W. et al., Thioalkylation of Nucleoside-H-Phosphonates and Its Application to Solid Phase Synthesis of Oligonucleotides, Tetrahedron Letters, 36(5):703-706 (1995).
Brooks, P.C. et al., Insulin-like Growth Factor Receptor Cooperates with Integrin $\alpha v \beta 5$ to Promote Tumor Cell Dissemination in Vivo, The Journal of Clinical Investigation, 99(6):1390-1398 (1997).
Brown, J.W.S. and Simpson, C.G., Splice Site Selection in Plant Pre-mRNA Splicing, Ann. Rev. Plant Physiol. Plant Mol. Biol., 49: 77-95 (1998).
Bumcrot, D et al., RNAi therapeutics: a potential new class of pharmaceutical drugs, Nat. Chem. Biol., 2: 711-9 (2006).
Bundgaard, H., (C) Means to Enhance Penetration. (1) Prodrugs as a means to improve the delivery of peptide drugs, Advanced Drug Delivery Reviews, 8:1-38 (1992).
Bundgaard, H., Design and Application of Prodrugs, A Textbook of Drug Design and Development, Edited by Krogsgaard-Larsen, P. and Bundgaard, H., Chapter 5: 113-191 (1991).
Bundgaard, H., Design of Prodrugs, Elsevier, 7-9 and 21-24 (Chapter 1) (1985).
Bunnell. B.A. et al., Targeted Delivery of Antisense Oligonucleotides by Molecular Conjugates, Somatic Cell and Molecular Genetics, 18(6):559-569 (1992).
Burgers et al., Absolute configuration of the diastereomers of adenosine 5'-O-(1-thiaotriphosphate): Consequences for the stereochemistry of polymerization by DNA-dependent RNA polymerase from *Escherichia coli*, Proceedings of the National Academy of Sciences of the United States of America 75(10): 4798-4800 (1978).
Burgers, P. M. J. et al., Stereochemistry of Hydrolysis by Snake Venom Phosphodiesterase, J. Biol. Chem., 254(16): 7476-7478 (1979).
Burgers, P.M.J. and Eckstein, F., A Study of the Mechanism of DNA Polymerase I from *Escherichia coli* with Diastereomeric Phosphorothioate Analogs of Deoxyadenosine Triphosphate, J. Biol. Chem., 254(15): 6889-6893 (1979).
Burgers, P.M.J. and Eckstein, F., Diastereomers of 5'-O-adenosyl 3'-O-uridyl phosphorothioate: chemical synthesis and enzymatic properties, Biochemistry, 18: 592-596 (1979).
Campbell, J. et al., Hybrid polymer/MOF membranes for Organic Solvent Nanofiltration (OSN): Chemical modification and the quest for perfection, Journal of Membrance Science, 503: 166-176 (2016).

(56) References Cited

OTHER PUBLICATIONS

Cankurtaran, E.S. et al., Clinical Experience with Risperidone and Memantine in the Treatment of Huntington's Disease, Journal of the National Medical Association, 98(8): 1353-1355 (2006).
Carbone, G.M. et al., Selective inhibition of transcription of the Ets2 gene in prostate cancer cells by a triplex-forming oligonucleotide, Nucl. Acid. Res., 31: 833-843 (2003).
Carrillo, H., and Lipman, D.J., The multiple sequence alignment problem in biology, SIAM J. Appl. Math., 48:1073-1082 (1988).
CAS Registry No. 1225524-67-3; STN Entry Date May 28, 2010; α-[(2-methylphenyl)methyl]-2-Pyrrolidinemethanol.
CAS Registry No. 1225524-68-4; STN Entry Date May 28, 2010; α-[(4-methylphenyl)methyl]-2-Pyrrolidinemethanol.
CAS Registry No. 1225545-00-5; STN Entry Date May 28, 2010; α-[(2,4,6-trimethylphenyl)methyl]-2-Pyrrolidinemethanol.
CAS Registry No. 1225554-20-0; STN Entry Date May 28, 2010; α-[(4-ethylphenyl)methyl]-2-Pyrrolidinemethanol.
CAS Registry No. 1225594-74-0; STN Entry Date May 28, 2010; α-[(2-chloro-6-fluorophenyl)methyl]-2-Pyrrolidinemethanol.
CAS Registry No. 1225682-42-7; STN Entry Date May 30, 2010; α-[(4-chlorophenyl)methyl]-2-Pyrrolidinemethanol.
CAS Registry No. 1226037-41-7; STN Entry Date May 30, 2010; α-[(3-chlorophenyl)methyl]-2-Pyrrolidinemethanol.
CAS Registry No. 1226118-97-3; STN Entry Date May 30, 2010; α-[(3-bromophenyl)methyl]-2-Pyrrolidinemethanol.
CAS Registry No. 1226119-02-3; STN Entry Date May 30, 2010; α-[(4-bromophenyl)methyl]-2-Pyrrolidinemethanol.
CAS Registry No. 1226146-65-1; STN Entry Date May 30, 2010; α-[(2,4-dimethylphenyl)methyl]-2-Pyrrolidinemethanol.
CAS Registry No. 1226160-20-8; STN Entry Date May 30, 2010; α-[(2,5-dimethylphenyl)methyl]-2-Pyrrolidinemethanol.
CAS Registry No. 1226178-36-4; STN Entry Date May 30, 2010; α-[(2-fluorophenyl)methyl]-2-Pyrrolidinemethanol.
CAS Registry No. 1226188-06-2; STN Entry Date May 30, 2010; α-[[4-(1-methylethyl)phenyl]methyl]-2-Pyrrolidinemethanol.
CAS Registry No. 1226204-20-1; STN Entry Date May 30, 2010; α-[(3-methylphenyl)methyl]-2-Pyrrolidinemethanol.
CAS Registry No. 1226231-44-2; STN Entry Date May 30, 2010; α-[(2-chlorophenyl)methyl]-2-Pyrrolidinemethanol.
CAS Registry No. 1226352-28-8; STN Entry Date May 30, 2010; α-[(2,4-dichlorophenyl)methyl]-2-Pyrrolidinemethanol.
CAS Registry No. 1226352-38-0; STN Entry Date May 30, 2010; α-[(3,4-dichlorophenyl)methyl]-2-Pyrrolidinemethanol.
CAS Registry No. 1226413-27-9; STN Entry Date May 30, 2010; α-(phenylmethyl)- 2-Pyrrolidinemethanol.
CAS Registry No. 1226419-15-3; STN Entry Date May 30, 2010; α-[(4-fluorophenyl)methyl]-2-Pyrrolidinemethanol.
CAS Registry No. 1263282-82-1 ; STN Entry Date Feb. 21, 2011; (S)-[(diphenyl)methyl]-2-Pyrrolidinemethanol.
CAS RN 78-96-6, Entered STN: Nov. 16, 1984.
Chak, L-L, and Okamura, K., Argonaute-dependent small RNAs derived from single-stranded, non-structured precursors, Frontiers in Genetics, 5(172): 1-15 (2014).
Chan, J.H.P. et al., Antisense Oligonucleotides: From Design to Therapeutic Application, Clinical and Experimental Pharmacology and Physiology, 33: 544-540 (2006).
Chang, W. et al., Systematic chemical modifications of single stranded siRNAs significantly improved CTNNB1 mRNA silencing, Bioorg. Med. Chem. Lett., 1-5 (2016), http://dx.doi.org/10.1016/j.bmcl.2016.07.064.
Chappell, C. et al., Involvement of human polynucleotide kinase in double-strand break repair by non-homologous end joining, The EMBO Journal, 21(11): 2827-2832 (2002).
Chatgilialoglu, C. and Snieckus, V., Chemical Synthesis: Gnosis to Prognosis, Kluwer Academic, 293-340 (1996).
Check, E., RNA interference: hitting the on switch, Nature, 448(7156): 855-858 (2007).
Cheloufi, S. et al., A Dicer-independent miRNA biogenesis pathway that requires Ago catalysis, Nature, 465(7298): 584-589 (2010).

Chen, B. and Bartlett, M., A One-Step Solid Phase Extraction Method for Bioanalysis of a Phosphorothioate Oligonucleotide and Its 3' n-1 Metabolite from Rat Plasma by uHPLC-MS/MS, The AAPS Journal, 14(4): 772-780 (2012).
Chiu, Y. and Rana, T.M., siRNA function in RNAi: A chemical modification analysis, RNA, 9(9):1034-1048 (2003).
Chmielewski, M.K. and Markiewicz, W.T., Novel Method of Synthesis of 5"-Phosphate 2'-O-ribosyl-ribonucleosides and Their 3'-Phosphoramidites, Molecules, 18:14780-14796 (2013).
Cieslak, J. et al., 31P NMR Study of the Desulfurization of Oligonucleoside Phosphorothioates Effected by "Aged" Trichloroacetic Acid Solutions, J. Org. Chem., 70: 3303-3306 (2005).
Cieslak, J. et al., Thermolytic 4-methylthio-1-butyl group for phosphate/thiophosphate protection in solid-phase synthesis of DNA oligonucleotides, Journal of Organic Chemistry, 69(7):2509-2515 (2004).
Clark, J.H, Flouride IOn as a Base in Organic Synthesis, Chemical Reviews, 1980 American Chemical Society 80(5): 429-452 (1980).
Communication Relating to the Results of the Partial International Search of PCT/IB2015/000395, Annex to Form PCT/ISA/206, 3 pages (dated Aug. 24, 2015).
Conway, N., The introduction of reporter groups at multiple and/or specific sites in DNA containing phosphorothioate diesters, Nucleic Acids Research, 43-44 (1989).
Cooney, M., et al., Site-Specific Oligonucleotide Binding Represses Transcription of the Human c-myc Gene in Vitro, Science, 241: 456-459 (1988).
Cosstick, R. and Eckstein, F., Synthesis of d(GC) and d(CG) Octamers Containing Alternating Phosphorothioate Linkages: Effect of the Phosphorothioate Group on the B-Z Transition, Biochemistry, 24: 3630-3638 (1985).
Coughlin, J.E. et al., Orally bioavailable anti-HBV dinucleotide acyloxyalkyl prodrugs, Bioorganic and Medicinal Chemistry Letters, 20(5):1783-1786 (2010).
Cox, J.R. and Ramsay, O.B., Mechanisms of Nucleophilic Substitution in Phosphate Esters, Chemical Reviews, 64(4): 317-352, (1964).
Crary, S.M. et al., Specific phosphorothioate substitutions probe the active site of *Bacilus subtilis* ribonuclease P, RNA, 8:933-947 (2002).
Crooke, S.T. and Geary, R.S. Clinical pharmacological properties of mipomersen (Kynamro), a second generation antisense inhibitor of apolipoprotein B, Br. J. Clin. Pharmacol., 76: 269-276 (2012).
Crooke, S.T., Antisense Strategies, Current Molecular Medicine, 4: 465-487 (2004).
Crooke, S.T., Molecular mechanisms of action of antisense drugs, Biochemica et Biophysica Acta, 1489: 31-44 (1999).
Crooke, S.T., Progress in Antisense Technology , Annu. Rev. Med., 55: 61-95 (2004).
Cullen, K.A. et al., Ambulatory surgery in the United States, 2006, National Health Statistics Reports, 11: 1-28 (Jan. 28, 2009—Revised Sep. 4, 2009).
Current Protocols in Nucleic Acid Chemistry, Edited by Beaucage, S.L. et al., Chapter 2: Protection of Nucleosides for Oligonucleotide Synthesis, 2.0.1.-2.16.31 (2012).
Davis, B.G. et al., Altering the specificity of subtilisin bacillus lentus through the introduction of positive charge at single amino acid sites, Bioorganic & Medicinal Chemistry, 7(11): 2303-2311 (1999).
De Koning, M.G. et al., Simple and Efficient Solution-Phase Synthesis of Oligonucleotides Using Extractive Work-Up, Organic Process Research & Developmen, 10: 1238-1245 (2006).
Dejesus-Hernandez, M. et al., Expanded GGGGCC hexanucleotide repeat in non-coding region of C9ORF72 causes chromosome 9p-linked frontotemporal dementia and amyotrophic lateral sclerosis, Neuron, 72(2): 245-256 (2011).
Deleavey, G.F. and Damha, M.J., Designing chemically modified oligonucleotides for targeted gene silencing. Chem. Biol., 19: 937-54 (2012).
Dellinger, D.J. et al., Streamlined Process for the Chemical Synthesis of RNA Using 2'-O-Thionocarbamate-Protected Nucleoside Phosphoramidites in the Solid Phase, J. Am. Chem. Soc., 133: 11540-11556 (2011).

(56) References Cited

OTHER PUBLICATIONS

Devereux, J. et al., A comprehensive set of sequence analysis programs for the VAX, Nucleic Acids Research, 12(1):387-395 (1984).
Dias, N. and Stein, C.A., Antisense Oligonucleotides: Basic Concepts and Mechanisms, Molecular Cancer Therapeutics, 1: 347-355 (2002).
Dietz, G.P.H. et al., Delivery of bioactive molecules into the cell: the Trojan horse approach, Molecular and Cellular Neuroscience, 27(2): 85-131 (2004).
Dikfidan, A. et al., RNA Specificity and Regulation of Catalysis in the Eukaryotic Polynucleotide Kinase Clp1, Molecular Cell, 54: 975-986 (2014).
Djukanovic, R. et al., Mucosal Inflammation in Asthma, Am. Rev. Respir. Dis., 142: 434-457 (1990).
Documents submitted to and/or received from the United States Securities and Exchange Commission; downloaded from EDGAR (Feb. 2, 2015 to Dec. 10, 2015).
Documents submitted to and/or received from the United States Securities and Exchange Commission; downloaded from EDGAR (Dec. 17, 2015 to Oct. 4, 2016).
Documents submitted to and/or received from the United States Securities and Exchange Commission; downloaded from EDGAR (Nov. 9, 2016 to May 10, 2017).
Donnelly, C.J. et al., RNA Toxicity from the ALS/FTD C90RF72 Expansion Is Mitigated by antisense Intervention, Neuron, 80:415-428 (2013).
Dorman et al., Synthesis of Oligodeoxynucleotides and Oligodeoxynucleotide Analogs using Phosphoramidite Intermediates, Tetrahedron, 40(1):95-102 (1984).
Dua, P. et al., Patents on SELEX and therapeutic aptamers, Recent Patents on DNA & Gene Sequences, 2(3):172-186 (2008).
Eaton, W.A. et al., Submillisecond kinetics of protein folding, Curr. Opin. Chem. Biol., 1:10-14 (1997).
Eckstein, F. et al., Stereochemistry of polymerization by DNA-dependent RNA-polymerase from *Escherichia coli*: an investigation with a diastereomeric ATP-analogue, Proc. Natl. Acad. Sci. USA, 73: 2987-90 (1976).
Eckstein, F. Phosphorothioates, Essential Components of Therapeutic Oligonucleotides, Nucleic Acid Therapeutics, 24(6): 374-387 (2014).
Eckstein, F., Oligonucleotides and Analogues A Practical Approach, IRL Press, 1-24 (1991).
Efimov, V.A. et al., Rapid synthesis of long-chain deoxyribooligonucleotides by the N-methylimidazolide phosphotriester method, Nucleic Acids Research, 11(23): 8369-8387 (1983).
Egholm, M. et al., PNA hybridizes to complementary oligonucleotides obeying the Watson-Crick hydrogen-bonding rules, Nature, 365, 566-568 (1993).
Egli, M. et al., Crystal structure of homo-DNA and nature's choice of pentose over hexose in the genetic system, Journal of the American Chemical Society, 128(33):10847-56 (2006).
Egli, M. et al., Probing the Influence of Stereoelectronic Effects on the Biophysical Properties of Oligonucleotides: Comprehensive Analysis of the RNA Affinity, Nuclease Resistance, and Crystal Structure of Ten 2'-0-Ribonucleic Acid Modifications, Biochemistry, 44: 9045-9057 (2005).
El Harchaoui, K. et al., Current and future pharmacologic options for the management of patients unable to achieve low-density lipoprotein-cholesterol goals with statins, Am. J. Cardiovasc. Drugs, 8(4): 233-242 (2008).
El-Sagheer, A.H. and Brown, T., Efficient RNA synthesis by in vitro transcription of a triazole-modified DNA template, Chem. Commun., 47(44):12057-12058 (2011).
El-Sagheer, A.H. and Brown, T., New strategy for the synthesis of chemically modified RNA constructs exemplified by hairpin and hammerhead ribozymes, PNAS, 107(35):15329-15334 (2010).
El-Sagheer, A.H. et al., Biocompatible artificial DNA linker that is read through by DNA polymerases and is functional in *Escherichia coli*, PNAS, 108(28):11338-11343 (2011).
Elbashir, S.M. et al., Duplexes of 21-nucleotide RNAs mediate RNA interference in cultured mammalian cells, Nature, 411: 494-498 (2001).
Elbashir, S.M. et al., Functional anatomy of siRNAs for mediating efficient RNAi in *Drosophila melanogaster* embryo lysate, The EMBO Journal, 20(23): 6877-6888 (2001).
Ellington, A.D. and Szostak, J.W., In vitro selection of RNA molecules that bind specific ligands, Nature, 346: 818-822 (1990).
Engelhardt, J.A. et al., Scientific and Regulatory Policy Committee Points-to-consider Paper: Drug-induced Vascular Injury Associated with Nonsmall Molecule Therapeutics in Preclinical Development: Part 2. Antisense Oligonucleotides, Toxicologic Pathology, XX: 1-10 (2015).
Epton, R., Innovation and Perspectives in Solid Phase Synthesis, Peptides, Proteins and Nucleic Acids, 21:157-162 (1994).
Erler, W. et al., Patient Advisory Board Meeting, Wave Life Sciences, London, 46 pages (Mar. 2, 2017).
Erler, W., Stereopure Exon 51-Skipping Oligonucleotide as a Potential Disease-Modifying Therapy for Duchenne Muscular Dystrophy, WAVE Life Sciences, 10 pages (2017).
Eschenmoser, A. et al., Why pentose- and not hexose-nucleic acids? Introduction to the problem, conformational analysis of oligonucleotide single strands containing 2', 3'-dideoxyglucopyranosyl building blocks ('homo-DNA'), and reflections on the conformation of A- and B-DNA, Helvetica Chimica Acta, 75:218-259 (1992).
Eschenmoser, A., Chemical etiology of nucleic acid structure, Science, 284(5423):2118-24 (1999).
Eschenmoser, A., Towards a Chemical Etiology of the Natural Nucleic Acids' Structure, Chemical Synthesis, Edited by Chatgilialoglu, C. and Snieckus, V., Kluwer Academic Publishers, 293-340 (1996).
Ewles, M. et al, Quantification of oligonucleotides by LC-MS/MS: the challenges of quantifying a phosphorothioate oligonucleotide and multiple metabolites, Bioanalysis, 6(4), 447-464 (2014).
Exiqon, Locked Nucleic Acid (LNA), Custom Oligonucleotides for RNA and DNA Research, 16 pages (Aug. 2009).
Famulok, M. Oligonucleotide aptamers that recognize small molecules, Curr. Opin. Struct. Biol., 9: 324-329 (1999).
Fearon, K. et al., Phosphorothioate oligodeoxynucleotides: large-scale synthesis and analysis, impurity characterization, and the effect of phosphorus stereochemistry, Oligonucleotides as Therapeutic Agents, Ciba Found. Symp. 209: 19-31 (1997).
Fendrich et al., Determination of the Absolute P-configuration of a Phthalidyl[ Phosphonate Thymidine-Thymidine Dimer, Nucleosides Nucleotides Nucleic Acids., 22(5-8): 1127-1129 (2003).
Ferreira, F. et al., Lewis acid deprotection of silyl-protected oligonucleotides and base-sensitive oligonucleotide analogues, Tetrahedron Letters, 45(33):6287-6290 (2004).
File Registry on STN, RN 18217-60-2, Entered STN: Nov. 16, 1984.
File Registry on STN, RN 871246-91-2, Entered STN: Jan. 5, 2006.
Fire, A. et al., Potent and specific RNA interference by double-stranded RNA in Caenorhadbditis elegans, Nature, 391: 806-811 (1998).
Forster, A.G. and Symons, R.H. Self-cleavage of plus and minus RNAs of a virusoid and a structural model for the active sites, Cell, 49(2): 211-220 (1987).
Forster, A.G. and Symons, R.H. Self-Cleavage of Virusoid RNA is performed by the Proposed 55-Nucleotide Active Site, Cell, 50: 9-16 (1987).
Frank-Kamenetsky, M. et al., Therapeutic RNAi targeting PCSK9 acutely lowers plasma cholesterol in rodents and LDL cholesterol in nonhuman primates. Proc. Natl. Acad. Sci. USA., 105(33): 11915-11920 (2008).
Frazier, K. et al., Potential Mechanisms of vascular toxicity in Monkeys with antisense oligonucleotides, TIDES oligo conference, 1-25 (May 15, 2014).
Frazier, K.S. Antisense Oligonucleotide Therapies: The Promise and the Challenges from a Toxicologic Pathologist's Perspective, Toxicology Pathology, 43: 78-89 (2015).
Frederiksen, J.K. et al., Separation of RNA Phosphorothioate Oligonucleotides by HPLC, Methods of Enzymology, 468:289-309 (2009).

(56) References Cited

OTHER PUBLICATIONS

Freier, S.M. et al., Improved free-energy parameters for predictions of RNA duplex stability, Proc. Nat. Acad. Sci. USA, 83: 9373-9377 (1986).
Freschauf, G., Identification of Small Molecule Inhibitors of the Human DNA Repair Enzyme Polynucleotide Kinase/Phosphatase, Master of Science in Experimental Oncology Thesis, University of Alberta, 155 pages (2011).
Froehler, B.C. et al., Synthesis of DNA via deoxynucleoside H-phosphonate intermediates, Nucleic Acids Research, 14(13): 5399-5407 (1986).
Fujii et al., Acylphosphonates. 5.1 A new method for stereospecific generation of phosphorothioate via aroylphosphonate intermediate, Tetrahedron Letters, 27(8): 935-938 (1986).
Fujii et al., Acylphosphonates. 7.1 A New Method for Stereospecific and Stereoselective Generation of Dideoxyribonucleoside Phosphorothioates via the Acylphosphonate Intermediates, Tetrahedron, 43: 3395-3407 (1987).
Gaffney, P.R.J. et al., Liquid-Phase Synthesis of 2'-Methyl-RNA on a Homostar Support through Organic-Solvent Nanofiltration, Chem. Eur. J., 21:1-10 (2015).
Gallier, F. et al., 5',6'-Nucleoside Phosphonate Analogues Architecture: Synthesis and Comparative Evaluation towards Metabolic Enzymes, Chem Med Chem, 6: 1094-1106 (2011).
Ganguly, A.K. et al., Structure of Halomicin B, J.C.S. Chem. Comm., 395-396 (1974).
Garegg, P.J. et al., Nucleoside H-Phosphonates. III. Chemical Synthesis of Oligodeoxyribonucleotides by the Hydrogenphosphonate Approach, Tetrahedron Letters, 27(34): 4051-4054 (1986).
Gauglitz, G.G. et al., Hypertrophic Scarring and Keloids: Pathomechanisms and Current Emerging Treatment Strategies, Mol. Med., 17(1-2): 113-125 (2011).
Giacometti, R.D. et al., Design, synthesis, and duplex-stabilizing properties of conformationally constrained tricyclic analogues of LNA, Org. Biomol. Chem., 14: 2034-2040 (2016).
Gijsen, H.J.M et al., Development of two diastereoselective rougtes towards trans-4-aminomethyl-piperidin-3-o1 building blocks, Tetrahedron 64(10): 2456-2464 (2008).
Goraczmiak, R. et al., Gene silencing by synthetic U1 Adaptors, Nature Biotechnology 27(3): 257-263 (2008).
Gosselin, G. et al., New insights regarding the potential of the pronucleotide approach in antiviral chemotherapy, 43(1):195-208 (1996).
Gough, G.R. et al., Recovery and recycling of synthetic units in the construction of oligodeoxyribonucleotides on solid supports, Tetrahedron Letters, 22(42): 4177-4180 (1981).
Gould, W.A. et al., Pyrrolidines. IX. 3-Aryl-3-pyrrolidinols, Journal of Medicinal Chemistry, 7(1): 60-67 (1964).
Graham, M.J. et al., Antisense inhibition of proprotein convertase subtilisin/kexin type 9 reduces serum LDL in hyperlipidemic mice, J. Lipid Res., 48(4): 763-767 (2007).
Grajkowski, A. et al., Design and Development of Thermolytic DNA Oligonucleotide Prodrugs, Annals of the New York Academy of Sciences, 1058:26-38 (2005).
Grajkowski, A. et al., Solid-Phase Synthesis of Thermolytic DNA Oligonucleotides Functionalized with a Single 4-Hydroxy-1-butyl or 4-Phosphato-/Thiophosphato-1-butyl Thiophosphate Protecting Group, Journal of Organic Chemistry, 72(3): 805-815 (2007).
Grajkowski, A. et al., Thermolytic CpG-containing DNA oligonucleotides as potential immunotherapeutic prodrugs, Nucleic Acids Research, 33(11):3550-3560 (2005).
Green, L.S. et al., Inhibitory DNA Ligands to Platelet-Derived Growth Factor B-Chain, Biochemistry, 35: 14413-14424 (1996).
Green, L.S. et al., Nuclease-resistant nucleic acid ligands to vascular permeability factor/vascular endothelial growth factor, Chem. Biol., 2(10): 683-695 (1995).
Griffiths-Jones, S. et al., miRBase: microRIVA sequences, targets and gene nomenclature, Nucleic Acids Research, 34 (Database Issue): D140-D144 (2006).
Griffiths-Jones, S. The microRNA Registry, Nucleic Acids Research, 32 (Database Issue): D109-D111 (2004).
Groebke, K. et al., Why pentose and not hexose nucleic acids? Part V. Purine-purine pairing in homo-DNA: guanine, isoguanine, 2,6-diaminopurine and xanthine. Helvetica Chimica Acta. 81: 375-474 (1998).
Gryaznov, S. and, Chen, J.-K., Oligodeoxyribonucleotide N3'4P5' Phosphoramidates: Synthesis and Hybridization Properties, J. Am. Chem. Soc., 116: 3143-3144 (1994).
Gude, L. et al., Mapping Targetable Sites on Human Telomerase RNA Pseudoknot/Template Domain Using 2'-OMe RNA-interacting Polynucleotide (RIPtide) Microarrays, J. Biol. Chem., 287(22): 18843-18853 (2012).
Guerciolini, R., Allele-selective Silencing of Mutant Huntingtin by Stereopure Oligonucleotides, WAVE Life Sciences, Huntington's Disease Society of America, HDSA Presentation 2016 (Jun. 3, 2016).
Guerlavais-Dagland, T et al., Fluoride-labile protecting groups for the synthesis of base-sensitive methyl-SATE oligonucleotide prodrugs, European Journal of Organic Chemistry, 2003(12):2327-2335 (2003).
Guga et al., Oxathiaphospholane Approach to the Synthesis of P-Chiral, Isotopomeric Deoxy(ribonucleoside phosphorothioate)s and Phosphates Labeled with an Oxygen Isotope. Angew Chem., 113(3): 630-633 (2001).
Guga et al., Unusual Thermal Stability of RNA/[RP-PS]-DNA/RNA Triplexes Containing a Homopurine DNA Strand, Biophys J., 92(7): 2507-2515 (2007).
Guga, P. and Stec, W.J., Synthesis of Phosphorothioate Oligonucleotides with Stereodefined Phsphorothioate Linkages, Current Protocols in Nucleic Acid Chemistry, Unit 4.17: 4.17.1-4.17.28 (2003).
Guga, P., P-chiral oligonucleotides in biological recognition processes, Current Topics in Medicinal Chemistry, 7:695-713 (2007).
Guo, M. et al., Solid-phase stereoselective synthesis of 2'-0-methyl-oligo-ribonucleoside phosphorothioates using nucleoside bicyclic oxazaphospholidines, Biorganic & Medicinal Chemistry Letters, 8(18):2539-2544 (1998).
Guzaev, A.P., Reactivity of 3H-1,2,4-dithiazole-3-thiones and 3H-1,2-dithiole-3-thiones as sulfurizing agents for oligonucleotide synthesis, Tetrahedron Letters, 52: 434-437 (2011).
Hacia, J.G. et al., Phosphorothioate oligonucleotide-directed triple helix formation, Biochemistry, 33:5367-5369 (1994).
Hagedorn, P.H. et al., Locked nucleic acid: modality, diversity, and drug discovery, Drug Discovery, 1-14 (Oct. 2017).
Hammond, S.M. and Wood, M.J. Genetic therapies for RNA mis-splicing diseases, Trends Genet., 27: 196-205 (2011).
Hanagata, N., Structure-dependent immunostimulatory effect of CpG oligodeoxynucleoties and their delivery system, Int. J. Nanomedicine, 7: 2181-95 (2012).
Hansen et al., Azaribofuranoside Analogues as Designed Inhibitors of Purine Nucleoside Phosphorylase, Synthesis and Biological Evaluation, Acta Chemis Scandinavica 52: 1214-1222 (1998).
Haringsma, H.J. et al., mRNA knockdown by single strand Rna is improved by chemical modifications, Nucleic Acids Research, 40(9): 4125-4136 (2012).
Harper, S.Q. et al., RNA interference improves motor and neuropathological abnormalities in a Huntington's disease mouse model, Proc. Natl. Acad. Sci. USA, 102(16): 5820-5825 (2005).
Hartmann, B. et al., Sequence effects on energetic and structural properties of phosphorothioate DNA: a molecular modelling study, Nucleic Acids Research, 27(16): 3342-3347 (1999).
Hartmann, G. et al., Delineation of a CpG Phosphorothioate Oligodeoxynucleotide for Activating Primate Immune Responses In Vitro and In Vivo, The Journal of Immunology, 164(3): 1617-1624 (2000).
Hau, P. et al., Results of G004, a phase lib actively controlled clinical trial with the TGF-b2 targeted compound AP 12009 for recurrent anaplastic astrocytoma, Journal of Clinical Oncology, 2006 ASCO Annual Meeting Proceedings (Post-Meeting Edition), 24(18, Jun. 20 Supplement): 1566 (2006).
Hayashi, S. et al., Studies on Antitumor Substances, Chemical & Pharmaceutical Bulletin, 12(11): 1271-1276 (1964).

(56) References Cited

OTHER PUBLICATIONS

Heemskerk, H.A. et al., In vivo comparison of 2'-O-methyl phosphorothioate and morpholino antisense oligonucleotides for Duchenne muscular dystrophy exon skipping, The Journal of Gene Medicine, 11:257-266 (2009).
Heger, W. et al., Embryotoxic effects of thalidomide derivatives on the non-human primate Callithrix jacchus; 3. Teratogenic potency of the EM 12 enantiomers, Arch. Toxicol., 62: 205-208 (1988).
Hendrix, C. et al., 1',5'-Anhydrohexitol Oligonucleotides: Synthesis, Base Pairing and Recognition by Regular Oligodeoxyribonucleotides and Oligoribonucleotides, Chem. Eur. J., 3(1): 110-120 (1997).
Henry, A.A. and Romesberg, F.E., Beyond A, C, G and T: augmenting nature's alphabet, Current Opinion in Chemical Biology, 7(6): 727-733 (2003).
Henry, S.P. et al., Activation of the Alternative Pathway of Complement by a Phosphorothioate Oligonucleotide: Potential Mechanism of Action, The Journal of Pharmacology and Experimental Therapeutics, 281(2): 810-816 (1997).
Herbert, B-S. et al., Nonradioactive detection of telomerase activity using the telomeric repeat amplification protocol, Nat. Protoc., 1(3): 1583-1590 (2006).
Herdewijn, Oligonucleotide Synthesis, Methods in Molecular Biology, 288: 1-435 (2005).
Heuberger, B.D. and Switzer, C., A Pre-RNA Candidate Revisited: Both Enantiomers of Flexible Nucleoside Triphosphates are DNA Polymerase Substrates, Journal of the American Chemical Society, 130(2):412-413 (2008).
Higuchi, T. et al., Pro-drugs as Novel Delivery Systems, ACS Symposium Series, 14 (1975).
Hirama, T. et al., PCR-Based Rapid Identification System Using Bridged Nucleic Acids for Detection of Clarithromycin-Resistant *Mycobacterium avium*-M. intracellulare Complex Isolates, Journal of Clinical Microbiology, 54(3): 699-704 (2016).
Hirao, I., Unnatural base pair systems for DNA/RNA-based biotechnology, Current Opinion in Chemical Biology,10:622-627 (2006).
Hirose, M. et al., MDM4 expression as an indicator of TP53 reactivation by combined targeting of MDM2 and MDM4 in cancer cells without TP53 mutation, Oncoscience, 1(12): (2014).
Hohjoh, H., Disease-Causing Allele-Specific Silencing by RNA Interference, Pharmaceuticals, 6: 522-535 (2013).
Hu, J. et al., Allele-Selective Inhibition of Huntingtin Expression by Switching to an miRNA-like RNAi Mechanism, Chemistry & Biology 17: 1183-1188 (2010).
Hu, J. et al., Exploring the Effect of Sequence Length and Composition on Allele-Selective Inhibition of Human Huntingtin Expression by Single-Stranded Silencing RNAs, Nucleic Acid Therapeutics, 24(3): 199-209 (2014).
Hu, J. et al., Recognition of c9orf72 Mutant RNA by Single-Stranded Silencing RNAs, Nucleic Acid Therapeutics, 8 (2016). Supplementary Figure, 1 page.
Hunziker, J. et al., Why Pentose—And Not Hexose-Nucleic Acids? Part III. Oligo(2',3'-dideoxy-(3-D-glucopyranosyl)nucleotides. ('Homo-DNA'): Base-Pairing Properties, Helvetica Chimica Acta, 76(1):259-352 (1993).
Hyrup., B. and Nielsen, P.E., Peptide Nucleic Acids (PNA): Synthesis, Properties and Potential Applications, Bioorg. Med. Chem., 4(1): 5-23 (1996).
Inagawa, T. et al., Inhibition of human immunodeficiency virus type 1 replication by P-stereodefined oligo(nucleoside phosphorothioate)s in a long-term infection model, FEBS Letters, 528(1-3): 48-52 (2002).
International Preliminary Report on Patentability for PCT/JP2010/065900, 6 pages (dated Mar. 29, 2012).
International Preliminary Report on Patentability for PCT/JP2010/065900, English Translation, 7 pages (dated Apr. 19, 2012).
International Preliminary Report on Patentability for PCT/JP2011/055018, English Translation, 5 pages (dated Oct. 11, 2012).
International Preliminary Report on Patentability for PCT/JP2011/071559, English Translation, 7 pages (dated Apr. 25, 2014).
International Preliminary Report on Patentability for PCT/JP2013/004303, 7 pages (dated Jan. 13, 2015).
International Preliminary Report on Patentability for PCT/JP2013/069107, English Translation, 10 pages (dated Jan. 15, 2015).
International Search Report for PCT/IB2009/007923, 4 pages (dated Sep. 6, 2010).
International Search Report for PCT/IB2015/000395, 7 pages (dated Oct. 30, 2015).
International Search Report for PCT/JP2010/065900, 1 page (dated Sep. 15, 2010).
International Search Report for PCT/JP2011/055018, 2 pages (dated Mar. 29, 2011).
International Search Report for PCT/JP2011/071559, 3 pages (dated Dec. 20, 2011).
International Search Report for PCT/JP2011/077313, 2 pages (dated Jan. 10, 2012).
International Search Report for PCT/JP2013/004303, 3 pages (dated Aug. 13, 2013).
International Search Report for PCT/JP2013/069107, 2 pages (dated Oct. 1, 2013).
International Search Report for PCT/JP2015/050714, and English Translation, 8 pages (dated Apr. 21, 2015).
International Search Report for PCT/JP2015/050716 and English Translation, 8 pages (dated Apr. 21, 2015).
International Search Report for PCT/JP2015/050718 and English Translation, 8 pages (dated Apr. 21, 2015).
International Search Report for PCT/US2010/041068, 1 page (dated Sep. 1, 2010).
International Search Report for PCT/US2011/064287, 2 pages (dated Apr. 12, 2012).
International Search Report for PCT/US2012/046805, 2 pages (dated Sep. 19, 2012).
International Search Report for PCT/US2013/050407, 5 pages (dated Jan. 9, 2014).
International Search Report for PCT/US2016/043542, 6 pages (dated Dec. 28, 2016).
International Search Report for PCT/US2016/043598, 4 pages (dated Nov. 28, 2016).
International Search Report for PCT/US2016/056123, 5 pages (dated Mar. 17, 2017).
International Search Report for PCT/US2017/022135, 3 pages (dated Jun. 6, 2017).
International Search Report for PCT/US2017/030753, 6 pages (dated Sep. 26, 2017).
International Search Report for PCT/US2017/030777, 5 pages (dated Oct. 2, 2017).
International Search Report for PCT/US2017/035837, 4 pages (dated Aug. 24, 2017).
International Search Report for PCT/US2017/043431, ISA/US, 5 pages (dated Dec. 21, 2017).
International Search Report for PCT/US2017/045218, 3 pages (dated Sep. 27, 2017).
International Search Report for PCT/US2017/055601, ISR/US, 6 pages (dated Feb. 15, 2018).
International Search Report for PCT/US2017/062996, 4 pages (dated Mar. 9, 2018).
Ionis Pharmaceuticals, Inc., Ionis Pharmaceuticals Licenses IONIS-HTT Rx to Partner Following Successful Phase 1/2a Study in Patients with Huntington's Disease, Press Release, 2 pages (Dec. 11, 2017).
Isis Pharmaceuticals, Inc. 2014 Annual Report, Improving Patients' Lives by Treating Disease Through Targeting RNA, 192 pages (2014).
*Isis Pharmaceuticals, Inc. v. Santaris Pharma A/S Corp.*, Order Denying Defendants' Motion for Summary Judgment Without Prejudice, Case No. 11cv02214 BTM (KSC), United States District Court, S.D. California, 5 pages (Sep. 19, 2012).
Isis Pharmaceuticals, Intellectual Property: Capturing Value From Innovation, Isis' Annual Meeting of Stockholders and Open House, Intellectual Property Poster, 1 page (2011). Received from Internet <http://www.isispharm.com/Site_Gfx/pdf/11-AnMtg_IntellectualProperty_TAB.pdf>.

(56) References Cited

OTHER PUBLICATIONS

Isis Pharmaceuticals, Intellectual Property: Capturing Value From Innovation, Isis' Annual Meeting of Stockholders and Open House, Intellectual Property Poster, 1 page (2012). Received from Internet <http://www.isispharm.com/Site_Gfx/pdf/2012_Annual_Meeting_IP_Poster.pdf>.
Iwamoto et al., Stereocontrolled Synthesis of H-phosphonate DNA, Nucleic Acids Symposium Series, (50):159-60 (2006).
Iwamoto, N. et al., Control of phosphorothioate stereochemistry substantially increases the efficacy of antisense oligonucleotides, Nature Biotechnology, Life Sciences Reporting Summary, 6 pages (2017).
Iwamoto, N. et al., Control of phosphorothioate stereochemistry substantially increases the efficacy of antisense oligonucleotides, Nature Biotechnology, pp. 1-9 (2017).
Iwamoto, N. et al., Control of phosphorothioate stereochemistry substantially increases the efficacy of antisense oligonucleotides, Nature Biotechnology, Supplementary Methods, Supplementary Tables 1-4, and Supplementary Note, 23 pages (2017).
Iwamoto, N. et al., Control of phosphorothioate stereochemistry substantially increases the efficacy of antisense oligonucleotides, Nature Biotechnology, Supplementary Text and Figures 1-9, 13 pages (2017).
Iwamoto, N. et al., Control of phosphorothioate stereochemistry substantially increases the efficacy of antisense oligonucleotides, Nature Biotechnology, with Supplemental Data, 19 pages (2017).
Iwamoto, N. et al., Optimization of Therapeutic Phosphorothioate Oligonucleotides by P-Chirality Control, WAVE Life Sciences, PSJ Congress: The Pharmaceutical Society of Japan, (Mar. 25, 2015-Mar. 28, 2016).
Iwamoto, N. et al., Stereocontrolled solid-phase synthesis of oligonucleoside H-phosphonates by an oxazaphospholidine approach, Angewandte Chemie International Edition, 48(3):496-499 (2009).
Iyer, R.P. et al., A novel nucleoside phosphoramidite synthon derived from 1R, 2S-ephedrine, Tetrahedron Asymmetry 6(5):1051-1054 (1995).
Iyer, R.P. et al., Acyloxyaryl prodrugs of oligonucleoside phosphorothioates, Bioorganic and Medicinal Chemistry Letters, 6(16):1917-1922 (1996).
Iyer, R.P. et al., Bioreversible oligonucleotide conjugates by site-specific derivatization, Bioorganic and Medicinal Chemistry Letters, 7:871-876 (1997).
Iyer, R.P. et al., Stereospecific Bio-Reversibility of Dinucleoside S-Alkyl Phosphorothiolates to Dinucleoside Phosphorothioates, Bioorganic & Medicinal Chemistry Letter, 4(20):2471-2476 (1994).
Iyer, R.P., et al., 3H-1,2-Benzodithiole-3-one 1,1-Dioxide as an Improved Sulfurizing Reagent in the Solid-Phase Synthesis of Oligodeoxyribonucleoside Phosphorothioates, Journal of the American Chemical Society, 112(3):1253-1254 (1990).
Iyer, R.P., et al., Prodrugs of Oligonucletides: The Acyloxyalkyl Esters of Oligodeoxyribonucleoside Phosphorothioates, Bioorganic Chemistry, 23:1-21 (1995).
Iyer, R.P., et al., Solid-phase stereoselective synthesis of oligonucleoside phosphorothioates: The nucleoside bicyclic oxazaphospholidines as novel synthons, Tetrahedron Letters, 39:2491-2494 (1998).
Jahns, H., et al., Stereochemical bias introduced during RNA synthesis modulates the activity of phosphorothioate siRNAs, Nat. Commun., 6: 6317 (2015).
Jepsen, J.S. et al., LNA-Antisense Rivals Sirna for Gene Silencing, Current Opinion in Drug Discovery and Development, 7(2): 188-194 (2004).
Jepsen, J.S. et al., Locked Nucleic Acid: A Potent Nucleic Acid Analog in Therapeutics and Biotechnology, Oligonucleotides,14: 130-146 (2004).
Jiang, J. et al., Allele-Specific Silencing of Mutant Myh6 Transcripts in Mice Suppresses Hypertrophic Cardiomyopathy, Science, 342: 111-114 (2013).
Jin et al., A Stereoselective Synthesis of Dinucleotide Boranophosphate, Using Chiral Indole-Oxazaphosphorine Intermediates, Tetrahedron Letters, 39: 6433-6436 (1998).

Jin et al., Stereoselective Synthesis of Dithymidine Phosphorothioates Using Xylose Derivatives as Chiral Auxiliaries, J. Org. Chem., 63(11): 3647-3654 (1998).
Johansson et al., Studies towards synthesis of dinucleoside arylphosphonates with metal complexing properties, Nucleosides Nucleotides & Nucleic Acids, 22(5-8): 1459-61 (2003).
Johansson et al., Synthesis of dinucleoside pyridylphosphonates involving palladium(o)-catalysed phosphorus-carbon bond formation as a key step, Chem. Commun., 2564-2565 (2001).
Johansson et al., The case for configurational stability of H-phosphonate diesters in the presence of diazabicyclo[5.4.0]undec-7-ene (DBU), Bioorg Med Chem., 9(9): 2315-22 (2001).
Jones, R.J. et al., Synthesis and binding properties of pyrimidine oligodeoxynucleoside analogs containing neutral phosphodiester replacements: The Formacetal and 3'-Thioformacetal Internucleoside Linkages, J. Org. Chem., 58: 2983-2991 (1993).
Jopling, C.L. et al., Modulation of Hepatitis C Vicus RNA Abundance by a Liver-Specific MicroRNA, Science, 309: 1577-1581 (2005).
Joyce, G.F. et al., The case for an ancestral genetic system involving simple analogues of the nucleotide, Proceedings of the National Academy of Sciences, 84:4398-4402 (1987).
Joyce, G.F. The antiquity of RNA-based evolution, Nature, 418(6894): 214-221 (2002).
Kakeya, N. et al., Studies on Prodrugs of Cephalosporins. I. Synthesis and Biological Properties of Glycyloxybenzoyloxymethyl and Glycylaminobenzoyloxymethyl Esters of 7-[2-(2- Aminothiazol-4-yl)-(Z)-2-methoxyiminoacetamido]-3-methyl-3-cephem-4-carboxylic Acid, Chem. Pharm. Bull., 32(2): 692-698 (1984).
Kamada, A.K. et al., Issues in the Use of Inhaled Glucocorticoids, Am. J. Respir. Crit. Care. Med., 153: 1739-1748 (1996).
Karwowski, B. et al., Stereocontrolled Synthesis of LNA Dinucleoside Phosphorothioate by the Oxathiaphospholane Approach, Bioorganic & Medicinal Chemistry Letters, 11: 1001-1003 (2001).
Kashida, H. et al., Acyclic artificial nucleic acids with phosphodiester bonds exhibit unique functions, Polymer Journal, 1-6 (2016).
Kaur, H. et al., Activation of natural killer-like YT-INDY cells by oligodeoxynucleotides and binding by homologous pattern recognition proteins, Scandinavian Journal of Immunology, 62: 361-370 (2005).
Kawasaki, A et. al., Uniformly Modified 2'-Deoxy-2'-fluoro Phosphorothioate Oligonucleotides as Nuclease-Resistant Antisense Compounds with High Affinity and Specificity for RNA Targets, J. Med. Chem., 36: 831-841 (1993).
Kay, C. et al., Huntingtin Haplotypes Provide Prioritized Target Panels for Allele-Specific Silencing in Huntington Disease Patients of European Ancestry, Molecular Therapy, Accepted Article Preview Online (Jul. 23, 2015).
Kay, C. et al., Huntingtin Haplotypes Provide Prioritized Target Panels for Allele-specific Silencing in Huntington Disease Patients of European Ancestry, The American Society of Gene & Cell Therapy, 1-13 (2015).
Kay, C. et al., Personalized gene silencing therapeutics for Huntington disease, Clinical Genetics, 1-8 (2014).
Kers et al., A new type of nucleotide analogue with 4-pyridylphosphonate internucleotide linkage, Tetrahedron Letters, 40(22): 4263-4266 (1999).
Kihara, M et al., New norepinephrine potentiators: synthesis and structure-actvity relastionships of a series of 4-phenyl-1,2,3,4-tetrahydroisoquinolin-4-ols, Chemical & Pharmaceutical Bulletin 42(1): 67-73 (1994).
Kim, D. et al., Immunostimulation and anti-DNA antibody production by backbone modified CpG-DNA, Biochemical and Biophysical Research Communications, 379(2): 362-367 (2009).
Kim, M., Beta conformation of polyglutamine track revealed by a crystal structure of Huntingtin N-terminal region with insertion of three histidine residues, Prion, 7(3): 221-228 (2013).
Kim, N.W. et al., Specific Association of Human Telomerase Activity with Immortal Cells and Cancer, Science, 226: 2011-2015 (1994).
Kim, S.-H. and Cech, T.R., Three-dimensional model of the active site of the selfsplicing rRNA precursor of Tetrahymena, Proc. Natl. Acad. Sci. U S A., 84(24): 8788-8792 (1987).

(56) References Cited

OTHER PUBLICATIONS

Kim, S-K. et al., Bridged Nucleic Acids (BNAs) as Molecular Tools, J Biochem Mol Biol Res., 1(3): 67-71 (2015).
Kim, S. et al., Liquid-Phase RNA Synthesis by Using Alkyl-Chain-Soluble Support, Chem. Eur. J., 19: 8615-8620 (2013).
Kiviniemi, a. et al., Solid-Supported 2'-O-Glycoconjugation of Oligonucleotides by Azidation and Click Reactions, Bioconjugate Chemistry, 22(6): 1249-1255 (2011).
Klose, J. et al., Preparation of 2-(2-Cyanoethyl)-sulfanyl-1H-isoindole-1,3-(2H)-dione and related sulfur transfer reagents, Tetrahedron, 53(42):14411-14416 (1997).
Koch, T., A New Dimension in LNA Therapeutics, Roche Innovation Center, Copenhagen, Denmark, Presentation, 39 pages (May 3, 2017).
Koizumi, M. et al., Triplex formation with 2'-O,4'-C-ethylene-bridged nucleic acids (ENA) having C3'-endo conformation at physiological pH, Nuc. Acids Res., 31(12): 3267-3273 (2003).
Kool, E.T., Replacing the Nucleobases in DNA with Designer Molecules, Accounts of Chemical Research, 35:936-943 (2002).
Kordasiewicz, H.B. et al., Sustained therapeutic reversal of Huntington's disease by transient repression of huntingtin synthesis, Neuron, 74(6): 1031-1044 (2012).
Koseoglu, M. et al., Effects of hemolysis interference on routine biochemistry parameters. Biochemia Medica., 21(1): 79-85 (2011). Retrieved May 18, 2017, URL: <http://www.biochemia-medica.com/2011/21/79>.
Koshkin, A.A. et al., LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition, Tetrahedron 54: 3607-3630 (1998).
Kozikowski, A.P. et al., Chemistry of the main group metals: A stereoselective synthesis of allyl vinyl thioethers for the thio-claisen reaction, Journal of Organometallic Chemistry, 164(3): C33-C37 (1979).
Koziolkewicz et al., Stability of Stereoregular Oligo-(nucleoside Phosphorothioate)s in Human Plasma: Diastereoselectiviy of Plasma 3'-Exonuclease, Antisense Nucl. Acid Drug Dev., 7: 43-48 (1997).
Koziolkewicz et al., Stereodifferentiation-the effect of P chirality of oligo(nucleoside phosphorothioates) on the activity of bacterial RNase H, Nucl. Acids Res., 23(24): 5000-5005 (1995).
Koziolkiewicz, M. et al., Effect of P-chirality of oligo(deoxyribonucleoside phosphorothioate)s) on the activity of terminal deoxyribonucleotidyl transferase, FEBS Letters, 434(1-2): 77-82 (1998).
Kraszewski et al., Studies on Reactions of Nucleoside H-phosphonates with Bifunctional Reagents. Part 1. Reaction with amino alcohols, J. Chem. Soc., Perkin Trans., 1: 1699-1704 (1993).
Kremer, B. et al., A Worldwide Study of the Huntington's Disease Mutation, The New England Journal of Medicine, 330(20): 1401-1406 (1994).
Kretschmer-Kazemi Far, R. and Sczakiel, G., The activity of siRNA in mammalian cells is related to structural target accessibility: a comparison with antisense oligonucleotides, Nucleic Acids Research, 31(15):4417-4424 (2003).
Krieg, A.M. et al., CpG motifs in bacterial DNA trigger direct B-cell activation, Nature, 374: 546-549 (1995).
Krieg, A.M. et al., P-Chirality-Dependent Immune Activation by Phosphorothioate CpG Oligodeoxynucleotides, Oligonucleotides, 13:491-499 (2003).
Krieg, A.M., Development of TLR9 agonists for cancer therapy, The Journal of Clinical Investigation, 117(5): 1184-1194 (2007).
Krieg, A.M., Therapeutic potential of Toll-like receptor 9 activation, Nature Reviews, 471-484 (2006).
Krotz, A.H. et al., Phosphorothioate Oligonucleotides with Low Phosphate Diester Content: Greater than 99.9% Sulfurization Efficiency with "Aged" Solutions of Phenylacetyl Disulfide (PADS), Organic Process Research & Development, 8: 852-858 (2004).

Krueger, A.T. et al., Synthesis and properties of size-expanded DNAs: toward designed, functional genetic systems, Accounts of Chemical Research, 40:141-150 (2007).
Krutzfeldt, J. et al., Silencing of microRNAs in vivo with 'antagomirs', Nature, 438: 685-689 (2005).
Kumar, R. et al., The First Analogues of LNA (Locked Nucleic Acids): Phosphorothioate-LNA and 2'-THIO-LNA, Bioo. Med. Chem. Let., 8: 2219-2222 (1998).
Kungurtsev, V. et al., Solution-Phase Synthesis of Short Oligo-2'-deoxyribonucleotides by Using Clustered Nucleosides as a Soluble Support, Eur. J. Org. Chem., 6687-6693 (2013).
Kuramoto, Y. et al., Mannosylated cationic liposomes/CpG DNA complex for the treatment of hepatic metastasis after intravenous administration in mice, Journal of Pharmaceutical Science, 98(3): 1193-1197 (2009).
Kwon, H.-J. et al., NF-kappaB-dependent regulation of tumor necrosis factor-alpha gene expression by CpG-oligodeoxynucleotides, Biochem. Biophys. Res. Commun., 311(1): 129-138 (2003).
Lahiri, N., Shooting the messenger with single-stranded RNA gene silencing, edited by Wild, E., HDBuzz, 7 pages (Sep. 24, 2012). Retrieved Oct. 7, 2015. URL: http://en.hdbuzz.net/099.
LaPlanche, L.A. et al., Phosphorothioate-modified oligodeoxyribonucleotides. III. NMR and UV spectroscopic studies of the Rp-Rp, Sp-Sp, and Rp-Sp duplexes, [d(GGsAATI'CC)2, derived from diastereomeric 0-ethyl phosphorothioates, Nucleic Acids Research, 14(22): 9081-9093 (1986).
Latimer, L.J.P. et al, Synthetic repeating sequence DNAs containing phosphorothioates: nuclease sensitivity and triplex formation, Nucleic Acids Research, 17(4): 1549-1561 (1989).
Laurent et al., Chiral and steric effects in the efficient binding of alpha-anomeric deoxyoligonucleoside N-alkylphosphoramidates to ssDNA and RNA, Nucleic Acids Res., 27(21): 4151-9 (1999).
Lauritsen, A. et al., Methylphosphonate LNA: A Locked Nucleic Acid with a Methylphosphonate Linkage, Bioo. Med. Chem. Lett., 13: 253-256 (2003).
Lauritsen, A. et al., Oligodeoxynucleotides containing amide-linked LNA-type dinucleotides: synthesis and high-affinity nucleic acid hybridization, Chem. Comm., 5: 530-531 (2002).
Lavergne, T. et al., A Base-Labile Group for 2'-OH Protection of Ribonucleosides: A Major Challenge for RNA Synthesis, Chem. Eur. J, 14, 9135-9138 (2008).
Lee, K-W et al., CG sequence- and phosphorothioate backbone modification-dependent activation of the NF-κB-responsive gene expression by CpG-oligodeoxynucleotides in human RPMI 8226 B cells, Molecular Immonulogy, 41: 955-964 (2004).
Lesnikowski et al., Studies on Stereospecific Formation of P-Chiral Internucleotide Linkage. Synthesis of (RP, RP)- and (SP, SP)-Thymidylyl (3', 5') Thymidylyl (3', 5') Thymidine DI (O,O-Phosphorothioate) Using 2-Nitrobenzyl Group as a New S-Protection, Tetrahedron Letters 30(29) 3821-3824 (1989).
Lesnikowski, Z. J. et al., Octa(thymidine methanephosphonates) of partially defined sterochemistry: synthesis and effect of chirality at phosphorus on binding to pentadecadeoxyriboadenylic acid, Nucleic Acids Research, 18(8): 2109-2115 (1990).
Levin, A.A. et al., Basic Principles of the Pharmacokinetics of Antisense Oligonucleotide Drugs, Antisense Drug Technology: Principles, Strategies, and Applications, Second Edition, Chapter 7: 183-215 (2008).
Leviten, M., Wave's Purity Progress, Biocentury, 1-6 (Sep. 28, 2017).
Li L.C., Small RNA Mediated Gene Activation, RNA and the Regulation of Gene Expression: A Hidden Layer of Complexity, Edited by Kevin V. Morris, Chapter 13, Caister Academic Press (2008).
Li, L-C. et al., Small dsRNAs induce transcriptional activation in human cells, PNAS, 103(46): 17337-17342 (2006).
Li, M. et al., Synthesis and cellular activity of stereochemically-pure 2'-O-(2-methoxyethyl)-phosphorothioate oligonucleotides, Chem. Commun., 53: 541-544 (2017).
Li-Tsang, C.W. et al., Prevalence of hypertrophic scar formation and its characteristics among the Chinese population, Burns, 31: 610-616 (2005).

(56) References Cited

OTHER PUBLICATIONS

Liang, X-h. et al., Identification and characterization of intracellular proteins that bind oligonucleotides with phosphorothioate linkages, Nucleic Acids Research, 43(5): 2927-2945, Supplemental Data pp. 1-20 (2015).
Lima, W. et al., Single-Stranded ssRNAi Activate RNAi in Animals, Cell, 150: 883-894 (2012).
Lima, W.F. et al., The influence of antisense oligonucleotide-induced RNA structure on Escherichia coli RNase H1 activity, J. Biol. Chem., 272(29):18191-9 (1997).
Lima, W.F., et al., Human RNase H1 discriminates between subtle variations in the structure of the heteroduplex substrate, Mol. Pharmacol., 71: 83-91 (2007).
Limbach, P.A. et al., Summary: the modified nucleosides of RNA, Nucleic Acids Research, 22(12):2183-2196 (1994).
Lin et al., Synthesis and resolution of dinucleotide (TpAZT) phosphoramidates, Synthetic Commun., 33(14): 2553-2562 (2003).
Linton, M.F., et al., Transgenic Mice Expressing High Plasma Concentrations of Human Apolipoproteins B100 and Lipoprotein (a), J. Clin. Invest., 92: 3029-37 (1993).
Liu, J. et al., Modulation of Splicing by Single-Stranded Silencing RNAs, Nucleic Acid Therapeutics, 25(3): 113-120 (2015).
Liu, W. et al., Increased Steady-State Mutant Huntingtin mRNA in Huntington's Disease Brain, Journal of Huntington's Disease 2: 491-500 (2013).
Lopez, C. et al., Inhibition of AAC(6')-Ib-Mediated Resistance to Amikacin in Acinetobacter baumannii by an Antisense Peptide-Conjugated 2',4'- Bridged Nucleic Acid-NC-DNA Hybrid Oligomer, Antimicrobial Agents and Chemotherapy, 59(9): 5798-5803 (2015).
Lu, X. et al., Antisense-Mediated Inhibition of Human Immunodeficiency Virus (HIV) Replication by Use of an HIV Type 1-Based Vector Results in Severely Attenuated Mutants Incapable of Developing Resistance, Journal of Virology, 78(13): 7079-7088 (2004).
Lu, Y. And Just, G., Stereoselective synthesis of dithymidine phosphorothioates using d-xylose derived chiral auxiliaries, Tetrahedron, 57(9):1677-1687 (2001).
Lu, Y. et al., Stereoselective Synthesis of R(P)- and S(P)-Dithymidine Phosphorothioates via Chiral Indolooxazaphosphorine Intermediates Derived from Tryptophan This work was financially supported by Natural Science and Engineering Research Council of Canada (NSERC). We thank Nadim Saadeh and Dr. Orval Mamer, McGill University biomedical mass spectroscopy unit, for recording mass spectra, Angewandte Chemie International Edition, 39(24):4521-4524 (2000).
Lu, Y., Recent advances in the stereocontrolled synthesis of antisense phosphorothioates, Mini Reviews in Medicinal Chemistry, 6(3): 319-330 (2006).
Machine Translation of JP 2010-265304 (2010). <http://dossier1.ipdl.inpit.go.jp/AIPN/odse_top_dn.ipdl?NOOOO=7400>.
Machytka et al., Extension of the Applicability of &I-Values for the Configurational Assignment of Diastereomeric Phosphate-Modified Dideoxynucleotides, Nucleosides and Nucleotides, 17(12): 2311-2322 (1998).
Machytka et al., Synthesis and NMR characterization of diastereomeric CPSMeG derivatives, Nucleosides Nucleotides Nucleic Acids., 19(5-6): 903-15 (2000).
Maher III, L.J., et al., Inhibition of DNA Binding Proteins by Oligonucleotide-Directed Triple Helix Formation, Science, 245: 725-730 (1989).
Mann, M.J. et al., Therapeutic applications of transcription factor decoy oligonucleotides, J. Clin. Invest., 106:1071-1075 (2000).
Mannironi, C. et al., In Vivo Selection of Dopamine RNA Ligands, Biochemistry, 36: 9726-9734 (1997).
Martin, P., A New Access to 2'-O-alkylated Ribonucleosides and Properties of 2'-O-Alkylated Oligoribonucleotides, Helv. Chim. Acta., Abstract Only, 78: 486-504 (1995).
Martin, P., Stereoselective Synthesis of 2'-O-(2-Methoxyethyl)ribonucleosides: Neighboring-Group Participation of the Methoxyethoxy Group in the Ribosylation Step, Helv. Chim. Acta, 79: 1930-1938 (1996).

Martinez, J. et al., Single-Stranded Antisense siRNAs Guide Target RNA Cleavage in RNAi, Cell, 110: 563-574 (2002).
Martinez-Montero, S. et al., Locked 2'-Deoxy-2',4'-Difluororibo Modified Nucleic Acids: Thermal Stability, Structural Studies, and siRNA Activity, ACS Chem. Biol., 10: 2016-2023 (2015).
Masahiro, T. et al., Nematicidal and antimicrobial constituents from Allium grayi Regel and *Allium fistulosum* L. var. *caespitosum*, Agricultural and Biological Chemistry, 52(9): 2383-2385 (1988).
Matranga, C. et al., Passenger-Strand Cleavage Facilitates Assembly of siRNA into Ago2-Containing RNAi Enzyme Complexes, Cell, 123: 607-620 (2005). Supplemental Data, 6 pages.
Matsui, M. et al., Argonaute 2-dependent Regulation of Gene Expression by Single-stranded miRNA Mimics, Molecular Therapy, 10 pages (2016).
Matsui, M. et al., Transcriptional Silencing by Single-Stranded RNAs Targeting a Noncoding RNA That Overlaps a Gene Promoter, ACS Chem. Biol., 8: 122-126 (2013).
Matsuno, Y. et al., Synthetic Method for Oligonucleotide Block by Using Alkyl-Chain-Soluble Support, Org. Lett., 18: 800-803 (2016).
Matysiak, S et al., Acetals as New 2'-O-Protecting Functions for the Synthesis of the Oligoribonucleotides: Synthesis of Uridine Building Blocks and Evaluatino of Their Relative Acid Stability, Helvetica Chimica Acta 81: 1545-1566 (1998).
Maung, J. et al., Alternatives to 1-H-tetrazole in the preparation of phosphonate diesters and phosphonamidates from phosphonyl dichlorides, Tetrahedron Lett., 45: 6497-6499 (2004).
Mauritz, R.P. et al., Elucidation of the Hydrolytical Properties of α-Hydroxybenzylphosphonates as a New Potential Pro-Oligonucleotide Concept, Nucleosides and Nucleotides, 18(6-7):1417-1418 (1999).
Mauritz, R.P. et al., Synthesis of 3',5'-Dithymidylyl-α-hydroxyphosphonate Dimer Building Blocks for Oligonucleotide Synthesis—A New Pro-oliguncleotide, Nucleosides and Nucleotides, 16(7-9):1209-1212 (1997).
McBride, J.L. et al., Prelinical Safety of RNAi-Mediated HTT Suppression in the Rhesus Macaque as a Potential Therapy for Huntington's Disease, Molecular Therapy, 19:1-11 (2011).
Meade, M.F., et al., Efficient delivery of RNAi prodrugs containing reversible charge-neutralizing phosphotriester backbone modifications, Nat. Biotech., 32: 1256-61 (2014).
Medical News Today, AVI BioPharma Announces FDA Clears IND Applications for Clinical Trials of RNA Therapeutic Agents for Treatment of Ebola and Marburg Viruses, Accessed Apil 2, 2015, 2 pages (Dec. 30, 2008).
Meena, Control of Human RNase H Mediated Cleavage by Stereopure Phosphorothioate Oligonucleotides, WAVE Life Sciences, TIDES Meeting, 23 pages (May 3-6, 2015).
Meena, Development of Allele Specific Antisense Oligonucleotides, WAVE Life Sciences, ACS Central Regional Meeting (CERM), Covington, KY (May 19, 2016).
Meena, Development of Allele Specific Antisense Oligonucleotides, WAVE Life Sciences, TIDES Meeting (May 11, 2016).
Meena, et al., Discovery and Early Clinical Development of the First Allele-Specific Stereopure ASO Drug Candidate with Disease-Modifying Potential for the Treatment of Huntington's Disease, WAVE Life Sciences, Poster, 1 page (2016).
Meena, et al., Therapeutic Implications of Controlling P-Chirality in Phosphorothioate Oligonucleotides, TIDES Poster (May 12-15, 2014).
Meena, et al., Therapeutic Implications of Controlling P-Chirality in Phosphorothioate Oligonucleotides, TIDES, San Diego, WAVE Life Sciences, Poster, 1 page (May 3-6, 2014).
Meena, Optimization of Antisense Drugs by P-Stereochemistry Control, WAVE Life Sciences, OTS Annual Meeting 2014, Oligonucleotide Therapeutics Society, 13 pages (Oct. 12-14, 2014).
Merki, E. et al., Antisense oligonucleotide directed to human apolipoprotein B-100 reduces lipoprotein(a) levels and oxidized phospholipids on human apolipoprotein B-1 00 particles in lipoprotein(a) transgenic mice, Circulation, 118(7): 743-53 (2008).
Mesmaeker, A.D. Backbone modifications in oligonucleotides and peptide nucleic acid systems, Current Opinion in Structural Biology, 5: 343-355 (1995).

(56) References Cited

OTHER PUBLICATIONS

Mesmaeker, A.D. et al. Amides as a New Type of Backbone Modification in Oligonucleotides, Angew. Chem., Int. Ed. Engl., 33: 226-229 (1994).
Methods in Enzymology, Edited by Widder, K. and Green, R., Drug and Enzyme Targeting, Academic Press, 112: 309-396 (1985).
Midturi, J. et al., Spectrum of Pulmonary Toxicity Associated with the Use of Interferon Therapy for Hepatitis C: Case Report and Review of the Literature, Clinical Infectious Diseases, 39(11): 1724-1729 (2004).
Mignet, N. et al., Synthesis and evaluation of glucuronic acid derivatives as alkylating agents for the reversible masking of internucleoside groups of antisense oligonucleotides, Carbohydrate Research, 303:17-24 (1997).
Mignet, N. et al., The Prooligonucleotide Approach. V: Influence of the phosphorus atom environment on the hydrolysis of enzymolabile dinucleoside phosphotriesters, Bioorganic and Medicinal Chemistry Letters, 7(7):851-854 (1997).
Milkowski, J.D. et al., Thiol Protection with the Acetamidomethyl Group: S-Acetamidomethyl-l-cysteine Hydrochloride, Organic Syntheses, 6: 5 (1988).
Misaki, S et al., Dehydration of 2-Trifluoromethyl-3,3,3-Trifluoropropanil with Base, Journal of Flourine Chemistry 24: 531-533 (1984).
Molenkamp, B.G. et al., Local Administration of PF-3512676 CpG-B Instigates Tumor-Specific CD8+ T-Cell Reactivity in Melanoma Patients, Clin. Cancer Res., 14(14): 4532-4542 (2008).
Molina, a.G. et al., Acetylated and Methylated β-Cyclodextrins asViable Soluble Supports for the Synthesis of Short 2'-Oligodeoxyribonucleotides in Solution, Molecules, 17: 12102-12120 (2012).
Molina, A.G. et al., Assembly of Short Oligoribonucleotides from Commercially Available Building Blocks on a Tetrapodal Soluble Support, Current Organic Synthesis, 12:1-6 (2015).
Molina, A.G. et al., Solution phase synthesis of short oligoribonucleotides on a precipitative tetrapodal support, Beilstein Journal of Organic Chemistry, 10: 2279-2285 (2014).
Molina, A.G., Synthesis of Short Oligonucleotides on a Soluble Support by the Phosphoramidite Method, University of Turku, 1-66 (2015).
Monteys, A.M. et al., Artificial miRNAs Targeting Mutant Huntingtin Show Preferential Silencing In Vitro and In Vivo, Molecular THerapy—Nucleic Acids, 4: e234 1-11 (2015).
Monteys, A.M. et al., Single nucleotide seed modification restores in vivo tolerability of a toxic artificial miRNA sequence in the mouse brain, Nucleic Acids Res., 42(21): 13315-13327 (2014).
Morales-Rojas, H. and Kool, E.T., A porphyrin C-nucleoside incorporated into DNA, Organic Letters, 4(25):4377-4380 (2002).
Morcos, P.A., Achieving targeted and quantifiable alteration of mRNA splicing with Morpholino oligos, Biochem. Biophys. Res. Commun., 358(2): 521-527 (2007).
Morita, K. et al., 2'-O,4'-C-Ethylene-bridged nucleic acids (ENA) with nuclease-resistance and high affnity for RNA, Nucl. Acids Res., Supp. 1: 241-242 (2001).
Morita, K. et al., 20-O,40-C-Ethylene-Bridged Nucleic Acids (ENA): Highly Nuclease-Resistant and Thermodynamically Stable Oligonucleotides for Antisense Drug, Bioo. Med. Chem. Lett., 12: 73-76 (2002).
Morita, K. et al., Synthesis and properties of 2'-O,4'-C-Ethylene-bridged nucleic acids (ENA) as effective antisense oligonucleotides, Bioorganic & Medicinal Chemistry, 11(10): 2211-2226 (2003).
Morvan, F. et al., Cellular uptake and intracellular quantification of fluorescent labeled T20 Me-SATE prooligonucleotides, Nucleosides Nucleotides Nucleic Acids, 20(4-7):1165-1168 (2001).
Morvan, F. et al., Kinetics study of the biotransformation of an oligonucleotide prodrug in cells extract by matrix-assisted laser desorption/ionization time-of-flight mass spectrometry, Nucleosides, Nucleotides and Nucleic Acids, 20(2-4):1159-1163 (2001).
Morvan, F. et al., The Oligonucleotide Prodrug Approach: The Pro-Oligonucleotides, Pharmaceutical Aspects of Oligonucleotides, 79-97 (2000).

Moser, H. E. et al., Sequence-Specific Cleavage of Double Helical DNA by Triple Helix Formation, Science, 238: 645-650 (1987).
Nawrot et al., DNA Oligonucleotides Containing Stereodefined Phosphorothioate Linkages in Selected Positions, Current Protocols in Nucleic Acid Chemistry, UNIT 4.34: 4.34.1-4.34.15 (2009).
Nencka, R. et al., Novel Conformationally Locked Nucleosides and Nucleotides, Collection Symposoim Series, 14: 119-122 (2014).
Nielsen, J. and Caruthers, M.H., Directed Arbuzov-type reactions of 2-cyano-1,1-dimethylethyl deoxynucleoside phosphites, J. Am. Chem. Soc., 110: 6275-6 (1988).
Nielsen, N.M. and Bundgaard, H. Glycolamide Esters as Biolabile Prodrugs of Carboxylic Acid Agents: Synthesis, Stability, Bioconversion, and Physicochemical Properties, Journal of Pharmaceutical Sciences, 77(4): 285-298 (1988).
Nielsen, P.E. and Haaima, G., Peptide nucleic acid (PNA). A DNA mimic with a pseudopeptide backbone, Chem. Soc. Rev., 73-78 (1997).
Nielsen, P.E. et al., Sequence-Selective Recognition of DNA by Strand Displacement with a Thymine-Substituted Polyamide, Science, 254(5037): 1497-1500 (1991).
Nielsen, P.E. et al., Synthesis of 29-O,39-C-linked bicyclic nucleosides and bicyclic Oligonucleotides, J. Chem. Soc. Perkins Trans., 1: 3423-3433 (1997).
Nieuwlandt, D. et al., In Vitro Selection of RNA Ligands to Substance P, Biochemistry, 34: 5651-5659 (1995).
Nilsson et al., Chemical and Stereochemical Aspects of Oxidative Coupling of H-Phosphonate and H-Phosphonothioate Diesters. Reactions with N,N-,N,O and O,O-Binucleophiles, Letters in Organic Chemistry, 2(2): 188-197 (2005).
Nilsson et al., Controlling Stereochemistry During Oxidative Coupling. Preparation of Rp or Sp Phosphoramidates from One P-chiral Precursor, Chem. Commun., (22): 2566-7 (2004).
Nilsson, J. et al., Chemoselectivity in oxidative coupling of bifunctional nucleophiles with dinucleoside H-phosphonate and dinucleoside H-phosphonothioate diesters, Nucleosides, Nucleotides & Nucleic Acids, 22(5-8):1467-1469 (2003).
Nowotny, M. et al., Structure of human RNase H1 complexed with an RNA/DNA hybrid: insight into HIV reverse transcription, Mol Cell, 28(2):264-76 (2007).
Nukaga, Y. et al., Stereocontrolled Solid-Phase Synthesis of Phosphate/Phosphorothioate (PO/PS) Chimeric Oligodeoxyribonucleotides on an Automated Synthesizer Using an Oxazaphospholidine-Phosphoramidite Method, J. Org. Chem., A-J, 10 pages (Publication Date (Web): Mar. 3, 2016).
Nukaga, Y. et al., Stereocontrolled Solid-Phase Synthesis of Phosphorothioate Oligoribonucleotides Using 2'-O-(2-Cyanoethoxymethyl)-nucleoside 3'-O-Oxazaphospholiidine Monomers, Journal of Organic Chemistry, 77(18):7913-7922 (2012).
O'Connell, D. et al., Calcium-dependent oligonucleotide antagonists specific for L-selectin, Proc. Natl. Acad. Sci. USA, 93: 5883-5887 (1996).
Obika et al. Stability and structural features of the duplexes containing nucleoside analogues with a fixed N-type conformation, 2'-O,4'-C-methyleneribonucleosides, Tetrahedron Lett. 39: 5401-5404 (1998).
Obika, S. et al., Synthesis of 2'-O,4'-C-Methyleneuridine and -cytidine. Novel Bicyclic Nucleosides Having a Fixed C a ,-endo Sugar Puckering, Tetrahedron Lett., 38(50): 8735-8 (1997).
Ohgi, T. et al., A New RNA Synthetic Method with a 2'-O-(2-Cyanoethoxymethyl) Protecting Group, Organic Letters, 7(16): 3477-3480 (2005).
Ohkubo et al., Synthesis of oligodeoxyribonucleotides containing hydroxymethylphosphonate bonds in the phosphoramidite method and their hybridization properties, Tetrahedron Letters, 46(51): 8953-8957 (2005).
Oka, N. and Wada, T., Stereocontrolled synthesis of oligonucleotide analogs containing chiral internucleotidic phosphorus atoms, Chemical Society Reviews, 40(12):5829-5843 (2011).
Oka, N. et al., An oxazaphospholidine approach for the stereocontrolled synthesis of oligonucleoside phosphorothioates, Journal of the America Chemical Society, 125(27):8307-8317 (2003).
Oka, N. et al., Diastereocontrolled Synthesis of Dinucleoside Phosphorothioates Using a Novel Class of Activators,

(56) References Cited

OTHER PUBLICATIONS

Dialkyl(cyanomethyl)ammonium Tetrafluoroborates, Journal of the American Chemical Society, 124(18):4962-4963 (2002).
Oka, N. et al., Solid-Phase Synthesis of Stereoregular Oligodeoxyribonucleoside Phosphorothioates Using Bicyclic Oxazaphospholidine Derivatives as Monomer Units, Journal of the American Chemical Society, 130(47):16031-16037 (2008).
Oka, N. et al., Stereocontrolled synthesis of dinucleoside boranophosphates by an oxazaphospholidine method, Nucleic Acids Symposium Series, (49): 131-132 (2005).
Oka, N. et al., Stereocontrolled synthesis of oligonucleoside phosphorothioates and PO/PS-chimeric oligonucleotides by using oxazaphospholidine derivatives, Nucleic Acids Symposium Series, 52: 335-336 (2008).
Oka, N. et al., Stereocontrolled Synthesis of Oligoribonucleoside Phosphorothioates by an Oxazaphospholidine Approach, Organic Letters, 11(4):967-970 (2009).
Onizuka, K. et al., Short Interfering RNA Guide Strand Modifiers from Computational Screening, J. Am. Chem. Soc., 135: 17069-17077 (2013).
Osawa, T. et al., Synthesis and Properties of the 5-Methyluridine Derivative of 3,4-Dihydro-2H-pyran-Bridged Nucleic Acid (DpNA), J. Org. Chem., 80: 10474-10481 (2015).
Ostergaard, M. et al., Rational design of antisense oligonucleotides targeting single nucleotide polymorphisms for potent and allele selective suppression of mutant Huntingtin in the CNS, Nucleic Acids Research, 41(21), 9634-9650 (2013).
Ostergaard, M.E. et al., Efficient Synthesis and Biological Evaluation of 5?-GalNAc Conjugated Antisense Oligonucleotides, Bioconjugate. Chem., 26: 1452-1455 (2015).
Otting, G. et al., Why Pentose- and Not Hexose-Nucleid Acids? Part IV. 'Homo-DNA': 1 H-, 13C-, 31P-, and 15N-NMR-Spectroscopic Investigation of ddGlc(A-A-A-A-A-T-T-T-T-T) in Aqueous Solution, Helvetica Chimica Acta, 76(8):2701-2756 (1993).
Padmanabhan, S. et al., Anti-HBV nucleotide prodrug analogs: Synthesis, bioreversibility, and cytotoxicity studies, Bioorganic and Medicinal Chemistry Letters, 16(15):1491-1494 (2006).
Pallan, P.S. et al., Structure and nuclease resistance of 20,40-constrained 20-O-methoxyethyl (cMOE) and 20-O-ethyl (cEt) modified DNAs, Chem. Comm., 48: 8195-8197 (2012).
Pan, Q-W. et al., New therapeutic opportunities for Hepatitis C based on small RNA, World J. Gastroenterol., 13(33): 4431-4436 (2007).
Panzara, M. et al., Duchenne Muscular Dystrophy Advisory Board Meeting, WAVE Life Sciences, 70 pages (Mar. 3, 2017).
Parmer, R. et al., 5'-(E)-Vinylphosphonate: A Stable Phosphate Mimic Can Improve the RNAi Activity of siRNA-GalNAc Conjugates, Chem. Bio. Chem., 17: 1-6 (2016).
Parrish et al., Functional Anatomy of a dsRNA Trigger: Differential Requirement for the Two Trigger Strands in RNA Interference, Molecular Cell, 6:1077-1087 (2000).
Patil et al., Syntheses and properties of oligothymidylate analogs containing stereoregulated phosphorothioate and phosphodiester linkages in an alternating manner, Bioorganic & Medicinal Chemistry Letters, 4(22): 2663-2666 (1994).
Pedersen, L. et al, A Kinetic Model Explains Why Shorter and Less Affine Enzyme-recruiting Oligonucleotides Can Be More Potent, Mol Ther Nucleic Acids, 3: e149 1-8 (2014).
Pendergraff, H.M. et al., Single-Stranded Silencing RNAs: Hit Rate and Chemical Modification, Nucleic Acid Therapeutics, 1-7 (2016).
Perrino, E. et al., New sulfurated derivatives of valproic acid with enhanced histone deacetylase inhibitory activity, Bioorganic & Medicinal Chemistry Letters, 18(6): 1893-1897 (2008).
Petersen, M. and Wengel, J., LNA: a versatile tool for therapeutics and genomics, Trends in Biotechnology, 21(2): 74-81 (2003).
Peyrottes, S. et al., SATE pronucleotide approaches: an overview, Mini-Reviews Medicinal Chemistry, 4(4):395-408 (2004).
Pfister, E.L. et al., Five siRNAs targeting three SNPs may provide therapy for three-quarters of Huntington's disease patients, 19(9): 774-778 (2009).

Pharmacology Review(s), Application No. 203568Orig1s000, Center for Drug Evaluation and Research, Food and Drug Administration, Department of Health & Human Services, 2013.
Pitsch, S. et al., Reliable Chemical Synthesis of Oligoribonucleotides (RNA) with 2'-O-[(Triisopropylsilypoxy]methyl(2'-O-tom)-Protected Phosphoramidites, Helvetica Chimica Acta, 84: 3773-3795 (2001).
Poijarvi, P. et al., 2,2-Bis(ethoxycarbonyl)- and 2-(Alkylaminocarbonyl)-2-cyano-Substituted 3-(Pivaloyloxy)propyl Groups as Biodegradable Phosphate Protections of Oligonucleotides, Bioconjugate Chemistry, 16(6):1564-1571 (2005).
Poijarvi, P. et al., The chemical stability of S-(2-acylthioethyl) and S-acyloxymethyl protected thymidyl1-3',5'-thymidine phosphoromonothiolates and their deacylation products in aqueous solution, Nucleosides Nucleotides and Nucleic Acids, 20(1-2):77-91 (2001).
Poijarvi, P. et al., Towards Nucleotide Prodrugs Derived from 2,2-Bis(hydroxymethyl)malonate and Its Congeners: Hydrolytic Cleavage of 2-Cyano-2-(hydroxymethyl)-3-methoxy-3-oxopropyl and 3-(Alkylamino)-2-cyano-2-(hydroxymethyl)-3-oxopropyl Protections from the Internucleosidic Phosphodiester and Phosphorothioate Linkages, Helvetica Chimica Acta, 85(7):1869-1876 (2002).
Poijarvi, P. et al., Towards Oligonucleotide Pro-Drugs: 2,2-Bis(ethoxycarbonyl) and 2-(Alkylaminocarbonyl)-2-cyano Substituted 3-(Pivaloyloxy)Propyl Groups as Biodegradable Protecting Groups for Internucleosidic Phosphoromonothioate Linkages, Letters in Organic Chemistry, 1(2):183-188 (2004).
Poijarvi, P., Prodrug Approaches of Nucleotides and Oligonucleotides, Current Medicinal Chemistry, 13(28):3441-3465 (2006).
Pon, R. T., Solid-Phase Supports for Oligonucleotide Synthesis, Current Protocols in Nucleic Acid Chemistry, 3.1.1-3.1.28 (2000).
Pontarollo, R.A. et al., Monocytes are required for optimum in vitro stimulation of bovine peripheral blood mononuclear cells by non-methylated CpG motifs, Veterinary Immunology and Immunopathology, 84(1-2): 43-59 (2002).
Pontiggia, R. et al., 2-C-Methyluridine modified hammerhead ribozyme against the estrogen receptor, Bioorganic & Medicinal Chemistry Letters, 20: 2806-2808 (2010).
Pontiggia, R. et al., DNAzymes and ribozymes carrying 2'-C-methyl nucleotides, Nucleic Acids Sumposium Series, 52: 521-522 (2008).
Potter et al, Stereospecificity of nucleases towards phosphorothioate-substituted RNA: stereochemistry of transcription by T7 RNA polymerase, Nucleinc Acids Research, 15(10): 4145-4162 (1987).
Potter, B.V.L. et al., Synthesis and Configurational Analysis of Dinucleoside Phosphate Isotopically Chiral at Phosphorus. Stereochmical Course of Penicillium citrum Nuclease P1 Reaction, Biochemistry, 22: 1369-1377 (1983).
Prakash, T.P. et al., 2'-O-[2-(Methylthio )ethyl]-Modified Oligonucleotide: An Analogue of 2'-O-[2-(Methoxy)-ethyl]-Modified Oligonucleotide with Improved Protein Binding Properties and High Binding Affinity to Target RNA, Biochemistry, 41: 11642-11648 (2002).
Prakash, T.P. et al., Identification of metabolically stable 5-phosphate analogs that support single-stranded siRNA activity, Nucleic Acids Research, 43(6): 2993-3011 (2015). Supplementary Data, 80 pages.
Prakash, T.P. et al., Lipid Nanoparticles Improve Activity of Single-Stranded siRNA and Gapmer Antisense Oligonucleotides in Animals, ACS Chem. Biol., 5 pages (2013), DOI: 10.1021/cb4001316.
Prakash, T.P. et al., Synergistic effect of phosphorothioate, 50-vinylphosphonate and GalNAc modifications for enhancing activity of synthetic siRNA, Bioorg. Med. Chem. Lett., 26: 2817-2820 (2016).
Prakash, T.P. et al., Targeted delivery of antisense oligonucleotides to hepatocytes using triantennary N-acetyl galactosamine improves potency 10-fold in mice, Nucleic Acids Res., 42(13): 8796-807 (2014).
Prhavc, M. et al., 2'-O-[2-[2-(N,N-Dimethylamino)ethoxy]ethyl] Modified Oligonucleotides: Symbiosis of Charge Interaction Factors and Stereoelectronic Effects, Organic Letters, 5(12): 2017-2020 (2003).

(56) References Cited

OTHER PUBLICATIONS

Pubchem, Substance Record for SID 174316404, Available Date: Mar. 31, 2014 (retrieved on Feb. 26, 2018). Retrieved from the Internet: <URL: https://pubchem.ncbi.nlm.nih.gov/substance/174316404>.

Pubchem, Substance Record for SID 174316700, Available Date: Mar. 31, 2014 (retrieved on Feb. 26, 2018). Retrieved from the Internet: <URL: https://pubchem.ncbi.nlm.nih.gov/substance/174316700>.

Pubchem, Substance Record for SID 174316999, Available Date: Mar. 31, 2014 {retrieved on Feb. 26, 2018). Retrieved from the Internet: <URL: https://pubchem.ncbi.nlm.nih.gov/substance/174316999>.

Puri, N. et al, Targeted Gene Knockout by 2'-O-Aminoethyl Modified Triplex Forming Oligonucleotides, J. Biol. Chem., 276: 28991-28998 (2001).

Puri, N. et al., The Synthesis and Reactivity of New 2-(N,N-Diisoprophylamino)-3-Methylsulfonyl-1,3,2-Benzoxazaphospholes. The Utility of the 5-Chloro analogue in the One-Pot Synthesis of Oligothiophosphates: [ApsppA, ApspppA, ppp5'A2'ps5'A, m7GpsppA, Apspppp, Apspp], Tetrahedron 51(10): 2991-3014 (1995).

Perez, B. et al., Antisense Mediated Splicing Modulation for Inherited Metabolic Diseases: Challenges for Delivery, Nucleic Acid Therapies, 24(1): 48-56 (2014).

Rajwanshi, V.K. et al., Lna stereoisomers: xylo-LNA (b-d-xylo configured locked nucleic acid) and a-l-LNA (a-l-ribo configured locked nucleic acid), Chem. Commun., 1395-1396 (1999).

Ravikumar, V.T. et al., Unylinker: An Efficient and Scaleable Synthesis of Oligonucleotides Utilizing a Universal Linker Molecule: A Novel Approach to Enhance the Purity of Drugs, Org. Process Res. Dev., 12(3): 399-410 (2008).

Ravn, J. et al., Stereodefined LNA Phosphorthioate Oligonucleotides, Roche Pharma Research and Early Development, RTR Research, Roche Innovation Center Copenhagen, RNA & Oligonucleotide Therapeutics Meeting, Poster, 1 page (Mar. 29-Apr. 1, 2017).

Reese, C.B. and Yan, H., Solution phase synthesis of ISIS 2922 (Vitravene) by the modified H-phophane approach, J. Chem. Soc., Perkin Trans. I, 2619-2633 (2002).

Regan, J.F. et al., A Rapid Molecular Approach for Chromosomal Phasing, PLOS ONE, 1-15 (2015).

Reither, S. and Jeltsch, A., Specificity of DNA triple helix formation analyzed by a FRET assay, BMC Biochemistry, 3: 9 pages (2002).

Revankar, G. R. and Rao, T.S., DNA with Altered Bases, DNA and Aspects of Molecular Biology, Comprehensive Natural Products Chemistry, 7.09: 313-339 (1999).

Robinson, D.S. et al., Predominant TH2-Like Bronchoalveolar T-Lymphocyte Population in Atopic Asthma, The New England Journal of Medicine, 326: 298-304 (1992).

Rossetti, G., Structural aspects of the Huntingtin protein investigated by biocomputing methods, Thesis, RWTH Aachen University, Forschungszentrum Juelich, 173 pages (2011).

Rozners, E. et al., Evaluation of 2'-hydroxyl protection in RNA-synthesis using the H-phosphonate approad, Nucleic Acids Research, 22(1): 94-99 (1994).

Saetrom, P., Predicting the efficacy of short oligonucleotides in antisense and RNAi experiments with boosted genetic programming, Bioinformatics, 20(17): 3055-3063 (2004).

Sakatsume, O. et al., Solid Phase Synthesis of Oligoribonucleotides by the Phosphoramidite Approach Using 2'-O-1-(2-Chloroethoxy)Ethyl Protection, Tetrahedron, 47(41): 8717-8728 (1991).

Saneyoshi, H. et al., A General Method for the Synthesis of 2'-0-Cyanoethylated Oligoribonucleotides Having Promising Hybridization Affinity for DNA and RNA and Enhanced Nuclease Resistance, The Journal of Organic Chemistry, 70(25): 10453-10460 (2005).

Sanhueza, C.A. et al., Efficient Liver Targeting by Polyvalent Display of a Compact Ligand for the Asialoglycoprotein Receptor, J. Am. Chem. Soc., 9 pages (2016).

Schirle, N. T. and Macrae, I.J., The Crystal Structure of Human Argonaute2, Science, 336(6084): 1037-1040 (2012).

Schirle, N.T. et al., Structural analysis of human Argonaute-2 bound to a modified siRNA guide, J. Am. Chem. Soc., 1-6 (2016).

Schirle, N.T. et al., Structural Basis for microRNA Targeting, Science, 346(6209): 608-613 (2014).

Schirle, N.T. et al., Water-mediated recognition of t1-adenosine anchors Argonaute2 to microRNA targets, eLife, 4: e07646 1-16 (2015).

Schmitz, C. et al., Synthesis of P-Stereogenic Phosphoramidite and Phosphorodiamidite Ligands and Their Application in Asymmetric Catalysis, Eur. J. Org. Chem., 6205-6230 (2015).

Schoning, K.-U. et al., Chemical Etiology of Nucleic Acid Structure: The α-Threofuranosyl-(3'->2') Oligonucleotide System, Science, 290(5495):1347-1351 (2000).

Schultz, C., Prodrugs of Biologically Active Phospate Esters, Bioorganic and Medicinal Chemistry, 11(6):885-898 (2003).

Schultz, R.G. and Gryaznov, S.M., Oligo-24-fluoro-24-deoxynucleotide N34_P54 phosphoramidates: synthesis and properties, Nucleic Acids Res., 24(15): 2966-2973 (1996).

Schulz, W.G. and Cai, S.L., Synthetic Genetics, Chemical and Engineering News, 5 (2012).

Scrimgeour, E.M. Huntington Disease (Chorea) in the Middle East, SQU. Med. J., 9(1): 16-23 (2009).

Seela et al, Diastereomerically pure Rp and Sp dinucleoside H-phosphonates. The stereochemical course of their conversion into P-methylphosphonates, phosphorothioates and [18O] chiral phosphates, Journal of Organic Chemistry, 56(12): 3861-3869 (1991).

Seidman, M.M. and Glazer, P.T. The potential for gene repair via triple helix formation, The Journal of Clinical Investigation, 112(4): 487-494 (2003).

Senn, J.J. et al., Non-CpG-Containing Antisense 2-Methoxyethyl Oligonucleotides Activate a Proinflammatory Response Independent of Toll-Like Receptor 9 or Myeloid DifferentiationFactor 88, The Journal of Pharmacology and Experimental Therapeutics, 314: 972-979 (2005).

Sergueeva et al., Synthesis of Dithymidine Boranophosphates via Stereospecific Boronation of H-phosphonate Diesters and Assignment of their Configuration, Tetrahedron Letters, 40: 2041-2044 (1999).

Seth, P., and Olson, R., Nucleic Acid Therapeutics—Making Sense of Antisesnse, 2016 Drug Design and Delivery Symposium, ACS Webinar, 1-36 (Jul. 26, 2016).

Seth, P.P. et al., An Exocyclic Methylene Group Acts as a Bioisostere of the 2'Oxygen Atom in LNA, J. Am. Chem. Soc, 132(42): 14942-14950 (2010).

Seth, P.P. et al., Configuration of the 50-Methyl Group Modulates the Biophysical and Biological Properties of Locked Nucleic Acid (LNA) Oligonucleotides, J. Med. Chem., 53: 8309-8318 (2010).

Seth, P.P. et al., Design, Synthesis and Evaluation of Constrained Methoxyethyl, (cMOE) and Constrained Ethyl (cEt) Nucleoside Analogs, Nucleic Acids Symposium Series, 52(1), 553-554 (2008).

Seth, P.P. et al., Short Antisense Oligonucleotides with Novel 2'-4' Conformationaly Restricted Nucleoside Analogues Show Improved Potency without Increased Toxicity in Animals, J. Med. Chem., 52: 10-13 (2009).

Seth, P.P. et al., Structural requirements for hybridization at the 50-position are different in a-L-LNA as compared to b-D-LNA, Bioo. Med. Chem. Lett., 22: 296-299 (2012).

Seth, P.P. et al., Structure Activity Relationships of α-I-LNA Modified, Phosphorothioate Gapmer Antisense Oligonucleotides in Animals, Mol. Ther-Nuc. Acids., 1: e47 1-8 (2012).

Seth, P.P. et al., Synthesis and Biophysical Evaluation of 2',4'-Constrained 2'O-Methoxyethyl and 2',4'-Constrained 2'O-Ethyl Nucleic Acid Analogues, J. Org. Chem., 75: 1569-1581 (2010).

Sharma, V.K. et al. Antisense oligonucleotides: modifications and clinical trials, Med. Chem. Commun., 5: 1454-71 (2014).

She, X. et al., Synergy between Anti-Endoglin (CD105) Monoclonal Antibodies and TGF-β in Suppression of Growth of Human Endothelial Cells, Int. J. Cancer, 108: 251-257 (2004).

Sheehan, J.P. and Phan, T.M. Phosphorothioate Oligonucleotides Inhibit the Intrinsic Tenase Complex by an Allosteric Mechanism, Biochemistry, 40: 4980-4989 (2001).

(56) References Cited

OTHER PUBLICATIONS

Shivalingam, A. et al., Molecular Requirements of High-Fidelity Replication-Competent DNA Backbones for Orthogonal Chemical Ligation, J. Am. Chem. Soc., 139(4):1575-1583 (2017).
Sierzchala et al., Oxathiaphospholane Method of Stereocontrolled Synthesis of Diribonucleoside 3', 5'-Phosphorotioates, Journal of Organic Chemistry 61(19): 6713-6716 (1996).
Silverman, R.H., A scientific journey through the 2-5A/RNase L system, Cytokine Growth Factor Reviews, 18(5-6):381-388 (2007).
Singh, P.P. et al., Universality of LNA-mediated high-affinity nucleic acid recognition, Chem. Comm., 1247-1248 (1998).
Singh, S.K. et al., Synthesis of 2'-Amino-LNA: A Novel Conformationally Restricted High-Affinity Oligonucleotide Analogue with a Handle, J. Org. Chem., 63: 10035-10039 (1998).
Singh, S.K. et al., Synthesis of Novel Bicyclo[2.2.1] Ribonucleosides: 2'-Amino- and 2'-Thio-LNA Monomeric Nucleosides, J. Org. Chem., 63: 6078-6079 (1998).
Singhrao, S.K. et al., Increased Complement Biosynthesis by Microglia and Complement Activation on Neurons in Huntington's Disease, Experimental Neurology, 159: 362-376 (1999).
Skotte, N.H. et al., Allele-specific suppression of mutant huntingtin using antisense oligonucleotides: providing a therapeutic option for all Huntington disease patients, PLoS One, 9(9): e107434 1-18 (2014).
Small, L.D. et al., Comparison of Some Properties of Thiolsulfonates and Thiolsulfinates, Journal of the American Chemical Society, 71(10): 3565-3566 (1949).
Smith, A. et al., The murine haemopexin receptor, Biochem. J., 276: 417-425 (1991).
Sobkowski, et al. Stereochemistry of internucleotide bond formation by the H?phosphonate method. 1. Synthesis and 31P NMR analysis of 16 diribonulceoside (3'-5')-H-phosphonates and the corresponding phosphorothioates, Nucleosides Nucleotides Nucleic Acids, 24(10-12): 1469-84 (2005).
Sobkowski, M. et al., Recent Advances in H-Phosphonate Chemistry. Part 1. H-Phosphonate Esters: Synthesis and Basic Reactions, Top Curr Chem, 361:137-177 (2014).
Sonveaux, E., Protecting Groups in Oligonucleotide Synthesis, Protocols for Oligonucleotide Conjugates, Methods in Molecular Biology, Edited by Agrawal, S., Humana Press, 26:1-71 (1994).
Sorensen, M.D., Functionalized LNA (locked nucleic acid): high-affinity hybridization of oligonucleotides containing N-acylated and N-alkylated 2'-amino-LNA monomers, Chem. Comm., 2130-2131 (2003).
Spinelli, N. et al., Use of Allylic Protecting Groups for the Synthesis of Base-Sensitive Prooligonucleotides, European Journal of Organic Chemistry, 49-56 (2002).
Sproat, B.S., RNA Synthesis Using 2'-O-(Tert-Butyldimethylsilyl) Protection, Methods in Molecular Biology, 288: 17-31 (2005).
Stawinski et al., Nucleoside H-phosphonates. 14. Synthesis of nucleoside phosphoroselenoates and phosphorothioselenoates via stereospecific selenization of the corresponding H-phosphonate and H-phosphonothioate diesters with the aid of new selenium-transfer reagent, 3H-1,2-benzothiaseleno1-3-one, J. Org. Chem., 59(1): 130-136 (1994).
Stawinski et al., Stereospecific oxidation and oxidative coupling of H-phosphonate and H-phosphonothioate diesters, Tetrahedron Letters, 33(22):3185-3188 (1992).
Stawinski, J. and Stromberg, R. Di- and Oligonucleotide Synthesis Using H-Phosphonate Chemistry, Methods in Molecular Biology, 288: 81-100 (2005).
Stawinski, J. and Thelin, M., 3-H-2,1-benzoxathiol-3-one 1-oxide—A New Reagent for Stereospecific Oxidation of Nucleoside H-Phosphonothioate Diesters, Tetrahedron Letters, 33(22): 3189-3192 (1992).
Stawinski, J. and Thelin, M., 3H-1,2-benzothiaseleno1-3-one. A new selenizing reagent for nucleoside H-phosphonate and H-phosphonothioate diesters, Tetrahedron Letters, 33(47): 7255-7258 (1992).
Stec, W.J. and Zon, G., Stereochemical Studies of the Formation of Chiral Internucleotide Linkages by Phosphormadite COupling in the Synthesis of Oligodeocyribonucleotides, Tetrahedron Letters, 25(46): 5279-5282 (1984).
Stec, W.J. et al., Automated Solid-Phase Synthesis, Separation, and Stereochemistry of Phosphorothioate Analogues of Oligodeocyribonucleotides, J. Am. Chem. Soc., 106: 6077-6079 (1984).
Stec, W.J. et al., Deoxyribonucleoside 3'-O-(2-Thio- and 2-Oxo-"spiro"-4,4-pentamethylene-1,3,2-oxathiaphospholane)s:? Monomers for Stereocontrolled Synthesis of Oligo(deoxyribonucleoside phosphorothioate)s and Chimeric PS/PO Oligonucleotides, J. Am. Chem. Soc., 120(29): 7156-7167 (1998).
Stec, W.J. et al., Diastereomers of Nucleoside 3'-O-(2-Thio-1,3,2-oxathia(selena)phospholanes): Building Blocks for Stereocontrolled Synthesis of Oligo(nucleoside phosphorothioate)s, Journal of the American Chemical Society, 117(49):12019-12029 (1995).
Stec, W.J. et al., Novel route to oligo(deoxyribonucleoside phosphorothioates). Stereocontrolled synthesis of P-chiral oligo(deoxyribonucleoside phosphorothioates), Nucleic Acids Research, 19(21):5883-5888 (1991).
Stec, W.J. et al., Stereocontrolled Synthesis of Oligo (nucleoside phosphorothioate)s , Angew. Chem. Int. Ed. Engl., 33:709-722 (1994).
Stec, W.J. et al., Stereodependent inhibition of plasminogen activator inhibitor type 1 by phosphorothioate oligonucleotides: proof of sequence specificity in cell culture and in vivo rat experiments, Antisense Nucleic Acid Drug Dev., 7(6):567-73 (1997).
Stec, W.J. et al., Stereospecific Synthesis of P-Chiral Analogs of Oligonucleotides, Methods in Molecular Biology, 20: 285-313 (1993).
Stec, W.J., Oligo(nucleoside Phosphorothioate)s: The Quest of P-Chirality, in Phosphorus, Sulfur, and Silicon, 177(6): 1775-1778 (2002).
Stein, C.A. and Cheng, Y.C., Antisense oligonucleotides as therapeutic agents—is the bullet really magical?, Science, 261(5124):1004-12 (1993).
Stout, A.K. et al., Inhibition of wound healing in mice by local interferon a/b injection, Int J Exp Pathol, 74 (1): 79-85 (1993).
Sureshbabu, V.V. et al., Synthesis of tetrazole analogues of amino acids using Fmoc chemistry: isolation of amino free tetrazoles and their incorporation into peptides, Tetrahedron Letters, 48(39): 7038-7041 (2007).
Surono, A. et al., Chimeric RNA/Ethylene Bridged Nucleic Acids Promote Dystrophin Expression in Myocytes of Duchenne Muscular Dystrophy by Inducing Skipping of the Nonsense Mutation-Encoding Econ, Human Gene Therapy, 15:749-757 (2004).
Suska, A. et al., Antisense oligonucleotides: Stereocontrolled synthesis of phosphorothioate oligonucleotides, Pure and Applied Chemistry, 65(4):707-714 (1993).
Suter, S.R. et al., Structure-Guided Control of siRNA Off Target Effects, J. Am. Chem. Soc., 1-9 (2016).
Swayze, E.E. and Bhat, B., The medicinal chemistry of oligonucleotides, Crooke, S.T. (ed) Antisense Drug Technology: Principles, Strategies, and Applications, CRC Press, Boca Raton, FL: 143-82 (2007).
Swayze, E.E. et al., Antisense oligonucleotides containing locked nucleic acid improve potency but cause significant hepatotoxicity in animals, Nucleic Acids Research, 35(20: 687-700 (2007).
Takahashi, D. et al., Novel diphenylmethyl-Derived Amide Protecting Group for Efficient Liquid-Phase Peptide Synthesis: AJIPHASE, Org. Lett., 14(17): 4514-4517 (2012).
Takahashi, T. et al., Interactions between the non-seed region of siRNA and RNA-binding RLC/RISC proteins, Ago and TRBP, in mammalian cells, Nucleic Acids Research, 42(8): 5256-5269 (2014).
Takeno, H. et al., Selection of an RNA Molecule that Specifically Inhibits the Protease Activity of Subtilisin, J. Biochem., 125: 1115-1119 (1999).
Takeshima, Y. et al., Oligonucleotides against a splicing enhancer sequence led to dystrophin production in muscle cells from a Duchenne muscular dystrophy patient, Brain & Development, 23:788-790 (2001).

(56) References Cited

OTHER PUBLICATIONS

Tam, Journal of Hematotherapy & Stem Cell Research, 12: 467-471 (2003).
Tamura et al., Preparation of Stereoregulated Antisense Oligodeoxyribonucleoside Phoshorothioate and Interaction with its Complementary DNA and RNA, Nucleosides & Nucleotides,17(1-3): 269-282 (1998).
Tang, J. et al., Enzymatic Synthesis of Stereoregular (All Rp) Oligonucleotide Phosphorothioate and Its Properties, Nucleosides Nucleotides, 14(3-5):985-990 (1995).
Tawarada, R. et al., Mechanistic studies on oxidative condensation of a thymidine 3'-H-phosphonate derivative with 3'-O-acetylthymidine, Archive for Organic Chemistry, (3):264-273 (2009).
Thayer, J.R. et al., Separation of oligonucleotide phosphorothioate distereoisomers by pellicular anion-exchange chromatography, Journal of Chromatography A, 1218: 802-808 (2011).
Tomoskozi et al., Stereospecific conversion of H-phosphonates into phosphoramidates. The use of vicinal carbon-phosphorus couplings for configurational determination of phosphorus, Tetrahedron, 51(24): 6797-6804 (1995).
Tosquellas, G. et al., First synthesis of alternating SATE-phosphotriester/phosphodiester prooligonucleotides on solid support, Bioorganic and Medicinal Chemistry Letters, 8(20): 2913-2918 (1998).
Tosquellas, G. et al., Prooligonucleotides exhibit less serum-protein binding than phosphodiester and phosphorothioate oligonucleotides, Nucleosides, Nucleotides and Nucleic Acids, 19(5-6):995-1003 (2000).
Tosquellas, G. et al., The pro-oligonucleotide approach: solid phase synthesis and preliminary evaluation of model pro-dodecathymidylates, Nucleic Acids Research, 26(9):2069-2074 (1998).
Tosquellas, G. et al., The Prooligonucleotide Approach III: Synthesis and bioreversibility of a chimeric phosphorodithioate prooligonucleotide, Bioorganic and Medicinal Chemistry Letters, 6(4):457-462 (1996).
Tosquellas, G. et al., The Prooligonucleotide Approach IV : Synthesis of chimeric prooligonucleotides with 6 enzymolabile masking groups and unexpected desulfurization side reaction, Bioorganic and Medicinal Chemistry Letters, 7(3):263-268 (1997).
Ts'o, P.O. et al., An Approach to Chemotherapy Based on Base Sequence Information and Nucleic Acid Chemistry, Ann. N. Y. Acad. Sci., 507: 220-241 (1988).
Tsai, C.H. et al., Enzymatic synthesis of DNA on glycerol nucleic acid templates without stable duplex formation between product and template, Proceedings of the National Academy of Science, 104(37):14598-14603 (2007).
Tuerk, C. and Gold, L., Systematic Evolution of Ligans by Exponential Enrichment: RNA Ligands to Bacteriophage T4 DNA Polymerase, Science, 249: 505-510 (1990).
Turner, D.H. et al, Improved Parameters for Prediction of RNA Structure, Cold Spring Harbor Symposia on Quantitative Biology, LII: 123-133 (1987).
Turner, D.H. et al., Free Energy Increments for Hydrogen Bonds in Nucleic Acid Base Pairs, J. Am. Chem. Soc., 109: 3783-3785 (1987).
U.S. Food and Drug Administration, Development of New Stereoisomeric Drugs, 8 pages (May 1, 1992). URL: http://www.fda.gov/Drugs/GuidanceComplianceRegulatoryInformation/Guidances/ucm122883.htm [Retrieved Jun. 15, 2016].
Umemoto, T et al., Oligoribonucleotide Synthesis by the use of 1-(2-cyanoethoxy)ethyl (Cee) as a 2'-hydroxy protecting group, Tetrahedron Letters 45: 9529-9531 (2004).
Uphoff, K.W. et al., in vitro selection of aptamers: the death of pure reason, Curr. Opin. Struct. Biol., 6: 281-288 (1996).
Usman, N et al., Automated Chemical Synthesis of Long Oligoribonucleotides Using 2'-O-Siylylated Ribonucleoside 3'-O-Phosphoramidites on a Controlled-Pore Glass Support, J. Am. Chem. Soc. 109(25): 7845-7854 (1987).
Uznanski, B. et al., Stereochemistry of base-catalyzed ring opening of 1,3,2-oxathiaphospholanes. Absolute configuration of 2-{N-[(Rc)-1-(.alpha.-naphthyl)ethyl]amino}-2-thiono-1,3,2-oxathiaphospholanes and O,S-dimethyl N-[(Rc)-1-(.alpha.-naphthypethyl]phosphoramidothioates, Journal of the American Chemical Society, 114(26):10197-10202 (1992).
Van Aerschot, A. et al., 1,5-Anhydrohexitol Nucleic Acids, a New Promising Antisense Construc, Angew. Chem. Int. Ed. Engl., 34: 1338-1339 (1995).
Van Der Veken, P. et al., Irreversible inhibition of dipeptidyl peptidase 8 by dipeptide-derived diaryl phosphonates, Journal of Medicinal Chemistry, 50(23): 5568-5570 (2007).
Van Deutekom, J.C.T. et al., Antisense-induced exon skipping restores dystrophin expression in DMD patient derived muscle cells, Human Molecular Genetics, 10(15):1547-1554 (2001).
Vasquez, K.M. et al., Chromosomal mutations induced by triplex-forming oligonucleotides in mammalian cells, Nucl. Acids Res. 27(4): 1176-1181 (1999).
Vasseur, J-J. et al., Oligonucleosides: Synthesis of a Novel Methylhydroxylamine-Linked Nucleoside Dimer and Its Incorporation into Antisense Sequences, J. Am. Chem. Soc., 114: 4006-4007 (1992).
Veedu, R.N. et al., Novel Applications of Locked Nucleic Acids, Nucleic Acids Symposium Series, 51: 29-30 (2007).
Verhagen et al., A Conformationally locked Aminomethyl C-Glycoside and Studies on Its N-Pyren-1-ylcarbonyl Derivative Inserted into Oligodeoxynucleotides, European Journal of Organic Chemistry, 2538-2548 (2006).
Verma, S. and Eckstein, F., Modified Oligonucleotides: Synthesis and Strategy for Users, Annu. Rev. Biochem., 67: 99-134 (1998).
Vermeulen, A. et al., Double-Stranded Regions Are Essential Design Components of Potent Inhibitors of RISC Function, RNA, 13: 723-730 (2007).
Vives, E. et al., Lipophilic pro-oligonucleotides are rapidly and efficiently internalized in HeLa cells, Nucleic Acids Research, 27(20):4071-4076 (1999).
Vlassov, V.V. et al., Transport of oligonucleotides across natural and model membranes, Biochimica et Biophysica Acta, 1197: 95-108 (1994).
Vu, H. and Hirschbein, B.L., Internucleotide Phosphite Sulfurization With Tetraethylthiuram Disulfide. Phosphorothioate Oligonucleotide Synthesis Via Phosphoramidite Chemistry, Tetrahedron Letters, 32(26):3005-3008 (1991).
Vuyisich, M. and Beal, P.A., Regulation of the RNA-dependent protein kinase by triple helix formation, Nuc, Acids Res., 28(12): 2369-74 (2000).
Wada et al., Stereocontrolled Synthesis of Phosphorothioate RNA by the Oxazaphospholidine Approach, Nucleic Acids Symp. Ser., 48: 57-58 (2004).
Wada, T. et al., Chemical synthesis and properties of stereoregulated phosphorothioate RNAs, Nucleic Acids Symposium Series, 51:119-120 (2007).
Wada, T. et al., Stereocontrolled synthesis of phosphorothioate DNA by an oxazaphospholidine approach, Nucleic Acids Research Supplement, 3:109-110 (2003).
Wada, Takeshi, Chapter I Development of nucleic acid medicines, 3.3 Chemical synthesis of phosphorous atom-modified nucleic acids, CMC Publication., Frontier of Development of Nucleic Acid Medicine: 67-75 (2009).
Wagner, C.R. et al., Pronucleotides: toward the in vivo delivery of antiviral and anticancer nucleotides, Medicinal Research Reviews, 20(6):417-451 (2000).
Walker, J.R. et al., Structure of the Ku heterodimer bound to DNA and its implications for double-strand break repair, Nature, 412: 607-614 (2001).
Wan et al., Synthesis of Second Generation Antisense Oligonucleotides Containing Chiral Phosphorothioate Linkages and Evaluation of their Biophysical Properties and Biological Activity, 10th Annual Meeting of the Oligonucleotide Therapeutics Society, abstract received by Applicant Oct. 7, 2014, poster setup prior to presentation (first known to Applicant late Oct. 12, 2014, PST), poster presentation Oct. 13, 2014.
Wan, W.B. and Seth, P.P., The Medicinal Chemistry of Therapeutic Oligonucleotides, J. Med. Chem., 59: 9645-9667 (2016).
Wan, W.B. et al., Synthesis, biophysical properties and biological activity of second generation antisense oligonucleoties containing

(56) References Cited

OTHER PUBLICATIONS chiral phosphorothioate linkages, Nucleic Acid Research, 42: 13456-13468 (2014). Supplementary Information, 14 pages.
Wang H, et al., Therapeutic gene silencing delivered by a chemically modified siRNA against mutant SOD 1 slows ALS progression, The Journal of Biological Chemistry, 283(23):15845-15852 (2008).
Wang, J.-C. et al., A stereoselective synthesis of dinucleotide phosphorothioate triesters through a chiral indol-oxazaphosphorine intermediate, Tetrahedron Letters, 38(5):705-708 (1997).
Wang, Y. et al., Structure of an argonaute silencing complex with a seed-containing guide DNA and target RNA duplex, Nature, 456(7224): 921-926 (2008).
Warby, S.C. et al., CAG expansion in the Huntington disease gene is associated with a specific and targetable predisposing haplogroup, Am. J. Hum. Genet., 84(3): 351-366 (2009).
Watts, J.K. and Corey, D.R., Gene silencing by siRNAs and antisense oligonucleotides in the laboratory and the clinic, J. Pathol. 226(2): 365-79 (2012).
WAVE Life Sciences Press Release, WAVE Life Sciences Added to the Russell 2000® Index, 2 pages (Jun. 27, 2016).
WAVE Life Sciences Press Release, WAVE Life Sciences Announces Plan to Deliver Six Clinical Programs by 2018, 6 pages (Jan. 29, 2016).
WAVE Life Sciences Press Release, WAVE Life Sciences Announces Pricing of Initial Public Offering, 3 pages (Nov. 11, 2015).
WAVE Life Sciences Press Release, WAVE Life Sciences Appoints Dr. Michael Panzara as Head of Neurology Franchise, 4 pages (Jul. 12, 2016).
WAVE Life Sciences Press Release, WAVE Life Sciences Appoints Keith Regnante as Chief Financial Officer, 4 pages (Aug. 17, 2016).
WAVE Life Sciences Press Release, WAVE Life Sciences Appoints Roberto Guerciolini, M. Senior Vice President and Head of Early Development, 2 pages (Apr. 7, 2015).
WAVE Life Sciences Press Release, WAVE Life Sciences Closed $18 Million Series a Financing to Advance Stereopure Nucleic Acid Therapeutics, 3 pages (Feb. 2, 2015).
WAVE Life Sciences Press Release, WAVE Life Sciences Enters Collaboration with Pfizer to Develop Genetically Targeted Therapies for the Treatment of Metabolic Diseases, 5 pages (May 5, 2016).
WAVE Life Sciences Press Release, WAVE Life Sciences Expands Stereopure Synthetic Chemistry Platform Capabilities, Augments Patent Portfolio with Addition of Single-Stranded RNAi (ssRNAi), 3 pages (Jun. 8, 2015).
WAVE Life Sciences Press Release, WAVE Life Sciences Raises $66 Million in Series B Financing, 3 pages (Aug. 18, 2015).
WAVE Life Sciences Press Release, WAVE Life Sciences Receives Orphan Drug Designation from Fda for its Lead Candidate Designed to Treat Huntington's Disease, 5 pages (Jun. 21, 2016).
WAVE Life Sciences Press Release, WAVE Life Sciences Reports First Quarter 2016 Financial Results and Provides Business Update, 9 pages (May 16, 2016).
WAVE Life Sciences Press Release, WAVE Life Sciences Reports Fourth Quarter and Full Year 2015 Financial Results and Provides Business Update, 10 pages (Mar. 30, 2016).
WAVE Life Sciences Press Release, WAVE Life Sciences Reports Second Quarter 2016 Financial Results and Provides Business Update, 10 pages (Aug. 15, 2016).
WAVE Life Sciences Press Release, WAVE Life Sciences to Advance Next-Generation Nucleic Acid Therapies to Address Unmet Need in Duchenne Muscular Dystrophy, 6 pages (May 9, 2016).
WAVE Life Sciences Press Release, WAVE Life Sciences to Present at the Deutsche Bank 41st Annual Health Care Conference, 2 pages (Apr. 29, 2016).
Wave Life Sciences Press Release, Wave Life Sciences to Present at the Jefferies 2016 Healthcare Conference, 2 pp. (Jun. 1, 2016).
WAVE Life Sciences Press Release, WAVE Life Sciences to Present at the Jmp Securities Life Sciences Conference, 2 pages (Jun. 15, 2016).
WAVE Life Sciences Press Release, WAVE Life Sciences to Present at the Leerink Partner 5th Annual Global Healthcare Conference, 2 pages (Feb. 3, 2016).
WAVE Life Sciences Press Release, WAVE Life Sciences to Present at the Leerink Partners Rare Disease & Immuno-Oncology Roundtable, 2 pages (Sep. 14, 2016).
WAVE Life Sciences Press Release, WAVE Life Sciences to Present at the SunTrust Robinson Humphrey 2016 Orphan Drug Day Conference, 2 pages (Feb. 16, 2016).
Weidner, J.P. et al., Alkyl and Aryl Thiolsulfonates, Journal of Medicinal Chemistry, 7(5): 671-673 (1964).
Weiner, G. J. et al., Immunostimulatory oligodeoxynucleotides containing the CpG motif are effective as immune adjuvants in tumor antigen immunization, 94(20): 10833-10837 (1997).
Weinfeld, M., et al., Influence of nucleic acid base aromaticity on substrate reactivity with enzymes acting on single-stranded DNA, Nucleic Acids Res., 21(3): 621-626 (1993).
Weiser, T.G., et al., An estimation of the global volume of surgery: a modeling strategy based on available data, Lancet, 372(9633): 139-144 (2008).
Welz et al., 5-(Benzylmercapto)-1 H-tetrazole as activator for 2'-O-TBDMS phosphoramidite building blocks in RNA synthesis, Tetrahedron Letters, 43: 795-797 (2002).
Wengel, J., Synthesis of 3'-C- and 4'-C-Branched Oligodeoxynucleotides and the Development of Locked Nucleic Acid (LNA), Ace. Chem. Res., 32: 301-310 (1999).
Whittaker, B. et al., Stereoselective synthesis of highly functionalised P-stereogenic nucleosides via palladium-catalysed P-C cross-coupling reactions, Tetrahedron Letters, 49: 6984-6987 (2008).
Widdison, W. C. et al., Semisynthetic Maytansine analogues for the targeted treatment of cancer, Journal of Medicinal Chemistry, 49(14): 4392-4408 (2006).
Wild, E. et al., Quantification of mutant huntingtin protein in cerebrospinal fluid from Huntington's disease patients, The Journal of Clinical Investigation, 125(5): 1979-1986 (2015).
Wilk, A. and Stec, W.J., Analysis of oligo(deoxynucleoside phosphorothioate)s and their diastereomeric composition, Nucleic Acids Research, 23(3):530-534 (1995).
Wilk, A. et al., Deoxyribonucleoside Cyclic N-Acylphosphoramidites as a New Class of Monomers for the Stereocontrolled Synthesis of Oligothymidylyl- and Oligodeoxycytidylyl-Phosphorothioates, Journal of the American Chemical Society, 122(10): 2149-2156 (2000).
Wong, Chui Ming, Synthesis of anisomycin. Part I. The stereospecific synthesis of N-benzoyl-2-(p-methoxybenzyl)-3-hydroxy-4-carboxamido pyrrolidine and the absolute configuration of anisomycin, Canadian journal of Chemistry 46: 1101-1104 (1968).
Woolf, T.M. et al., Specificity of antisense oligonucleotides in vivo, Prov. Natl. Aca. Sci. USA, 89: 7305-7309 (1992).
Wright, P. et al., Large scale synthesis of oligonucleotides via phosphoramidite nucleosides and a high-loaded polystyrene support, Tetrahedron Letters, 34(21):3373-3736 (1993).
Written Opinion for PCT/IB2009/007923, 8 pages (dated Sep. 6, 2010).
Written Opinion for PCT/IB2015/000395, 10 pages (dated Oct. 30, 2015).
Written Opinion for PCT/JP11/55018, 3 pages (dated Mar. 29, 2011).
Written Opinion for PCT/JP11/71559, 6 pages (dated Dec. 20, 2011).
Written Opinion for PCT/JP15/50716 and English Translation, 11 pages (dated Apr. 21, 2015).
Written Opinion for PCT/JP2010/065900, 5 pages (dated Sep. 15, 2010).
Written Opinion for PCT/JP2013/004303, 6 pages (dated Aug. 13, 2013).
Written Opinion for PCT/JP2015/050714, and English Translation, 11 pages (dated Apr. 21, 2015).
Written Opinion for PCT/JP2015/050718 and English Translation, 6 pages ( dated Apr. 21, 2015).
Written Opinion for PCT/US2010/041068, 11 pages, (dated Sep. 1, 2010).
Written Opinion for PCT/US2011/064287, 14 pages (dated Apr. 12, 2012).

(56) References Cited

OTHER PUBLICATIONS

Written Opinion for PCT/US2012/046805, 9 pages (dated Sep. 19, 2012).
Written Opinion for PCT/US2013/050407, 12 pages (dated Jan. 9, 2014).
Written Opinion for PCT/US2016/043542, 14 pages (dated Dec. 28, 2016).
Written Opinion for PCT/US2016/043598, 10 pages (dated Nov. 28, 2016).
Written Opinion for PCT/US2016/056123, 15 pages (dated Mar. 17, 2017).
Written Opinion for PCT/US2017/022135, 11 pages (dated Jun. 6, 2017).
Written Opinion for PCT/US2017/030753, 13 pages (dated Sep. 26, 2017).
Written Opinion for PCT/US2017/030777, 10 pages (dated Oct. 2, 2017).
Written Opinion for PCT/US2017/035837, 15 pages (dated Aug. 24, 2017).
Written Opinion for PCT/US2017/043431, ISA/US, 38 pages (dated Dec. 21, 2017).
Written Opinion for PCT/US2017/045218, 11 pages (dated Sep. 27, 2017).
Written Opinion for PCT/US2017/055601, ISR/US, 16 pages (dated Feb. 15, 2018).
Written Opinion for PCT/US2017/062996, 9 pages (dated Mar. 9, 2018).
Wu, X. et al., Synthesis of 5'-C- and 2'-O-(Bromoalkyl)-Substituted Ribonucleoside Phosphoramidites for the Post-synthetic Functionalization of Oligonucleotides on Solid Support, Helvetica Chimica Acta, 83: 1127-1144 (2000).
Xiang, Y. et al., Effects of RNase L mutations associated with prostate cancer on apoptosis induced by 2',5'-oligoadenylates, Cancer Research, 63(20):6795-6801 (2003).
Xiong, H.Y. et al., The human splicing code reveals new insights into the genetic determinants of disease, Science, 347(6218): 144 1254806-1-1254806-8 (2015).
Xu, D. and Esko, J.D., Demystifying Heparan Sulfate-Protein Interactions, Annu. Rev. Biochem., 83: 129-157 (2014).
Xu, L. et al., Cyclic ADP-ribose analogues containing the methylenebisphosphonate linkage: effect of pyrophosphate modifications on Ca2+ release activity, J. Med. Chem., 48(12): 4177-4181 (2005).
Xu, Y. et al., Functional comparison of single- and double-stranded siRNAs in mammalian cells, Biochemical and Biophysical Research Communications, 316: 680-687 (2004).
Yamada, O. et al., Diastereoselective Synthesis of 3,4-Dimethoxy-7-morphinanone: A Potential Route to Morphine, Organic Letters, 2(18): 2785-2788 (2000).
Yamakage, S-i. et al., 1-(2-Chloroethoxy)Ethyl Group for the Protection of 2'-Hydroxyl Group in the Synthesis of Oligoribonucleotides, Tetrahedron Letters, 30(46): 6361-6364 (1989).
Yamamoto, S. et al., Unique Palindromic Sequences in Synthetic Oligonucleotides are Required to Induce INF and Augment INF-Mediated Natural Killer Activity, J. Immunol., 148(12): 4072-4076 (1992).
Yamato, K. et al., Enhanced specificity of HPV16 E6E7 siRNA by RNA-DNA chimera modification, Cancer Gene Therapy, 18: 587-597 (2011).
Yanai, H. et al., Suppression of immune responses by nonimmunogenic oligodeoxynucleotides with high affinity for high-mobility group box proteins (HMGBs), PNAS Early Edition, 1-6 (2011).
Yasuda, K. et al., CpG motif-independent activation of TLR9 upon endosomal translocation of "natural" phosphodiester DNA, European Journal of Immunology, 431-436 (2006).
Ye, S. et al., An efficient procedure for genotyping single nucleotide polymorphisms, Nucleic Acids Research, 29(17): e88 1-8 (2001).
Yu, D. et al., Accessible 5'-end of CpGcontaining phosphorothioate oligodeoxynucleotides is essential for immunostimulatory activity, Bioorganic & Medicinal Chemistry Letters, 10: 2585-2588 (2000).
Yu, D. et al., Single-Stranded RNAs Use RNAi to Potently and Allele-Selectively Inhibit Mutant Huntingtin Expression, Cell, 150: 895-908 (2012).
Yu, D. et al., Stereo-Enriched Phosphorothioate Oligodeoxynucleotides: Synthesis, Biophysical and Biological Properties, Bioorganic & Medicinal Chemitry, 8: 275-284 (2000).
Yu, R.Z. et al., Cross-species comparison of in vivo PK/PD relationships for second-generation antisense oligonucleotides targeting apolipoprotein B-100, Biochem. Pharmacol., 77: 910-919 (2009).
Yu, S. et al., A One-Pot Formal [4+2] Cycloaddition Approach to Substituted Piperidines, Indolizidines, and Quinolizidines. Total Synthesis of Indolizidine (-)-209I, Journal of Organic Chemicals, 70:7364-7370 (2005).
Zhang, J. et al., Optimization of Exon Skipping Therapies for Duchenne Muscular Dystrophy, WAVE Life Sciences, PPMD: Parent Project Muscular Dystrophy Meeting, Orlando, FL, Poster, 1 page (Jul. 25, 2016).
Zhang, L. et al., A simple glycol nucleic acid, Journal of the American Chemical Society,127(12):4174-4175 (2005).
Zhang, R.S. et al., Synthesis of two mirror image 4-helix junctions derived from glycerol nucleic acid, Journal of the American Chemical Society, 130(18):5846-5847 (2008).
Zhang, Y. et al., Structural Isosteres of Phosphate Groups in the Protein Data Bank, J. Chem. Inf. Model, 1-18 (2017).
Zhang, Y., Investigating phosphate structural replacements through computational and experimental approaches, Academic Dissertain, University of Helsinki, 119 pages (2014).
Zhao, J. et al., Genome-wide Identification of Polycomb-Associated RNAs by RIP-seq, Molecular Cell, 40: 939-953 (2010).
Zhong, Z. et al., WAVE Life Sciences: Developing Stereopure Nucleic Acid Therapies for the Treatment of Genetic Neurological Diseases, World CNS Summit 2017, Boston, MA, WAVE Life Sciences, Poster, 1 page (Feb. 20-22, 2017).
Zlatev et al., Phosphoramidate dinucleosides as hepatitis C virus polymerase inhibitors, J Med Chem., 51(18): 5745-57 (2008).
Zlatev, I. et al., 5'-C-Malonyl RNA: Small Interfering RNAs Modified with 5'-Monophosphate Bioisostere Demonstrate Gene Silencing Activity, ACS Chem. Biol., 8 pages (2015).
Zon, Automated synthesis of phosphorus-sulfur analogs of nucleic acids-25 years on: potential therapeutic agents and proven utility in biotechnology, New J. Chem., 34(5): 795-804 (2010).
Zon, G and Stec, W.J., Phosphorothioate oligonucleotides, Oligonucleotides and Analogues: A Practical Approach, 87-108 (1991).
ALS Association, The ALS Association and the Packard Center Partner to Develop Animal Model Systems for Most Common Cause of Familial Als, 4 pages (Mar. 1, 2012). URL: http://www.alsa.org/news/archive/new-animal-model-systems.html [Retrieved Dec. 14, 2017].
CAS Registry File RN 121563-98-2; Chemical Abstracts Accession No. 1989:450484, 2 pages (2018).
CAS Registry No. 1223431-57-9, Chemical Abstracts Accession No. 2000:10625, 2 pages (2018).
Donnelly, C.J. et al., M1415. Development of C9orf72 ALS Biomarkers and Therapeutics, Annals of Neurology, 72 (suppl 16): S67-S68 (2012).
Krishna, H. et al., Alkynyl Phosphonate DNA: A Versatile "Click-"able Backbone for DNA-Based Biological Applications, J. Am. Chem. Soc., 134: 11618?11631 (2012).
Lee, K.-W. et al., CG sequence- and phosphorothioate backbone modification-dependent activation of the NF-κB-responsive gene expression by CpG-oligodeoxynucleotides in human RPMI 8226 B cells, Molecular Immunology, 41: 955-964 (2004).
Liu, S. et al., Evaluation of protective effect of multi-epitope DNA vaccine encoding six antigen segments of Toxoplasma gondii in mice Parasitol Res, 105:267-274 (2009).
Madsen, A., Antisense Against C90RF72, MDA/ALS News Magazine, 2 pages (Jul. 1, 2012). URL: http://alsn.mda.org/article/antisense-against-c90rf72 [Retrieved Dec. 14, 2017].

(56) References Cited

OTHER PUBLICATIONS

Martinez, J.M.L. et al, NMR Characterization of Hydrate and Aldehyde Forms of Imidazole-2-carboxaldehyde and Derivatives, Journal of Organic Chemistry, 75: 3208-3213 (2010).
Nishina, K. et al., DNA/RNA heteroduplex oligonucleotide for highly efficient gene silencing, Nature Communications, 6:7969, pp. 1-13 (2015).
Renton, A.E. et al., A Hexanucleotide Repeat Expansion in C9ORF72 Is the Cause of Chromosome 9p21-Linked ALS-FTD, Neuron 72, 257-268 (Oct. 20, 2011).
Sha, S.J. and Boxer, A., Treatment implications of C9ORF72, Alzheimer's Research & Therapy, 4(46): 7 pages (2012).
Simon-Sanchez, J. et al., The clinical and pathological phenotype of C9ORF72 hexanucleotide repeat expansions, Brain, 135: 723-735 (2012).
Tulic, M.K. et al Amb a 1-immunostimulatory oligodeoxynucleotide conjugate immunotherapy decreases the nasal inflammatory response, J. Allergy Clin. Immunol., 235-241 (2004).

\* cited by examiner

METHODS FOR THE SYNTHESIS OF FUNCTIONALIZED NUCLEIC ACIDS

CROSS-REFERENCE TO RELATED APPLICATIONS

This application is a continuation application of U.S. patent application Ser. No. 15/222,910, filed Jul. 28, 2016, which is a continuation of U.S. patent application Ser. No. 14/233,579, filed Feb. 27, 2014 (now U.S. Pat. No. 9,605,019), which is a 371 national phase entry of International Application No. PCT/US12/46805, which claims priority to U.S. Provisional Application No. 61/509,526, filed Jul. 19, 2011. The contents of these priority applications are hereby incorporated by reference in their entirety.

BACKGROUND OF THE INVENTION

Oligonucleotides are useful in therapeutic, diagnostic, research and nanomaterials applications. The use of natural sequences of DNA or RNA for therapeutics is limited because of their instability against extra and intracellular nucleases, poor cell penetration and distribution. Additionally, in vitro studies have shown that the properties of antisense nucleotides such as binding affinity, sequence specific binding to the complementary RNA (Cosstick and Eckstein, 1985; LaPlanche et al., 1986; Latimer et al., 1989; Hacia et al., 1994; Mesmaeker et al., 1995), stability to nucleases are affected by the configurations of the phosphorous atoms Therefore, there is a need for modified oligonucleotides to impart stability towards ubiquitous nucleases, increase binding affinity towards complementary RNA and increase cell penetration and bio-distribution for a number of in-vitro and in-vivo applications.

SUMMARY OF THE INVENTION

Described herein are methods for the synthesis of novel functionalized nucleic acids and nucleic acid prodrugs. In some embodiments, the nucleic acids comprise chiral phosphorous moieties.

One embodiment provides a process for the preparation of phosphorothiotriesters of structure IIIa comprising the steps of:
i) reacting an H-phosphonate of structure Ia with an silylating reagent to provide a silyloxyphosphonate; and
ii) reacting the silyloxyphosphonate with a thiosulfonate reagent of structure IIa to provide a phosphorothiotriester of structure IIIa;
wherein,
the H-phosphonate of structure Ia has the following structure:

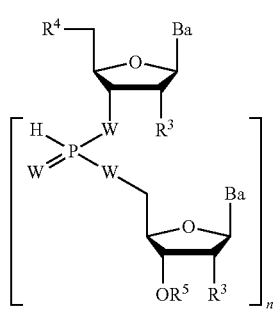

Structure Ia wherein,
W is independently selected from O, S, NH, or $CH_2$;
$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —P(O)(Re)$_2$, —HP(O)(Re), —$OR^a$ or —$SR^c$;
$Y^1$ is O, $NR^d$, S, or Se;
$R^a$ is a blocking group;
$R^c$ is a blocking group;
each instance of $R^d$ is independently hydrogen, alkyl, alkenyl, alkynyl, aryl, acyl, substituted silyl, carbamate, —P(O)($R^e$)$_2$, or —HP(O)($R^e$);
each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;
$Y^2$ is O, $NR^d$, or S;
each instance of $R^4$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, and $R^b$ is a blocking group;
each instance of Ba is independently a blocked or unblocked adenine, cytosine, guanine, thymine, uracil or modified nucleobase;
$R^5$ is hydrogen, a blocking group, a linking moiety connected to a solid support or a linking moiety connected to a nucleic acid; and
n is between 1 and about 200; and
the thiosulfonate reagent of structure IIa has the following structure:

Structure IIa wherein,
X is alkyl, cycloalkyl, or heteroaryl;
R is alkyl, alkenyl, alkynyl, cycloalkyl, aryl, aralkyl, heteroaryl, heteroaralkyl, or $R^1$-$R^2$;
$R^1$ is selected from —S-alkenylene-, —S-alkylene-, —S-alkylene-aryl-alkylene-, —S—CO-aryl-alkylene-, or —S—CO-alkylene-aryl-alkylene-;
$R^2$ is selected from heterocyclo-alkylene-S—, heterocyclo-alkenylene-S—, aminoalkyl-S—, or (alkyl)$_4$N-alkylene-S—;
and the phosphorothiotriester of structure IIIa has the following structure:

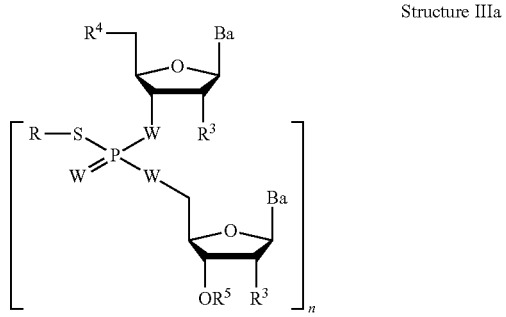

Structure IIIa wherein,

W is independently selected from O, S, NH, or $CH_2$;

R is alkyl, alkenyl, alkynyl, cycloalkyl, aryl, aralkyl, heteroaryl, heteroaralkyl, or $R^1$-$R^2$;

$R^1$ is selected from —S-alkenylene-, —S-alkylene-, —S-alkylene-aryl-alkylene-, —S—CO-aryl-alkylene-, or —S—CO-alkylene-aryl-alkylene-;

$R^2$ is selected from heterocyclo-alkylene-S—, heterocyclo-alkenylene-S—, aminoalkyl-S—, or $(alkyl)_4N$-alkylene-S—;

$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$P(O)(R^e)_2$, —$HP(O)(R^e)$, —$OR^a$ or —$SR^c$;

$Y^1$ is O, $NR^d$, S, or Se;

$R^a$ is a blocking group;

$R^c$ is a blocking group;

each instance of $R^d$ is independently hydrogen, alkyl, alkenyl, alkynyl, aryl, acyl, substituted silyl, carbamate, —$P(O)(R^e)_2$, or —$HP(O)(R^e)$;

each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;

$Y^2$ is O, $NR^d$, or S;

each instance of $R^4$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, and $R^b$ is a blocking group;

each instance of Ba is independently a blocked or unblocked adenine, cytosine, guanine, thymine, uracil or modified nucleobase;

$R^5$ is hydrogen, a blocking group, a linking moiety connected to a solid support or a linking moiety connected to a nucleic acid; and n is between 1 and about 200.

Another embodiment provides a process for the preparation of phosphorothiotriesters of structure IIIa, wherein W is O.

Another embodiment provides a process for the preparation of phosphorothiotriesters of structure IIIa, wherein $R^1$ is selected from:

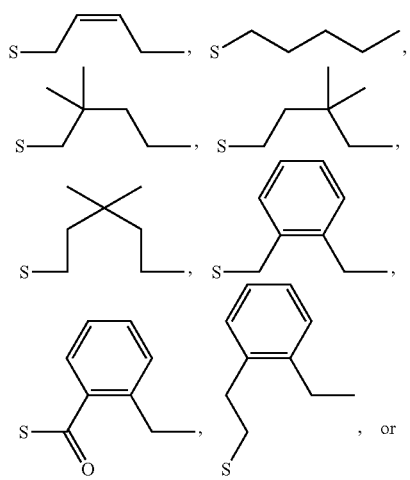

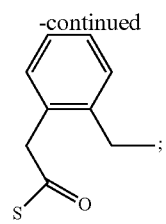

and $R^2$ is selected from:

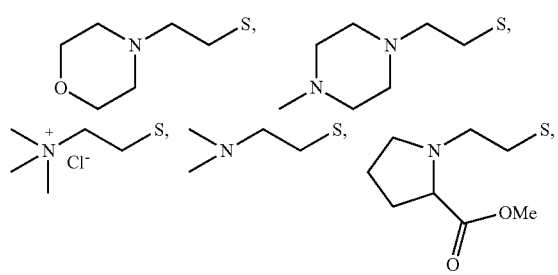

Another embodiment provides a process for the preparation of phosphorothiotriesters of structure IIIa, wherein the silylating reagent is selected from
1,1,3,3-tetramethyl-1,3-diphenyldisilazane;
1,3-dimethyl-1,1,3,3-tetraphenyldisilazane;
1-(trimethylsilyl)imidazole;
N-trimethylsilyl-N-methyl trifluoroacetamide;
bis(dimethylamino)dimethylsilane;
bromotrimethylsilane;
chlorodimethyl(pentafluorophenyl)silane;
chlorotriethylsilane;
chlorotriisopropylsilane;
chlorotrimethylsilane;
dichlorodimethylsilane;
hexamethyldisilazane;
N,N'-bis(trimethylsilyl)urea;
N,N-bis(trimethylsilyl)methylamine;
N,N-dimethyltrimethylsilylamine;
N,O-bis(trimethylsilyl)acetamide;
N,O-bis(trimethylsilyl)carbamate;
N,O-bis(trimethylsilyl)trifluoroacetamide;
N-methyl-N-(trimethylsilyl)trifluoroacetamide;
N-methyl-N-trimethylsilylacetamide;
N-methyl-N-trimethylsilylheptafluorobutyramide;
N-tert-butyldimethylsilyl-N-methyltrifluoroacetamide;
N-methyl-N-trimethylsilylheptafluorobutyramide;
trimethylsilyltriflate;
triethylsilyltriflate;
triisopropylsilyltriflate; or
tert-butyldimethyl silyltriflate.

Another embodiment provides the process, wherein the silylating reagent is selected from N,O-bis(trimethylsilyl)trifluoroacetamide, trimethyl silyltriflate, chlorotrimethylsilane, or 1-(trimethyl silyl)imidazole.

Another embodiment provides the process, wherein the silylating reagent is selected from N,O-bis(trimethylsilyl)trifluoroacetamide.

Another embodiment provides the process, wherein the H-phosphonate is covalently linked to a solid phase.

One embodiment provides a process for the preparation of phosphorothiotriesters comprising non-stereorandom phosphorous linkages of structure IIIb comprising the steps of:

i) reacting a H-phosphonate comprising non-stereorandom phosphorous linkages of structure Ib with an silylating reagent to provide a silyloxyphosphonate; and ii) reacting the silyloxyphosphonate with a thiosulfonate reagent of structure IIb to provide a phosphorothiotriester comprising non-stereorandom phosphorous linkages of structure IIIb;

wherein,
the H-phosphonate comprising non-stereorandom phosphorous linkages of structure Ib has the following structure:

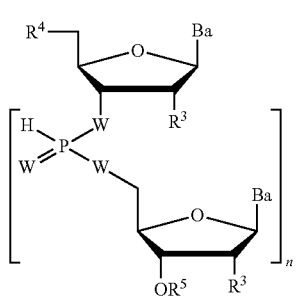

Structure Ib wherein,
W is independently selected from O, NH, or $CH_2$;
$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —P(O)$(R^e)_2$, —HP(O)($R^e$), —$OR^a$ or —$SR^c$;
$Y^1$ is O, $NR^d$, S, or Se;
$R^a$ is a blocking group;
$R^c$ is a blocking group;
each instance of $R^d$ is independently hydrogen, alkyl, alkenyl, alkynyl, aryl, acyl, substituted silyl, carbamate, —P(O)$(R^e)_2$, or —HP(O)($R^e$);
each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;
$Y^2$ is O, $NR^d$, or S;
each instance of $R^4$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, and $R^b$ is a blocking group;
each instance of Ba is independently a blocked or unblocked adenine, cytosine, guanine, thymine, uracil or modified nucleobase;
$R^5$ is hydrogen, a blocking group, a linking moiety connected to a solid support or a linking moiety connected to a nucleic acid; and
n is between 1 and about 200; and
the thiosulfonate reagent of structure IIb has the following structure:

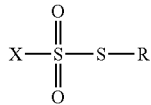

Structure IIb wherein,
X is alkyl, cycloalkyl, aryl, or heteroaryl;
R is alkyl, alkenyl, alkynyl, cycloalkyl, aryl, aralkyl, heteroaryl, heteroaralkyl, or $R^1$-$R^2$;
$R^1$ is selected from —S-alkenylene-, —S-alkylene-, —S-alkylene-aryl-alkylene-, —S—CO-aryl-alkylene-, or —S—CO-alkylene-aryl-alkylene-;
$R^2$ is selected from heterocyclo-alkylene-S—, heterocyclo-alkenylene-S—, aminoalkyl-S—, or $(alkyl)_4N$-alkylene-S—;
and the chiral phosphorothiotriester comprising non-stereorandom phosphorous linkages of structure IIIb has the following structure:

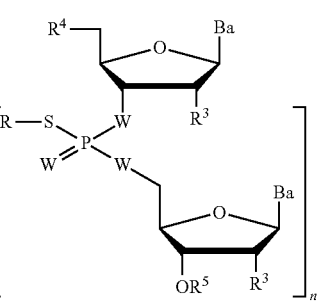

Structure IIIb wherein,
W is independently selected from O, NH, or $CH_2$;
R is alkyl, alkenyl, alkynyl, cycloalkyl, aryl, aralkyl, heteroaryl, heteroaralkyl, or $R^1$-$R^2$;
$R^1$ is selected from —S-alkenylene-, —S-alkylene-, —S-alkylene-aryl-alkylene-, —S—CO-aryl-alkylene-, or —S—CO-alkylene-aryl-alkylene-;
$R^2$ is selected from heterocyclo-alkylene-S—, heterocyclo-alkenylene-S—, aminoalkyl-S—, or $(alkyl)_4N$-alkylene-S—;
$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —P(O)$(R^e)_2$, —HP(O)($R^e$), —$OR^a$ or —$SR^c$;
$Y^1$ is O, $NR^d$, S, or Se;
$R^a$ is a blocking group;
$R^c$ is a blocking group;
each instance of $R^d$ is independently hydrogen, alkyl, alkenyl, alkynyl, aryl, acyl, substituted silyl, carbamate, —P(O)$(R^e)_2$, or —HP(O)($R^e$);
each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;
$Y^2$ is O, $NR^d$, or S;
each instance of $R^4$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, and $R^b$ is a blocking group;
each instance of Ba is independently a blocked or unblocked adenine, cytosine, guanine, thymine, uracil or modified nucleobase;
$R^5$ is hydrogen, a blocking group, a linking moiety connected to a solid support or a linking moiety connected to a nucleic acid; and
n is between 1 and about 200.

Another embodiment provides a process for the preparation of phosphorothiotriesters comprising non-stereorandom phosphorous linkages of structure IIIb, wherein W is O.

Another embodiment provides a process for the preparation of phosphorothiotriesters comprising non-stereorandom phosphorous linkages of structure IIIb, wherein $R^1$ is selected from:

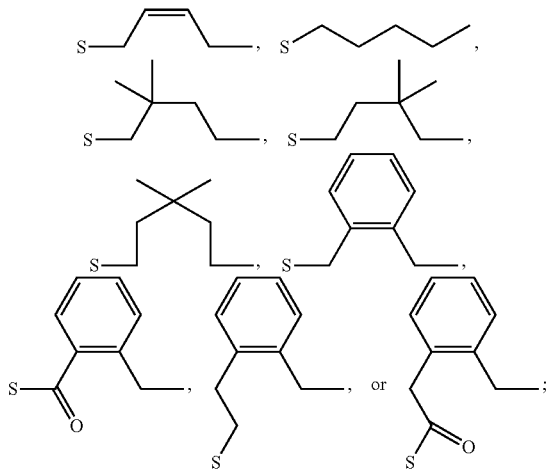

and
$R^2$ is selected from:

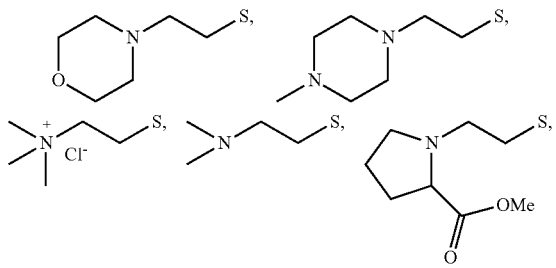

Another embodiment provides a process for the preparation of phosphorothiotriesters comprising non-stereorandom phosphorous linkages of structure IIIb, wherein the silylating reagent is selected from
1,1,3,3-tetramethyl-1,3-diphenyldisilazane;
1,3-dimethyl-1,1,3,3-tetraphenyldisilazane;
1-(trimethylsilyl)imidazole;
N-trimethylsilyl-N-methyl trifluoroacetamide;
bis(dimethylamino)dimethylsilane;
bromotrimethylsilane;
chlorodimethyl(pentafluorophenyl)silane;
chlorotriethylsilane;
chlorotriisopropylsilane;
chlorotrimethylsilane;
dichlorodimethylsilane;
hexamethyldisilazane;
N,N'-bis(trimethylsilyl)urea;
N,N-bis(trimethylsilyl)methylamine;
N,N-dimethyltrimethylsilylamine;
N,O-bis(trimethylsilyl)acetamide;
N,O-bis(trimethylsilyl)carbamate;
N,O-bis(trimethylsilyl)trifluoroacetamide;
N-methyl-N-(trimethylsilyl)trifluoroacetamide;
N-methyl-N-trimethylsilylacetamide;
N-methyl-N-trimethylsilylheptafluorobutyramide;
N-tert-butyldimethylsilyl-N-methyltrifluoroacetamide;
N-methyl-N-trimethylsilylheptafluorobutyramide;
trimethyl silyltriflate;
triethylsilyltriflate;
triisopropylsilyltriflate; or
tert-butyldimethyl silyltriflate.

Another embodiment provides the process, wherein the silylating reagent is selected from N,O-bis(trimethylsilyl)trifluoroacetamide, trimethyl silyltriflate, chlorotrimethylsilane, or 1-(trimethyl silyl)imidazole.

Another embodiment provides the process, wherein the silylating reagent is selected from N,O-bis(trimethylsilyl)trifluoroacetamide.

Another embodiment provides the process, wherein the H-phosphonate is covalently linked to a solid phase.

One embodiment provides a process for the preparation of phosphorothiotriesters of structure IIIc comprising the steps of:
i) reacting a H-phosphonate of structure Ic with an silylating reagent to provide a silyloxyphosphonate;
ii) reacting the silyloxyphosphonate with a bis(thiosulfonate) reagent of structure IVc to provide a phosphorothiotriester comprising a thiosulfonate group of structure Vc;
iii) reacting the phosphorothiotriester comprising a thiosulfonate group of structure Vc with a nucleophile of structure VIc to provide the phosphorothiotriesters of structure IIIc;
wherein,
the H-phosphonate of structure Ic has the following structure:

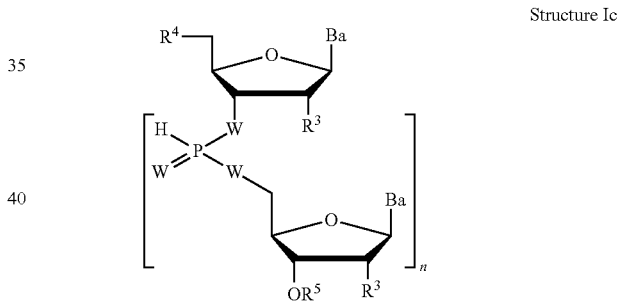

Structure Ic wherein,
W is independently selected from O, S, NH, or $CH_2$;
$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, $P(O)(R^e)_2$, —$HP(O)(R^e)$, —$OR^a$ or —$SR^c$;
$Y^1$ is O, $NR^d$, S, or Se;
$R^a$ is a blocking group;
$R^c$ is a blocking group;
each instance of $R^d$ is independently hydrogen, alkyl, alkenyl, alkynyl, aryl, acyl, substituted silyl, carbamate, —$P(O)(R^e)_2$, or —$HP(O)(R^e)$;
each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;
$Y^2$ is O, $NR^d$, or S;
each instance of $R^4$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, and $R^b$ is a blocking group;

each instance of Ba is independently a blocked or unblocked adenine, cytosine, guanine, thymine, uracil or modified nucleobase;

$R^5$ is hydrogen, a blocking group, a linking moiety connected to a solid support or a linking moiety connected to a nucleic acid; and n is between 1 and about 200; and the bis(thiosulfonate) reagent of structure IVc has the following structure:

$$R^6-\overset{\overset{O}{\|}}{\underset{\underset{O}{\|}}{S}}-S-X-S-\overset{\overset{O}{\|}}{\underset{\underset{O}{\|}}{S}}-R^6 \quad \text{Structure IVc}$$

wherein,

X is alkylene, alkenylene, arylene, or heteroarylene;

each $R^6$ is independently alkyl, cycloalkyl, aryl, or heteroaryl;

the nucleophile of structure VIc has the following structure:

$R^7$—SH, wherein $R^7$ is selected from alkyl, alkenyl, aryl, heterocyclo, aminoalkyl, or (heterocyclo)alkyl;

and phosphorothiotriesters of structure IIIc has the following structure:

Structure IIIc wherein,

W is independently selected from O, S, NH, or $CH_2$;

R is $R^7$—S—S—X—

$R^7$ is alkyl, alkenyl, aryl, heterocyclo, aminoalkyl, or (heterocyclo)alkyl;

X is alkylene, alkenylene, arylene, or heteroarylene;

$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —P(O)$(R^e)_2$, —HP(O)$(R^e)$, —$OR^a$ or —$SR^c$;

$Y^1$ is O, $NR^d$, S, or Se;

$R^a$ is a blocking group;

$R^c$ is a blocking group;

each instance of $R^d$ is independently hydrogen, alkyl, alkenyl, alkynyl, aryl, acyl, substituted silyl, carbamate, —P(O)$(R^e)_2$, or —HP(O)$(R^e)$;

each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;

$Y^2$ is O, $NR^d$, or S;

each instance of $R^4$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, and $R^b$ is a blocking group;

each instance of Ba is independently a blocked or unblocked adenine, cytosine, guanine, thymine, uracil or modified nucleobase;

$R^5$ is hydrogen, a blocking group, a linking moiety connected to a solid support or a linking moiety connected to a nucleic acid;

n is between 1 and about 200; and wherein the phosphorous linkages of the H-phosphonate of structure Ic, the phosphorothiotriester comprising a thiosulfonate group of structure Vc, and the phosphorothiotriesters of structure IIIc may optionally comprise non-stereorandom phosphorous linkages.

Another embodiment provides the process wherein the phosphorothiotriesters of structure IIIb comprise non-stereorandom phosphorous linkages and the H-phosphonate of structure Ic comprise non-stereorandom phosphorous linkages; and W is independently selected from O, NH, or $CH_2$.

Another embodiment provides the process wherein W is O.

Another embodiment provides the process wherein $R^6$ is methyl.

Another embodiment provides the process wherein bis (thiosulfonate) reagent of structure IVc is selected from:

$$H_3C-\overset{\overset{O}{\|}}{\underset{\underset{O}{\|}}{S}}-S-CH_2-S-\overset{\overset{O}{\|}}{\underset{\underset{O}{\|}}{S}}-CH_3,$$

$$H_3C-\overset{\overset{O}{\|}}{\underset{\underset{O}{\|}}{S}}-S-\phantom{xx}-S-\overset{\overset{O}{\|}}{\underset{\underset{O}{\|}}{S}}-CH_3, \text{ or}$$

$$H_3C-\overset{\overset{O}{\|}}{\underset{\underset{O}{\|}}{S}}-S-\phantom{xx}-S-\overset{\overset{O}{\|}}{\underset{\underset{O}{\|}}{S}}-CH_3.$$

Another embodiment provides the process wherein the nucleophile of structure VIc has the following structure:

Another embodiment provides a process for the preparation of phosphorothiotriesters of structure IIIa, wherein the silylating reagent is selected from 1,1,3,3-tetramethyl-1,3-diphenyldisilazane;
1,3-dimethyl-1,1,3,3-tetraphenyldisilazane;
1-(trimethylsilyl)imidazole;
N-trimethylsilyl-N-methyl trifluoroacetamide;
bis(dimethylamino)dimethylsilane;
bromotrimethylsilane;
chlorodimethyl(pentafluorophenyl)silane;
chlorotriethylsilane;
chlorotriisopropylsilane;
chlorotrimethylsilane;
dichlorodimethylsilane;
hexamethyldisilazane;
N,N'-bis(trimethylsilyl)urea;
N,N-bis(trimethylsilyl)methylamine;
N,N-dimethyltrimethylsilylamine;
N,O-bis(trimethylsilyl)acetamide;
N,O-bis(trimethylsilyl)carbamate;
N,O-bis(trimethylsilyl)trifluoroacetamide;
N-methyl-N-(trimethylsilyl)trifluoroacetamide;
N-methyl-N-trimethylsilylacetamide;
N-methyl-N-trimethylsilylheptafluorobutyramide;
N-tert-butyldimethylsilyl-N-methyltrifluoroacetamide;
N-methyl-N-trimethylsilylheptafluorobutyramide;
trimethyl silyltriflate;
triethylsilyltriflate;
triisopropylsilyltriflate; or
tert-butyldimethyl silyltriflate.

Another embodiment provides the process, wherein the silylating reagent is selected from N,O-bis(trimethylsilyl) trifluoroacetamide, trimethyl silyltriflate, chlorotrimethylsilane, or 1-(trimethyl silyl)imidazole.

Another embodiment provides the process, wherein the silylating reagent is selected from N,O-bis(trimethylsilyl) trifluoroacetamide.

Another embodiment provides the process, wherein the H-phosphonate is covalently linked to a solid phase.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
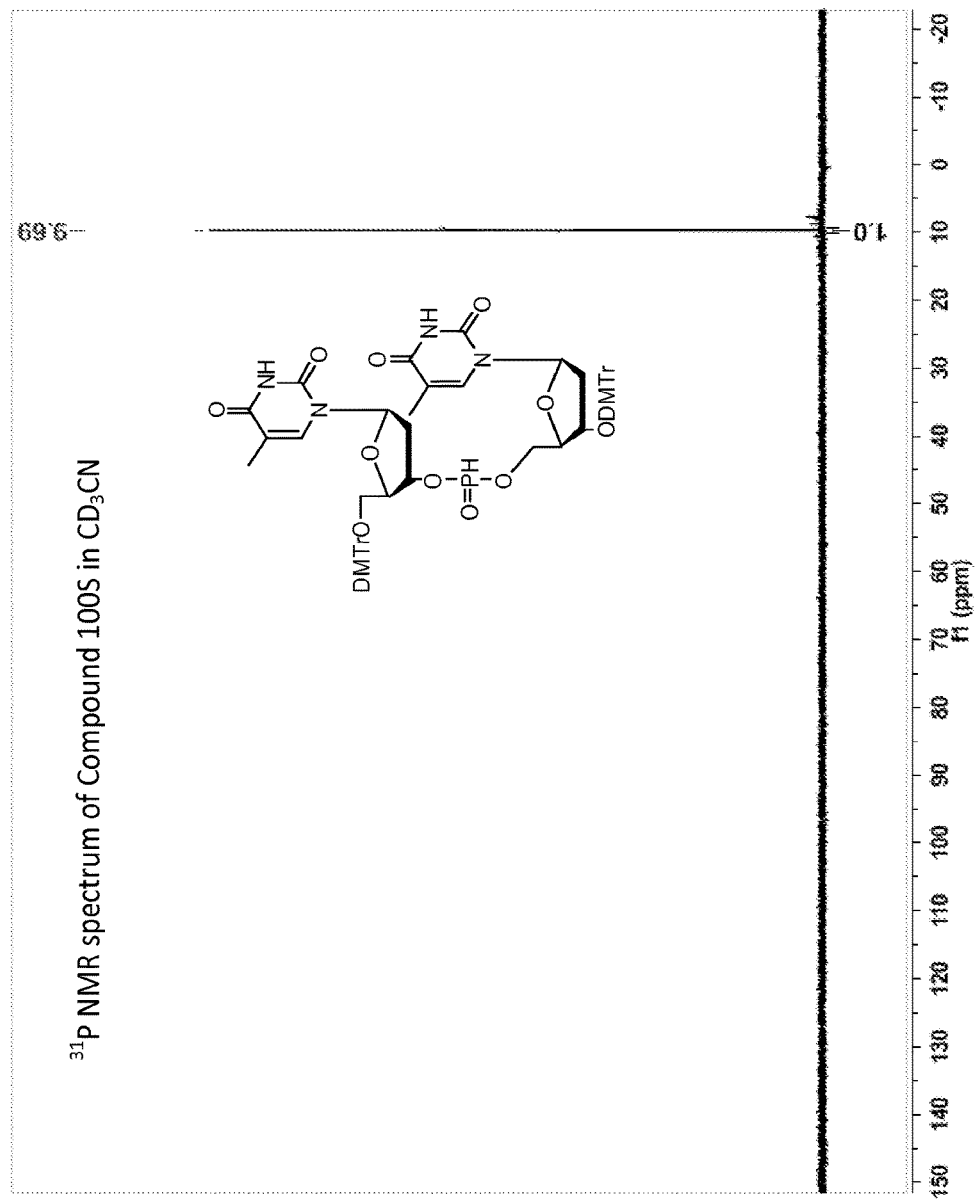
FIG. 1 provides the $^{31}$P NMR spectrum of Compound 100S in CD$_3$CN as described in Example 6.
Figure 2:
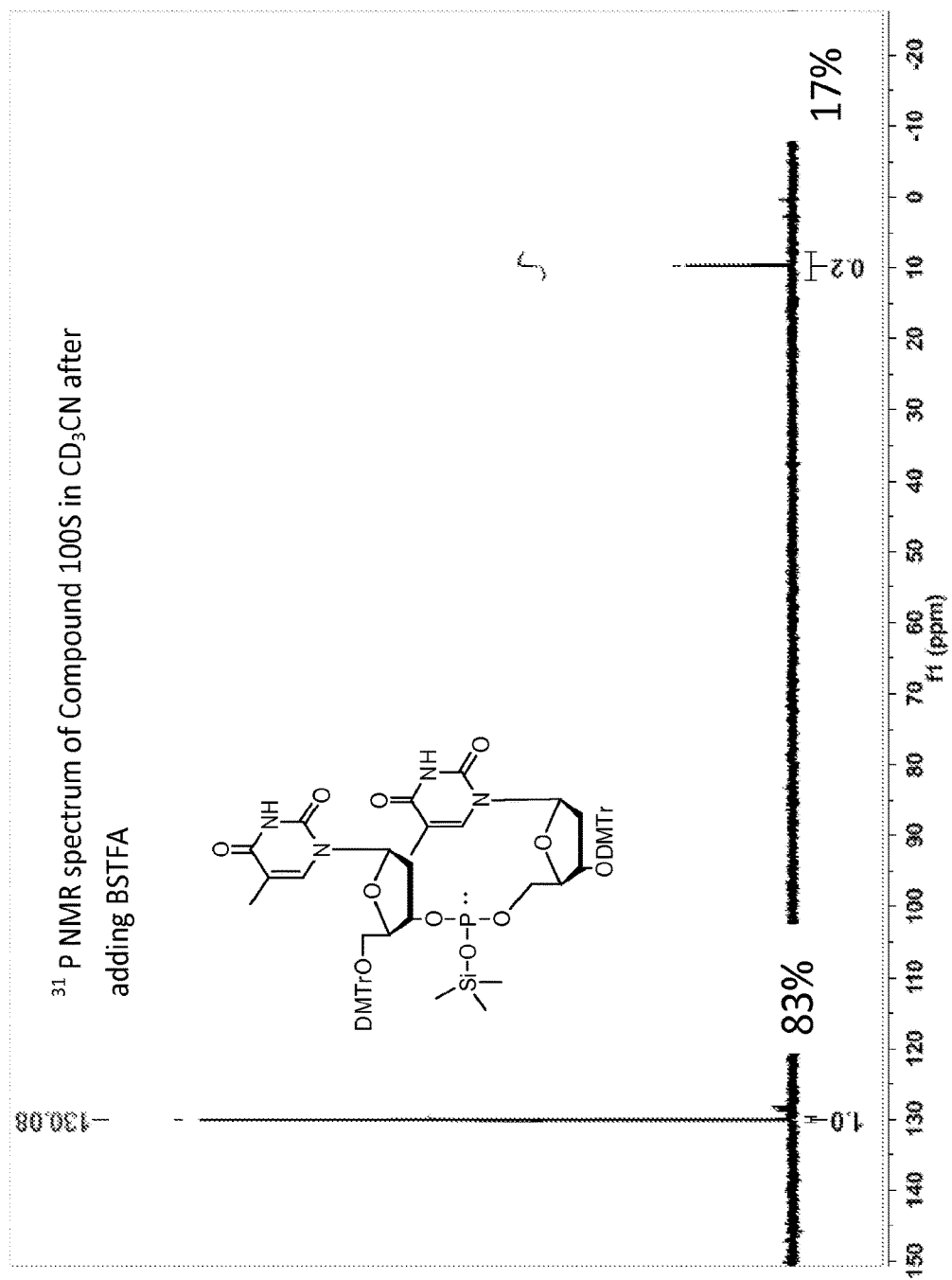
FIG. 2 provides the $^{31}$P NMR spectrum of Compound 100S in CD$_3$CN after adding BSTFA as described in Example 6.
Figure 3:
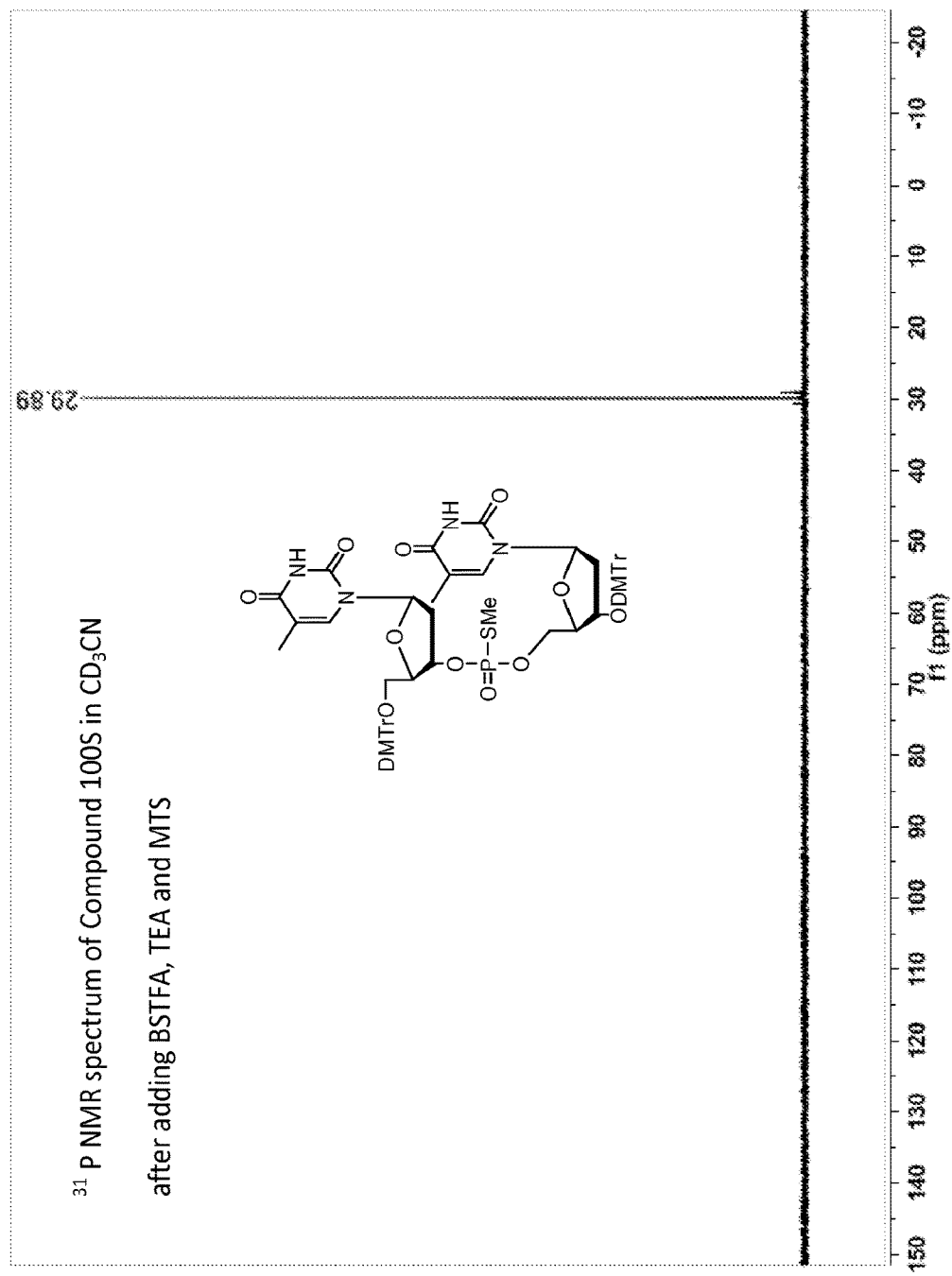
FIG. 3 provides the $^{31}$P NMR spectrum of Compound 100S in CD$_3$CN after adding BSTFA, TEA and MTS as described in Example 6.
Figure 4:
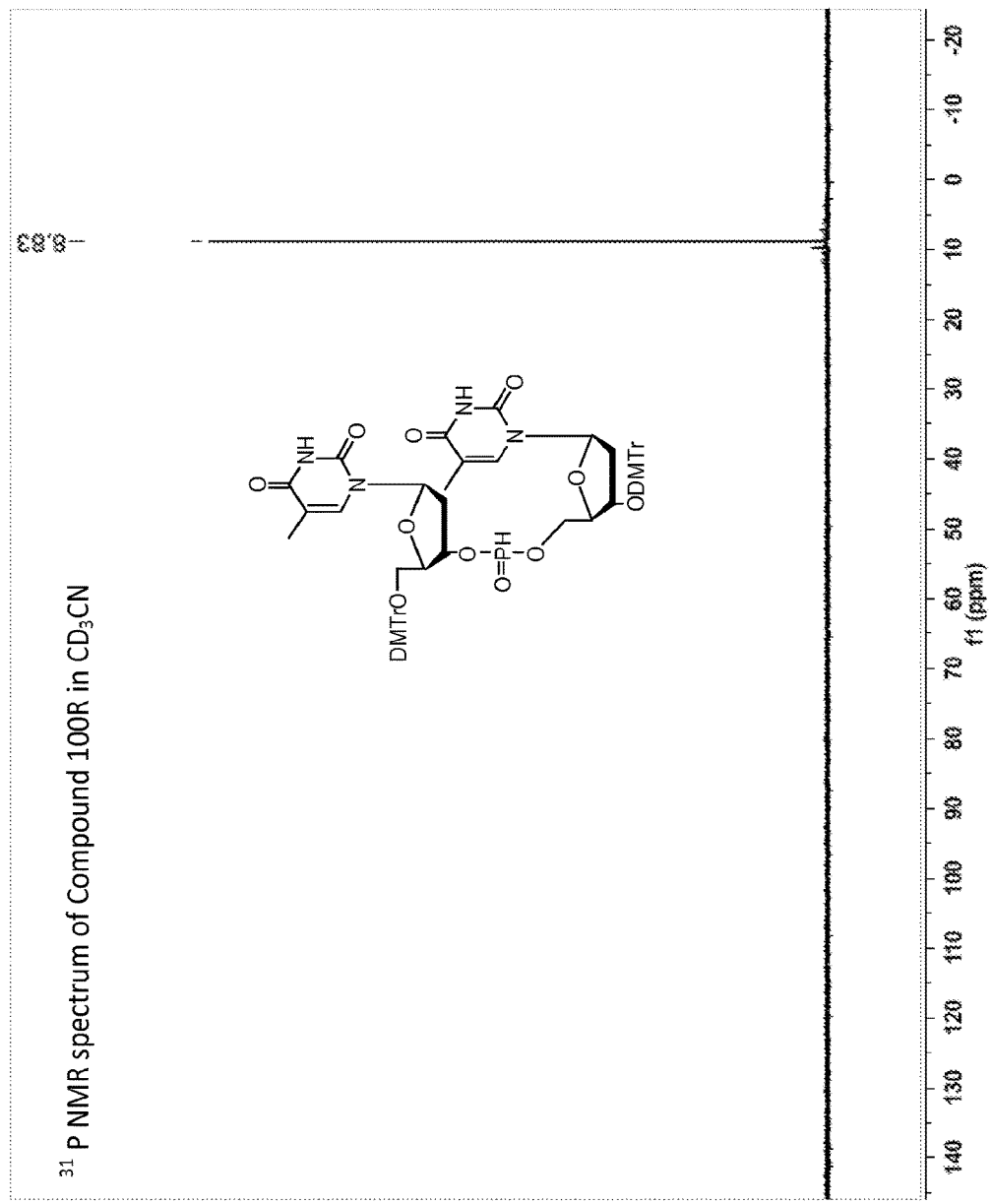
FIG. 4 provides the $^{31}$P NMR spectrum of Compound 100R in CD$_3$CN as described in Example 6.
Figure 5:
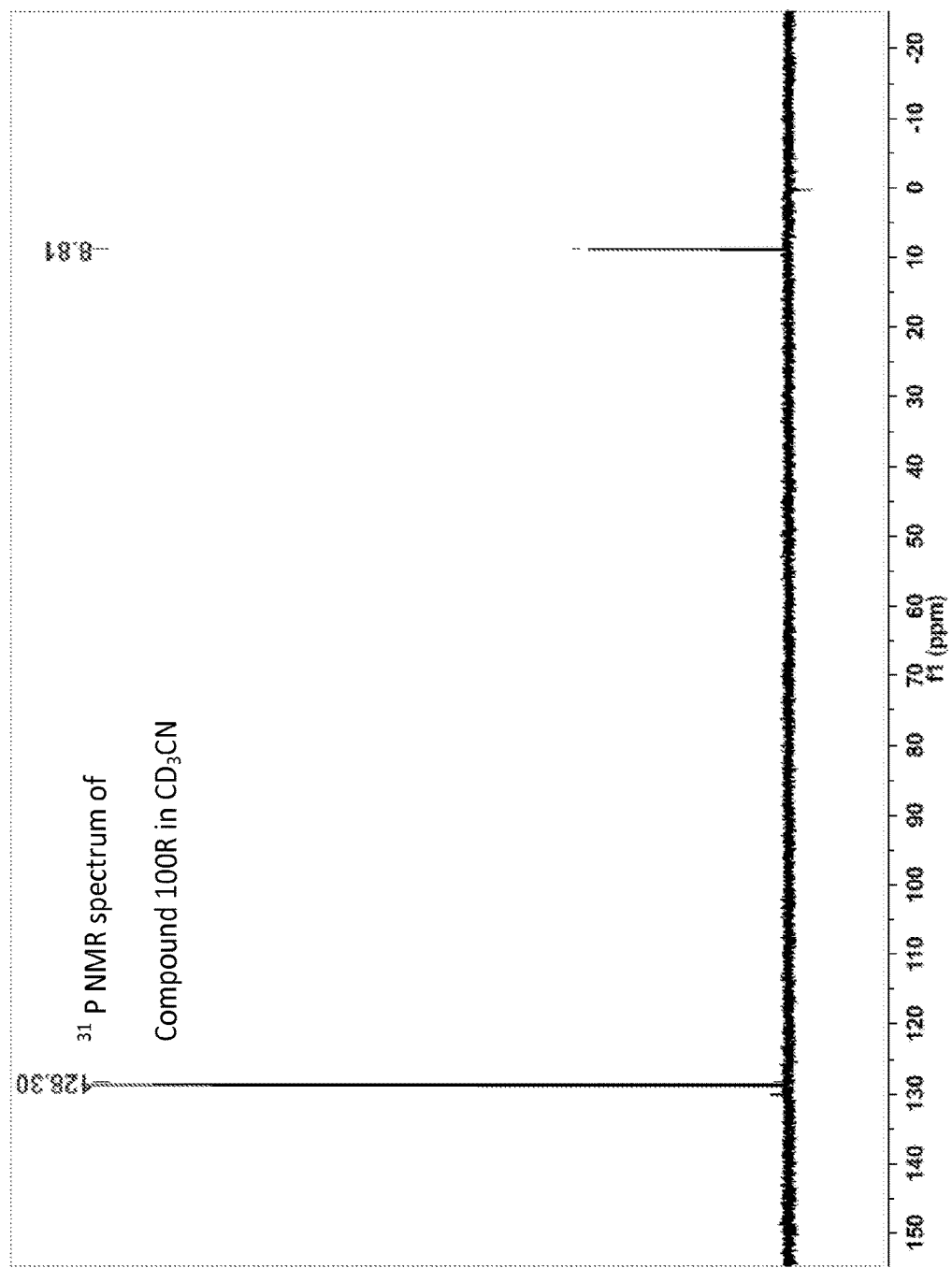
FIG. 5 provides the $^{31}$P NMR spectrum of Compound 100R in CD$_3$CN as described in Example 6.
Figure 6:
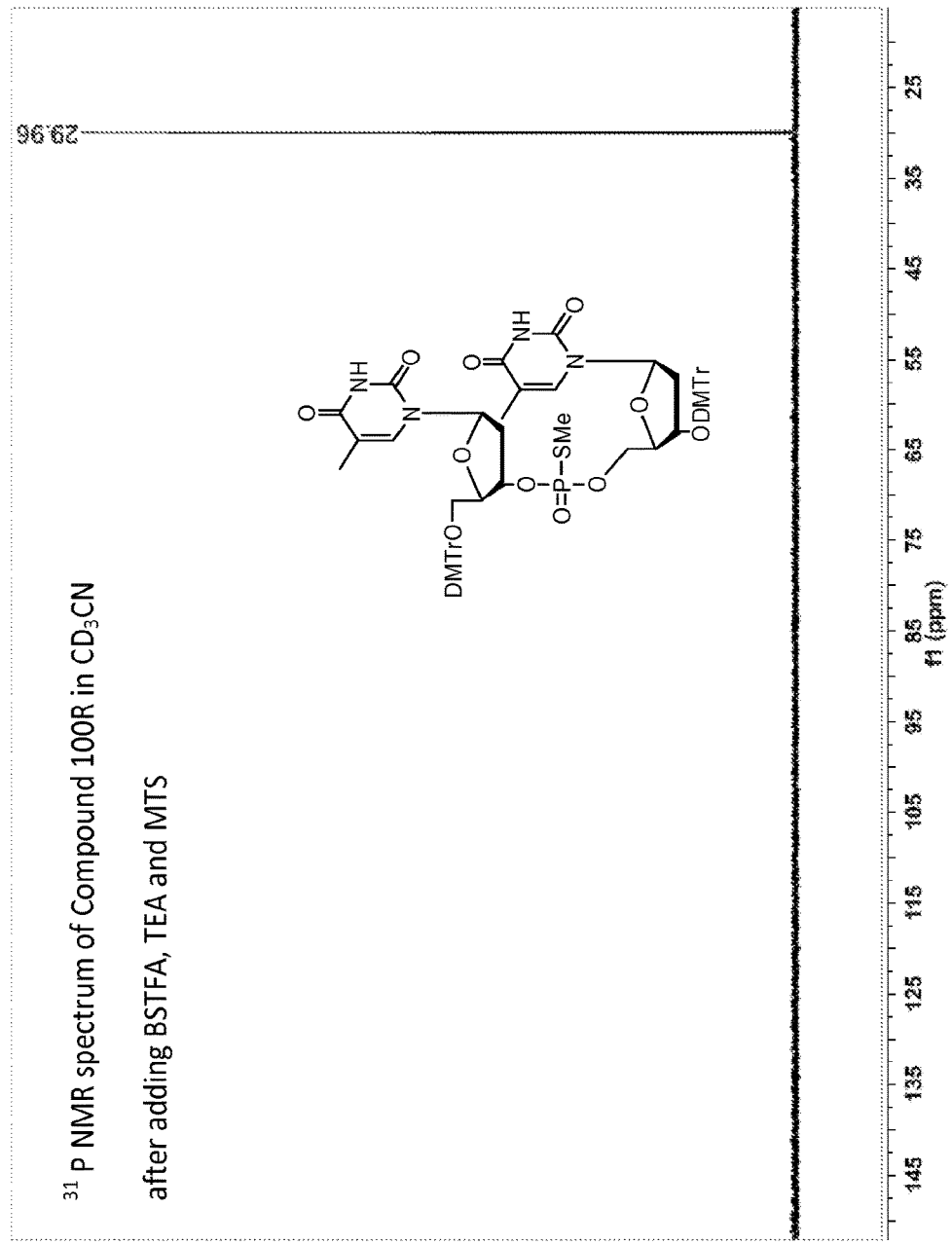
FIG. 6 provides the $^{31}$P NMR spectrum of Compound 100R in CD$_3$CN after adding BSTFA, TEA and MTS as described in Example 6.

Unless otherwise stated, the following terms used in this application, including the specification and claims, have the definitions given below. It must be noted that, as used in the specification and the appended claims, the singular forms "a" "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes" and "included" is not limiting.

Certain Chemical Terminology

Unless otherwise noted, the use of general chemical terms, such as though not limited to "alkyl," "amine," "aryl," are unsubstituted.

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The terms "heteroatom" or "hetero" as used herein, alone or in combination, refer to an atom other than carbon or hydrogen. Heteroatoms are may be independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to a straight-chain or branched-chain saturated hydrocarbon monoradical having from one to about ten carbon atoms, or one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms. In one embodiment, the "alkyl" is substituted. Unless otherwise indicated, the "alkyl" is unsubstituted.

The term "alkenyl" as used herein, alone or in combination, refers to a straight-chain or branched-chain hydrocarbon monoradical having one or more carbon-carbon double-bonds and having from two to about ten carbon atoms, or two to about six carbon atoms. The group may be in either the cis or trans conformation about the double bond(s), and should be understood to include both isomers. Examples include, but are not limited to ethenyl (—CH═CH$_2$), 1-propenyl (—CH$_2$CH═CH$_2$), isopropenyl [—C(CH$_3$)═CH$_2$], butenyl, 1,3-butadienyl and the like. Whenever it appears herein, a numerical range such as "C$_2$-C$_6$ alkenyl" or "C$_{2-6}$ alkenyl", means that the alkenyl group may consist of 2 carbon atoms, 3 carbon atoms, 4 carbon atoms, 5 carbon atoms or 6 carbon atoms. In one embodiment, the "alkenyl" is substituted. Unless otherwise indicated, the "alkenyl" is unsubstituted.

The term "alkynyl" as used herein, alone or in combination, refers to a straight-chain or branched-chain hydrocarbon monoradical having one or more carbon-carbon triple-bonds and having from two to about ten carbon atoms, or from two to about six carbon atoms. Examples include, but are not limited to ethynyl, 2-propynyl, 2-butynyl, 1,3-butadiynyl and the like. Whenever it appears herein, a numerical range such as "C$_2$-C$_6$ alkynyl" or "C$_{2-6}$ alkynyl", means that the alkynyl group may consist of 2 carbon atoms, 3 carbon atoms, 4 carbon atoms, 5 carbon atoms or 6 carbon atoms. In one embodiment, the "alkynyl" is substituted. Unless otherwise indicated, the "alkynyl" is unsubstituted.

The terms "heteroalkyl", "heteroalkenyl" and "heteroalkynyl" as used herein, alone or in combination, refer to alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, N—N═, —N═N—, —N═N—NH—, —P(O)$_2$—, —O—P(O)$_2$—, —P(O)$_2$—O—, —S(O)—, —S(O)$_2$—, —SnH$_2$— and the like.

The terms "haloalkyl", "haloalkenyl" and "haloalkynyl" as used herein, alone or in combination, refer to alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl, chloromethyl and bromoethyl. A non-limiting example of a haloalkenyl group is bromoethenyl. A non-limiting example of a haloalkynyl group is chloroethynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The term "cycloalkyl" as used herein, alone or in combination, refers to a saturated, hydrocarbon monoradical ring, containing from three to about fifteen ring carbon atoms or from three to about ten ring carbon atoms, though may include additional, non-ring carbon atoms as substituents (e.g. methylcyclopropyl). Whenever it appears herein, a numerical range such as "C$_3$-C$_6$ cycloalkyl" or "C$_{3-6}$ cycloalkyl", means that the cycloalkyl group may consist of 3 carbon atoms, 4 carbon atoms, 5 carbon atoms or 6 carbon atoms, i.e., is cyclopropyl, cyclobutyl, cyclopentyl or cyclohepty, although the present definition also covers the occurrence of the term "cycloalkyl" where no numerical range is designated. The term includes fused, non-fused, bridged and spiro radicals. A fused cycloalkyl may contain from two to four fused rings where the ring of attachment is a cycloalkyl ring, and the other individual rings may be alicyclic, heterocyclic, aromatic, heteroaromatic or any combination thereof. Examples include, but are not limited to cyclopropyl, cyclopentyl, cyclohexyl, decalinyl, and bicyclo [2.2.1] heptyl and adamantyl ring systems. Illustrative examples include, but are not limited to the following moieties:

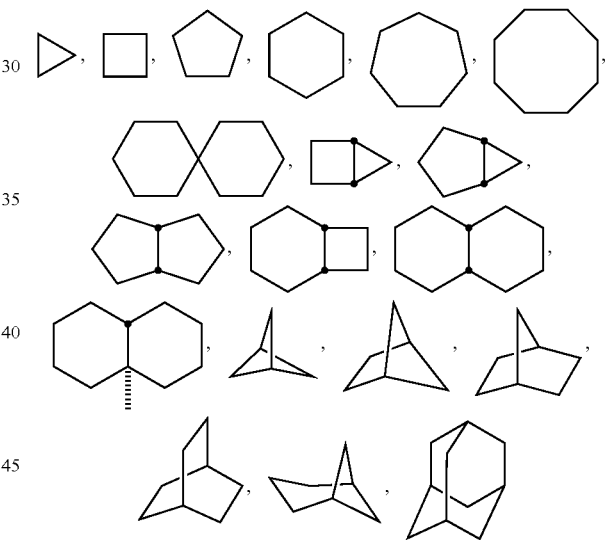

and the like.

In one embodiment, the "cycloalkyl" is substituted. Unless otherwise indicated, the "cycloalkyl" is unsubstituted.

The terms "non-aromatic heterocyclyl" and "heteroalicyclyl" as used herein, alone or in combination, refer to a saturated, partially unsaturated, or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. In embodiments in which two or more heteroatoms are present in the ring, the two or more heteroatoms can be the same as each another, or some or all of the two or more heteroatoms can each be different from the others. The terms include fused, non-fused, bridged and spiro radicals. A fused non-aromatic heterocyclic radical may contain from two to four fused rings where the attaching ring is a non-aromatic heterocycle, and the other individual rings may be alicyclic, heterocyclic, aromatic, heteroaromatic or any combination thereof. Fused ring systems may be fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. Attachment of a non-aromatic heterocyclic subunit to its parent molecule can be via a heteroatom or a carbon atom. Likewise, additional substitution can be via a heteroatom or a carbon atom. As a non-limiting example, an imidazolidine non-aromatic heterocycle may be attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

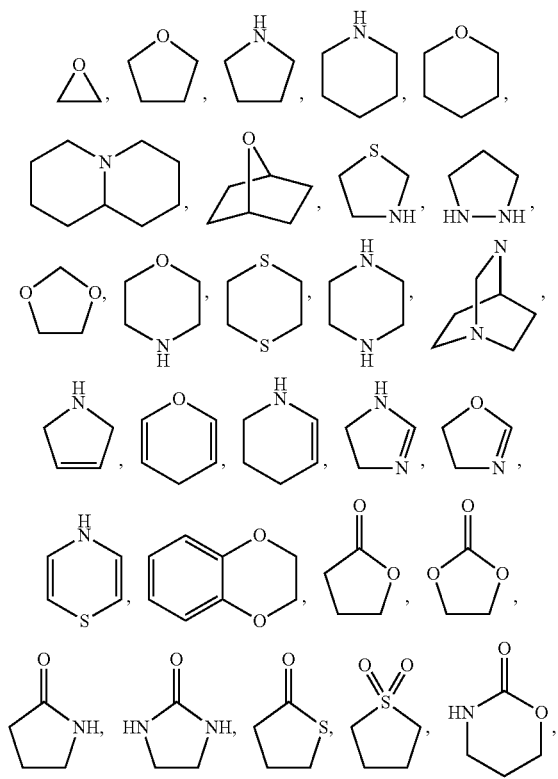

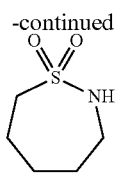

and the like.

The terms also include all ring forms of the carbohydrates, including but not limited to the monosaccharides, the disaccharides and the oligosaccharides. In one embodiment, the "non-aromatic heterocyclyl" or "heteroalicyclyl" is substituted. Unless otherwise indicated, the "non-aromatic heterocyclyl" or "heteroalicyclyl" is unsubstituted.

The term "aryl" as used herein, alone or in combination, refers to an aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused biaryl group includes biphenyl. In one embodiment, the "aryl" is substituted. Unless otherwise indicated, the "aryl" is unsubstituted.

The term "heteroaryl" as used herein, alone or in combination, refers to an aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

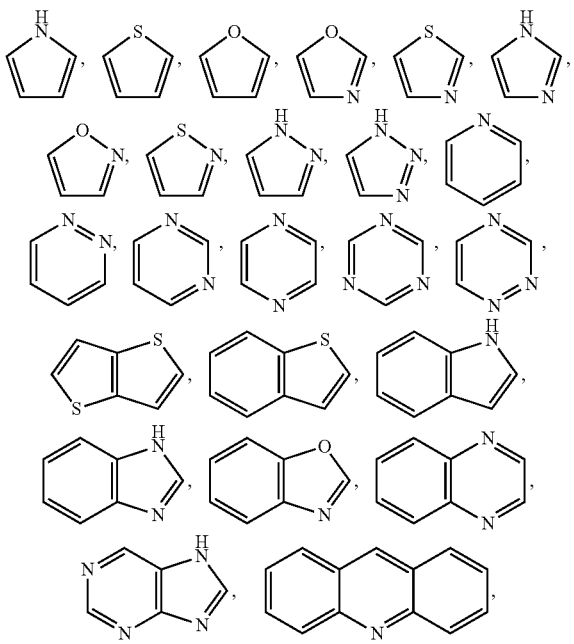

and the like.

In one embodiment, the "heteroaryl" is substituted. Unless otherwise indicated, the "heteroaryl" is unsubstituted.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring.

Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom. In one embodiment, the "heterocyclyl" is substituted. Unless otherwise indicated, the "heterocycyl" is unsubstituted.

The terms "halogen", "halo" or "halide" as used herein, alone or in combination refer to fluoro, chloro, bromo and/or iodo.

The compounds, or their pharmaceutically acceptable salts may contain one or more asymmetric centers and may thus give rise to enantiomers, diastereomers, and other stereoisomeric forms that may be defined, in terms of absolute stereochemistry, such as (R)- or (S)-. When the compounds described herein contain olefinic double bonds or other centers of geometric asymmetry, and unless specified otherwise, it is intended that the compounds include both Z and E geometric isomers (e.g., cis or trans). Likewise, all possible isomers, as well as their racemic and optically pure forms, and all tautomeric forms are also intended to be included.

A "stereoisomer" refers to the relationship between two or more compounds made up of the same atoms bonded by the same bonds but having different three-dimensional structures, which are not superimposable. The term "enantiomer" refers to two stereoisomers that are nonsuperimposeable mirror images of one another. It is contemplated that the various stereoisomers of the compounds disclosed herein, and mixtures thereof, are within the scope of the present disclosure and specifically includes enantiomers.

A "tautomer" refers to a compound wherein a proton shift from one atom of a molecule to another atom of the same molecule is possible. The compounds presented herein may exist as tautomers. In solutions where tautomerization is possible, a chemical equilibrium of the tautomers will exist. The exact ratio of the tautomers depends on several factors, including temperature, solvent, and pH. Some examples of tautomeric equilibrium are shown below.

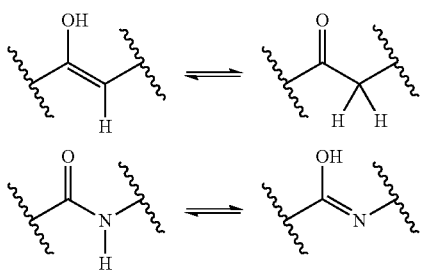

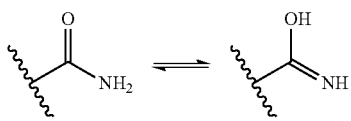

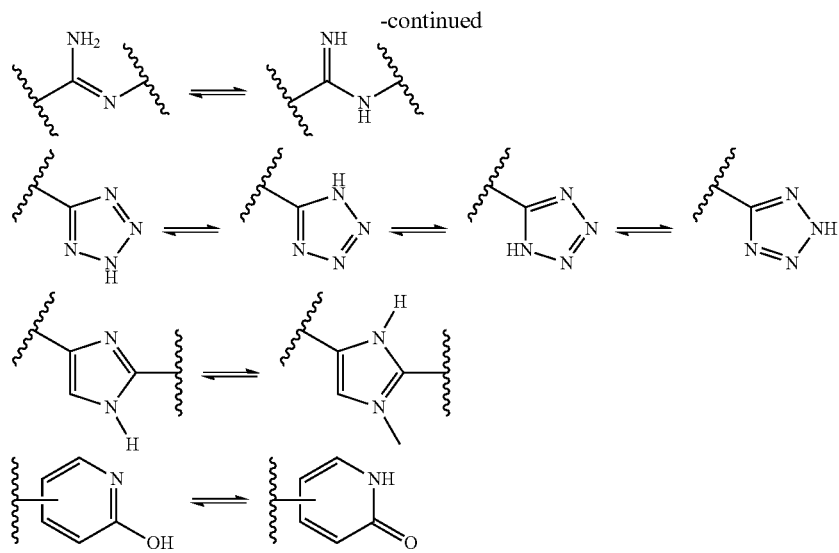

The term "non-stereorandom phosphorous linkage(s)" as used herein refers to a chiral phosphorous atom in the phosphodiester, or other isosteric linkage type, internucleotide linkage. For embodiments comprising more than one phosphorous internucleotide linkage, the handedness of chirality at phosphorous is independently selected at each phosphorous atom. In one embodiment, the oligonucleotide described herein is a pure diastereomer. In another embodiment, the oligonucleotide is greater that 95% diastereomeric purity. In another embodiment, the oligonucleotide is greater that 90% diastereomeric purity.

"Optional" or "optionally" means that a subsequently described event or circumstance may or may not occur and that the description includes instances when the event or circumstance occurs and instances in which it does not. For example, "optionally substituted alkyl" means that the alkyl radical may or may not be substituted and that the description includes both substituted aryl radicals and aryl radicals having no substitution.

Certain Nucleic Acid Terminology

Natural nucleic acids have a phosphate backbone; artificial nucleic acids may contain other types of backbones, but contain the same bases.

The term "nucleotide" as used herein refers to a monomeric unit of a polynucleotide that consists of a heterocyclic base, a sugar, and one or more phosphate groups. The naturally occurring bases, (guanine, (G), adenine (A), cytosine (C), thymine (T), and uracil (U)) are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are linked via phosphate bonds to form nucleic acids, or polynucleotides, though many other linkages are known in the art (such as, though not limited to phosphorothioates, boranophosphates, and the like). Artificial nucleic acids include PNAs (peptide nucleic acids), phosphothionates, and other variants of the phosphate backbone of native nucleic acids.

The term "nucleoside" refers to a moiety wherein a nucleobase or a modified nucleobase is covalently bound to a sugar or modified sugar.

The term "sugar" refers to a monosaccharide in closed and/or open form. Sugars include, but are not limited to, ribose, deoxyribose, pentofuranose, pentopyranose, and hexopyranose moieties.

The term "modified sugar" refers to a moiety that can replace a sugar. The modified sugar mimics the spatial arrangement, electronic properties, or some other physicochemical property of a sugar.

The terms "nucleic acid" and "polynucleotide" as used herein refer to a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from nucleotide analogs and modified polynucleotides such as, though not limited to, methylated and/or capped polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorous-atom bridges. The term encompasses nucleic acids containing any combinations of nucleobases, modified nucleobases, sugars, modified sugars, phosphate bridges or modified phosphorous atom bridges. Examples include, and are not limited to, nucleic acids containing ribose moieties, the nucleic acids containing deoxy-ribose moieties, nucleic acids containing both ribose and deoxyribose moieties, nucleic acids containing ribose and modified ribose moieties. The prefix poly- refers to a nucleic acid containing about 1 to about 10,000 nucleotide monomer units and wherein the prefix oligo- refers to a nucleic acid containing about 1 to about 200 nucleotide monomer units.

The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T).

The term "modified nucleobase" refers to a moiety that can replace a nucleobase. The modified nucleobase mimics the spatial arrangement, electronic properties, or some other physicochemical property of the nucleobase and retains the property of hydrogen-bonding that binds one nucleic acid strand to another in a sequence specific manner. A modified nucleobase can pair with all of the five naturally occurring bases (uracil, thymine, adenine, cytosine, or guanine) without substantially affecting the melting behavior, recognition by intracellular enzymes or activity of the oligonucleotide duplex.

The term "chiral reagent" refers to a compound that is chiral or enantiopure and can be used for asymmetric induction in nucleic acid synthesis.

The term "chiral ligand" or "chiral auxiliary" refers to a moiety that is chiral or enantiopure and controls the stereochemical outcome of a reaction.

In a condensation reaction, the term "condensing reagent" refers to a reagent that activates a less reactive site and renders it more susceptible to attack by a nucleophile.

The term "blocking group" refers to a group that transiently masks the reactivity of a functional group. The functional group can be subsequently unmasked by removal of the blocking group.

The term "moiety" refers to a specific segment or functional group of a molecule. Chemical moieties are often recognized chemical entities embedded in or appended to a molecule.

The term "solid support" refers to any support which enables synthetic mass production of nucleic acids and can be reutilized at need. As used herein, the term refers to a polymer, that is insoluble in the media employed in the reaction steps performed to synthesize nucleic acids, and is derivatized to comprise reactive groups.

The term "linking moiety" refers to any moiety optionally positioned between the terminal nucleoside and the solid support or between the terminal nucleoside and another nucleoside, nucleotide, or nucleic acid.

A "DNA molecule" refers to the polymeric form of deoxyribonucleotides (adenine, guanine, thymine, or cytosine) in its either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can hydrogen bond to a sense nucleic acid molecule.

As used herein, a "complementary DNA" or "cDNA" includes recombinant polynucleotides synthesized by reverse transcription of mRNA and from which intervening sequences (introns) have been removed.

Synthetic Methods for the Preparation Novel Functionalized Nucleic Acids and Nucleic Acid Prodrugs Described herein are methods for the synthesis of novel functionalized nucleic acids and nucleic acid prodrugs. In some embodiments, the nucleic acids comprise chiral phosphorous moieties.

One embodiment provides a process for the preparation of phosphorothiotriesters of structure IIIa comprising the steps of:

i) reacting an H-phosphonate of structure Ia with an silylating reagent to provide a silyloxyphosphonate; and ii) reacting the silyloxyphosphonate with a thiosulfonate reagent of structure IIa to provide a phosphorothiotriester of structure IIIa;

wherein, the H-phosphonate of structure Ia has the following structure:

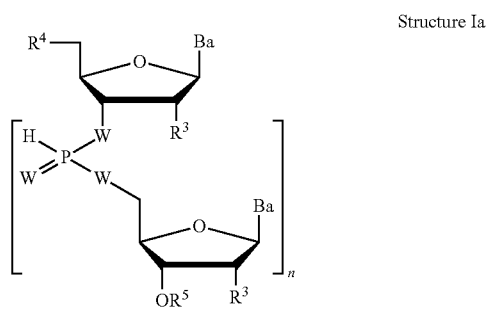

Structure Ia wherein,

W is independently selected from O, S, NH, or $CH_2$;

$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —P(O)($R^e$)$_2$, —HP(O)($R^e$), —$OR^a$ or —$SR^c$;

$Y^1$ is O, $NR^d$, S, or Se;

$R^a$ is a blocking group;

$R^c$ is a blocking group;

each instance of $R^d$ is independently hydrogen, alkyl, alkenyl, alkynyl, aryl, acyl, substituted silyl, carbamate, —P(O)($R^e$)$_2$, or —HP(O)($R^e$);

each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;

$Y^2$ is O, $NR^d$, or S;

each instance of $R^4$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, and $R^b$ is a blocking group;

each instance of Ba is independently a blocked or unblocked adenine, cytosine, guanine, thymine, uracil or modified nucleobase;

$R^5$ is hydrogen, a blocking group, a linking moiety connected to a solid support or a linking moiety connected to a nucleic acid; and n is between 1 and about 200; and the thiosulfonate reagent of structure IIa has the following structure:

Structure IIa $$X-\underset{\underset{O}{\|}}{\overset{\overset{O}{\|}}{S}}-S-R$$

wherein,
X is alkyl, cycloalkyl, or heteroaryl;
R is alkyl, alkenyl, alkynyl, cycloalkyl, aryl, aralkyl, heteroaryl, heteroaralkyl, or $R^1$-$R^2$;
$R^1$ is selected from —S-alkenylene-, —S-alkylene-, —S-alkylene-aryl-alkylene-, —S—CO-aryl-alkylene-, or —S—CO-alkylene-aryl-alkylene-;
$R^2$ is selected from heterocyclo-alkylene-S—, heterocyclo-alkenylene-S—, aminoalkyl-S—, or (alkyl)$_4$N-alkylene-S—;
and the phosphorothiotriester of structure IIIa has the following structure:

Structure IIIa

[structure diagram]

wherein,
W is independently selected from O, S, NH, or $CH_2$;
R is alkyl, alkenyl, alkynyl, cycloalkyl, aryl, aralkyl, heteroaryl, heteroaralkyl, or $R^1$-$R^2$;
$R^1$ is selected from —S-alkenylene-, —S-alkylene-, —S-alkylene-aryl-alkylene-, —S—CO-aryl-alkylene-, or —S—CO-alkylene-aryl-alkylene-;
$R^2$ is selected from heterocyclo-alkylene-S—, heterocyclo-alkenylene-S—, aminoalkyl-S—, or (alkyl)$_4$N-alkylene-S—;
$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —P(O)($R^e$)$_2$, —HP(O)($R^e$), —$OR^a$ or —$SR^c$;
$Y^1$ is O, $NR^d$, S, or Se;
$R^a$ is a blocking group;
$R^c$ is a blocking group;
each instance of $R^d$ is independently hydrogen, alkyl, alkenyl, alkynyl, aryl, acyl, substituted silyl, carbamate, —P(O)($R^e$)$_2$, or —HP(O)($R^e$);
each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;
$Y^2$ is O, $NR^d$, or S;
each instance of $R^4$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, and $R^b$ is a blocking group;
each instance of Ba is independently a blocked or unblocked adenine, cytosine, guanine, thymine, uracil or modified nucleobase;

$R^5$ is hydrogen, a blocking group, a linking moiety connected to a solid support or a linking moiety connected to a nucleic acid; and
n is between 1 and about 200.

Another embodiment provides a process for the preparation of phosphorothiotriesters of structure IIIa, wherein W is O.

Another embodiment provides a process for the preparation of phosphorothiotriesters of structure IIIa, wherein $R^1$ is selected from:

[structure diagrams]

and
$R^2$ is selected from:

[structure diagrams]

Another embodiment provides a process for the preparation of phosphorothiotriesters of structure IIIa, wherein the silylating reagent is selected from
1,1,3,3-tetramethyl-1,3-diphenyldisilazane;
1,3-dimethyl-1,1,3,3-tetraphenyldisilazane;
1-(trimethylsilyl)imidazole;
N-trimethylsilyl-N-methyl trifluoroacetamide;
bis(dimethylamino)dimethylsilane;
bromotrimethylsilane;
chlorodimethyl(pentafluorophenyl)silane;
chlorotriethylsilane;
chlorotriisopropylsilane;
chlorotrimethylsilane;
dichlorodimethylsilane;
hexamethyldisilazane;
N,N'-bis(trimethylsilyl)urea;
N,N-bis(trimethylsilyl)methylamine;
N,N-dimethyltrimethylsilylamine;
N,O-bis(trimethylsilyl)acetamide;
N,O-bis(trimethylsilyl)carbamate;

N,O-bis(trimethylsilyl)trifluoroacetamide;
N-methyl-N-(trimethylsilyl)trifluoroacetamide;
N-methyl-N-trimethylsilylacetamide;
N-methyl-N-trimethylsilylheptafluorobutyramide;
N-tert-butyldimethylsilyl-N-methyltrifluoroacetamide;
N-methyl-N-trimethylsilylheptafluorobutyramide;
trimethyl silyltriflate;
triethylsilyltriflate;
triisopropylsilyltriflate; or
tert-butyldimethyl silyltriflate.

Another embodiment provides the process, wherein the silylating reagent is selected from N,O-bis(trimethylsilyl)trifluoroacetamide, trimethyl silyltriflate, chlorotrimethylsilane, or 1-(trimethyl silyl)imidazole.

Another embodiment provides the process, wherein the silylating reagent is selected from N,O-bis(trimethylsilyl)trifluoroacetamide.

Another embodiment provides the process, wherein the H-phosphonate is covalently linked to a solid phase.

One embodiment provides a process for the preparation of phosphorothiotriesters comprising non-stereorandom phosphorous linkages of structure IIIb comprising the steps of:
  i) reacting a H-phosphonate comprising non-stereorandom phosphorous linkages of structure Ib with an silylating reagent to provide a silyloxyphosphonate; and
  ii) reacting the silyloxyphosphonate with a thiosulfonate reagent of structure IIb to provide a phosphorothiotriester comprising non-stereorandom phosphorous linkages of structure IIIb;
wherein,
the H-phosphonate comprising non-stereorandom phosphorous linkages of structure Ib has the following structure:

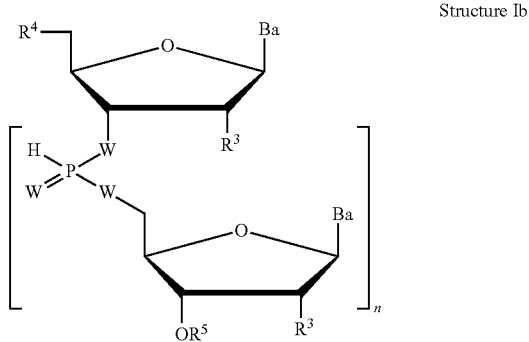

Structure Ib wherein,
W is independently selected from O, NH, or $CH_2$;
$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —P(O)$(R^e)_2$, —HP(O)$(R^e)$, —$OR^a$ or —$SR^c$;
$Y^1$ is O, $NR^d$, S, or Se;
$R^a$ is a blocking group;
$R^c$ is a blocking group;
each instance of $R^d$ is independently hydrogen, alkyl, alkenyl, alkynyl, aryl, acyl, substituted silyl, carbamate, —P(O)$(R^e)_2$, or —HP(O)$(R^e)$;
each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;

$Y^2$ is O, $NR^d$, or S;
each instance of $R^4$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, and $R^b$ is a blocking group;
each instance of Ba is independently a blocked or unblocked adenine, cytosine, guanine, thymine, uracil or modified nucleobase;
$R^5$ is hydrogen, a blocking group, a linking moiety connected to a solid support or a linking moiety connected to a nucleic acid; and
n is between 1 and about 200; and
the thiosulfonate reagent of structure IIb has the following structure:

Structure IIb wherein,
X is alkyl, cycloalkyl, aryl, or heteroaryl;
R is alkyl, alkenyl, alkynyl, cycloalkyl, aryl, aralkyl, heteroaryl, heteroaralkyl, or $R^1$-$R^2$;
$R^1$ is selected from —S-alkenylene-, —S-alkylene-, —S-alkylene-aryl-alkylene-, —S—CO-aryl-alkylene-, or —S—CO-alkylene-aryl-alkylene-;
$R^2$ is selected from heterocyclo-alkylene-S—, heterocyclo-alkenylene-S—, aminoalkyl-S—, or $(alkyl)_4$N-alkylene-S—;
and the chiral phosphorothiotriester comprising non-stereorandom phosphorous linkages of structure IIIb has the following structure:

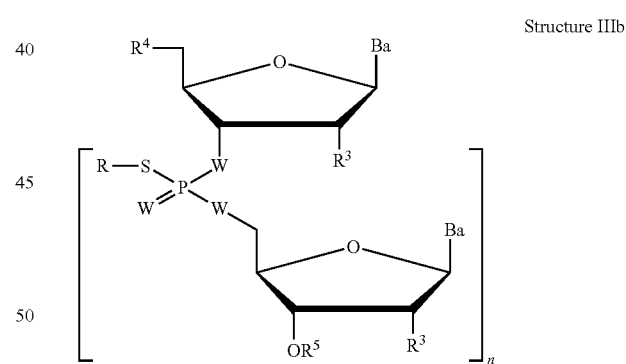

Structure IIIb wherein,
W is independently selected from O, NH, or $CH_2$;
R is alkyl, alkenyl, alkynyl, cycloalkyl, aryl, aralkyl, heteroaryl, heteroaralkyl, or $R^1$-$R^2$;
$R^1$ is selected from —S-alkenylene-, —S-alkylene-, —S-alkylene-aryl-alkylene-, —S—CO-aryl-alkylene-, or —S—CO-alkylene-aryl-alkylene-;
$R^2$ is selected from heterocyclo-alkylene-S—, heterocyclo-alkenylene-S—, aminoalkyl-S—, or $(alkyl)_4$N-alkylene-S—;
$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —P(O)$(R^e)_2$, —HP(O)$(R^e)$, —$OR^a$ or —$SR^c$;

Y¹ is O, $NR^d$, S, or Se;

$R^a$ is a blocking group;

$R^c$ is a blocking group;

each instance of $R^d$ is independently hydrogen, alkyl, alkenyl, alkynyl, aryl, acyl, substituted silyl, carbamate, —P(O)($R^e$)$_2$, or —HP(O)($R^e$);

each instance of $R^e$ is independently hydrogen, alkyl, aryl, alkenyl, alkynyl, alkyl-Y²—, alkenyl-Y²—, alkynyl-Y²—, aryl-Y²—, or heteroaryl-Y²—, or a cation which is $Na^{+1}$, $Li^{+1}$, or $K^{+1}$;

Y² is O, $NR^d$, or S;

each instance of R⁴ is independently hydrogen, —OH, —SH, —$NR^dR^d$, —N₃, halogen, alkyl, alkenyl, alkynyl, alkyl-Y¹—, alkenyl-Y¹—, alkynyl-Y¹—, aryl-Y¹—, heteroaryl-Y¹—, —$OR^b$, or —$SR^c$, and $R^b$ is a blocking group;

each instance of Ba is independently a blocked or unblocked adenine, cytosine, guanine, thymine, uracil or modified nucleobase;

R⁵ is hydrogen, a blocking group, a linking moiety connected to a solid support or a linking moiety connected to a nucleic acid; and n is between 1 and about 200.

Another embodiment provides a process for the preparation of phosphorothiotriesters comprising non-stereorandom phosphorous linkages of structure IIIb, wherein W is O.

Another embodiment provides a process for the preparation of phosphorothiotriesters comprising non-stereorandom phosphorous linkages of structure IIIb, wherein R¹ is selected from:

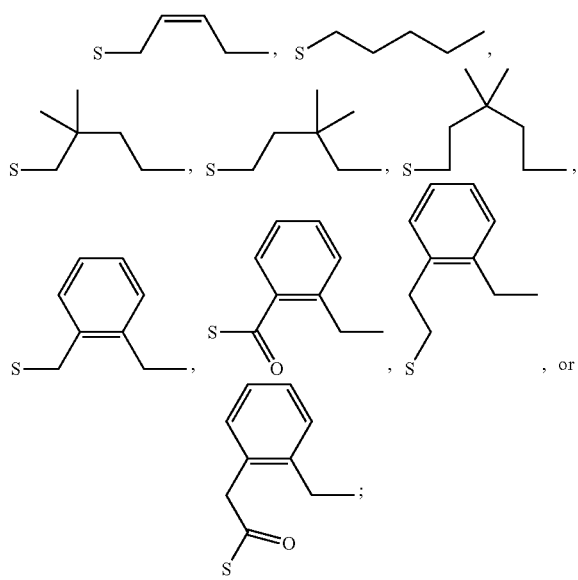

and

R² is selected from:

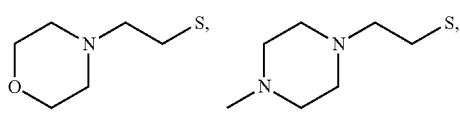

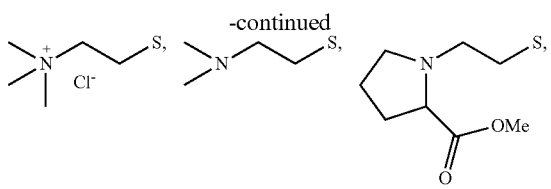

Another embodiment provides a process for the preparation of phosphorothiotriesters comprising non-stereorandom phosphorous linkages of structure IIIb, wherein the silylating reagent is selected from 1,1,3,3-tetramethyl-1,3-diphenyldisilazane;
1,3-dimethyl-1,1,3,3-tetraphenyldisilazane;
1-(trimethylsilyl)imidazole;
N-trimethylsilyl-N-methyl trifluoroacetamide;
bis(dimethylamino)dimethylsilane;
bromotrimethylsilane;
chlorodimethyl(pentafluorophenyl)silane;
chlorotriethylsilane;
chlorotriisopropylsilane;
chlorotrimethylsilane;
dichlorodimethylsilane;
hexamethyldisilazane;
N,N'-bis(trimethylsilyl)urea;
N,N-bis(trimethylsilyl)methylamine;
N,N-dimethyltrimethylsilylamine;
N,O-bis(trimethylsilyl)acetamide;
N,O-bis(trimethylsilyl)carbamate;
N,O-bis(trimethylsilyl)trifluoroacetamide;
N-methyl-N-(trimethylsilyl)trifluoroacetamide;
N-methyl-N-trimethylsilylacetamide;
N-methyl-N-trimethylsilylheptafluorobutyramide;
N-tert-butyldimethylsilyl-N-methyltrifluoroacetamide;
N-methyl-N-trimethylsilylheptafluorobutyramide;
trimethyl silyltriflate;
triethylsilyltriflate;
triisopropylsilyltriflate; or
tert-butyldimethyl silyltriflate.

Another embodiment provides the process, wherein the silylating reagent is selected from N,O-bis(trimethylsilyl)trifluoroacetamide, trimethyl silyltriflate, chlorotrimethylsilane, or 1-(trimethyl silyl)imidazole.

Another embodiment provides the process, wherein the silylating reagent is selected from N,O-bis(trimethylsilyl)trifluoroacetamide.

Another embodiment provides the process, wherein the H-phosphonate is covalently linked to a solid phase.

One embodiment provides a process for the preparation of phosphorothiotriesters of structure IIIc comprising the steps of:

i) reacting a H-phosphonate of structure Ic with an silylating reagent to provide a silyloxyphosphonate;

ii) reacting the silyloxyphosphonate with a bis(thiosulfonate) reagent of structure IVc to provide a phosphorothiotriester comprising a thiosulfonate group of structure Vc;

iii) reacting the phosphorothiotriester comprising a thiosulfonate group of structure Vc with a nucleophile of structure VIc to provide the phosphorothiotriesters of structure IIIc;

wherein, the H-phosphonate of structure Ic has the following structure:

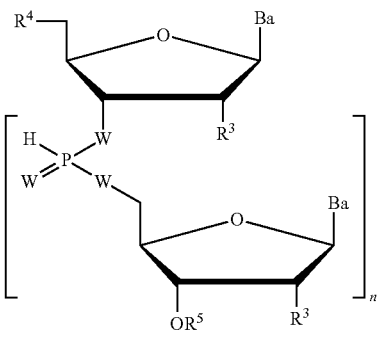

Structure Ic wherein,

W is independently selected from O, S, NH, or $CH_2$;

$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, $P(O)(R^e)_2$, —$HP(O)(R^e)$, —$OR^a$ or —$SR^c$;

$Y^1$ is O, $NR^d$, S, or Se;

$R^a$ is a blocking group;

$R^c$ is a blocking group;

each instance of $R^d$ is independently hydrogen, alkyl, alkenyl, alkynyl, aryl, acyl, substituted silyl, carbamate, —$P(O)(R^e)_2$, or —$HP(O)(R^e)$;

each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;

$Y^2$ is O, $NR^d$, or S;

each instance of $R^4$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, and $R^b$ is a blocking group;

each instance of Ba is independently a blocked or unblocked adenine, cytosine, guanine, thymine, uracil or modified nucleobase;

$R^5$ is hydrogen, a blocking group, a linking moiety connected to a solid support or a linking moiety connected to a nucleic acid; and n is between 1 and about 200; and the bis(thiosulfonate) reagent of structure IVc has the following structure:

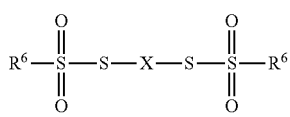

Structure IVc wherein,

X is alkylene, alkenylene, arylene, or heteroarylene;

each $R^6$ is independently alkyl, cycloalkyl, aryl, or heteroaryl;

the nucleophile of structure VIc has the following structure:

$R^7$—SH, wherein $R^7$ is selected from alkyl, alkenyl, aryl, heterocyclo, aminoalkyl, or (heterocyclo)alkyl;

and phosphorothiotriesters of structure IIIc has the following structure:

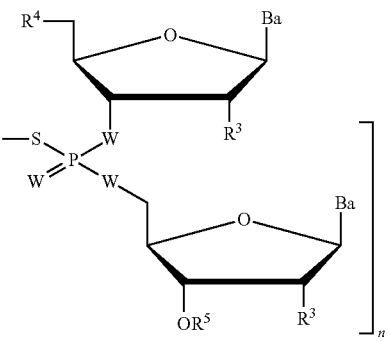

Structure IIIc wherein,

W is independently selected from O, S, NH, or $CH_2$;

R is $R^7$—S—S—X—

$R^7$ is alkyl, alkenyl, aryl, heterocyclo, aminoalkyl, or (heterocyclo)alkyl;

X is alkylene, alkenylene, arylene, or heteroarylene;

$R^3$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$P(O)(R^e)_2$, —$HP(O)(R^e)$, —$OR^a$ or —$SR^c$;

$Y^1$ is O, $NR^d$, S, or Se;

$R^a$ is a blocking group;

$R^c$ is a blocking group;

each instance of $R^d$ is independently hydrogen, alkyl, alkenyl, alkynyl, aryl, acyl, substituted silyl, carbamate, —$P(O)(R^e)_2$, or —$HP(O)(R^e)$;

each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;

$Y^2$ is O, $NR^d$, or S;

each instance of $R^4$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, and $R^b$ is a blocking group;

each instance of Ba is independently a blocked or unblocked adenine, cytosine, guanine, thymine, uracil or modified nucleobase;

$R^5$ is hydrogen, a blocking group, a linking moiety connected to a solid support or a linking moiety connected to a nucleic acid;

n is between 1 and about 200; and wherein the phosphorous linkages of the H-phosphonate of structure Ic, the phosphorothiotriester comprising a thiosulfonate group of structure Vc, and the phosphorothiotriesters of structure IIIc may optionally comprise non-stereorandom phosphorous linkages.

Another embodiment provides the process wherein the phosphorothiotriesters of structure IIIb comprise non-stereorandom phosphorous linkages and the H-phosphonate of structure Ic comprise non-stereorandom phosphorous linkages; and W is independently selected from O, NH, or $CH_2$. Another embodiment provides the process wherein W is O.

Another embodiment provides the process wherein $R^6$ is methyl.

Another embodiment provides the process wherein bis(thiosulfonate) reagent of structure IVc is selected from:

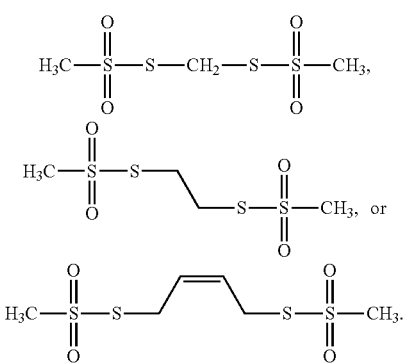

Another embodiment provides the process wherein the nucleophile of structure VIc has the following structure:

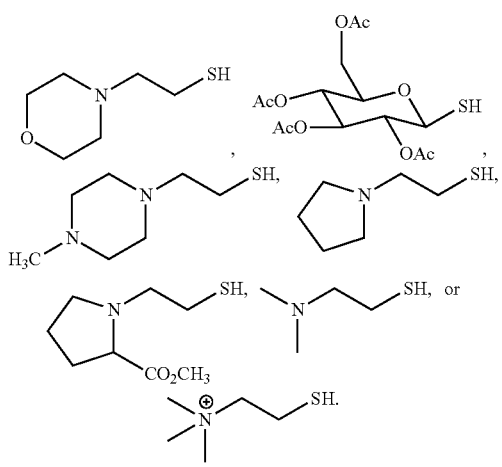

Another embodiment provides a process for the preparation of phosphorothiotriesters of structure IIIa, wherein the silylating reagent is selected from
1,1,3,3-tetramethyl-1,3-diphenyldisilazane;
1,3-dimethyl-1,1,3,3-tetraphenyldisilazane;
1-(trimethylsilyl)imidazole;
N-trimethylsilyl-N-methyl trifluoroacetamide;
bis(dimethylamino)dimethylsilane;
bromotrimethylsilane;
chlorodimethyl(pentafluorophenyl)silane;
chlorotriethylsilane;
chlorotriisopropylsilane;
chlorotrimethylsilane;
dichlorodimethylsilane;
hexamethyldisilazane;
N,N'-bis(trimethylsilyl)urea;
N,N-bis(trimethylsilyl)methylamine;
N,N-dimethyltrimethylsilylamine;
N,O-bis(trimethylsilyl)acetamide;
N,O-bis(trimethylsilyl)carbamate;
N,O-bis(trimethylsilyl)trifluoroacetamide;
N-methyl-N-(trimethylsilyl)trifluoroacetamide;
N-methyl-N-trimethylsilylacetamide;
N-methyl-N-trimethylsilylheptafluorobutyramide;
N-tert-butyldimethylsilyl-N-methyltrifluoroacetamide;
N-methyl-N-trimethylsilylheptafluorobutyramide;
trimethyl silyltriflate;
triethylsilyltriflate;
triisopropylsilyltriflate; or
tert-butyldimethyl silyltriflate.

Another embodiment provides the process, wherein the silylating reagent is selected from N,O-bis(trimethylsilyl)trifluoroacetamide, trimethyl silyltriflate, chlorotrimethylsilane, or 1-(trimethyl silyl)imidazole.

Another embodiment provides the process, wherein the silylating reagent is selected from N,O-bis(trimethylsilyl)trifluoroacetamide.

Another embodiment provides the process, wherein the H-phosphonate is covalently linked to a solid phase.

Modified Oligonucleotides

Oligonucleotides have several pharmaceutical properties which can be improved through the application of prodrug strategies. In particular, oligonucleotides are rapidly degraded by nucleases and exhibit poor cellular uptake through the cytoplasmic cell membrane (Poijarvi-Virta et al., Curr. Med. Chem. (2006), 13(28); 3441-65; Wagner et al., Med. Res. Rev. (2000), 20(6):417-51; Peyrottes et al., Mini Rev. Med. Chem. (2004), 4(4):395-408; Gosselin et al., (1996), 43(1):196-208; Bologna et al., (2002), Antisense & Nucleic Acid Drug Development 12:33-41). In one example, Vives et al., (Nucleic Acids Research (1999), 27(20):4071-76) found that tert-butyl SATE pro-oligonucleotides displayed markedly increased cellular penetration compared to the parent oligonucleotide. Described herein are methods for the synthesis of modified oligonucleotides or pronucleotides.

Reaction Conditions and Reagents Used in the Methods of the Invention.

Conditions

The steps of reacting a molecule comprising an achiral H-phosphonate moiety and a nucleoside comprising a 5'-OH moiety to form a condensed intermediate can occur without isolating any intermediates. In some embodiments, the steps of reacting a molecule comprising an achiral H-phosphonate moiety and a nucleoside comprising a 5'-OH moiety to form a condensed intermediate occurs is a one-pot reaction. In an embodiment, a molecule comprising an achiral H-phosphonate moiety, condensing reagent, chiral reagent, and compound comprising a free nucleophilic moiety are added to the reaction mixture at different times. In another embodiment, a molecule comprising an achiral H-phosphonate moiety, condensing reagent, and chiral reagent are present in the same reaction vessel or same pot. In another embodiment, a molecule comprising an achiral H-phosphonate moiety, condensing reagent, chiral reagent, and compound comprising a free nucleophilic moiety are present in the same reaction or same pot. This allows the reaction to be performed without isolation of intermediates and eliminates time-consuming steps, resulting in an economical and efficient synthesis. In specific embodiments, the achiral H-phosphonate, condensing reagent, chiral amino alcohol, 5'-OH nucleoside are present at the same time in a reaction. In a further embodiment, the formation of the chiral intermediate for condensation is formed in situ and is not isolated prior to the condensation reaction. In another embodiment, a molecule comprising an achiral H-phosphonate moiety has been activated by reaction with a condensing reagent, chiral reagent in a different reaction vessel from that used when reacting the chiral intermediate with the compound comprising a free 5'-OH moiety.

Synthesis on Solid Support

In some embodiments, the synthesis of the nucleic acid is performed in solution. In other embodiments, the synthesis of the nucleic acid is performed on solid phase. The reactive groups of a solid support may be unprotected or protected.

During oligonucleotide synthesis a solid support is treated with various reagents in several synthesis cycles to achieve the stepwise elongation of a growing oligonucleotide chain with individual nucleotide units. The nucleoside unit at the end of the chain which is directly linked to the solid support is termed "the first nucleoside" as used herein. The first nucleoside is bound to the solid support via a linker moiety, i.e. a diradical with covalent bonds to both the polymer of the solid support and the nucleoside. The linker stays intact during the synthesis cycles performed to assemble the oligonucleotide chain and is cleaved after the chain assembly to liberate the oligonucleotide from the support.

Solid supports for solid-phase nucleic acid synthesis include the supports described in, e.g., U.S. Pat. Nos. 4,659,774, 5,141,813, 4,458,066; Caruthers U.S. Pat. Nos. 4,415,732, 4,458,066, 4,500,707, 4,668,777, 4,973,679, and 5,132,418; Andrus et al. U.S. Pat. Nos. 5,047,524, 5,262,530; and Koster U.S. Pat. No. 4,725,677 (reissued as Re34,069). In some embodiments, the solid phase is an organic polymer support. In other embodiments, the solid phase is an inorganic polymer support. In some embodiments, the organic polymer support is polystyrene, aminomethyl polystyrene, a polyethylene glycol-polystyrene graft copolymer, polyacrylamide, polymethacrylate, polyvinylalcohol, highly cross-linked polymer (HCP), or other synthetic polymers, carbohydrates such as cellulose and starch or other polymeric carbohydrates, or other organic polymers and any copolymers, composite materials or combination of the above inorganic or organic materials. In other embodiments, the inorganic polymer support is silica, alumina, controlled poreglass (CPG), which is a silica-gel support, or aminopropyl CPG. Other useful solid supports include fluorous solid supports (see e.g., WO/2005/070859), long chain alkylamine (LCAA) controlled pore glass (CPG) solid supports (see e.g., S. P. Adams, K. S. Kavka, E. J. Wykes, S. B. Holder and G. R. Galluppi, *J. Am. Chem. Soc.,* 1983, 105, 661-663; G. R. Gough, M. J. Bruden and P. T. Gilham, *Tetrahedron Lett.,* 1981, 22, 4177-4180). Membrane supports and polymeric membranes (see e.g. Innovation and Perspectives in Solid Phase Synthesis, Peptides, Proteins and Nucleic Acids, ch 21 pp 157-162, 1994, Ed. Roger Epton and U.S. Pat. No. 4,923,901) are also useful for the synthesis of nucleic acids. Once formed, a membrane can be chemically functionalized for use in nucleic acid synthesis. In addition to the attachment of a functional group to the membrane, the use of a linker or spacer group attached to the membrane may be used to minimize steric hindrance between the membrane and the synthesized chain.

Other suitable solid supports include those generally known in the art to be suitable for use in solid phase methodologies, including, for example, glass sold as Primer™ 200 support, controlled pore glass (CPG), oxalyl-controlled pore glass (see, e.g., Alul, et al., *Nucleic Acids Research,* 1991, 19, 1527), TentaGel Support—an aminopolyethyleneglycol derivatized support (see, e.g., Wright, et al., *Tetrahedron Lett.,* 1993, 34, 3373), and Poros-a copolymer of polystyrene/divinylbenzene.

Surface activated polymers have been demonstrated for use in synthesis of natural and modified nucleic acids and proteins on several solid supports mediums. The solid support material can be any polymer suitably uniform in porosity, has sufficient amine content, and sufficiently flexible to undergo any attendant manipulations without losing integrity. Examples of suitable selected materials include nylon, polypropylene, polyester, polytetrafluoroethylene, polystyrene, polycarbonate, and nitrocellulose. Other materials can serve as the solid support, depending on the design of the investigator. In consideration of some designs, for example, a coated metal, in particular gold or platinum can be selected (see e.g., US publication No. 20010055761). In one embodiment of oligonucleotide synthesis, for example, a nucleoside is anchored to a solid support which is functionalized with hydroxyl or amino residues. Alternatively, the solid support is derivatized to provide an acid labile trialkoxytrityl group, such as a trimethoxytrityl group (TMT). Without being bound by theory, it is expected that the presence of the trialkoxytrityl protecting group will permit initial detritylation under conditions commonly used on DNA synthesizers. For a faster release of oligonucleotide material in solution with aqueous ammonia, a diglycoate linker is optionally introduced onto the support.

Linking Moiety

A linking moiety or linker is optionally used to connect the solid support to the compound comprising a free nucleophilic moiety. Suitable linkers are known such as short molecules which serve to connect a solid support to functional groups (e.g., hydroxyl groups) of initial nucleosides molecules in solid phase synthetic techniques. In some embodiments, the linking moiety is a succinamic acid linker, or a succinate linker (—CO—CH$_2$—CH$_2$—CO—), or an oxalyl linker (—CO—CO—). In other embodiments, the linking moiety and the nucleoside are bonded together through an ester bond. In other embodiments, the linking moiety and the nucleoside are bonded together through an amide bond. In further embodiments, the linking moiety connects the nucleoside to another nucleotide or nucleic acid. Suitable linkers are disclosed in, for example, Oligonucleotides And Analogues A Practical Approach, Ekstein, F. Ed., IRL Press, N.Y., 1991, Chapter 1.

A linker moiety is used to connect the compound comprising a free nucleophilic moiety to another nucleoside, nucleotide, or nucleic acid. In some embodiments, the linking moiety is a phosphodiester linkage. In other embodiments, the linking moiety is an H-phosphonate moiety. In yet other embodiments, the linking moiety is an X-phosphonate moiety.

Solvents for Synthesis

Synthesis of the nucleic acids is performed in an aprotic organic solvent. In some embodiments, the solvent is acetonitrile, pyridine, or NMP. In some embodiments, the solvent is acetone, acetonitrile, NMP, ethyl acetate, THF, dioxane, DMF, DMSO, DCM, chloroform, pyridine, 2,6-lutidine, HMPA, HMPT, DMA, glyme, diglyme, sulfone, methyl tert-butyl ether, or combinations thereof. In some embodiments, the solvent is a polar, aprotic organic solvent. In some embodiments, the solvent is anhydrous.

Acidification Conditions to Remove Blocking Groups.

Acidification to remove blocking groups is accomplished by a Brønsted acid or Lewis acid. In some embodiments, acidification is used to remove $R^1$ blocking groups. Useful Brønsted acids are carboxylic acids, alkylsulfonic acids, arylsulfonic acids, phosphoric acid and its derivatives, phosphonic acid and its derivatives, alkylphosphonic acids and their derivatives, arylphosphonic acids and their derivatives, phosphinic acid, dialkylphosphinic acids, and diarylphosphinic acids which have a pKa (25° C. in water) value of −0.6 (trifluoroacetic acid) to 4.76 (acetic acid) in an organic solvent or water (in the case of 80% acetic acid). The concentration of the acid (1 to 80%) used in the acidification step depends on the acidity of the acid. Consideration to the acid strength must be taken into account as strong acid conditions will result in depurination/depyrimidination, wherein purinyl or pyrimidinyl bases are cleaved from ribose ring.

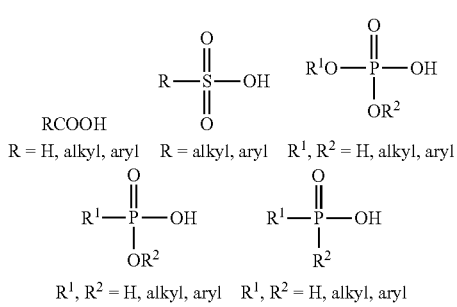

In some embodiments, acidification is accomplished by a Lewis acid in an organic solvent. Useful Lewis acids are $ZnX_2$ wherein X is Cl, Br, I, or $CF_3SO_3$.

In some embodiments, the acidifying comprises adding an amount of a Brønsted or Lewis acid effective to convert the condensed intermediate into the compound of Formula 4 without removing purine moieties from the condensed intermediate.

Acids that are useful in the acidifying step also include, but are not limited to 10% phosphoric acid in an organic solvent, 10% hydrochloric acid in an organic solvent, 1% trifluoroacetic acid in an organic solvent, 3% dichloroacetic acid in an organic solvent or 80% acetic acid in water. The concentration of any Brønsted or Lewis acid used in the process is selected such that the concentration of the acid does not exceed a concentration that causes cleavage of the nucleobase from the sugar moiety.

In some embodiments, acidification comprises adding 1% trifluoroacetic acid in an organic solvent. In some embodiments, acidification comprises adding about 0.1% to about 8% trifluoroacetic acid in an organic solvent. In other embodiments, acidification comprises adding 3% dichloroacetic acid in an organic solvent. In other embodiments, acidification comprises adding about 0.1% to about 10% dichloroacetic acid in an organic solvent. In yet other embodiments, acidification comprises adding 3% trichloroacetic acid in an organic solvent. In yet other embodiments, acidification comprises adding about 0.1% to about 10% trichloroacetic acid in an organic solvent. In some embodiments, acidification comprises adding 80% acetic acid in water. In some embodiments, acidification comprises adding about 50% to about 90%, or about 50% to about 80%, about 50% to about 70%, about 50% to about 60%, about 70% to about 90% acetic acid in water. In some embodiments, the acidification comprises the further addition of cation scavengers to the acidic solvent. In specific embodiments, the cation scavengers can be triethylsilane or triisopropylsilane. In some embodiments, $R^1$ is deblocked prior to the step of acidifying the condensed intermediate. In some embodiments, $R^1$ is deblocked by acidification, which comprises adding 1% trifluoroacetic acid in an organic solvent. In some embodiments, $R^1$ is deblocked by acidification, which comprises adding 3% dichloroacetic acid in an organic solvent. In some embodiments, $R^1$ is deblocked by acidification, which comprises adding 3% trichloroacetic acid in an organic solvent.

Removal of Blocking Moieties or Groups

Functional groups such as hydroxyl or amino moieties which are located on nucleobases or sugar moieties are routinely blocked with blocking (protecting) groups (moieties) during synthesis and subsequently deblocked. In general, a blocking group renders a chemical functionality of a molecule inert to specific reaction conditions and can later be removed from such functionality in a molecule without substantially damaging the remainder of the molecule (see e.g., Green and Wuts, Protective Groups in Organic Synthesis, $2^{nd}$ Ed., John Wiley & Sons, New York, 1991). For example, amino groups can be blocked with nitrogen blocking groups such as phthalimido, 9-fluorenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). Carboxyl groups can be protected as acetyl groups. Hydroxy groups can be protected such as tetrahydropyranyl (THP), t-butyldimethylsilyl (TBDMS), 1-[(2-chloro-4-methyl)phenyl]-4-methoxypiperidin-4-yl (Ctmp), 1-(2-fluorophenyl)-4-methoxypiperidin-4-yl (Fpmp), 1-(2-chloroethoxy)ethyl, 3-methoxy-1,5-dicarbomethoxypentan-3-yl (MDP), bis(2-acetoxyethoxy)methyl (ACE), triisopropylsilyloxymethyl (TOM), 1-(2-cyanoethoxy)ethyl (CEE), 2-cyanoethoxymethyl (CEM), [4-(N-dichloroacetyl-N-methylamino)benzyloxy]methyl, 2-cyanoethyl (CN), pivaloyloxymethyl (PivOM), levunyloxymethyl (ALE). Other representative hydroxyl blocking groups have been described (see e.g., Beaucage et al., *Tetrahedron*, 1992, 46, 2223). In some embodiments, hydroxyl blocking groups are acid-labile groups, such as the trityl, monomethoxytrityl, dimethoxytrityl, trimethoxytrityl, 9-phenylxanthin-9-yl (Pixyl) and 9-(p-methoxyphenyl)xanthin-9-yl (MOX). Chemical functional groups can also be blocked by including them in a precursor form. Thus an azido group can be considered a blocked form of an amine as the azido group is easily converted to the amine. Further representative protecting groups utilized in nucleic acid synthesis are known (see e.g. Agrawal et al., Protocols for Oligonucleotide Conjugates, Eds., Humana Press, New Jersey, 1994, Vol. 26, pp. 1-72).

Various methods are known and used for removal of blocking groups from the nucleic acids. In some embodiments, all blocking groups are removed. In other embodiments, the blocking groups are partially removed. In yet other embodiments, reaction conditions can be adjusted to remove blocking groups on certain moieties. In certain embodiments where $R^2$ is a blocking group, removal of the blocking group at $R^2$ is orthogonal to the removal of the blocking group at $R^1$. The blocking groups at $R^1$ and $R^2$ remain intact during the synthesis steps and are collectively removed after the chain assembly. In some embodiments, the $R^2$ blocking group are removed simultaneously with the cleavage of the nucleic acids from the solid support and with the removal of the nucleobase blocking groups. In specific embodiments, the blocking group at $R^1$ is removed while the blocking groups at $R^2$ and nucleobases remain intact. Blocking groups at $R^1$ are cleavable on solid supports with an organic base such as a primary amine, a secondary amine, or a mixture thereof. Deblocking of the $R^1$ position is commonly referred to as front end deprotection.

In an embodiment, the nucleobase blocking groups, if present, are cleavable after the assembly of the respective nucleic acid with an acidic reagent. In another embodiment, one or more of the nucleobase blocking groups is cleavable under neither acidic nor basic conditions, e.g. cleavable with fluoride salts or hydrofluoric acid complexes. In yet another embodiment, one or more of the nucleobase blocking groups are cleavable after the assembly of the respective nucleic acid in the presence of base or a basic solvent, and wherein the nucleobase blocking group is stable to the conditions of the front end deprotection step with amines.

In some embodiments, blocking groups for nucleobases are not required. In other embodiments, blocking groups for nucleobases are required. In yet other embodiments, certain nucleobases require blocking group while other nucleobases do not require blocking groups. In embodiments where the nucleobases are blocked, the blocking groups are either completely or partially removed under conditions appropriate to remove the blocking group at the front end. For example, $R^1$ can denote $OR^a$, wherein $R^a$ is acyl, and Ba denotes guanine blocked with an acyl group including, but not limited to isobutyryl, acetyl or 4-(tert-butylphenoxy) acetyl. The acyl groups at $R^1$ and Ba will be removed or partially removed during the same deblocking step.

Stereochemistry of Oligonucleoside Phosphorothioate Linkages

Oligonucleoside phosphorothioates have shown therapeutic potential (Stein et al., Science (1993), 261:1004-12; Agrawal et al., Antisence Res. and Dev. (1992), 2:261-66; Bayever et al., Antisense Res. and Dev. (1993), 3:383-390). Oligonucleoside phosphorothioates prepared without regard to the sterochemistry of the phosphorothioate exist as a mixture of $2^n$ diastereomers, where n is the number of internucleotide phosphorothioates linkages. The chemical and biological properties of these diastereomeric phosphorothioates can be distinct. For example, Wada et al (Nucleic Acids Symposium Series No. 51 p. 119-120; doi:10.1093/nass/nrm060) found that stereodefined-(Rp)-(Ups)$_9$U/(Ap)$_9$A duplex showed a higher Tm value than that of natural-(Up)$_9$U/(Ap)$_9$A and stereodefined-(Sp)-(Ups)$_9$U did not form a duplex. In another example, in a study by Tang et al., (Nucleosides Nucleotides (1995), 14:985-990) stereopure Rp-oligodeoxyribonucleoside phosphorothioates were found to possess lower stability to nucleases endogenous to human serum that the parent oligodeoxyribonucleoside phosphorothioates with undefined phosphorous chirality.

Nucleobases and Modified Nucleobases

The nucleobase Ba utilized in the compounds and methods described herein is a natural nucleobase or a modified nucleobase derived from natural nucleobases. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. *Nucleic Acids Research,* 1994, 22, 2183-2196 and Revankar and Rao, *Comprehensive Natural Products Chemistry*, vol. 7, 313, are also contemplated as Ba moieties of the compounds and methods described herein.

Compounds represented by the following general formulae are also contemplated as modified nucleobases:

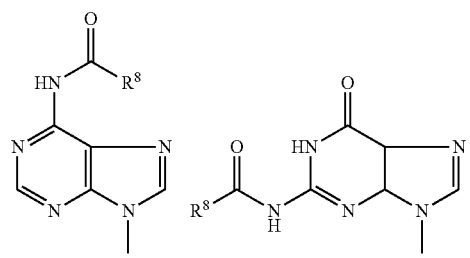

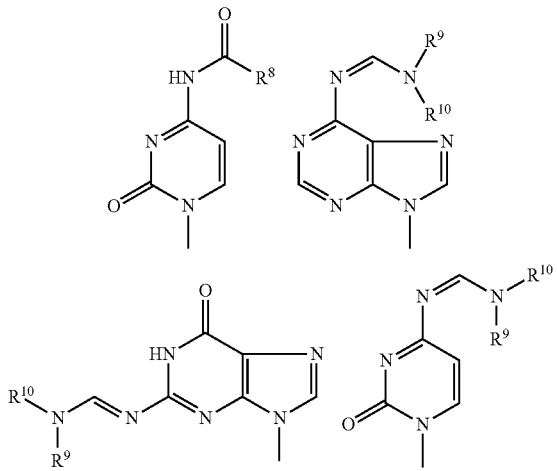

In the formulae above, $R^8$ is a linear or branched alkyl, aryl, aralkyl, or aryloxylalkyl group having 1 to 15 carbon atoms, including, by way of example only, a methyl, isopropyl, phenyl, benzyl, or phenoxymethyl group; and each of $R^9$ and $R^{10}$ represents a linear or branched alkyl group having 1 to 4 carbon atoms.

Modified nucleobases also include expanded-size nucleobases in which one or more benzene rings has been added. Nucleic base replacements described in the Glen Research catalog (www.glenresearch.com); Krueger A T et al, *Acc. Chem. Res.,* 2007, 40, 141-150; Kool, E T, *Acc. Chem. Res.,* 2002, 35, 936-943; Benner S. A., et al., *Nat. Rev. Genet.,* 2005, 6, 553-543; Romesberg, F. E., et al., *Curr. Opin. Chem. Biol.,* 2003, 7, 723-733; Hirao, I., *Curr. Opin. Chem. Biol.,* 2006, 10, 622-627, are contemplated as useful for the synthesis of the nucleic acids described herein. Some examples of these expanded-size nucleobases are shown below:

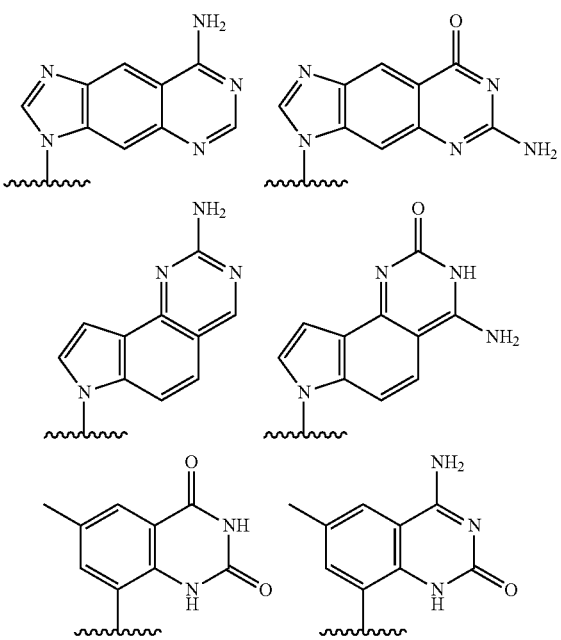

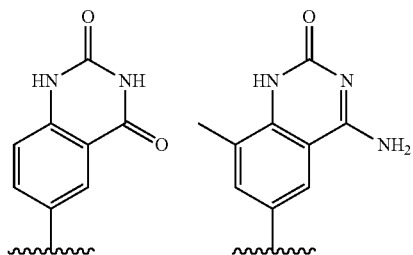

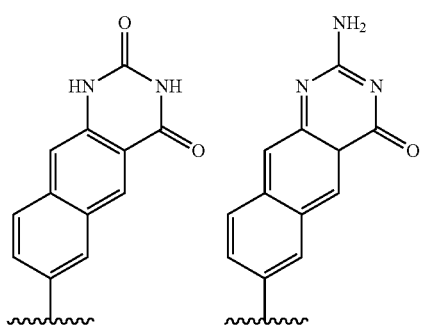

Herein, modified nucleobases also encompass structures that are not considered nucleobases but are other moieties such as, but not limited to, corrin- or porphyrin-derived rings. Porphyrin-derived base replacements have been described in Morales-Roj as, H and Kool, E T, *Org. Lett.*, 2002, 4, 4377-4380. Shown below is an example of a porphyrin-derived ring which can be used as a base replacement:

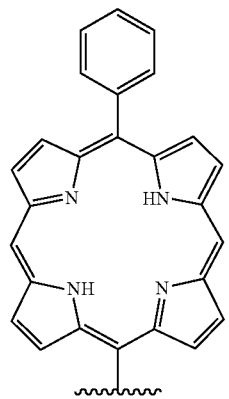 [SMILES: *c1c2nc(cc3ccc([nH]3)c(-c3ccccc3)c3nc(cc4ccc1[nH]4)C=C3)C=C2]

Other modified nucleobases also include base replacements such as those shown below:

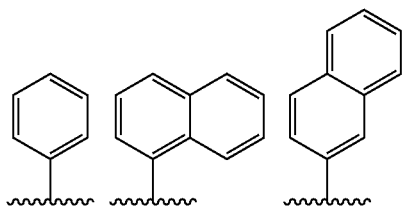

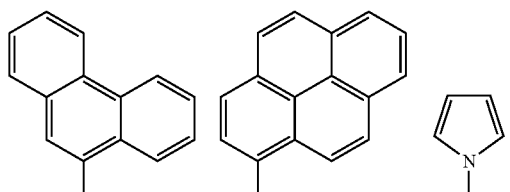

Modified nucleobases which are fluorescent are also contemplated. Non-limiting examples of these base replacements include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:

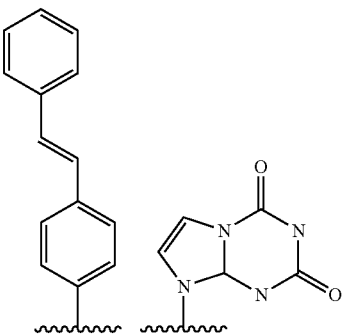

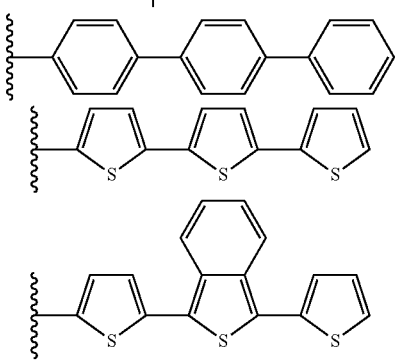

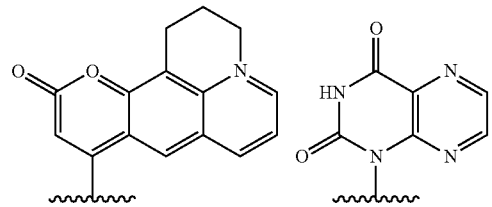

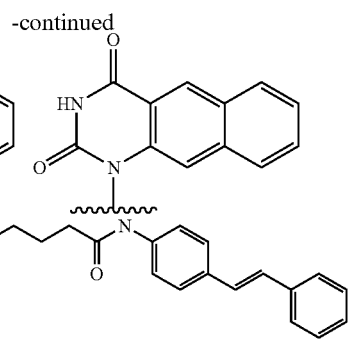

The modified nucleobases can be unsubstituted or contain further substitutions such as heteroatoms, alkyl groups, or linking moieties connected to fluorescent moieties, biotin or avidin moieties, or other protein or peptides. Modified nucleobases also include certain 'universal bases' that are not nucleobases in the most classical sense, but function similarly to nucleobases. One representative example of such a universal base is 3-nitropyrrole.

Other nucleosides can also be used in the process disclosed herein and include nucleosides that incorporate modified nucleobases, or nucleobases covalently bound to modified sugars. Some examples of nucleosides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In other embodiments, nucleosides include 5'-modified bicyclic nucleoside analogs that have either (R) or (S)-chirality at the 5'-position and include the analogs described in US Patent Application Publication No. 20070287831.

In some embodiments, the nucleobases or modified nucleobases comprises biomolecule binding moieties such as antibodies, antibody fragments, biotin, avidin, streptavidin, receptor ligands, or chelating moieties. In other embodiments, Ba is 5-bromouracil, 5-iodouracil, or 2,6-diaminopurine. In yet other embodiments, Ba is modified by substitution with a fluorescent or biomolecule binding moiety. In some embodiments, the substituent on Ba is a fluorescent moiety. In other embodiments, the substituent on Ba is biotin or avidin.

Modified Sugars of the Nucleotide/Nucleoside.

The most common naturally occurring nucleotides are ribose sugars linked to the nucleobases adenosine (A), cytosine (C), guanine (G), and thymine (T) or uracil (U). Also contemplated are modified nucleotides wherein the phosphate group or the modified phosphorous atom moieties in the nucleotides can be linked to various positions of the sugar or modified sugar. As non-limiting examples, the phosphate group or the modified phosphorous-atom moiety can be linked to the 2', 3', 4' or 5' hydroxyl moiety of a sugar or modified sugar. Nucleotides that incorporate the modified nucleobases described above can also be used in the process disclosed herein. In some embodiments, nucleotides or modified nucleotides comprising an unprotected —OH moiety are used in the process disclosed herein.

In addition to the ribose moiety described in Schemes 1-4b, other modified sugars can also be incorporated in the nucleic acids disclosed herein. In some embodiments, the modified sugars contain one or more substituents at the 2' position including one of the following: F; $CF_3$, CN, $N_3$, NO, $NO_2$, O-, S-, or N-alkyl; O-, S-, or N-alkenyl; O-, S- or N-alkynyl; or O-alkyl-O-alkyl, O-alkyl-N-alkyl or N-alkyl-O-alkyl wherein the alkyl, alkenyl and alkynyl may be substituted or unsubstituted $C_1$-$C_{10}$ alkyl or $C_2$-$C_{10}$ alkenyl and alkynyl. Examples of substituents include, and are not limited to, $O(CH_2)_nOCH_3$, and $O(CH_2)NH_2$, wherein n is from 1 to about 10, MOE, DMAOE, DMAEOE. Also contemplated herein are modified sugars described in WO 2001/088198; and Martin et al., Helv. Chim. Acta, 1995, 78, 486-504. In some embodiments, modified sugars comprise substituted silyl groups, an RNA cleaving group, a reporter group, a fluorescent label, an intercalator, a group for improving the pharmacokinetic properties of a nucleic acid, or a group for improving the pharmacodynamic properties of a nucleic acid, and other substituents having similar properties. The modifications may be made at the at the 2', 3', 4', 5', or 6' positions of the sugar or modified sugar, including the 3' position of the sugar on the 3'-terminal nucleotide or in the 5' position of the 5'-terminal nucleotide.

Modified sugars also include sugar mimetics such as cyclobutyl or cyclopentyl moieties in place of the pentofuranosyl sugar. Representative United States patents that teach the preparation of such modified sugar structures include, but are not limited to, U.S. Pat. Nos. 4,981,957; 5,118,800; 5,319,080; and 5,359,044. Some modified sugars that are contemplated include:

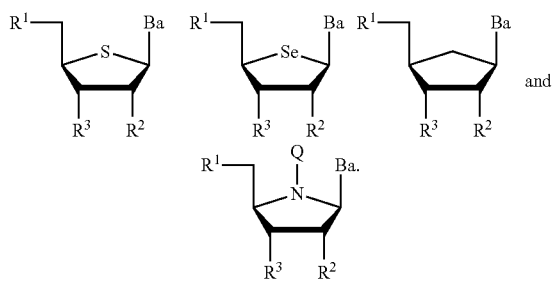

Q = Me, Et, i-Pr

Other non-limiting examples of modified sugars include glycerol, which form glycerol nucleic acid (GNA) analogues. One example of a GNA analogue is shown below and is described in Zhang, R et al., J. Am. Chem. Soc., 2008, 130, 5846-5847; Zhang L, et al., J. Am. Chem. Soc., 2005, 127, 4174-4175 and Tsai C H et al., PNAS, 2007, 14598-14603:

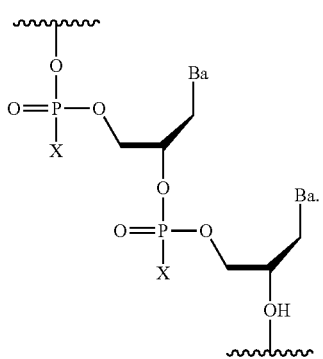

wherein X is as defined herein. Another example of a GNA derived analogue, flexible nucleic acid (FNA) based on the mixed acetal aminal of formyl glycerol, is described in Joyce G F et al., *PNAS*, 1987, 84, 4398-4402 and Heuberger B D and Switzer C, *J. Am. Chem. Soc.*, 2008, 130, 412-413, and is shown below:

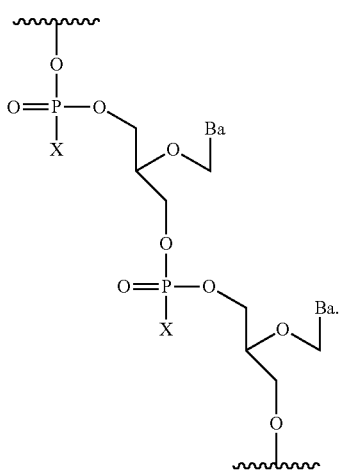

Other non-limiting examples of modified sugars include hexopyranosyl (6' to 4'), pentopyranosyl (4' to 2'), pentopyranosyl (4' to 3'), or tetrofuranosyl (3' to 2') sugars.

Hexopyranosyl (6' to 4') sugars contemplated include:

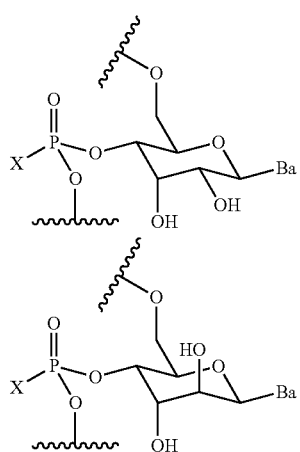

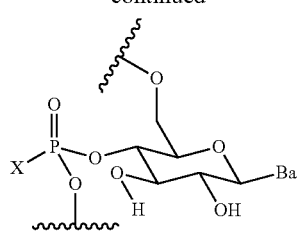

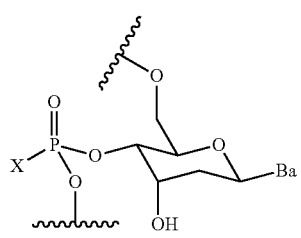

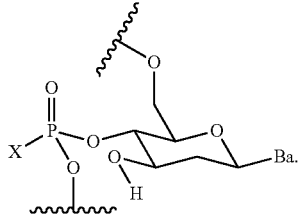

Pentopyranosyl (4' to 2') sugars contemplated include:

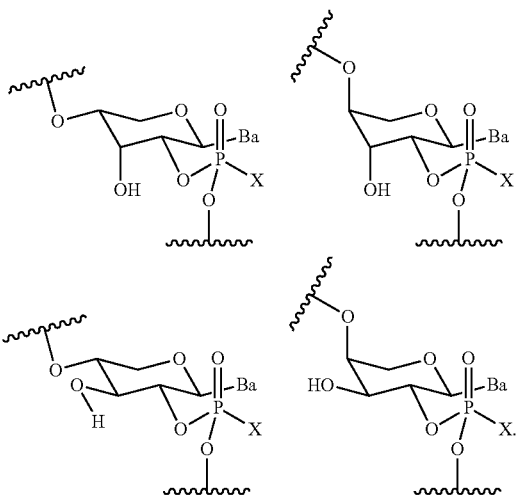

Pentopyranosyl (4' to 3') sugars contemplated include:

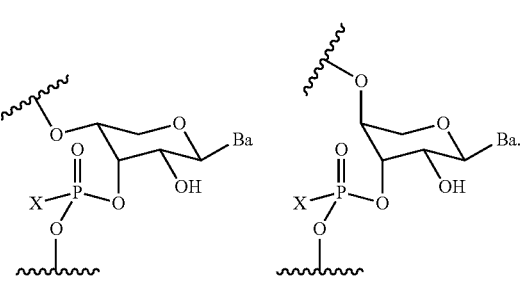

Tetrofuranosyl (3' to 2') sugars contemplated include:
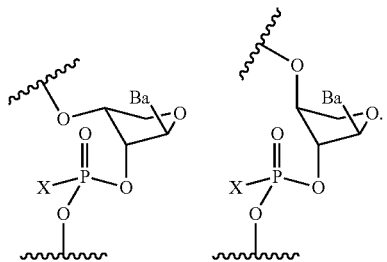
Other modified sugars contemplated include:
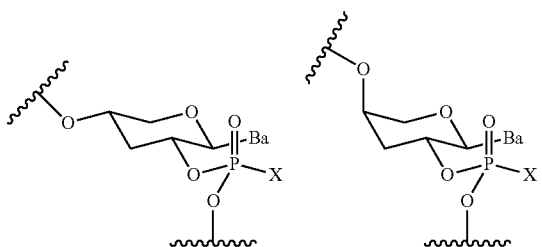
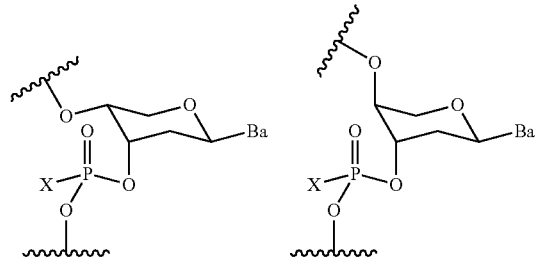
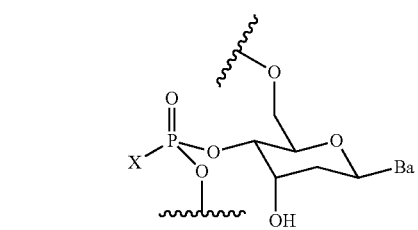
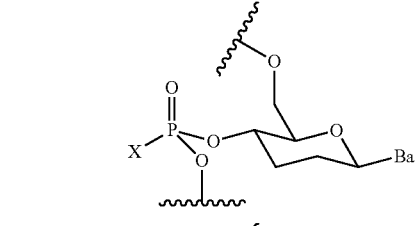
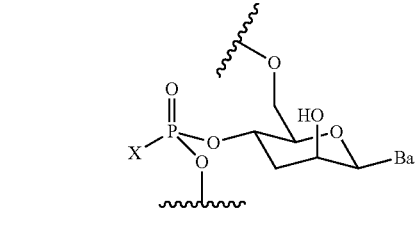
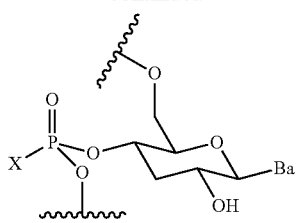
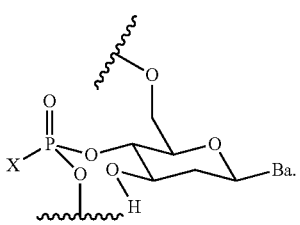
Further contemplated are the sugar mimetics illustrated below wherein X is selected from S, Se, $CH_2$, N-Me, N-Et or N-iPr.
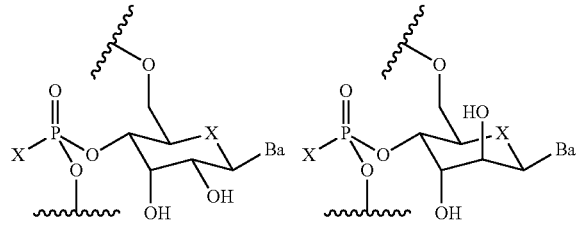
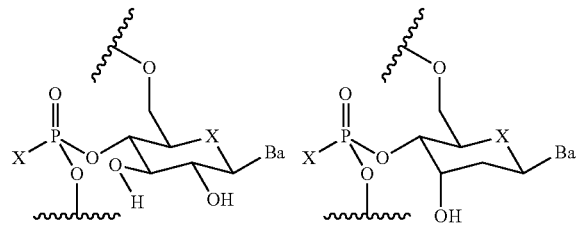
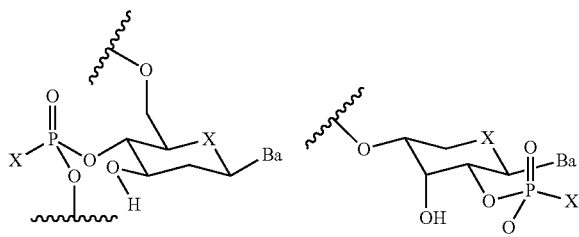
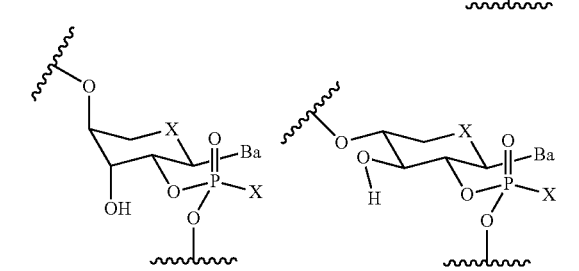

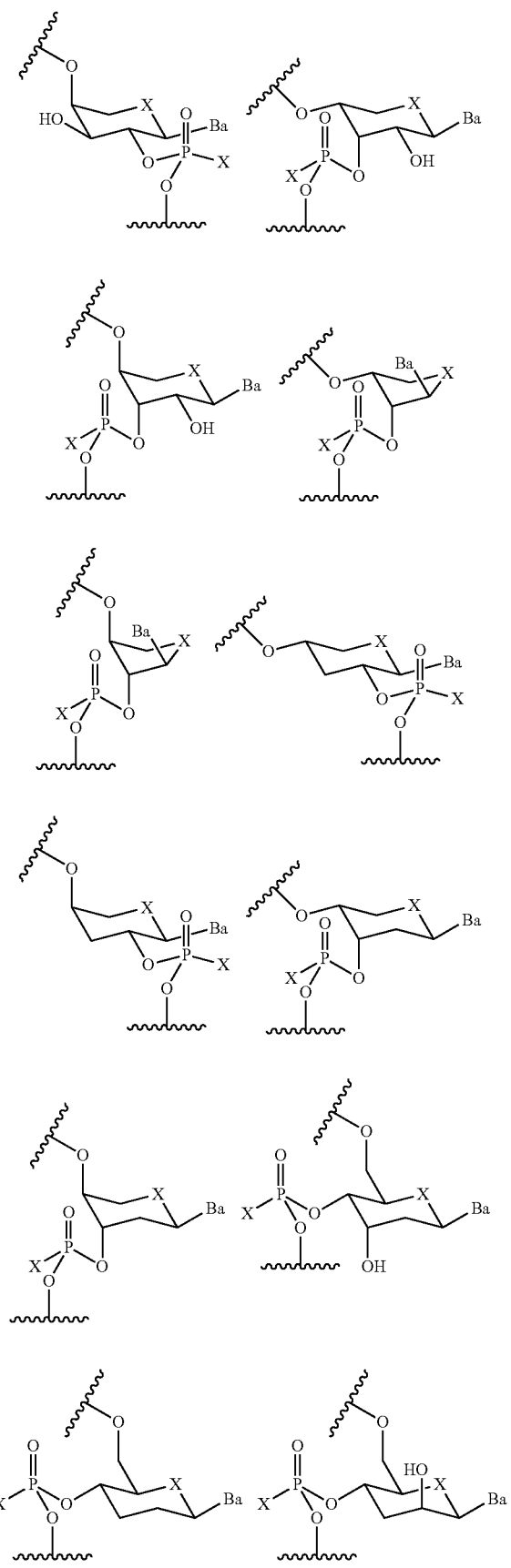
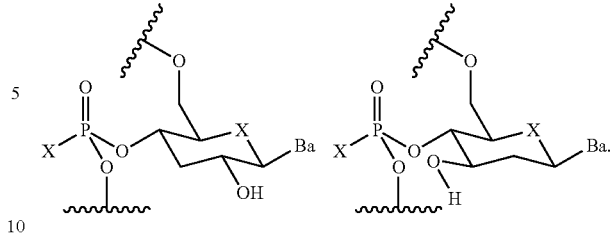

The modified sugars and sugar mimetics can be prepared by methods known in the art, including, but not limited to: A. Eschenmoser, Science (1999), 284:2118; M. Bohringer et al, Helv. Chim. Acta (1992), 75:1416-1477; M. Egli et al, J. Am. Chem. Soc. (2006), 128(33):10847-56; A. Eschenmoser in *Chemical Synthesis: Gnosis to Prognosis*, C. Chatgilialoglu and V. Sniekus, Ed., (Kluwer Academic, Netherlands, 1996), p. 293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118.

Blocking Groups

In the reactions described, it is necessary in certain embodiments to protect reactive functional groups, for example hydroxy, amino, thiol or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group is removable by a different means. Protective groups that are cleaved under totally disparate reaction conditions fulfill the requirement of differential removal. In some embodiments, protective groups are removed by acid, base, and/or hydrogenolysis. Groups such as trityl, dimethoxytrityl, acetal and t-butyldimethylsilyl are acid labile and are used in certain embodiments to protect carboxy and hydroxy reactive moieties in the presence of amino groups protected with Cbz groups, which are removable by hydrogenolysis, and/or Fmoc groups, which are base labile. In other embodiments, carboxylic acid and hydroxy reactive moieties are blocked with base labile groups such as, but not limited to, methyl, ethyl, and acetyl in the presence of amines blocked with acid labile groups such as t-butylcarbamate or with carbamates that are both acid and base stable but hydrolytically removable.

In another embodiment, hydroxy reactive moieties are blocked with hydrolytically removable protective groups such as the benzyl group, while amine groups capable of hydrogen bonding with acids are blocked with base labile groups such as Fmoc. In another embodiment, carboxylic acid reactive moieties are protected by conversion to simple ester compounds, or they are, in yet another embodiment, blocked with oxidatively-removable protective groups such as 2,4-dimethoxybenzyl, while co-existing amino groups are blocked with fluoride labile silyl or carbamate blocking groups.

Allyl blocking groups are useful in the presence of acid- and base-protecting groups since the former are stable and can be subsequently removed by metal or pi-acid catalysts. For example, an allyl-blocked hydroxy groups can be deprotected with a Pd(0)-catalyzed reaction in the presence of acid labile t-butylcarbamate or base-labile acetate amine protecting groups. Yet another form of protecting group is a resin to which a compound or intermediate is attached. As long as the residue is attached to the resin, that functional group is blocked and cannot react. Once released from the resin, the functional group is available to react.

Typically blocking/protecting groups useful in the synthesis of the compounds described herein are, by way of example only:

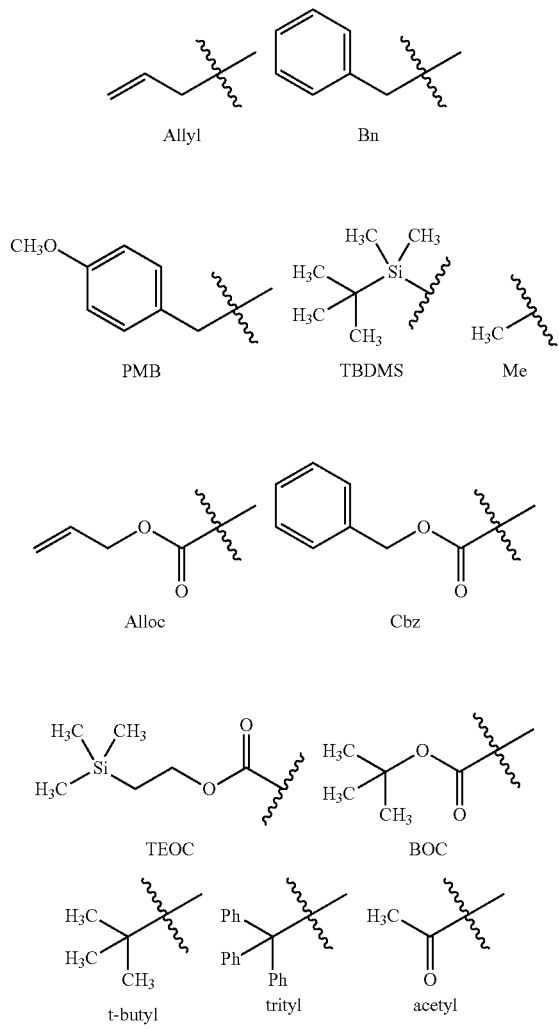

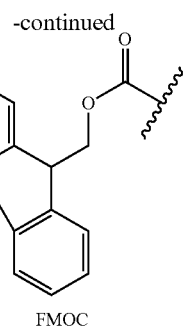

FMOC

Representative protecting groups useful to protect nucleotides during synthesis include base labile protecting groups and acid labile protecting groups. Base labile protecting groups are used to protect the exocyclic amino groups of the heterocyclic nucleobases. This type of protection is generally achieved by acylation. Three commonly used acylating groups for this purpose are benzoyl chloride, phenoxyacetic anhydride, and isobutyryl chloride. These protecting groups are stable to the reaction conditions used during nucleic acid synthesis and are cleaved at approximately equal rates during the base treatment at the end of synthesis.

In some embodiments, the 5'-protecting group is trityl, monomethoxy trityl, dimethoxytrityl, trimethoxytrityl, 2-chlorotrityl, DATE, TBTr, 9-phenylxanthine-9-yl (Pixyl), or 9-(p-methoxyphenyl)xanthine-9-yl (MOX).

In some embodiments, thiol moieties are incorporated in the compounds described herein and are protected. In some embodiments, the protecting groups include, but are not limited to, pixyl, trityl, benzyl, p-methoxybenzyl (PMB), or tert-butyl (t-Bu).

Other protecting groups, plus a detailed description of techniques applicable to the creation of protecting groups and their removal are described in Greene and Wuts, Protective Groups in Organic Synthesis, 3$^{rd}$ Ed., John Wiley & Sons, New York, N.Y., 1999, and Kocienski, Protective Groups, Thieme Verlag, New York, N.Y., 1994, which are incorporated herein by reference for such disclosure.

The examples provided below further illustrate and exemplify the compounds of the present invention and methods of preparing such compounds. It is to be understood that the scope of the present invention is not limited in any way by the scope of the following examples and preparations.

EXAMPLES

Example 1—Synthesis of Methanethiosulfonate Reagents

Scheme 1

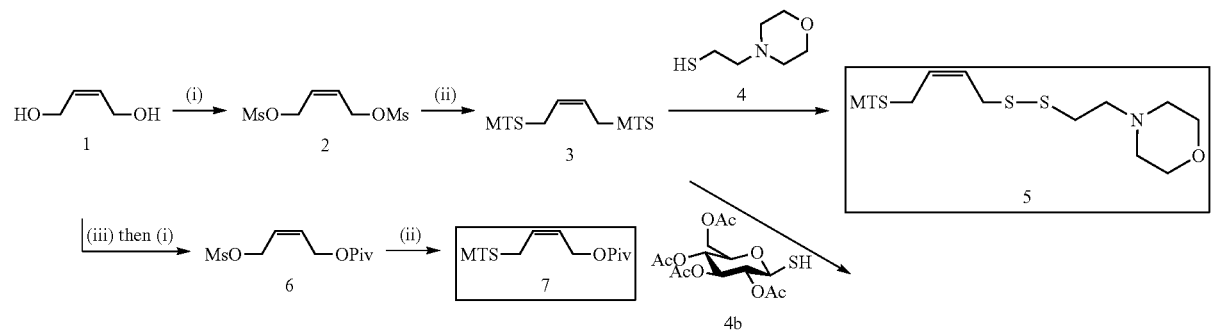

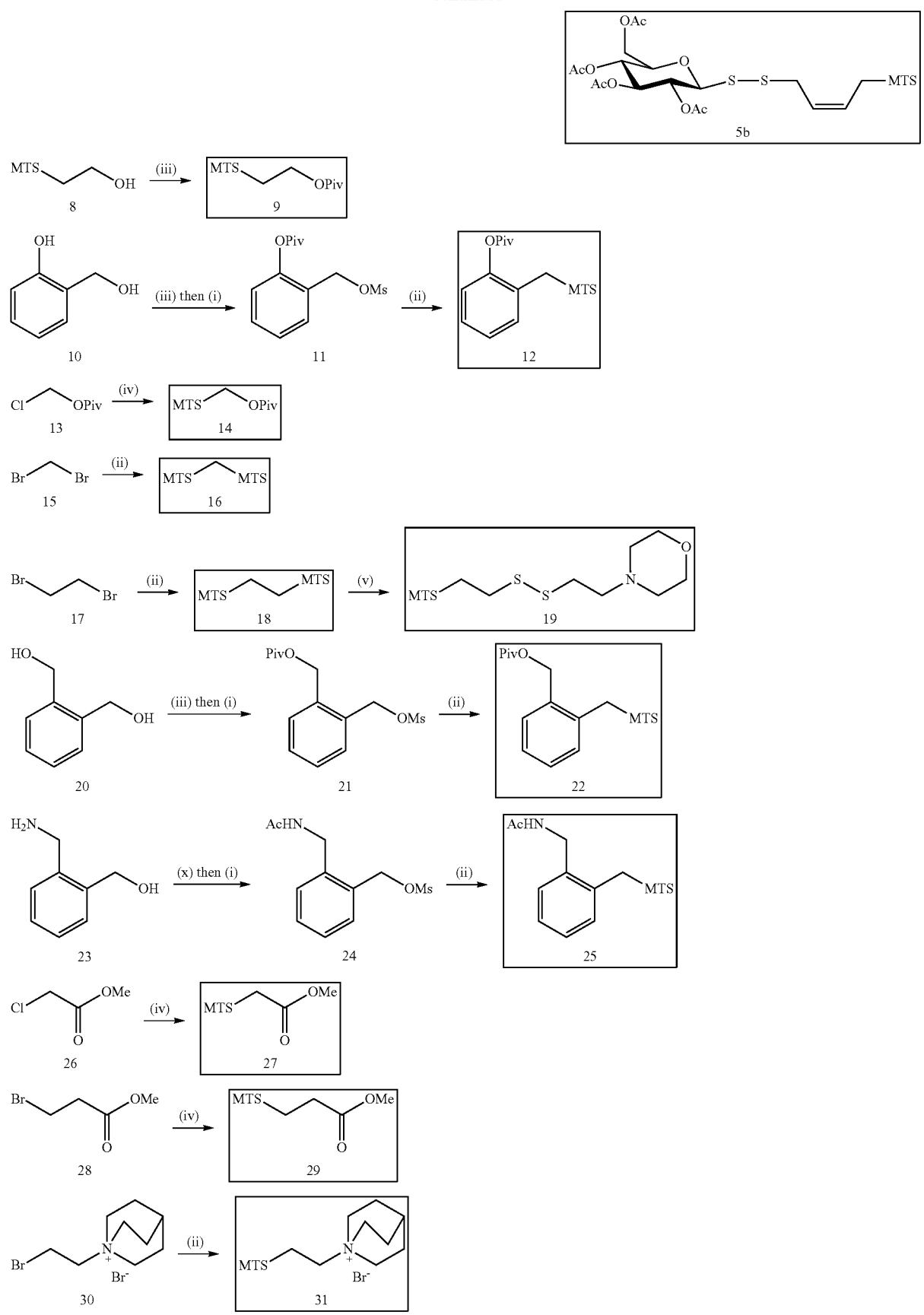

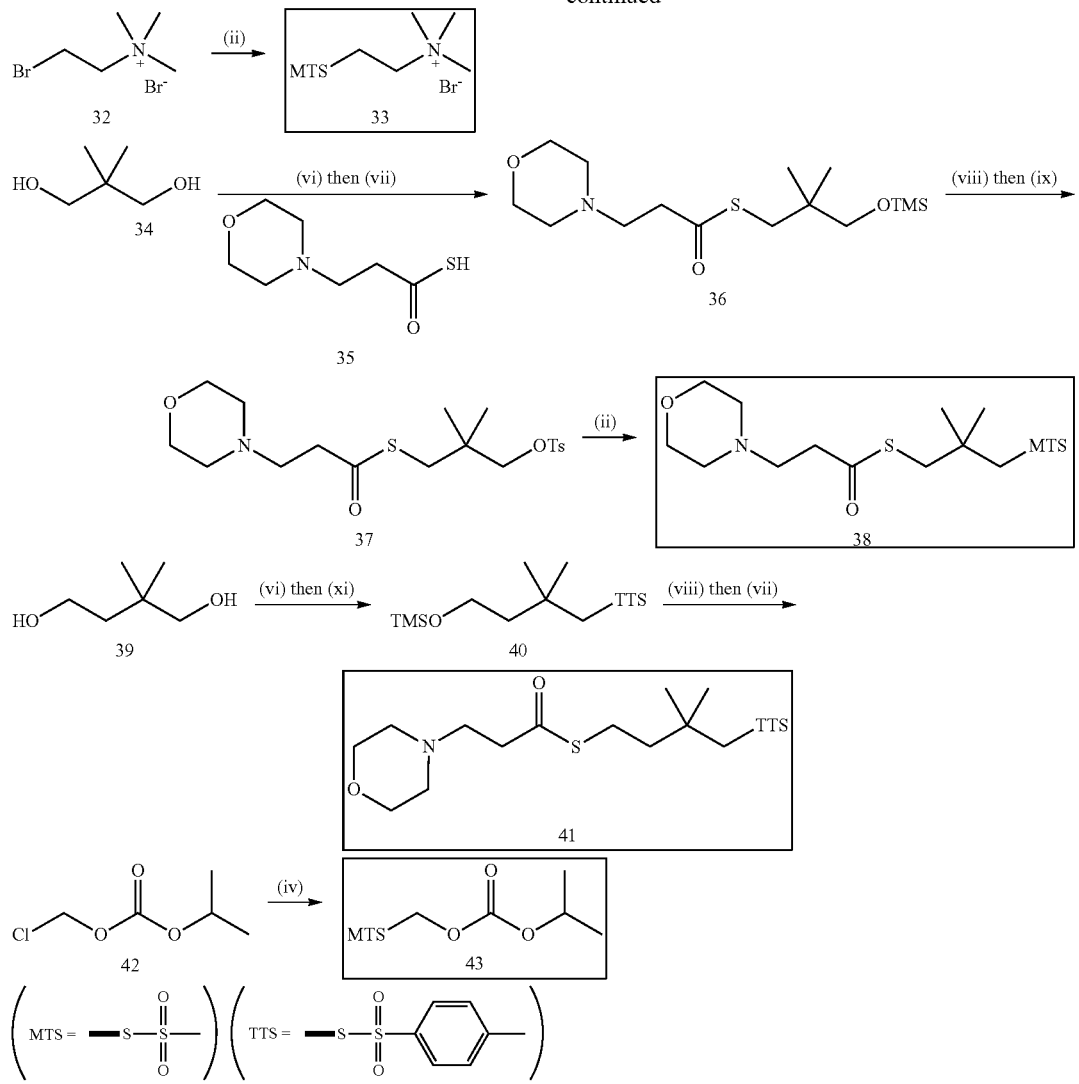

(i) MsCl, NEt₃, (ii) NaMTS, (iii) PivCl, NEt₃, (iv) NaMTS, NaI, (v) compound 4, (vi) TMSCl, NEt₃, (vii) compound 35, DEAD, PPh₃
(viii) TBAF, (ix) TsCl, Pyridine, (x) Ac₂O, Pyridine (xi) NaTTS Compound 2

A solution of (Z)-but-2-ene-1,4-diol (0.93 ml, 11.3 mmol) and triethylamine (3.3 ml, 24 mmol) in DCM (50 mL) was added in a dropwise fashion to a stirring ice cold solution of methanesulfonyl chloride (1.9 ml, 24 mmol) in DCM (50 mL). After stirring for 0.5h at r.t. the mixture was poured onto ice and extracted. The organic layer was collected, dried (MgSO₄), filtered and reduced to 2.66 g, 96% of compound 2, which was judged by NMR to be sufficiently pure for direct use in the next step of the reaction.

¹H NMR (399 MHz, CDCl₃) δ 5.94 (ddd, J=5.4, 4.1, 1.3 Hz, 2H), 4.83 (dd, J=4.1, 1.3 Hz, 4H), 3.04 (s, 6H); ¹³C NMR 128.34, 64.38, 38.27; MS (ESI+ve): calc (M+NH₄): 262.04, found: 262.05. R$_f$=0.3 (1:1 EtOAc/hexane).

Compound 3

A solution of sodium methanesulfonothioate (1.51 g, 11.3 mmol) in MeOH (20 ml) was treated with neat (Z)-but-2-ene-1,4-diyl dimethanesulfonate (1.25 g, 5.12 mmol) at r.t. After 5 min, precipitation was observed to occur. After 36 h, the mixture was partitioned between water and DCM. The organic layer was separated, dried (MgSO₄), filtered and reduced to afford a colorless oil. Column chromatography (ISCO) gave the pure product as a pale colorless oil. Column chromatography gave pure compound 3 (0.89 g, 63%) as a colorless oil.

¹H NMR (399 MHz, CDCl₃) δ 5.84 (ddd, J=6.6, 5.1, 1.5 Hz, 2H), 3.92 (dd, J=5.1, 1.5 HZ, 4H), 3.33 (s, 6H); ¹³C NMR 128.1, 51.47, 33.13; MS (ESI+ve): calc (M+NH₄): 294.00, found: 294.04. R$_f$=0.4 (1:1 EtOAc/hexane).

Compound 4

Under argon atmosphere, morpholine (10 g, 115 mmol) was added to ethylene sulfide (15 g, 250 mmol) in a round bottom flask. The reaction was stirred for 7 hrs and was directly loaded on to a silica gel column. The column was washed with DCM first and then 2% MeOH/DCM was used to obtain compound 4 (15.3 g, 91%) as colorless oil.

$^1$H NMR (399 MHz, CDCl$_3$) δ 3.67-3.59 (m, 4H), 2.63-2.52 (m, 2H), 2.51-2.45 (m, 2H), 2.44-2.34 (m, 4H); MS (ESI+ve): calc (M+H)+=148.07, found: 148.1.

Compound 5

A DCM solution (1 mL) of 2-morpholinoethanethiol (0.21 g, 1.44 mmol) was added dropwise via syringe to a stirring solution compound 3 (0.40 g, 1.44 mmol) in DCM (10 mL) at r.t. Immediately after addition, the TLC was checked, to reveal rapid formation of product and some quantity of dimer. After 0.5 h, the mixture was partitioned by addition of water. Upon extraction, the organic layer was separated then dried (MgSO$_4$), filtered and reduced in vacuo. Column chromatography gave compound 5 (0.29 g, 58%) as colorless oil.

$^1$H NMR (399 MHz, CDCl$_3$) δ 5.78 (m, 2H), 3.92 (d, J=7.3 Hz, 2H), 3.70 (t, J=4.7 Hz, 4H), 3.46 (d, J=5.5 Hz, 2H), 3.31 (s, 3H), 2.84 (dd, J=7.8, 6.7 Hz, 2H), 2.66 (dd, J=7.8, 6.7, 2H), 2.48 (t, J=4.6 Hz, 4H); $^{13}$C NMR 130.35, 126.27, 66.97, 58.20, 53.67, 51.52, 36.22, 35.16, 33.67; MS (ESI+ve): calc (M+H): 344.05, found: 344.06. R$_f$=0.3 (EtOAc).

Compound 5b

A DCM solution (1 mL) of compound 4b (395 mg, 1.085 mmol) was added dropwise via syringe to a stirring DCM (15 mL) solution compound 3 (300 mg, 1.085 mmol) at r.t. After 1h, the resulting solution was partitioned by addition of water. Upon extraction, the organic layer was separated then dried (MgSO$_4$), filtered and reduced in vacuo. Column chromatography gave compound 5b as a colorless oil (0.35 g, 58%). $^1$H NMR (399 MHz, CDCl$_3$) δ 5.83-5.70 (m, 2H), 5.35-5.21 (dt, J=26.0, 9.3 Hz, 2H), 5.16-5.07 (m, 1H), 4.59-4.54 (d, J=9.5 Hz, 1H), 4.29-4.23 (m, 1H), 4.23-4.18 (m, 1H), 3.99-3.88 (dd, J=6.7, 1.2 Hz, 2H), 3.80-3.72 (ddd, J=10.1, 4.6, 2.6 Hz, 1H), 3.64-3.56 (m, 1H), 3.50-3.43 (m, 1H), 3.31 (s, 3H), 2.09 (s, 3H), 2.03 (s, 6H), 2.00 (s, 3H); $^{13}$C NMR (100 MHz, CDCl$_3$) δ 170.68, 170.30, 169.51, 169.30, 129.43, 127.14, 87.73, 76.49, 73.89, 69.16, 67.99, 61.99, 51.64, 35.89, 33.58, 20.95, 20.80, 20.74, 20.71; MS (ESI+ve): calc (M+NH$_4$+): 578.07, found: 577.96. R$_f$=0.5 (1:1 EtOAc/hexane).

Compound 6

An ice cold solution of (Z)-but-2-ene-1,4-diol (0.93 ml, 11.3 mmol) and triethylamine (1.6 mL, 11.5 mmol) in DCM (50 ml) was treated dropwise via syringe with pivaloyl chloride (1.4 ml, 11.4 mmol) over 2 min. After 1 h, TLC showed good reaction.

The resulting mixture was partitioned by addition of water. Upon extraction, the organic layer was separated then dried (MgSO$_4$), filtered and reduced in vacuo. This crude compound was found: by TLC (Rf=0.6, 1:1 EtOAc/hexane) to contain no starting diol and was used crude to prepare the mesylate. The crude material was taken up in DCM (50 ml) containing triethylamine (1.7 mL, 12 mmol) and cooled on an ice bath. Methanesulfonyl chloride (0.98 ml, 12.66 mmol) was added dropwise via syringe over 2 min. TLC immediately after addition indicated complete consumption of starting material. The resulting mixture was partioned by addition of water. Upon extraction, the organic layer was separated then dried (MgSO$_4$), filtered and reduced in vacuo. Column chromatography gave pure compound 6, 1.48 g, 52%, as a colorless oil.

1H NMR (399 MHz, CDCl3) δ 5.89-5.75 (m, 2H), 4.89-4.84 (d, J=5.7 Hz, 2H), 4.68-4.63 (d, J=5.9 Hz, 2H), 3.03 (s, 3H), 1.19 (s, 9H); 13C NMR (100 MHz, CDCl3) δ 178.28, 130.61, 126.11, 65.08, 59.65, 38.84, 38.21, 27.25; MS (ESI+ve): calc (M+NH4): 268.12, found: 268.20; Rf=0.3 (20% EtOAc/hexane).

Compound 7

A MeOH (10 ml) solution of sodium methanesulfonothioate (0.63 g, 4.70 mmol) and (Z)-4-(methylsulfonyloxy)but-2-enyl pivalate (1.00 g, 4.00 mmol) was stirred at r.t. for 18 h with formation of a white precipitate (after 10 min). The resulting mixture was partitioned by addition of water and DCM. Upon extraction into DCM, the organic layer was separated then dried (MgSO$_4$), filtered and reduced in vacuo. Column chromatography gave compound 7, 0.83 g, 78% as a colorless oil.

$^1$H NMR (399 MHz, CDCl$_3$) δ 5.82-5.73 (m, 2H), 4.73-4.66 (m, 2H), 3.95-3.87 (m, 2H), 3.32 (s, 3H), 1.19 (s, 9H); $^{13}$C NMR (100 MHz, CDCl$_3$) δ 178.35, 129.37, 127.32, 59.50, 51.44, 38.84, 33.61, 27.28; MS (ESI+ve): calc (M+NH$_4$): 284.10, found: 284.19; R$_f$=0.4 (20% EtOAc/hexane).

Compound 9

Pivaloyl chloride (0.60 g, 5.0 mmol) was added in a dropwise fashion to a stirring solution of S-2-hydroxyethyl methanesulfonothioate (0.65 g, 4.16 mmol) in DCM (20 ml). After 2 h at r.t. the resulting mixture with white precipitate was partitioned with water. The organic layer was separated, dried (Ns$_2$SO$_4$), filtered and reduced to an oil. Column gave compound 9 as a colorless oil (0.45 g, 45%). $^1$H NMR (399 MHz, CDCl$_3$) δ 4.39-4.34 (t, J=6.3 Hz, 2H), 3.44-3.39 (t, J=6.3 Hz, 2H), 3.36 (s, 3H), 1.20 (s, 9H); $^{13}$C NMR (100 MHz, CDCl$_3$) δ 62.10, 51.11, 38.96, 35.19, 27.24; MS (ESI+ve): calc (M+NH$_4$): 158.08, found: 158.04. R$_f$=0.3 (20% EtOAc/hexane).

Compound 11

Pivaloyl chloride (4.96 ml, 40.3 mmol) was added dropwise via syringe to an ice cold DCM solution (50 mL) of 2-(hydroxymethyl)phenol (5 g, 40.3 mmol) and triethylamine (5.61 ml, 40.3 mmol). An ice-cold solution of the crude pivalate ester was treated with triethylamine (6.74 ml, 48.4 mmol) and 50 mL DCM. Methanesulfonyl chloride (3.43 ml, 44.3 mmol) was then added slowly (5 min) via syringe and the resulting mixture was warmed to r.t. The mixture was poured onto ice and the organic layer was separated then washed with sat NaHCO$_3$ (aq), dried (MgSO$_4$), filtered and reduced to 10.5 g crude pale yellow oil.

Column (ISCO) gave pure 11 5.45 g, 47%.

$^1$H NMR (399 MHz, CDCl$_3$) δ 7.53-7.46 (dd, 7.7, 1.8 Hz, 1H), 7.46-7.40 (dt, 7.7, 1.8 Hz, 1H), 7.32-7.24 (t, 7.7 Hz, 1H), 7.13-7.06 (d, 7.7 Hz, 1H), 5.21 (s, 2H), 2.79 (s, 3H), 1.40 (s, 9H); $^{13}$C NMR (100 MHz, CDCl$_3$) δ 177.05, 150.06, 131.18, 131.07, 126.35, 125.94, 123.21, 66.88, 39.48, 38.82, 27.30, 27.26. MS (ESI+ve): calc (M+NH$_4$): 304.12, found: 303.99. R$_f$=0.4 (20% EtOAc/hexane).

Compound 12

A MeOH (20 mL) solution of sodium methanesulfonothioate (0.825 g, 6.15 mmol) was treated with 2-((methylsulfonyloxy)methyl)phenyl pivalate (1.76 g, 6.15 mmol) at r.t.

and left to stir for 18 h. The mixture was partitioned between water and DCM. The organic layer was separated, dried (MgSO$_4$), filtered and reduced to afford a colorless oil. Column chromatography gave pure compound 12 as a pale colorless oil, 0.754 g, 41%.

$^1$H NMR (399 MHz, CDCl$_3$) δ 7.48-7.44 (dd, J 7.7, 1.7 Hz, 1H), 7.39-7.34 (td, J 7.8, 1.7 Hz, 1H), 7.25-7.20 (td, J 7.6, 1.2 Hz, 1H), 7.10-7.06 (dd, J 8.2, 1.2 Hz, 1H), 4.29 (s, 2H), 2.90 (s, 3H), 1.39 (s, 9H); $^{13}$C NMR (100 MHz, CDCl$_3$) δ 176.69, 149.59, 131.17, 129.85, 127.41, 126.18, 123.40, 51.43, 39.47, 36.01, 27.30; MS (ESI+ve): calc (M+NH$_4$): 320.10, found: 320.09. R$_f$=0.4 (20% EtOAc/hexane).

Compound 14

Chloromethyl pivalate (0.478 ml, 3.32 mmol) was added to a stirring mixture of sodium iodide (0.050 g, 0.33 mmol) and sodium methanesulfonothioate (0.445 g, 3.32 mmol) in acetone (7 ml) at r.t. After 24 h, TLC showed good conversion to product. The solvent was removed, and the residue was partitioned between water and DCM. The organic layer was separated and dried (MgSO$_4$), filtered and reduced to afford a colorless oil. Column chromatography gave pure 14 as a slightly pink solid, 0.41 g, 55%.

$^1$H NMR (399 MHz, CDCl$_3$) δ 5.67 (s, 2H), 3.39 (s, 3H), 1.24 (s, 9H); $^{13}$C NMR (100 MHz, CDCl$_3$) δ 177.35, 67.84, 52.20, 38.93, 27.05. R$_f$=0.5 (20% EtOAc/hexane).

Compound 16

Prepared from 15 and NaMTS as described previously: U.S. Pat. No. 3,484,473 $^1$H NMR (399 MHz, CDCl$_3$) δ 4.86 (s, 2H), 3.45 (s, 6H); $^{13}$C NMR (100 MHz, CDCl$_3$) δ 52.15, 41.50.

Compound 18

Prepared from 17 and NaMTS as described previously: Chem. Pharm. Bull. Vol. 12(11) p. 1271, 1964.

$^1$H NMR (399 MHz, CDCl$_3$) δ 3.55 (s, 4H), 3.40 (s, 6H); $^{13}$C NMR (100 MHz, CDCl$_3$) δ 50.67, 35.96.

Compound 19

A DCM solution (1 mL) of 2-morpholinoethanethiol (0.17 g, 1.2 mmol) was added dropwise via syringe to a stirring solution of compound 18 (300 mg, 1.2 mmol) in DCM (10 mL) at r.t. Immediately after addition, the TLC was checked, to reveal rapid formation of product and some dimer. After 0.5 h, the mixture was partitioned by addition of NaHCO$_3$. Upon extraction, the organic layer was separated then dried (MgSO$_4$), filtered and reduced in vacuo. Column chromatography gave pure 19 (0.20 g, 53%) as a colorless oil. $^1$H NMR (399 MHz, CDCl$_3$) δ 3.73-3.67 (t, J=4.7 Hz, 4H), 3.51-3.46 (m, 2H), 3.35 (s, 3H), 3.07-3.01 (m, 2H), 2.88-2.83 (m, 2H), 2.69-2.63 (m, 2H), 2.52-2.43 (t, J=4.6 Hz, 4H); $^{13}$C NMR (100 MHz, CDCl$_3$) δ 66.96, 57.91, 53.58, 50.79, 37.66, 36.10, 35.52; MS (ESI+ve): calc (M+H): 318.03, found: 318.04. R$_f$=0.3 (EtOAc).

Compound 21

Compound 20 is converted to compound 21 by a procedure analogous to that described for compound 11.

Compound 22

Compound 21 is converted to compound 22 by a procedure analogous to that described for compound 12.

Compound 23

Compound 23 is prepared according to a literature method (Journal of Medicinal Chemistry, 50(23), 5568-5570; 2007.)

Compound 24

An ice-cold pyridine solution (10 mL) of compound 23 (1 mmol) is treated successively, in a dropwise fashion with acetyl chloride (1 mmol), then after 5 min with MsCl (1.1 mmol). The solution is warmed to room temperature then the solvent is removed. The residue is dissolved in EtOAc, washed with water, dried (MgSO$_4$), filtered and reduced in vacuo. Purification by column chromatography affords pure compound 24.

Compound 25

Compound 24 is converted to compound 25 by a procedure analogous to that described for compound 12.

Compound 27

Compound 26 is converted to compound 27 by a procedure analogous to that described for compound 14.

Compound 29

Compound 28 is converted to compound 29 by a procedure analogous to that described for compound 14.

Compound 30

Compound 30 is prepared according to a literature method (Tetrahedron, 42(2), 601-7; 1986.)

Compound 31

Compound 31 is prepared from compound 30 according to a patent procedure (US 20090181444)

Compound 33

Compound 33 is prepared from compound 32 according to a patent procedure (US 20090181444)

Compound 36

An ice-cold DCM (20 mL) solution of compound 34 (1 mmol) is treated with NEt$_3$ (1 mmol) followed by the dropwise addition of TMS-Cl (1.1 mmol). After 1 h, the solution is washed with water, dried (MgSO$_4$), filtered and reduced in vacuo. The crude TMS protected material is redissolved in THF (10 mL), whereon PPh$_3$ (1.2 mmol), compound 35 (1.2 mmol), then DEAD (1.2 mmol, dropwise) are added in succession. After stirring at r.t. for 18 h, the solvent is removed under vacuum, the residue is redissolved in DCM, the solution of which is washed with water, dried (MgSO$_4$), filtered and reduced in vacuo. Purification by column chromatography affords pure compound 36.

Compound 37

A THF (10 mL) solution of compound 36 (0.5 mmol) is treated with TBAF (1 mmol of a 1M solution in THF), with monitoring by TLC. On completion of TMS cleavage, the solvent is removed under vacuum, the residue is redissolved in DCM, the solution of which is washed with water, dried (MgSO₄), filtered and reduced in vacuo. The crude alcohol is redissolved in pyridine (5 mL), and TsCl (0.55 mmol) is added. After 18 h at r.t., the solvent is removed, the residue is redissolved in DCM, the solution of which is washed with water, dried (MgSO₄), filtered and reduced in vacuo. Purification by column chromatography affords pure compound 37.

Compound 38

Compound 37 is converted to compound 38 by a procedure analogous to that described for compound 12.

Compound 40

An ice-cold DCM (20 mL) solution of compound 39 (1 mmol) is treated with NEt₃ (1 mmol) followed by the dropwise addition of TMS-Cl (1.1 mmol). After 1 h, the solution is washed with water, dried (MgSO₄), filtered and reduced in vacuo. The crude TMS protected material is redissolved in THF (10 mL), whereon PPh₃ (1.2 mmol), potassium p-toluenethiosulfonate (KTTS, 1.2 mmol), anhydrous ZnCl₂ (1 mmol) then DEAD (1.2 mmol, dropwise) are added in succession. After stirring at r.t. for 18 h, the solvent is removed under vacuum, the residue is redissolved in DCM, the solution of which is washed with water, dried (MgSO₄), filtered and reduced in vacuo. Purification by column chromatography affords pure compound 40.

Compound 41

A THF (10 mL) solution of compound 40 (0.5 mmol) is treated with TBAF (1 mmol of a 1M solution in THF), with monitoring by TLC. On completion of TMS cleavage, the solvent is removed under vacuum, the residue is redissolved in DCM, the solution of which is washed with water, dried (MgSO₄), filtered and reduced in vacuo. The crude alcohol is redissolved in THF (10 mL), whereon PPh₃ (1.2 mmol), compound 35 (1.2 mmol), then DEAD (1.2 mmol, dropwise) are added in succession. After stirring at r.t. for 18 h, the solvent is removed under vacuum, the residue is redissolved in DCM, the solution of which is washed with water, dried (MgSO₄), filtered and reduced in vacuo. Purification by column chromatography affords pure compound 40.

Compound 42

Compound 41 is converted to compound 42 by a procedure analogous to that described for compound 14.

Example 2—Thioalkylation of H-Phosphonates to Provide Phosphorothiotriesters in Solution Phase Scheme 2

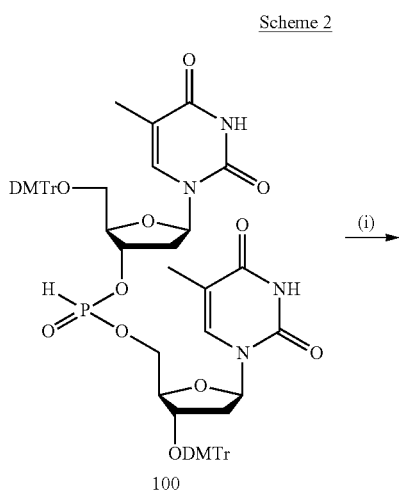

100

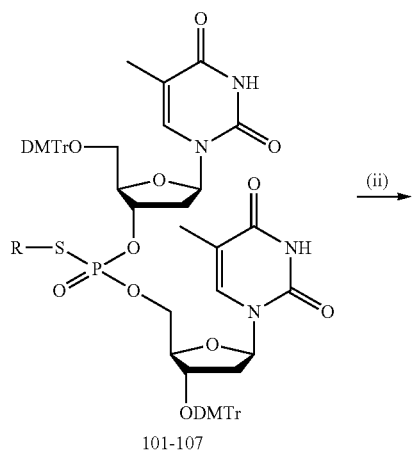

101-107

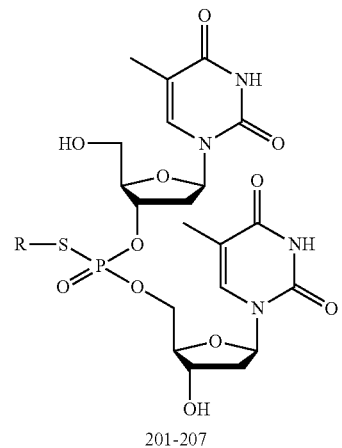

201-207

-continued (i) BSTFA, MTS—R, (ii) 3% TCA in DCM

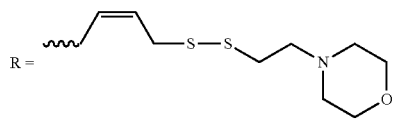

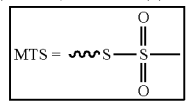

Compounds 101 and 201

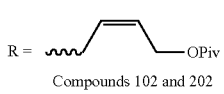
Compounds 102 and 202

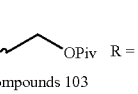
Compounds 103 and 203

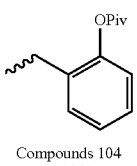
Compounds 104 and 204

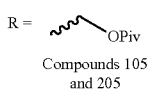
Compounds 105 and 205

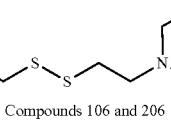
Compounds 106 and 206

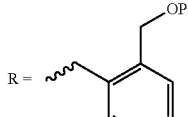
Compounds 107 and 207

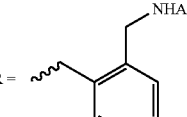
Compounds 108 and 208

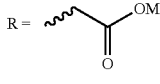
Compounds 109 and 209

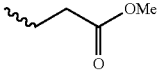
Compounds 110 and 210

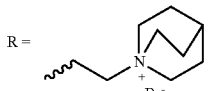
Compounds 111 and 211

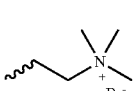
Compounds 112 and 212

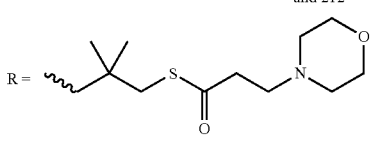
Compounds 113 and 213

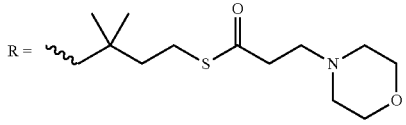
Compounds 114 and 214

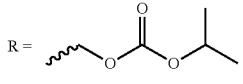
Compounds 115 and 215

BSTFA = N,O-bis(trimethylsilyl)trifluoroacetamide: CF$_3$C=NSi(CH$_3$)$_3$OSi(CH$_3$)$_3$ Compound 100

The synthetic procedure for Di-DMTr H-phosphonate TT dimer (100) has been previously described described (Froehler, Brian C.; Ng, Peter G.; Matteucci, Mark D., Nucleic Acids Research (1986), 14(13), 5399-5407; Garegg, Per J.; Lindh, Ingvar; Regberg, Tor; Stawinski, Jacek; Stroemberg, Roger; Henrichson, Christina Tetrahedron Letters (1986), 27(34), 4051-4054).

Compound 101

Compound 100, mixture of diastereomers (200 mg, 0.176 mmol) was dissolved in ACN (6 mL) then trimethylsilyl 2,2,2-trifluoro-N-(trimethylsilyl)acetimidate (227 mg, 0.882 mmol) was added. A solution of (Z)—S-4-((2-morpholinoethyl)disulfanyl)but-2-enyl methanesulfonothioate (121 mg, 0.353 mmol) in ACN (2 mL) was then added, over the course of 1 h in 3 approximately equal portions, with monitoring by TLC and HPLC/MS. After 3 h, the resulting solution was partitioned by addition of water. Upon extraction, the organic layer was separated then dried (MgSO$_4$), filtered and reduced in vacuo. Column chromatography gave compound 101 as a white foam, 225 mg, 91%.

$^1$H NMR (399 MHz, CDCl$_3$) δ 9.72 (d, br, 1H), 9.27, (d, br, 1H), 7.53 (dd, J 25.0, 1 Hz, 1H), 7.42, (t, J 7.0 Hz, 2H), 7.37-7.16 (m, 17H), 6.83 (m, 8H), 6.43-6.28 (m, 2H), 5.63-5.42 (m, 2H), 5.21 (q, J 7.1 Hz, 1H), 4.27 (m, br, 1H), 3.94 (m, br, 2H), 3.77 (m, 12H), 3.74-3.60 (m, 6H), 3.51-3.22 (m, 5H), 2.82-2.76 (m, 2H), 2.68-2.60 (m, 2H), 2.59-2.46 (m, 5H), 2.44-2.33 (m, 2H), 2.03-1.88 (m, 1H), 1.84 (m, 3H), 1.75-1.66 (m, 1H), 1.48-1.32 (dd, J 11.8, 1.2 Hz, 3H); $^{13}$C NMR (100 MHz, CDCl$_3$) δ 164.10, 164.07, 164.00, 163.94, 159.14, 159.10, 150.80, 150.78, 150.75, 150.63, 145.09, 144.30, 144.27, 136.31, 136.27, 136.22, 136.18, 135.95, 135.82, 135.43, 135.35, 135.33, 135.24, 135.22, 130.52, 130.43, 130.40, 129.49, 129.30, 128.54, 128.43, 128.39, 127.64, 127.57, 113.78, 113.76, 113.73, 113.67, 112.05, 111.56, 87.77, 87.66, 87.58, 85.77, 85.59, 84.63, 84.51, 74.42, 74.33, 67.02, 66.95, 63.63, 63.49, 58.27, 58.23, 55.60, 55.58, 53.69, 53.62, 39.48, 39.26, 39.18, 35.88, 35.61, 35.43, 35.36, 28.18, 12.83, 12.79, 12.02, 11.95.; $^{31}$P NMR (162 MHz, CDCl$_3$) δ 29.25, 29.12; MS (ESI+ve): calc (M+H): 1398.46, found: 1398.64. R$_f$=0.4 (5% MeOH/DCM).

Compound 201

Compound 101 (0.150 g, 0.107 mmol) was stirred with 3% TCA/DCM (10 mL) over 10 min. TLC and HPLC/MS showed that the reaction was complete. 10 mL of MeOH was added and stirring continued for 2 min. Solvents were evaporated and the residue was purified by column chromatography to give compound 201 (85 mg, 100%) as a white solid.

$^1$H NMR (399 MHz, CD$_3$OD) δ 7.78 (dd, J=7.2, 1.3 Hz, 1H), 7.53 (d, J=1.3 Hz, 1H), 6.33-6.27 (m, 2H), 5.83-5.70 (m, 2H), 5.25-5.19 (m, 1H), 4.47-4.30 (m, 3H), 4.27-4.22 (m, 1H), 4.11-4.05 (m, 1H), 3.89-3.82 (t, J=4.8 Hz, 4H), 3.85 (m, 2H), 3.76-3.70 (ddd, J=15.5, 7.2, 1.7 Hz, 2H), 3.52 (dd, J=7.3, 3.7 Hz, 2H), 3.28-3.19 (br, 2H), 3.16-3.05 (br, 4H), 3.05-2.98 (ddd, J=9.8, 5.5, 2.0 Hz, 2H), 2.62-2.52 (tdd, J=11.5, 5.7, 1.9 Hz, 1H), 2.47-2.36 (m, 1H), 2.33-2.28 (m, 2H), 1.92-1.87 (m, 6H); $^{31}$P NMR (162 MHz, CD$_3$OD) δ 30.22, 30.19; MS (ESI+ve): calc (M+H): 794.20, found: 794.18. R$_f$=0.3 (10% MeOH/DCM).

Compound 102

Compound 100 (400 mg, 0.352 mmol) was converted to compound 102 by a procedure analogous to that described for compound 101 (417 mg, 90%).

$^1$H NMR (399 MHz, CDCl$_3$) δ 9.17 (d, J=6.0 Hz, 1H), 9.13-9.00 (d, J=25.7 Hz, 1H), 7.58-7.49 (dd, J=26.3, 1.5 Hz,

1H), 7.45-7.40 (ddd, J=8.0, 5.2, 1.3 Hz, 2H), 7.40-7.18 (m, 17H), 6.87-6.81 (m, 8H), 6.44-6.30 (m, 2H), 5.65-5.53 (m, 1H), 5.53-5.44 (m, 1H), 5.26-5.16 (quintet, J=6.4 Hz, 1H), 4.61-4.54 (m, 2H), 4.30-4.24 (m, 1H), 4.19-4.13 (m, 1H), 3.97-3.88 (m, 2H), 3.80-3.72 (m, 12H), 3.69-3.57 (m, 1H), 3.54-3.30 (m, 5H), 2.61-2.49 (dt, J=14.4, 5.4 Hz, 1H), 2.44-2.32 (m, 1H), 2.02-1.91 (dt, J=12.5, 5.4 Hz, 1H), 1.85-1.80 (dd, J=5.0, 1.3 Hz, 3H), 1.76-1.63 (m, 1H), 1.43-1.36 (dd, J=10.2, 1.2 Hz, 3H), 1.19-1.14 (d, J=2.0 Hz, 8H); $^{13}$C NMR (100 MHz, CDCl$_3$) δ 178.22, 178.17, 163.82, 163.80, 163.75, 158.92, 158.88, 150.52, 150.43, 144.90, 144.88, 144.10, 144.05, 136.11, 136.08, 136.05, 136.01, 135.59, 135.28, 135.16, 135.03, 135.01, 130.30, 130.23, 130.19, 130.16, 128.69, 128.64, 128.59, 128.39, 128.34, 128.23, 128.21, 128.17, 127.42, 127.34, 113.54, 113.45, 111.85, 111.82, 111.41, 111.36, 87.59, 87.43, 87.37, 85.47, 85.33, 84.43, 84.29, 84.08, 84.00, 83.92, 74.24, 67.36, 63.38, 63.26, 59.42, 55.37, 39.22, 38.77, 27.94, 27.24, 12.57, 11.80, 11.74; $^{31}$P NMR (162 MHz, CDCl$_3$) δ 29.23, 28.97; MS (ESI+ve): calc (M+H): 1338.51, found: 1338.84. R$_f$=0.5 (5% MeOH/DCM).

Compound 202

Compound 102 (200 mg, 0.151 mmol) was converted to compound 202 by a procedure analogous to that described for compound 101 (105 mg, 97%).
$^1$H NMR (399 MHz, CD$_3$OD) δ 7.81-7.75 (dd, J=8.2, 1.3 Hz, 1H), 7.57-7.51 (dd, J=8.2, 1.3 Hz, 1H), 6.33-6.23 (m, 2H), 5.85-5.75 (m, 1H), 5.75-5.66 (m, 1H), 5.26-5.19 (m, 1H), 4.72-4.66 (m, 2H), 4.47-4.30 (m, 3H), 4.27-4.20 (m, 1H), 4.11-4.04 (m, 1H), 3.83-3.76 (m, 2H), 3.74-3.64 (m, 2H), 2.62-2.51 (m, 1H), 2.45-2.35 (td, J=8.7, 6.5 Hz, 1H), 2.32-2.24 (m, 2H), 1.93-1.82 (m, 6H), 1.20-1.15 (d, J=2.1 Hz, 9H); $^{13}$C NMR (126 MHz, CD$_3$OD) δ 179.65, 166.28, 152.30, 152.28, 152.22, 137.90, 137.81, 137.79, 130.07, 130.04, 129.26, 129.24, 111.93, 111.88, 111.87, 87.26, 87.22, 86.96, 86.90, 86.76, 86.54, 86.12, 86.07, 85.98, 85.92, 85.88, 85.82, 80.54, 80.49, 80.46, 80.41, 71.84, 71.67, 68.71, 68.66, 68.45, 68.40, 62.58, 62.50, 60.72, 40.51, 40.44, 39.70, 39.52, 39.48, 28.67, 28.64, 28.61, 27.53, 12.64, 12.48; $^{31}$P NMR (162 MHz, CDCl$_3$) δ 29.23, 28.97; MS (ESI+ve): calc (M+H): 717.22, found: 717.23. R$_f$=0.5 (10% MeOH/DCM).

Compound 103

Compound 100 (400 mg, 0.352 mmol) was converted to compound 103 by a procedure analogous to that described for compound 101 (379 mg, 83%).
$^1$H NMR (399 MHz, CDCl$_3$) δ 9.48 (s, 1H), 9.41-9.29 (m, 1H), 7.60-7.48 (dd, J=9.0, 1.0 Hz, 1H), 7.46-7.40 (dt, J=6.9, 1.2 Hz, 2H), 7.39-7.17 (m, 17H), 6.89-6.79 (m, 8H), 6.44-6.31 (m, 2H), 5.27-5.20 (t, J=6.5 Hz, 1H), 4.30-4.24 (t, J=6.1 Hz, 1H), 4.19-4.15 (m, 2H), 4.13-4.07 (t, J=7.1 Hz, 1H), 3.99-3.90 (m, 2H), 3.79-3.74 (m, 12H), 3.70-3.58 (m, 1H), 3.51-3.43 (td, J=8.8, 7.2, 2.3 Hz, 1H), 3.40-3.32 (m, 1H), 3.02-2.85 (m, 2H), 2.61-2.49 (dt, J=18.5, 7.0 Hz, 1H), 2.47-2.33 (m, 1H), 1.98-1.90 (dt, J=10.2, 5.0 Hz, 1H), 1.85-1.81 (m, 3H), 1.74-1.62 (td, J=14.2, 7.1 Hz, 1H), 1.42-1.36 (m, 3H), 1.19-1.13 (d, J=4.9 Hz, 9H); $^{31}$P NMR (162 MHz, CDCl$_3$) δ 29.36, 29.18; $^{13}$C NMR (126 MHz, CDCl$_3$) δ 177.97, 177.89, 163.94, 163.91, 163.90, 163.86, 158.91, 158.87, 150.63, 150.54, 150.53, 150.50, 144.88, 144.85, 144.10, 144.04, 136.09, 135.99, 135.52, 135.50, 135.24, 135.16, 135.12, 135.04, 135.00, 130.31, 130.29, 130.20, 130.16, 130.13, 128.34, 128.20, 128.18, 128.14, 127.39, 127.31, 124.89, 113.55, 113.52, 113.43, 111.84, 111.38, 87.58, 87.42, 87.36, 85.30, 84.98, 84.95, 84.40, 84.33, 84.27, 83.98, 83.91, 83.84, 79.31, 79.27, 78.88, 78.84, 74.16, 74.08, 67.56, 67.50, 67.46, 67.41, 63.33, 63.24, 62.79, 62.75, 55.34, 39.21, 39.16, 39.04, 39.00, 38.85, 38.82, 29.95, 29.92, 29.66, 29.63, 27.17, 12.53, 11.80, 11.72; MS (ESI+ve): calc (M+H): 1312.69, found: 1312.49. R$_f$=0.4 (5% MeOH/DCM).

Compound 203

Compound 103 (200 mg, 0.154 mmol) was converted to compound 203 by a procedure analogous to that described for compound 201 (103 mg, 98%).
$^1$H NMR (399 MHz, CD$_3$OD) δ 7.80-7.76 (dd, J=8.2, 1.2 Hz, 1H), 7.55-7.51 (dd, 7.1, 1.2 Hz, 1H), 6.32-6.24 (m, 2H), 5.26-5.19 (m, 1H), 4.46-4.20 (m, 6H), 4.10-4.05 (m, 1H), 3.82-3.78 (dd, J=6.5, 3.2 Hz, 2H), 3.22-3.14 (ddd, J=16.6, 7.0, 5.8 Hz, 2H), 2.61-2.51 (tdd, J=13.0, 5.9, 2.1 Hz, 1H), 2.46-2.37 (ddd, J=14.3, 8.3, 6.0 Hz, 1H), 2.31-2.26 (t, J=5.8 Hz, 2H), 1.91-1.86 (dt, J=11.0, 1.2 Hz, 6H), 1.21-1.17 (m, 9H); $^{31}$P NMR (162 MHz, CD$_3$OD) δ 30.15; $^{13}$C NMR (100 MHz, CD$_3$OD) δ 179.45, 179.42, 166.29, 152.31, 152.29, 152.23, 137.82, 137.80, 137.78, 111.91, 111.88, 87.21, 87.17, 86.94, 86.87, 86.63, 86.52, 86.11, 86.06, 85.92, 85.84, 85.77, 80.67, 80.60, 80.49, 80.43, 71.79, 71.64, 68.80, 68.74, 68.58, 68.52, 64.11, 64.07, 64.02, 62.54, 62.44, 40.48, 40.43, 39.81, 39.71, 39.68, 39.52, 39.47, 30.74, 30.72, 30.68, 27.52, 12.65, 12.50; MS (ESI+ve): calc (M+H): 691.21, found: 691.09. R$_f$=0.5 (10% MeOH/DCM).

Compound 104

Compound 100 (400 mg, 0.352 mmol) was converted to compound 104 by a procedure analogous to that described for compound 101 (451 mg, 94%).
$^1$H NMR (399 MHz, CDCl$_3$) δ 9.17-9.01 (m, 2H), 7.51-7.46 (dd, J 7.8, 1.5 Hz, 1H), 7.45-7.38 (m, 2H), 7.37-7.09 (m, 19H), 7.01-6.90 (m, 2H), 6.87-6.78 (m, 8H), 6.39-6.27 (m, 2H), 5.15-5.01 (m, 1H), 4.20-4.13 (m, 1H), 3.96-3.90 (m, 1H), 3.90-3.83 (m, 2H), 3.80-3.68 (m, 14H), 3.52-3.20 (m, 3H), 2.45-2.16 (m, 2H), 2.01-1.88 (ddd, J 23.3, 13.6, 5.6 Hz, 1H), 1.85-1.79 (dd, J 9.3, 1.2 Hz, 3H), 1.69-1.53 (m, 1H), 1.40-1.31 (m, 12H); $^{13}$C NMR (100 MHz, CDCl$_3$) δ 176.46, 176.37, 163.84, 163.78, 158.90, 158.87, 150.52, 150.50, 150.43, 149.38, 149.28, 144.95, 144.88, 144.16, 144.10, 136.13, 136.11, 136.09, 136.03, 135.57, 135.49, 135.37, 135.26, 135.21, 135.08, 135.04, 130.83, 130.74, 130.29, 130.21, 130.16, 129.51, 129.49, 129.40, 129.36, 129.35, 129.31, 128.38, 128.35, 128.27, 128.23, 128.19, 128.14, 127.39, 127.33, 126.05, 125.94, 122.94, 122.86, 113.53, 113.42, 111.77, 111.73, 111.39, 111.28, 87.55, 87.52, 87.37, 87.32, 85.33, 84.95, 84.90, 84.29, 84.20, 84.00, 83.92, 83.87, 83.79, 79.05, 79.00, 74.29, 74.24, 67.31, 67.24, 67.17, 67.11, 63.37, 55.37, 55.35, 39.37, 39.32, 39.15, 39.10, 38.64, 30.51, 30.41, 30.36, 27.28, 27.24, 12.59, 12.51, 11.75, 11.67; $^{31}$P NMR (162 MHz, CDCl$_3$) δ 29.12, 28.49; MS (ESI+ve): calc (M+NH$_4$): 1374.51, found: 1374.74. R$_f$=0.4 (5% MeOH/DCM).

Compound 204

Compound 104 (200 mg, 0.147 mmol) was converted to compound 204 by a procedure analogous to that described for compound 201 (98 mg, 88%).
$^1$H NMR (399 MHz, CD$_3$OD) δ 7.77-7.73 (m, 1H), 7.51-7.43 (m, 2H), 7.38-7.31 (m, 1H), 7.25-7.19 (ddd, J=9.2, 5.4, 1.6 Hz, 1H), 7.08-7.02 (ddd, J=8.0, 3.8, 1.3 Hz, 1H), 6.28-6.17 (m, 2H), 5.10-5.01 (m, 1H), 4.30-4.16 (m, 3H), 4.11-4.03 (m, 3H), 4.03-3.97 (d, J=5.3 Hz, 2H), 3.74-3.63 (m, 2H), 2.48-2.11 (m, 5H), 1.90-1.82 (m, 6H), 1.43-1.36 (d, J=3.4 Hz, 9H); $^{13}$C NMR (100 MHz, CD$_3$OD) δ 178.05, 166.26, 152.25, 152.19, 150.78, 137.80, 137.76, 132.13, 132.09, 130.61, 130.56, 127.24, 124.10, 111.92, 111.84, 111.79, 87.14, 87.09, 86.80, 86.71, 86.50, 85.98, 85.95, 85.92, 85.87, 85.83, 85.75, 80.55, 80.48, 80.32, 80.27, 71.97, 71.73, 68.67, 68.61, 68.35, 68.29, 62.51, 62.42, 40.41, 40.36, 40.32, 39.66, 39.64, 39.35, 39.29, 31.08, 31.04, 27.61, 12.68, 12.65, 12.49; $^{31}$P NMR (162 MHz, CD$_3$OD) δ 29.54, 29.29; MS (ESI+ve): calc (M+H): 753.22, found: 753.12. R$_f$=0.5 (10% MeOH/DCM).

Compound 105

Compound 100 (200 mg, 0.176 mmol) was converted to compound 105 by using compound 14 in a procedure analogous to that described for compound 101 (158 mg, 70%).

$^1$H NMR (400 MHz, CDCl$_3$) δ 7.46-7.39 (m, 2H) 7.38-7.16 (m, 18H), 6.90-6.77 (m, 8H), 6.43-6.27 (m, 1H), 5.39-5.18 (m, 2H), 4.31-4.23 (dd, J=12.0, 6.2 Hz, 1H), 4.20-4.12 (m, 1H), 3.98-3.86 (m, 1H), 3.82-3.70 (m, 12H), 3.69-3.52 (m, 1H), 3.50-3.43 (td, J=9.9, 8.9, 2.7 Hz, 1H), 3.41-3.29 (ddd, J=17.2, 10.8, 2.5 Hz, 1H), 2.59-2.49 (m, 1H), 2.44-2.30 (m, 1H), 2.03-1.93 (m, 1H), 1.86-1.79 (d, J=2.9 Hz, 3H), 1.75-1.67 (m, 4H), 1.43-1.36 (d, 3H), 1.16-1.08 (d, J=9.3 Hz, 9H); $^{31}$P NMR (162 MHz, CDCl$_3$) δ 28.14, 27.81 (two diastereomers). MS (ESI+ve): calc (M+H): 1281.4, found: 1281.1 (M+H)$^+$ and 1298.6 (M+NH$_4$)$^+$ Compound 205

Compound 105 (137 mg, 0.107 mmol) was converted to compound 205 by a procedure analogous to that described for compound 201 (66 mg, 91%). $^1$H NMR (399 MHz, CD$_3$OD) δ 7.83-7.76 (m, 1H), 7.56-7.50 (m, 1H), 6.34-6.22 (m, 2H), 5.51-5.43 (m, H), 5.28-5.20 (qt, J=7.8, 1.8 Hz, 1H), 4.47-4.31 (m, 3H), 4.29-4.21 (m, 1H), 4.10-4.05 (m, 1H), 3.87-3.73 (dd, J=7.6, 3.1 Hz, 2H), 2.62-2.50 (tdd, J=16.9, 5.7, 1.9 Hz, 1H), 2.45-2.36 (m, 1H), 2.32-2.25 (ddd, J=6.9, 5.4, 1.5 Hz, 3H), 1.92-1.84 (m, 6H), 1.22-1.18 (d, J=5.3 Hz, 9H); $^{31}$P NMR (162 MHz, CD$_3$OD) δ 28.71, 28.42 (two diastereomers). MS (ESI+ve): calc (M+H): 677.2, found: 677.2 (M+H)$^+$, 694.2 (M+NH$_4$)$^+$ Compound 106

Compound 100 (405 mg, 0.357 mmol) was converted to compound 106 by using compound 19 and following a procedure analogous to that described for compound 101 (0.35 g, 71%). $^1$H NMR (399 MHz, CDCl$_3$) δ 9.97-9.42 (m, 2H), 7.58-7.47 (m, 1H), 7.46-7.39 (m, 2H), 7.39-7.13 (m, 17H), 6.87-6.78 (m, 8H), 6.44-6.29 (dtd, J=20.4, 9.2, 4.7 Hz, 2H), 5.27-5.16 (dt, J=14.7, 7.3 Hz, 1H), 4.30-4.22 (m, 1H), 4.22-4.12 (m, 1H), 4.02-3.90 (q, J=3.8, 3.4 Hz, 2H), 3.80-3.73 (m, 12H), 3.72-3.65 (m, 5H), 3.51-3.43 (m, 1H), 3.40-3.31 (m, 1H), 3.14-2.93 (m, 2H), 2.85-2.72 (m, 4H), 2.67-2.59 (m, 2H), 2.57-2.34 (m, 6H), 1.97-1.87 (td, J=13.7, 13.1, 5.7 Hz, 1H), 1.84 (s, 3H), 1.73-1.61 (td, J=14.1, 6.8 Hz, 1H), 1.42-1.37 (d, J=6.7 Hz, 3H); $^{13}$C NMR (100 MHz, CDCl$_3$) δ 163.97, 163.94, 163.91, 158.88, 158.84, 150.64, 150.60, 150.52, 144.86, 144.83, 144.09, 144.04, 136.06, 136.04, 135.95, 135.93, 135.54, 135.19, 135.09, 135.03, 134.99, 130.28, 130.17, 130.13, 128.29, 128.17, 128.14, 127.38, 127.31, 113.51, 113.42, 111.82, 111.79, 111.44, 111.38, 87.53, 87.38, 87.33, 85.29, 85.26, 84.89, 84.85, 84.41, 84.36, 84.29, 84.25, 83.88, 83.85, 83.80, 83.76, 79.28, 79.23, 78.72, 78.67, 74.04, 67.53, 67.46, 67.37, 67.29, 66.77, 63.33, 63.21, 57.84, 55.34, 53.41, 53.34, 39.23, 39.09, 39.01, 38.92, 38.55, 38.51, 38.46, 38.42, 35.64, 35.59, 30.35, 30.30, 30.26, 12.60, 11.79, 11.74; $^{31}$P NMR (162 MHz, CDCl$_3$) δ 29.30, 29.14; MS (ESI+ve): calc (M+H): 1372.44, found: 1372.79. R$_f$=0.4 (5% MeOH/DCM).

Compound 206

Compound 106 (200 mg, 0.146 mmol) was converted to compound 206 by a procedure analogous to that described for compound 201 (110 mg, 98%). $^1$H NMR (399 MHz, CD$_3$OD) δ 7.83-7.75 (dd, J=7.6, 1.4 Hz, 1H), 7.56-7.48 (d, J=1.6 Hz, 1H), 6.35-6.23 (m, 2H), 5.27-5.20 (m, 1H), 4.48-4.31 (m, 3H), 4.28-4.21 (dd, J=9.7, 2.1 Hz, 1H), 4.11-4.04 (t, J=4.0 Hz, 1H), 3.97-3.84 (br, 4H), 3.83-3.77 (dd, J=6.0, 3.2 Hz, 2H), 3.43-3.36 (m, 2H), 3.29-3.18 (m, 6H), 3.11-3.00 (m, 4H), 2.62-2.51 (tdd, J=11.7, 5.7, 1.7 Hz, 1H), 2.47-2.38 (ddd, J=14.3, 8.4, 6.0 Hz, 1H), 2.38-2.25 (q, J=5.3, 4.8 Hz, 2H), 1.91 (s, 3H), 1.88 (s, 3H); $^{31}$P NMR (162 MHz, CD$_3$OD) δ 30.19, 30.12; $^{13}$C NMR (100 MHz, CD$_3$OD) δ 166.28, 166.24, 166.23, 152.32, 152.27, 152.24, 138.05, 138.00, 137.77, 137.75, 112.08, 112.03, 111.97, 111.94, 87.28, 87.24, 87.01, 86.96, 86.62, 86.51, 86.10, 86.06, 85.76, 85.68, 71.73, 71.51, 68.91, 68.58, 68.51, 65.44, 62.60, 62.50, 57.50, 53.50, 40.25, 40.16, 39.64, 39.57, 39.20, 39.16, 39.06, 32.56, 32.55, 31.04, 31.00, 12.73, 12.69, 12.52; MS (ESI+ve): calc (M+H): 768.18, found: 768.14. R$_f$=0.3 (10% MeOH/DCM).

Compound 107

Using compound 22 in place of compound 5, compound 100 is converted to compound 107 by a procedure analogous to that described for compound 101.

Compound 207

Compound 107 is converted to compound 207 by a procedure analogous to that described for compound 201.

Compound 108

Using compound 25 in place of compound 5, compound 100 is converted to compound 108 by a procedure analogous to that described for compound 101.

Compound 208

Compound 108 is converted to compound 208 by a procedure analogous to that described for compound 201.

Compound 109

Using compound 27 in place of compound 5, compound 100 is converted to compound 109 by a procedure analogous to that described for compound 101.

Compound 209

Compound 109 is converted to compound 209 by a procedure analogous to that described for compound 201.

Compound 110

Using compound 29 in place of compound 5, compound 100 is converted to compound 110 by a procedure analogous to that described for compound 101.

Compound 210

Compound 110 is converted to compound 210 by a procedure analogous to that described for compound 201.

Compound 111

Using compound 31 in place of compound 5, compound 100 is converted to compound 111 by a procedure analogous to that described for compound 101.

Compound 211

Compound 111 is converted to compound 211 by a procedure analogous to that described for compound 201.

Compound 112

Using compound 33 in place of compound 5, compound 100 is converted to compound 112 by a procedure analogous to that described for compound 101.

Compound 212

Compound 112 is converted to compound 212 by a procedure analogous to that described for compound 201.

Compound 113

Using compound 38 in place of compound 5, compound 100 is converted to compound 113 by a procedure analogous to that described for compound 101.

Compound 213

Compound 113 is converted to compound 213 by a procedure analogous to that described for compound 201.

Compound 114

Using compound 41 in place of compound 5, compound 100 is converted to compound 114 by a procedure analogous to that described for compound 101.

Compound 214

Compound 114 is converted to compound 214 by a procedure analogous to that described for compound 201.

Compound 115

Using compound 43 in place of compound 5, compound 100 is converted to compound 115 by a procedure analogous to that described for compound 101.

Compound 215

Compound 115 is converted to compound 215 by a procedure analogous to that described for compound 201.

Example 3—Alternative Synthesis of Phosphorothiotriesters Using Bis(Methanethiosulfonate) Reagents Scheme 3

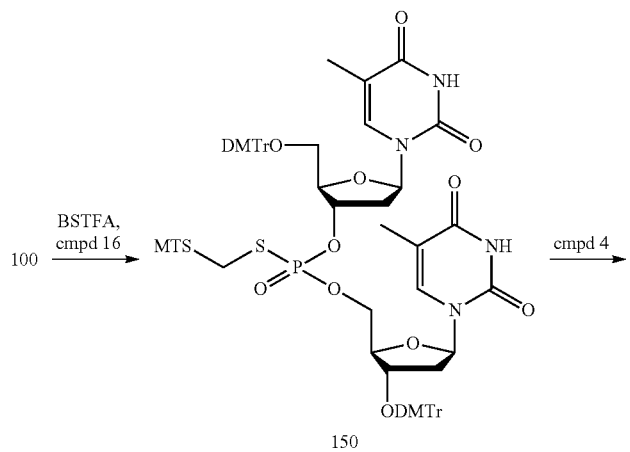

150

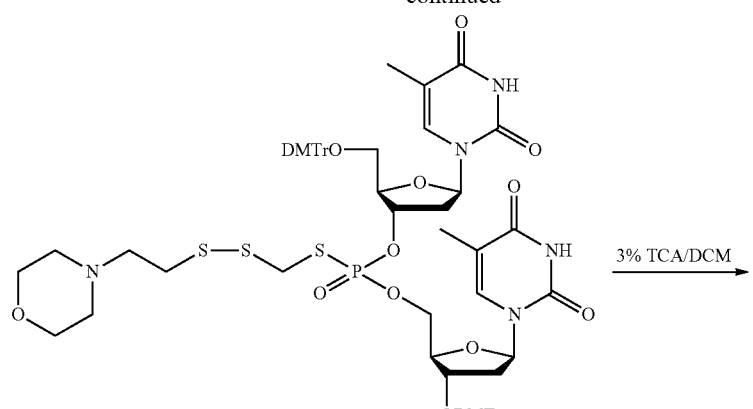
151
3% TCA/DCM →
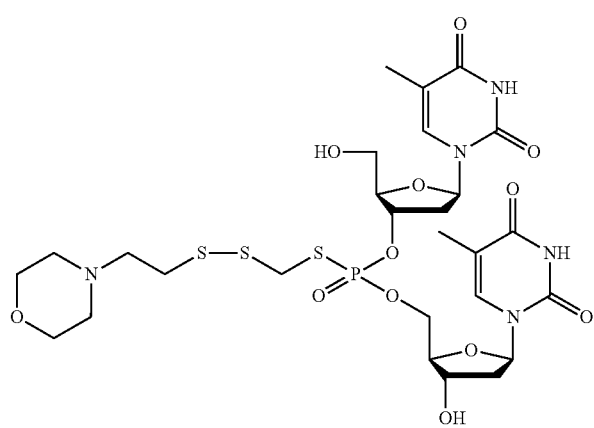
251
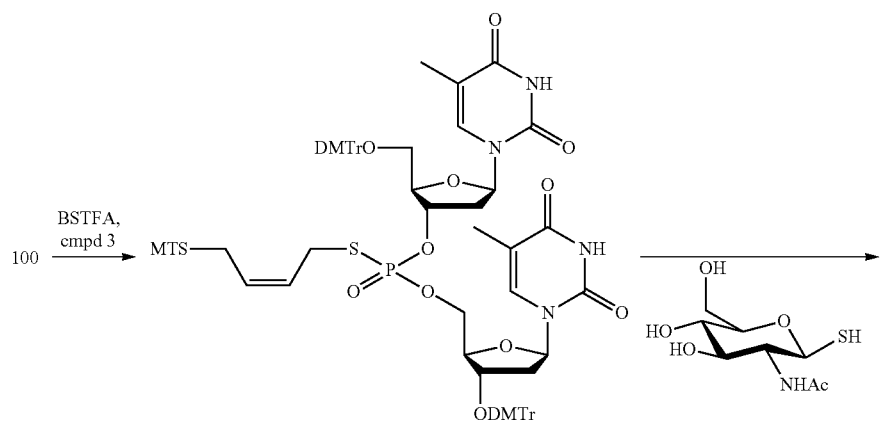
152

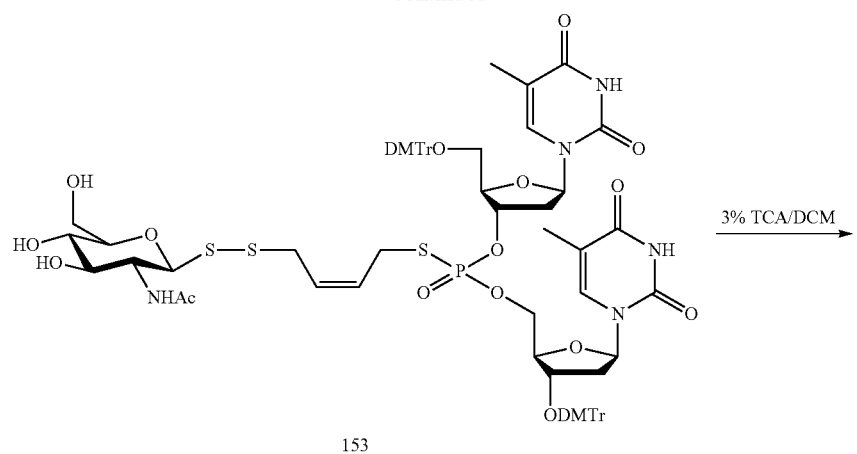
153
3% TCA/DCM →
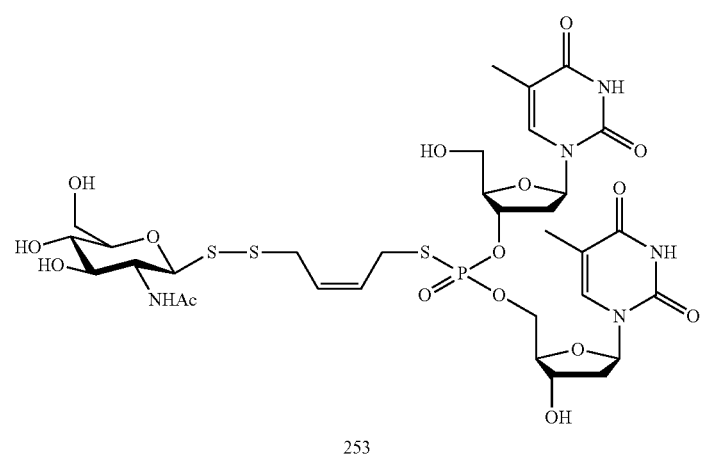
253
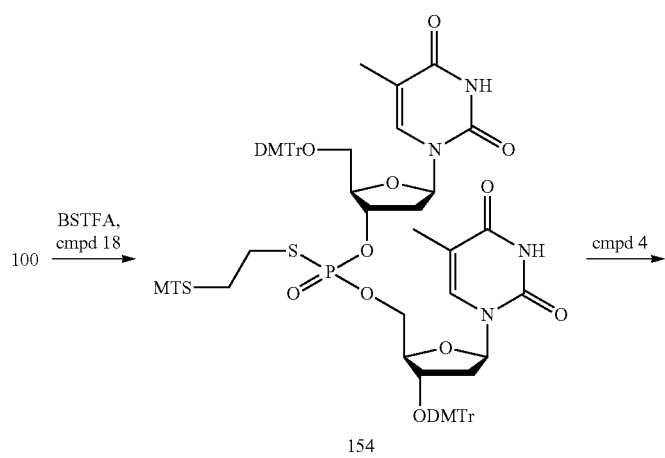
154

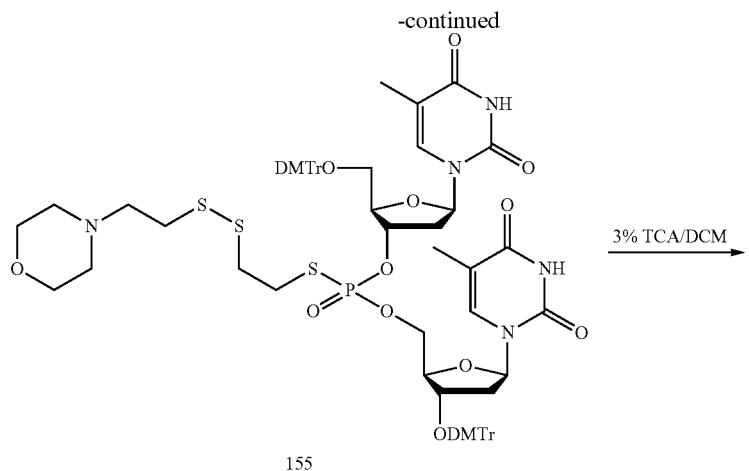

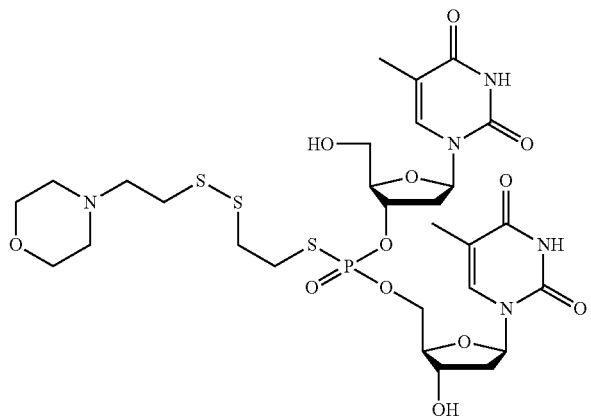

| Compound 150 | Compound 151 |

Compound 100 (300 mg, 0.264 mmol) was converted to compound 150 by a procedure analogous to that described for compound 101 (170 mg, 50%).

$^1$H NMR (399 MHz, CDCl$_3$) δ 9.34-9.30 (s, 1H), 9.28-9.17 (d, J 30.6 Hz, 1H), 7.57-7.47 (m, 1H), 7.47-7.40 (m, 2H), 7.38-7.18 (m, 17H), 7.18-7.07 (d, J 1.4 Hz, 1H), 6.88-6.77 (dd, J 9.0, 1.5 Hz, 8H), 6.44-6.34 (ddd, J 15.6, 8.9, 5.4 Hz, 1H), 6.32-6.21 (ddd, J 18.9, 8.5, 5.9 Hz, 1H), 5.27-5.19 (q, J 5.9 Hz, 1H), 4.46-4.33 (m, 2H), 4.31-4.16 (m, 2H), 4.03-3.91 (m, 2H), 3.81-3.67 (m, 12H), 3.54-3.46 (m, 1H), 3.42-3.34 (m, 1H), 3.34-3.25 (d, J 20.2 Hz, 3H), 2.64-2.53 (td, J 13.4, 5.4 Hz, 1H), 2.47-2.34 (dq, J 19.9, 6.5, 5.9 Hz, 1H), 1.99-1.91 (m, 1H), 1.85-1.80 (t, J 1.5 Hz, 3H), 1.78-1.65 (tt, J 14.1, 7.5 Hz, 1H), 1.44-1.37 (dd, J 7.3, 1.2 Hz, 3H); $^{13}$C NMR (100 MHz, CDCl$_3$) δ 171.27, 163.83, 163.80, 158.95, 158.93, 158.90, 150.64, 150.53, 150.46, 150.38, 144.91, 144.88, 144.09, 144.02, 136.00, 135.98, 135.94, 135.81, 135.11, 135.04, 134.98, 134.97, 130.34, 130.27, 130.20, 128.30, 128.23, 128.20, 127.46, 127.36, 113.59, 113.56, 113.48, 111.95, 111.38, 87.60, 87.47, 87.43, 86.03, 85.83, 84.44, 84.34, 83.81, 79.82, 79.58, 73.99, 73.91, 67.85, 67.78, 63.31, 63.20, 55.39, 51.77, 51.70, 39.16, 38.99, 38.90, 37.21, 37.16, 37.12, 37.05, 12.63, 12.57, 11.85, 11.80; $^{31}$P NMR (162 MHz, CDCl$_3$) δ 26.15, 25.60; MS (ESI+ve): calc (M+H): 1308.37, found: 1308.70. R$_f$=0.5 (5% MeOH/DCM).

A DCM (5 mL) solution of compound 150 (150 mg, 0.116 mmol) was treated with 2-morpholinoethanethiol (17 mg, 0.116 mmol) at r.t. with monitoring by TLC. After 0.5 h, the mixture was washed with NaHCO$_3$, extracting 5× into DCM. The organic extracts were dried (MgSO$_4$), filtered and reduced. Column chromatography gave compound 151 as a colorless solid foam (81 mg, 51%).

$^1$H NMR (399 MHz, CDCl$_3$) δ 9.68-9.54 (m, 1H), 9.44 (s, 1H), 7.59-7.48 (m, 1H), 7.47-7.40 (m, 2H), 7.40-7.13 (m, 17H), 6.90-6.76 (ddd, J=9.3, 4.4, 2.7 Hz, 8H), 6.45-6.27 (m, 2H), 5.32-5.22 (dd, J=8.5, 5.7 Hz, 1H), 4.34-4.25 (m, 1H), 4.23-4.14 (m, 1H), 4.07-3.89 (m, 2H), 3.79-3.74 (m, 12H), 3.74-3.65 (m, 6H), 3.51-3.33 (m, 2H), 2.90-2.79 (dd, J=14.2, 7.6 Hz, 2H), 2.73-2.55 (m, 3H), 2.55-2.34 (m, 6H), 2.02-1.91 (m, 1H), 1.87-1.81 (dd, J=4.9, 1.2 Hz, 3H), 1.77-1.66 (ddd, J=14.2, 8.7, 6.4 Hz, 1H), 1.41-1.35 (dd, J=6.6, 1.2 Hz, 3H); $^{13}$C NMR (100 MHz, CDCl$_3$) δ 163.97, 163.93, 163.88, 158.90, 158.86, 158.71, 150.64, 150.59, 150.53, 150.50, 144.92, 144.88, 144.13, 144.08, 136.11, 136.07, 136.03, 136.00, 135.73, 135.60, 135.22, 135.14, 135.08, 135.04, 135.02, 130.32, 130.30, 130.23, 130.18, 128.33, 128.19, 128.17, 127.39, 127.33, 113.56, 113.52, 113.45, 111.85, 111.82, 111.38, 111.29, 87.56, 87.41, 87.38, 85.71, 85.35, 84.91, 84.38, 84.27, 84.22, 84.05, 83.97, 83.85, 83.78, 79.36, 79.11, 79.05, 74.25, 74.07, 67.39, 66.88, 66.79, 63.27, 57.80, 55.36, 53.55, 53.51, 53.40, 43.06, 40.72, 40.54, 39.25, 39.16, 39.01, 35.91, 12.64, 12.60, 11.78, 11.74; $^{31}$P NMR (162 MHz, CDCl$_3$) δ 27.76, 27.46; MS (ESI+ve): calc (M+H): 1358.43, found: 1358.74. R$_f$=0.4 (5% MeOH/DCM).

75

Compound 251

Compound 151 (75 mg, 0.055 mmol) was converted to compound 251 by a procedure analogous to that described for compound 201 (10 mg, 24%). MS (ESI+ve): calc (M+H): 754.17, found: 754.19. $R_f$=0.3 (10% MeOH/DCM).

Compound 152

Compound 100 is converted to compound 152 by a procedure analogous to that described for compound 101.

76

Compound 153

Using 1-Thio-β-D-glucose tetraacetate in place of compound 4, compound 152 is converted to compound 153 by a procedure analogous to that described for compound 151.

Compound 253

Compound 153 is converted to compound 253 by a procedure analogous to that described for compound 201.

Scheme 4. Synthesis of phosphorothioate triesters on support

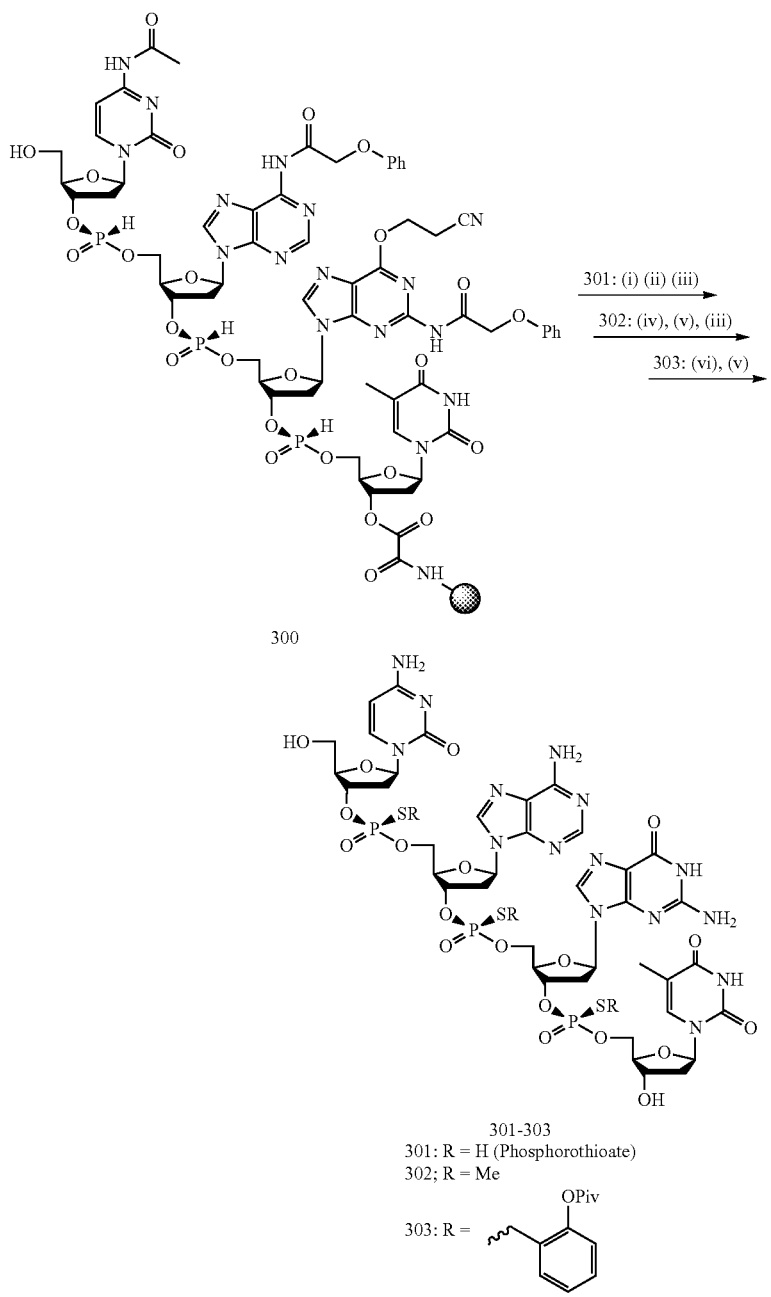

301-303
301: R = H (Phosphorothioate)
302: R = Me
303: R = [2-OPiv phenyl]

(i) Beaucase Reagent, BSA, ACN, (ii) 28% NH3 aq., (iii) NH4OAc (AA) buffer, (iv) MTS—Me, BSTFA, Et3N, ACN, (v) PrNH2, ACN, (vi) Compound 12, BSTFA, ACN,

Compound 154

Compound 100 is converted to compound 154 by a procedure analogous to that described for compound 101.

Compound 155

Compound 154 is converted to compound 155 by a procedure analogous to that described for compound 151.

Compound 255

Compound 155 is converted to compound 255 by a procedure analogous to that described for compound 201.

Example 4—Thioalkylation of H-Phosphonates to Provide Phosphorothiotriesters in Solid Phase

Compound 300

Synthesis of (Rp)-CAGT-H-phosphonate-oxalyl linker-CPG was carried out on an Applied Biosystems 394 DNA/RNA synthesizer according to the reported methods (*Journal of American Chemical Society* 2008, 130, 16031-16037; *Angewandte Chemie International Edition* 2009, 48, 496-499).

Compound 301: (Sp)-CAGT-phosphorothioate (R=H)

(Rp)-CAGT-H-phosphonate-oxalyl linker-CPG was treated by 0.2 M Beaucage Reagent/$CH_3CN$-BSA (9:1, v/v), stirred for 1 h at rt, then washed successively with $CS_2$ and acetonitrile and dried under reduced pressure. The resultant CPG was treated with 2 mL of 28% aqueous $NH_3$ and stirred for 18 h at rt. After removal of $NH_3$ under reduced pressure, the resulting product was analyzed by LC/MS and HPLC.

Compound 302: (Sp)-CAGT-S-methyl phosphorothiotriester (R=Me)

BSTFA (50 μL, 188 μmol) and acetonitrile (500 μL) were added to (Rp)-CAGT-H-phosphonate-oxalyl linker-CPG (14.7 mg, 1 μmol) then the mixture was shaken for 20 min at rt. S-methyl methane sulfonothioate (20 μL, 212 μmol) and $NEt_3$ (50 μL) were added and shaking was continued for 1 h at rt. The CPG was washed with $CH_3CN$ then dried in vacuo. 20% $PrNH_2$ in dry $CH_3CN$ (2 mL) was added to the CPG and the mixture was stirred for 16 h at rt. Solvents were removed under reduced pressure and $CH_3CN$ was added to the mixture. The CPG was removed by filtration and the filtrate was concentrated under reduced pressure. $CH_3CN$/DMSO/0.5 M AA buffer (1:1:1, v/v/v) was added, the mixture was stirred for 16 h at rt, then analyzed by LC/MS and HPLC.

Compound 303

Compound 303 is prepared by sulfurization of compound 300 on support followed by cleavage. ACN (450 μL), BSTFA (50 μL) and compound 12 (20 mg) are added to compound 300 (1 μmol) which is shaken for 18 h. The CPG is collected by filtration resuspended in 20% $PrNH_2$ in dry $CH_3CN$ (2 mL) and shaken for 16 h at rt. Solvents were removed under reduced pressure and the residue is purified by RPHPLC to provide pure compound 303.

Example 5—Thioalkylation of H-Phosphonates to Provide Phosphorothiotriesters in Solution Phase Scheme 5. Synthesis of phosphorothioate triesters in solution.

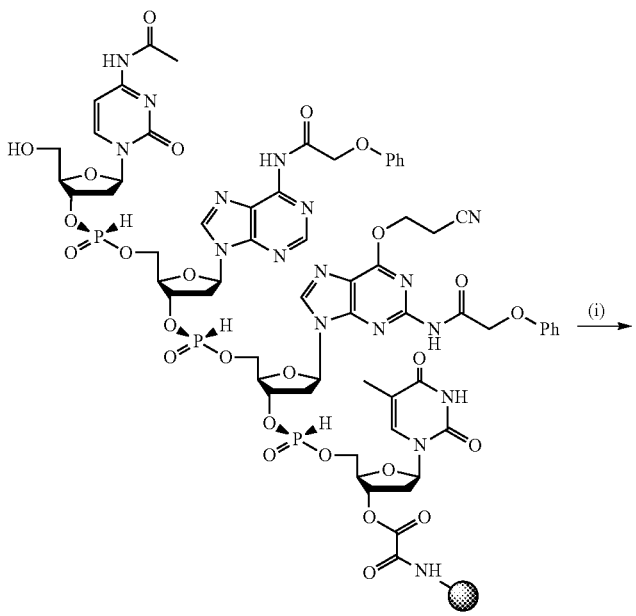

300

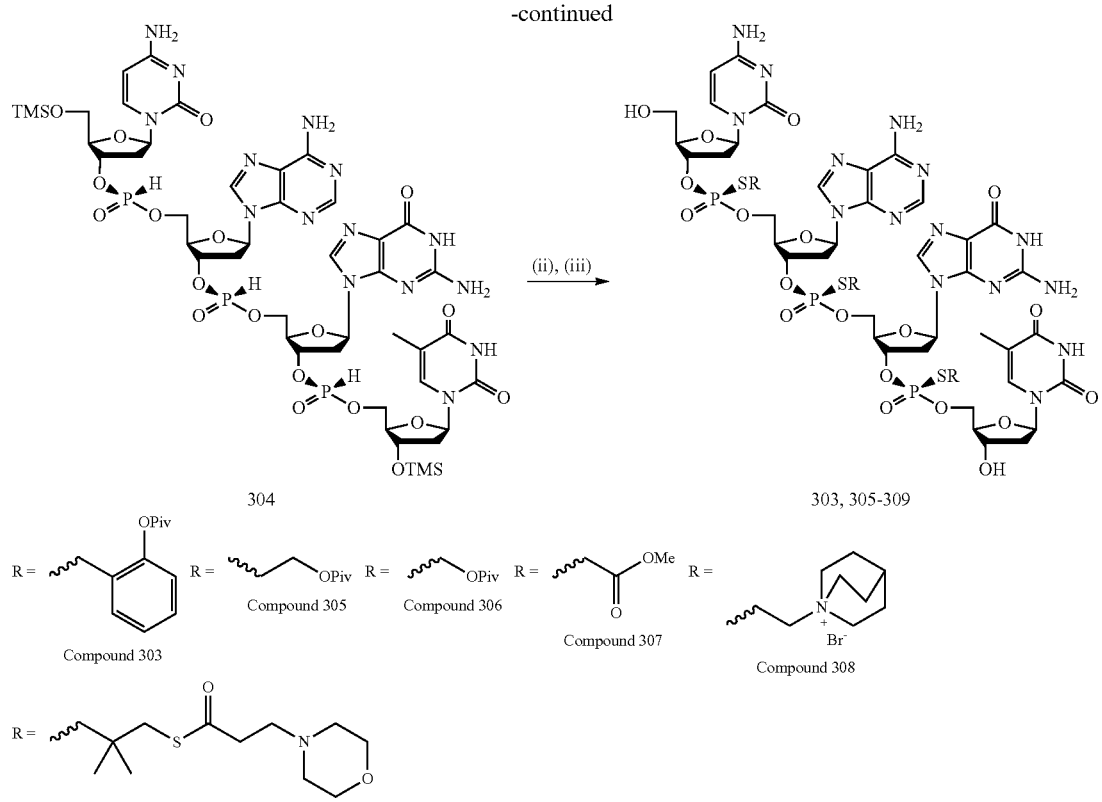

(i) 2:1:2 v/v/v ACN:BSTFA:PRNH2, 18 h rt, (ii) Pyridine, BSTFA, R—MTS, rt, (iii) 1:1 v/v MeOH:0.5M TEAA, 18 h rt.

Compound 305

Compound 300 (0.5 μmol) was taken up in ACN (125 μL) then BSTFA (62 μL) was added and the mixture was shaken for 20 min. PrNH$_2$ (125 μL) was added and the vial was rotated for 18 h. After filtration and washing with 1 mL ACN, the solvent was removed in vacuo and the residue was co-evaporated 3× with toluene to provide crude compound 304. The residue was redissolved in pyridine (375 μL) and treated with BSTFA for (16 Cl, 60.0 μmol) followed by compound 9 (7.2 mg, 30.0 μmol) with stirring under Ar. After 2 h at r.t. the solvent was removed and the residue was treated with MeOH (0.125 mL) for 1 h, then AA (0.5 M, 0.125 mL) was added and the mixture was stirred at r.t. for 2 h. The product was purified by RPHPLC to provide compound 305.

Compound 303

Substituting compound 12 for compound 9, compound 303 was prepared by a procedure analogous to that described for compound 305.

Compound 306

Substituting compound 12 for compound 14, compound 306 was prepared by a procedure analogous to that described for compound 305.

Compound 307

Substituting compound 12 for compound 29, compound 307 is prepared by a procedure analogous to that described for compound 305.

Compound 308

Substituting compound 12 for compound 31, compound 308 is prepared by a procedure analogous to that described for compound 305.

Compound 309

Substituting compound 12 for compound 38, compound 309 is prepared by a procedure analogous to that described for compound 305.

Example 6—Stereoselective Thioalkylation of H-Phosphanates

Objective: To demonstrate that the reaction of MTS reagents to H-phosphonate to generate phosphorothio triester is stereospecific. $^{31}$P NMR was used to trace the changes during the course of the reaction.

Scheme 5

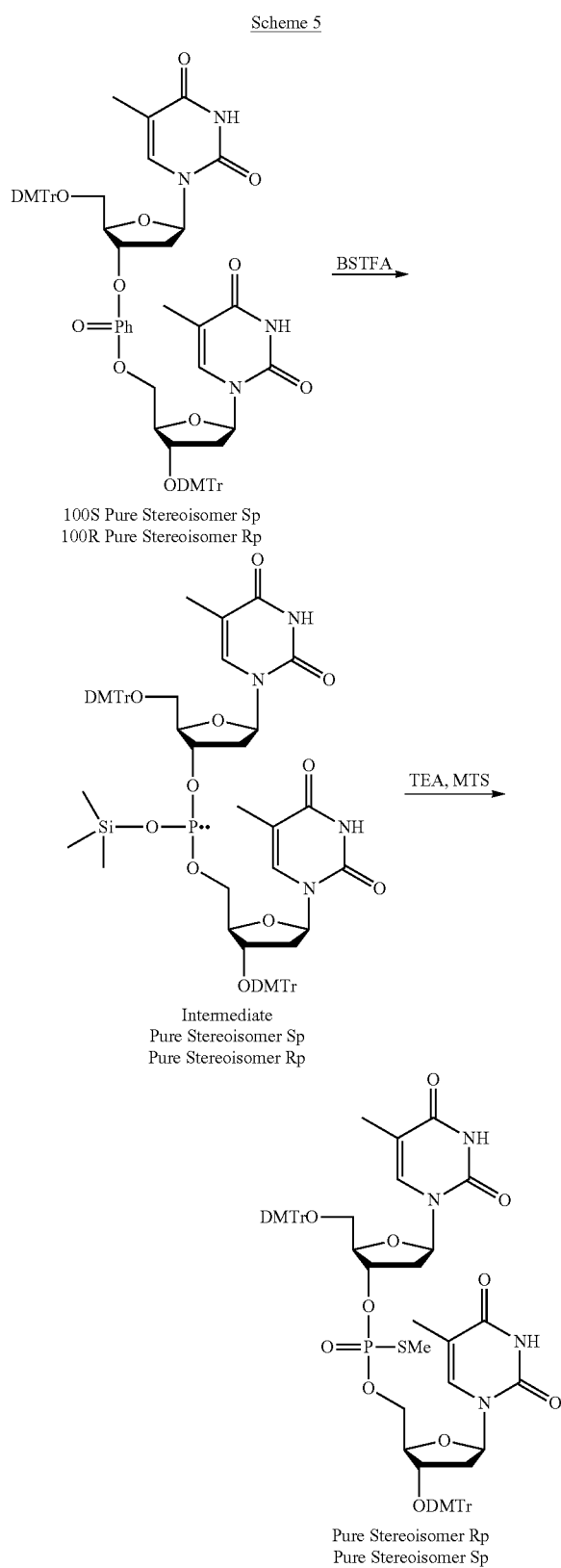

100S Pure Stereoisomer Sp
100R Pure Stereoisomer Rp

Intermediate
Pure Stereoisomer Sp
Pure Stereoisomer Rp

Pure Stereoisomer Rp
Pure Stereoisomer Sp

Experimental procedure: In an NMR tube was added compound 100S 5'-O-(4,4'-dimethoxytrityl)thymidin-3'-yl 3'-O-(4,4'-dimethoxytrityl)thymidin-5'-yl H-phosphonate (20 mg, 18 μmol) in 0.8 mL CD$_3$CN and the $^{31}$P NMR spectrum was recorded. BSTFA (17 μL, 176 μmol) was added to same NMR tube and after 5 min $^{31}$P NMR spectrum was recorded again. Triethylamine (49 μL, 352 μmol) and S-methyl methanethiosulfonate (22 μL, 88 μmol) were added to same NMR tube and $^{31}$P NMR spectrum was recorded immediately.

The same procedure was repeated for Rp isomer (compound 100R). The $^{31}$P NMR spectrum recorded for the starting material, intermediate and the product show that the stereochemistry at phosphorus atom is retained during the reaction.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A thiosulfonate compound of structure IIa:

Structure IIa wherein,
X is alkyl, cycloalkyl, or heteroaryl;
R is —R$^1$-R$^2$;
R$^1$ is selected from alkenylenyl-S—, -alkylenyl-S—, -alkylenyl-aryl-alkylenyl-S—, -alkylenyl-aryl-CO—S— and alkylenyl-aryl-alkylenyl-CO—S—; and
R$^2$ is selected from —S-alkylenyl-heterocyclo, —S-alkenylenyl-heterocyclo, —S-aminoalkyl, and —S-alkylenyl-N(alkyl)$_4$.

2. The thiosulfonate compound of claim 1, wherein R$^1$ is selected from -alkenylenyl-S— and -alkylenyl-S—.

3. The thiosulfonate compound of claim 1, wherein R$^2$ is —S-alkylenyl-heterocyclo.

4. The thiosulfonate compound of claim 1, wherein R$^1$ is selected from:

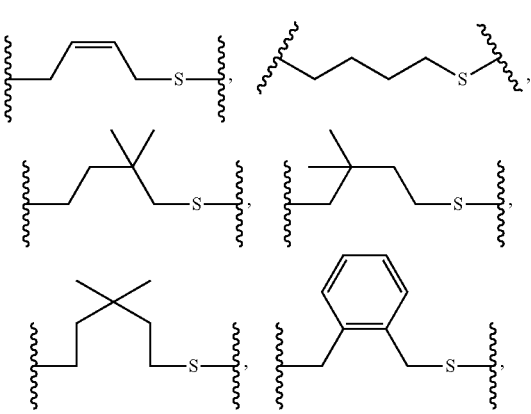

-continued

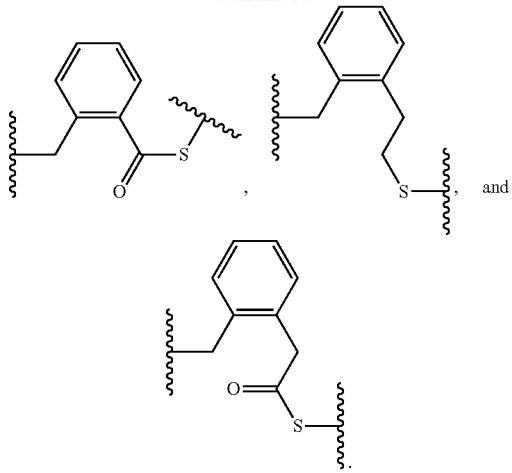

5. The thiosulfonate compound of claim 1, wherein $R^2$ is selected from:

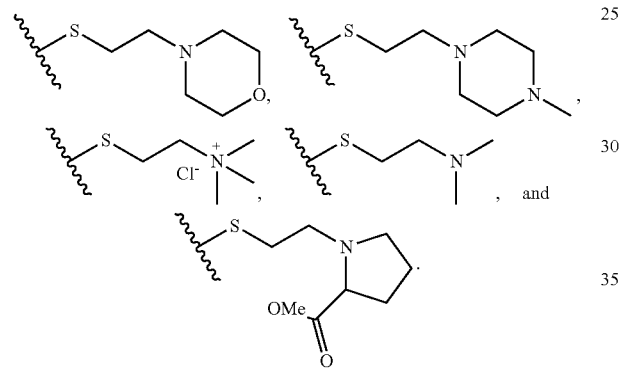

6. The thiosulfonate compound of claim 1, wherein X is alkyl.

7. The thiosulfonate compound of claim 6, wherein X is methyl.

8. A compound selected from

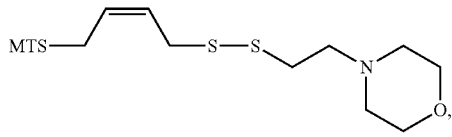

-continued

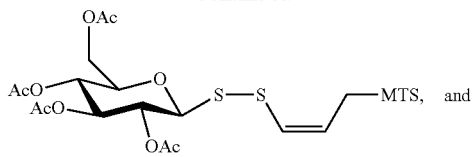

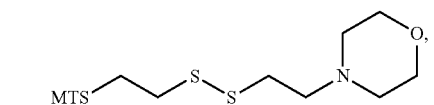

wherein MTS is $CH_3-S(O)_2-S-$.

9. The compound of claim 8, wherein the compound is

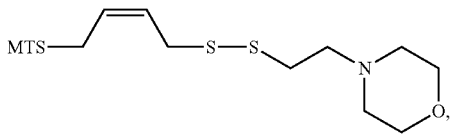

wherein MTS is $CH_3-S(O)_2-S-$.

10. The compound of claim 8, wherein the compound is

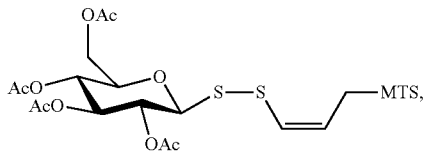

wherein MTS is $CH_3-S(O)_2-S-$.

11. The compound of claim 8, wherein the compound is

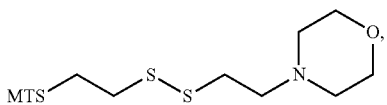

wherein MTS is $CH_3-S(O)_2-S-$.

* * * * *